United States Patent [19]
Loosmore et al.

[11] Patent Number: 5,922,562
[45] Date of Patent: Jul. 13, 1999

[54] NUCLEIC ACIDS ENCODING TRANSFERRIN RECEPTORS

[75] Inventors: Sheena Loosmore, Aurora; Robin Harkness, Willowdale; Anthony Schryvers, Calgary; Pele Chong, Richmond Hill; Scott Gray-Owen, Calgary; Yan-Ping Yang, Willowdale; Andrew Murdin, Newmarket; Michel Klein, Willowdale, all of Canada

[73] Assignee: Connaught Laboratories Limited, North York, Canada

[21] Appl. No.: 08/337,483

[22] Filed: Nov. 8, 1994

Related U.S. Application Data

[63] Continuation-in-part of application No. 08/175,116, Dec. 29, 1993, abandoned, which is a continuation-in-part of application No. 08/148,968, Nov. 8, 1993, abandoned.

[51] Int. Cl.$^6$ .......................... C12N 15/09; C07K 14/705
[52] U.S. Cl. ............... 435/69.1; 435/252.3; 435/254.11; 435/320.1; 435/325; 536/23.1; 530/412
[58] Field of Search .......................... 536/23.1; 435/69.1, 435/320.1, 240.1, 252.3, 254.11, 325; 530/412

[56] References Cited

U.S. PATENT DOCUMENTS

| | | | |
|---|---|---|---|
| 4,258,029 | 3/1981 | Moloney et al. | 424/88 |
| 4,496,538 | 1/1985 | Gordon | 424/92 |
| 4,596,792 | 6/1986 | Vyas | 514/21 |
| 4,599,230 | 7/1986 | Milich et al. | 424/89 |
| 4,599,231 | 7/1986 | Milich et al. | 424/89 |
| 4,601,903 | 7/1986 | Frasch | 424/92 |
| 4,855,283 | 8/1989 | Lockhoff et al. | 514/8 |
| 4,952,496 | 8/1990 | Studier et al. | 435/91 |
| 5,141,743 | 8/1992 | Schryvers | 424/92 |
| 5,194,254 | 3/1993 | Barber et al. | 424/85.8 |

FOREIGN PATENT DOCUMENTS

WO 92/17167  10/1992  WIPO.

OTHER PUBLICATIONS

Holland et al., FEMS Microbiology Letters, vol. 77, pp. 283–288, 1991.
Sambrook et al., Molecular Cloning, A Lab Manual, vol. 3, pp. 16.2–16.30 and pp. 17.2–17.28, $2^{nd}$ edition, Cold Spring Harbor Lab. Press.
Ghrayeb et al., Embo J., vol. 3, pp. 2437–2442, 1984.
Thomas et al., Methods in Enzymology, vol. 182, pp. 499–520, 1990.
Barcak et al., (1991) Methods Enzymol. 204: 321–342.
Berkowitz et al., (1987) J. Pediatr. 110:509.
Black et al., (1991) Pediatr. Infect. Dis. J. 10:97.
Bluestone, N. (1982) Engl. J. Med. 306:1399.
Chang et al., (1978) Nature 375:615.
Chou, et al., (1978). Annual Reviews of Biochemistry 47, 251–276.
Claesson et al., (1989) J. Pediatr. 114:97.
Cornelissen et al., (1992) J. Bacteriol. 174:5788.
Danve, et al., (1993). Vaccine 11, 1214–1220.
Deres et al., (1989) Nature 342:651.
Gerlach, et al., (1992) Infect. Immun. 608:325.
Goeddel et al., (1979) Nature 281:544.
Goeddel et al., (1980) Nucl. Acids Res. 8:4057.
Harkness et al., (1992) J. Bacteriol. 174:2425.
Holland et al., (1992) Infect. Immun. 60:2986.
Hopp, T.P. (1986) Journal of Immunological Methods 88, 1–18.
Itakura et al., (1977) Science 198:1056.
Jarosik et al., (1994). Infection and Immunity 62, 2470–2477.
Legrain et al., (1993). Gene 130:73.
Lockhoff et al., (1991) Chem. Int. Ed. Engl. 30:1611.
Mickelsen and Sparling, (1981) Infect. Immun. 33:555.
Morton et al., (1993) Infection and Immunity 61, 4033–4037.
Murdin et al., (1992) J. Gen. Viral 73: 607.
Murdin et al., (1991) Microbial Pathogenesis 10:27.
Nixon–George et al., (1990) J. Immunol. 14:4798.
Ogunnariwo, and Schryvers, (1992) Avian Dis. 36:655.
O'Hagan (1992) Clin Pharmokinet. 22:1.
Panezutti et al., (1993) Infection and Immunity 61, 1867–1872.
Roosi–Campos et al., (1992) Vaccine 10, 512–518.
Schryvers, (1988) Molec. Microbiol. 2:467.
Schryvers and Lee, (1989) Can. J. Microbiol. 35:409.
Schryvers and Gray–Owen, (1992) J. Infect. Dis. 165 suppl 1:S103.
Schryvers (1989) Med. Microbiol. 29:121.
Short et al., (1988) Nucl. Acids Res. 16:7583.
Ulmer et al., (1993) Curr. Opinion Invest. Drugs. 2 (9): 983–989.
Van der Werf et al., (1986) Proc. Natl. Acad. Sci. 83: 2330.
Weismuller et al., (1989) Vaccine 8:29.
Wilton et al., (1993) FEMS Microbiology Letters 107, 59–66.

*Primary Examiner*—Stephen Walsh
*Assistant Examiner*—Sally P. Teng
*Attorney, Agent, or Firm*—Sim & McBurney

[57] ABSTRACT

Purified and isolated nucleic acid is provided which encodes a transferrin receptor protein of a strain of Haemophilus or a fragment or an analog of the transferrin receptor protein. The nucleic acid sequence may be used to produce peptides free of contaminants derived from bacteria normally containing the Tbp1 or Tbp2 proteins for purposes of diagnostics and medical treatment. Furthermore, the nucleic acid molecule may be used in the diagnosis of infection. Also provided are recombinant Tbp1 or Tbp2 and methods for purification of the same. Live vectors expressing epitopes of transferrin receptor protein for vaccination are provided.

21 Claims, 141 Drawing Sheets

FIG.3A.

```
TATAACTCA ATG AAA TCT GTA CCT CTT ATC TCT GGT GGA CTT TCC TTT
          Met Lys Ser Val Pro Leu Ile Ser Gly Gly Leu Ser Phe
           1                   5                          10

TTA CTA AGT GCT TGT AGC GGA GGG GGG TCT TTT GAT GTA GAT AAC GTC
Leu Leu Ser Ala Cys Ser Gly Gly Gly Ser Phe Asp Val Asp Asn Val
         15                  20                  25

TCT AAT ACC CCC TCT TCT AAA CCA CGT TAT CAA GAC GAT ACT TCA AGT
Ser Asn Thr Pro Ser Ser Lys Pro Arg Tyr Gln Asp Asp Thr Ser Ser
 30                  35                  40                  45

TCA AGA ACA AAA TCT AAA TTG GAA AAG TTG TCC ATT CCT TCT TTA GGG
Ser Arg Thr Lys Ser Lys Leu Glu Lys Leu Ser Ile Pro Ser Leu Gly
         50                  55                  60

GGA GGG ATG AAG TTA GCG GCT CTG AAT CTT TTT GAT AGG AAC AAA CCT
Gly Gly Met Lys Leu Ala Ala Leu Asn Leu Phe Asp Arg Asn Lys Pro
 65                  70                  75

AGT CTC TTA AAT GAA GAT AGC TAT ATG ATA TTT TCC TCA CGT TCT ACG
Ser Leu Leu Asn Glu Asp Ser Tyr Met Ile Phe Ser Ser Arg Ser Thr
         80                  85                  90
```

FIG. 3B.

```
ATT GAA GAG GAT GTT AAA AAT GAC AAT CAA AAC GGC GAG CAC CCT ATT
Ile Glu Glu Asp Val Lys Asn Asp Asn Gln Asn Gly Glu His Pro Ile
 95                         100                         105

GAC TCA ATA GTC GAT CCT AGA GCA CCA AAT TCA AAC GAA AAT CGT CAT
Asp Ser Ile Val Asp Pro Arg Ala Pro Asn Ser Asn Glu Asn Arg His
110                         115                         120                 125

GGA CAA AAA TAT GTA TAT TCA GGG CTT TAT TAT TCA GGT TAC TAT GGA TAT
Gly Gln Lys Tyr Val Tyr Ser Gly Leu Tyr Tyr Ile Gln Ser Trp Ser
                            130                         135                 140

CTA AGA GAT TTA CCA AAT ACA ACT GCC TCT GCA TTA CCT GTA GGT GGC
Leu Arg Asp Leu Pro Asn Lys Lys Phe Tyr Ser Gly Tyr Tyr Gly Tyr
            145                         150                         155

GCG TAT TAC TTT GGC AAT ACA ACT GCC TCT GCA TTA CCT GTA GGT GGC
Ala Tyr Tyr Phe Gly Asn Thr Thr Ala Ser Ala Leu Pro Val Gly Gly
            160                         165                         170

GTA GCA ACG TAT AAA GGA ACT TGG AGC TTC ATC ACC GCA GCT GAA AAT
Val Ala Thr Tyr Lys Gly Thr Trp Ser Phe Ile Thr Ala Ala Glu Asn
175                         180                         185
```

FIG. 3C.

GGC AAG AAT TAT GAA TTG TTA AGA AAT TCT GGT GGC GGT CAA GCT TAT
Gly Lys Asn Tyr Glu Leu Leu Arg Asn Ser Gly Gly Gly Gln Ala Tyr
190                     195                 200                 205

TCT CGA CGT AGT GCT ACT CCA GAA GAT ATT GAT TTA GAT CGT AAG ACG
Ser Arg Arg Ser Ala Thr Pro Glu Asp Ile Asp Leu Asp Arg Lys Thr
        210                 215                 220

GGC TTA ACA AGT GAA TTT ACT GTC AAT TTT GGT ACA AAA AAG CTC ACT
Gly Leu Thr Ser Glu Phe Thr Val Asn Phe Gly Thr Lys Lys Leu Thr
            225                 230                 235

GGA GGA CTT TAT TAT TTA CGT GAA ACA GAT GCT AAT AAA TCA CAA
Gly Gly Leu Tyr Tyr Asn Leu Arg Glu Thr Asp Ala Asn Lys Ser Gln
                240                 245                 250

AAT AGA ACA CAT AAA CTC TAC GAT CTA GAA GCT GAT GTT CAT AGC AAC
Asn Arg Thr His Lys Leu Tyr Asp Leu Glu Ala Asp Val His Ser Asn
            255                 260                 265

CGA TTC AGG GGT AAA GTA AAG CCA ACC AAA AAA GAG TCT TCT GAA GAA
Arg Phe Arg Gly Lys Val Lys Pro Thr Lys Lys Glu Ser Ser Glu Glu
270                 275                 280                 285

FIG. 3D.

```
CAT CCC TTT ACC AGC GAG GGA ACA TTA GAA GGT GGT TTT TAC GGG CCT
His Pro Phe Thr Ser Glu Gly Thr Leu Glu Gly Gly Phe Tyr Gly Pro
        290                     295                     300

GAG GGT CAA GAA TTA GGA GGA AAG TTT TTA GCT CAC GAC AAA AAA GTT
Glu Gly Gln Glu Leu Gly Gly Lys Phe Leu Ala His Asp Lys Lys Val
        305                     310                     315

TTG GGG GTA TTT AGT GCC AAA GAA CAG CAA GAA ACG TCA GAA AAC AAA
Leu Gly Val Phe Ser Ala Lys Glu Gln Gln Glu Thr Ser Glu Asn Lys
        320                     325                     330

AAA TTA CCC AAA GAA ACC TTA ATT GAT GGC AAG CTA ACT ACT TTT AAA
Lys Leu Pro Lys Glu Thr Leu Ile Asp Gly Lys Leu Thr Thr Phe Lys
        335                     340                     345

ACA ACC AAT GCA ACA GCC AAT GCA ACA ACC GAT GCA ACA ACC AGT ACA
Thr Thr Asn Ala Thr Ala Asn Ala Thr Thr Asp Ala Thr Thr Ser Thr
        350                     355                     360                 365

ACA GCC AGT ACA AAA ACC GAT ACA ACA ACC AAT GCA ACA GCC AAT ACA
Thr Ala Ser Thr Lys Thr Asp Thr Thr Thr Asn Ala Thr Ala Asn Thr
        370                     375                     380
```

FIG. 3E.

GAA AAC TTT ACG ACA AAA GAT ATA CCA AGT TTG GGT GAA GCT GAT TAT
Glu Asn Phe Thr Thr Lys Asp Ile Pro Ser Leu Gly Glu Ala Asp Tyr
385                          390                          395

CTT TTA ATT GAT AAT TAC CCT GTT CCT CTT TTC CCT GAG AGT GGT GAT
Leu Leu Ile Asp Asn Tyr Pro Val Pro Leu Phe Pro Glu Ser Gly Asp
400                          405                          410

TTC ATA AGT AGT AAG CAC CAT ACT GTA GGA AAG AAA ACC TAT CAA GTA
Phe Ile Ser Ser Lys His His Thr Val Gly Lys Lys Thr Tyr Gln Val
415                          420                          425

GAA GCA TGT TGC AGT AAT CTA AGC TAT GTA AAA TTT GGT ATG TAT TAT
Glu Ala Cys Cys Ser Asn Leu Ser Tyr Val Lys Phe Gly Met Tyr Tyr
430                          435                          440                          445

GAA GCC CCA CCT AAA GAA GAA GAA AAA GAA AAA GAC AAA GAC
Glu Ala Pro Pro Lys Glu Glu Glu Lys Glu Lys Lys Asp Lys Asp
450                          455                          460

AAA GAA AAA GAA AAA CAA GCG ACA ACA TCT ATC AAG ACT TAT TAT CAA
Lys Glu Lys Glu Lys Gln Ala Thr Thr Ser Ile Lys Thr Tyr Tyr Gln
465                          470                          475

FIG. 3F.

TTC TTA GGT CTC CGT ACT CCC AGT TCT GAA ATA CCT AAA GAA GGA
Phe Leu Gly Leu Arg Thr Pro Ser Ser Glu Ile Pro Lys Glu Gly
480                      485                      490

AGT GCA AAA TAT CAT GGT AAT TGG TTT GGT TAT ATT AGT GAT GGC GAG
Ser Ala Lys Tyr His Gly Asn Trp Phe Gly Tyr Ile Ser Asp Gly Glu
495                      500                      505

ACA TCT TAC TCC GCC AGT GGT GAT AAG GAA CGC AGT AAA AAT GCT GTC
Thr Ser Tyr Ser Ala Ser Gly Asp Lys Glu Arg Ser Lys Asn Ala Val
510                      515                      520                  525

GCC GAG TTT AAT GTA AAT TTT GCC GAG AAA ACA TTA ACA GGC GAA TTA
Ala Glu Phe Asn Val Asn Phe Ala Glu Lys Thr Leu Thr Gly Glu Leu
530                      535                      540

AAA CGA CAC GAT ACT CAA AAT CCC GTA TTT AAA ATT AAT GCA ACC TTT
Lys Arg His Asp Thr Gln Asn Pro Val Phe Lys Ile Asn Ala Thr Phe
545                      550                      555

CAA AGT GGT AAG AAT GAC TTC ACT GGT ACA GCA ACC GCA AAA GAT TTA
Gln Ser Gly Lys Asn Asp Phe Thr Gly Thr Ala Thr Ala Lys Asp Leu
560                      565                      570

FIG. 3G.

```
GCA ATA GAT GGT AAA AAT ACA CAA GGC ACA TCT AAA GTC AAT TTC ACG
Ala Ile Asp Gly Lys Asn Thr Gln Gly Thr Ser Lys Val Asn Phe Thr
575                     580                     585

GCA ACA GTA AAC GGG GCA TTT TAT GGT CCG CAC GCT ACA GAA TTA GGC
Ala Thr Val Asn Gly Ala Phe Tyr Gly Pro His Ala Thr Glu Leu Gly
590                     595                     600                605

GGT TAT TTC ACC TAT AAC GGA AAC AAT CCT ACA GAT AAA AAT TCA TCA
Gly Tyr Phe Thr Tyr Asn Gly Asn Asn Pro Thr Asp Lys Asn Ser Ser
610                     615                     620

TCC AAT TCA GAA AAG GCA AGA GCT GCC GTT GTG TTT GGA GCT AAA AAA
Ser Asn Ser Glu Lys Ala Arg Ala Ala Val Val Phe Gly Ala Lys Lys
625                     630                     635

CAA CAA GTA GAA ACA ACC AA  GTAATGAAT ACTAAA A ATG ACT AAA AAA
Gln Gln Val Glu Thr Thr Lys                   Met Thr Lys Lys
640                                           645

CCC TAT TTT CGC CTA AGT ATT ATT TCT TGT CTT TTA ATT TCA TGC TAT
Pro Tyr Phe Arg Leu Ser Ile Ile Ser Cys Leu Leu Ile Ser Cys Tyr
650                     655                     660
```

FIG. 3H.

GTA AAA GCA GAA ACT CAA AGT ATA AAA GAT ACA AAA GAA GCT ATA TCA
Val Lys Ala Glu Thr Gln Ser Ile Lys Asp Thr Lys Glu Ala Ile Ser
665                     670                     675                 680

TCT GAA GTG GAC ACT CAA AGT ACA GAA GAT TCA GAA TTA GAA ACT ATC
Ser Glu Val Asp Thr Gln Ser Thr Glu Asp Ser Glu Leu Glu Thr Ile
            685                     690                     695

TCA GTC ACT GCA GAA AAA GTT AGA GAT CGT AAA GAT AAT GAA GTA ACT
Ser Val Thr Ala Glu Lys Val Arg Asp Arg Lys Asp Asn Glu Val Thr
            700                     705                     710

GGA CTT GGC AAA ATT ATA AAA ACT AGT GAA AGT ATC AGC CGA GAA CAA
Gly Leu Gly Lys Ile Ile Lys Thr Ser Glu Ser Ile Ser Arg Glu Gln
            715                     720                     725

GTA TTA AAT ATT CGT GAT CTA ACA CGC TAT GAT CCA GGG ATT TCA GTT
Val Leu Asn Ile Arg Asp Leu Thr Arg Tyr Asp Pro Gly Ile Ser Val
            730                     735                     740

GTA GAA CAA GGT CGC GGT GCA AGT TCT GGA TAT TCT ATT CGT GGT ATG
Val Glu Gln Gly Arg Gly Ala Ser Ser Gly Tyr Ser Ile Arg Gly Met
745                     750                     755                 760

FIG. 31.

GAC AGA AAT AGA GTT GCT TTA GTA GAT GGT TTA CCT CAA ACG CAA
Asp Arg Asn Arg Val Ala Leu Leu Val Asp Gly Leu Pro Gln Thr Gln
765                          770                         775

TCT TAT GTA GTG CAA AGC CCT TTA GTT GCT CGT TCA GGA TAT TCT GGC
Ser Tyr Val Val Gln Ser Pro Leu Val Ala Arg Ser Gly Tyr Ser Gly
        780                         785                     790

ACT GGT GCA ATT AAT GAA ATT GAA TAT GAA AAT GTA AAG GCC GTC GAA
Thr Gly Ala Ile Asn Glu Ile Glu Tyr Glu Asn Val Lys Ala Val Glu
    795                         800                     805

ATA AGC AAG GGG GGA AGT TCT TCT GAG TAT GGT AAT GGA GCA CTA GCT
Ile Ser Lys Gly Gly Ser Ser Ser Glu Tyr Gly Asn Gly Ala Leu Ala
810                         815                     820

GGT TCT GTA ACA TTT CAA AGC AAA TCA GCA GCC GAT ATC TTA GAA GGA
Gly Ser Val Thr Phe Gln Ser Lys Ser Ala Ala Asp Ile Leu Glu Gly
825                     830                     835         840

GAC AAA TCA TGG GGA ATT CAA ACT AAA AAT GCT TAT TCA AGC AAA AAT
Asp Lys Ser Trp Gly Ile Gln Thr Lys Asn Ala Tyr Ser Ser Lys Asn
                845                     850                 855

FIG. 3J.

AAA GGC TTT ACC CAT TCT TTA GCT GTA GCA GGA AAA CAA GGT GGA TTT
Lys Gly Phe Thr His Ser Leu Ala Val Ala Gly Lys Gln Gly Gly Phe
            860                     865                     870

GAA GGG GTC GCC ATT TAC ACT CAC CGA AAT TCA ATT GAA ACC CAA GTC
Glu Gly Val Ala Ile Tyr Thr His Arg Asn Ser Ile Glu Thr Gln Val
            875                     880                     885

CAT AAA GAT GCA TTA AAA GGC GTG CAA AGT TAT GAT CGA TTC ATC GCC
His Lys Asp Ala Leu Lys Gly Val Gln Ser Tyr Asp Arg Phe Ile Ala
            890                     895                     900

ACA ACA GAG GAT CAA TCT GCA TAC TTT GTG ATG CAA GAT GAG TGT CTA
Thr Thr Glu Asp Gln Ser Ala Tyr Phe Val Met Gln Asp Glu Cys Leu
            905                     910                     915                     920

GAT GGT TAT GAC AAG TGT AAA ACT TCA CCC AAA CGA CCT GCG ACT TTA
Asp Gly Tyr Asp Lys Cys Lys Thr Ser Pro Lys Arg Pro Ala Thr Leu
            925                     930                     935

TCC ACC CAA AGA GAA ACC GTA AGC GTT TCA GAT TAT ACG GGG GCT AAC
Ser Thr Gln Arg Glu Thr Val Ser Val Ser Asp Tyr Thr Gly Ala Asn
            940                     945                     950

FIG. 3K.

```
CGT ATC AAA CCT AAT CCA ATG AAA TAT GAA AGC CAG TCT TGG TTT TTA
Arg Ile Lys Pro Asn Pro Met Lys Tyr Glu Ser Gln Ser Trp Phe Leu
        955                 960                 965

AGA GGA GGT TAT CAT TTT TCT GAA CAA CAC TAT ATT GGT GGT ATT TTT
Arg Gly Gly Tyr His Phe Ser Glu Gln His Tyr Ile Gly Gly Ile Phe
        970                 975                 980

GAA TTC ACA CAA CAA AAA TTT GAT ATC CGT GAT ATG ACA TTT CCC GCT
Glu Phe Thr Gln Gln Lys Phe Asp Ile Arg Asp Met Thr Phe Pro Ala
985                 990                 995                 1000

TAT TTA AGG CCA ACA GAA GAC AAG GAT TTA CAA AGT CGC CCT TTT TAT
Tyr Leu Arg Pro Thr Glu Asp Lys Asp Leu Gln Ser Arg Pro Phe Tyr
                1005                1010                1015

CCA AAG CAA GAT TAT GGT GCA TAT CAA CAT ATT GGT GAT GGC AGA GGC
Pro Lys Gln Asp Tyr Gly Ala Tyr Gln His Ile Gly Asp Gly Arg Gly
        1020                1025                1030

GTT AAA TAT GCA AGT GGG CTT TAT TTC GAT GAA CAC CAT AGA AAA CAG
Val Lys Tyr Ala Ser Gly Leu Tyr Phe Asp Glu His His Arg Lys Gln
        1035                1040                1045
```

FIG. 3L.

CGT GTA GGT ATT GAA TAT ATT TAC GAA AAT AAG AAC AAA GCG GGC ATC
Arg Val Gly Ile Glu Tyr Ile Tyr Glu Asn Lys Asn Lys Ala Gly Ile
1050                          1055                         1060

ATT GAC AAA GCG GTG TTA AGT GCT AAT CAA CAA ACA TCA TAC TTG ACA
Ile Asp Lys Ala Val Leu Ser Ala Asn Gln Gln Thr Ser Tyr Leu Thr
1065                         1070                          1075                     1080

GTT ATA TGC GAC ATA CGC ATT GCA GTC TTT ATC CAT AAT CCA AGT AAG
Val Ile Cys Asp Ile Arg Ile Ala Val Phe Ile His Asn Pro Ser Lys
              1085                          1090                         1095

AAT TGC CGC CCA ACA CTT GAT AAA CCT TAT TCA TAC TAT CAT TCT GAT
Asn Cys Arg Pro Thr Leu Asp Lys Pro Tyr Ser Tyr Tyr His Ser Asp
                         1100                         1105                         1110

AGA AAT GTT TAT AAA GAA AAA CAT AAC ATG TTG CAA TTG CAA TTA GAG
Arg Asn Val Tyr Lys Glu Lys His Asn Met Leu Gln Leu Gln Leu Glu
             1115                          1120                         1125

AAA AAA ATT CAA CAA AAT TGG CTT ACT CAT CAA ATT GCC TTC AAT CTT
Lys Lys Ile Gln Gln Asn Trp Leu Thr His Gln Ile Ala Phe Asn Leu
1130                         1135                         1140

FIG. 3M.

GGT TTT GAT GAC TTT ACT TCC GCA CTT CAG CAT AAA GAT TAT TTA ACT
Gly Phe Asp Asp Phe Thr Ser Ala Leu Gln His Lys Asp Tyr Leu Thr
1145                          1150                         1155                    1160

CGA CGT GTT ATC GCT ACG GCA AGT AGT ATT TCA GAG AAA CGT GGT GAA
Arg Arg Val Ile Ala Thr Ala Ser Ser Ile Ser Glu Lys Arg Gly Glu
                              1165                        1170                        1175

GCA AGA AGA AAT GGT TTA CAA TCA AGT CCT TAC TTA TAC CCA ACA CCA
Ala Arg Arg Asn Gly Leu Gln Ser Ser Pro Tyr Leu Tyr Pro Thr Pro
                1180                            1185                        1190

AAA GCA GAG TTG GTA GGA GGA GAT CTT TGT AAT TAT CAA GGT AAG TCC
Lys Ala Glu Leu Val Gly Gly Asp Leu Cys Asn Tyr Gln Gly Lys Ser
          1195                            1200                        1205

TCT AAT TAC AGT GAC TGT AAA GTG CGG TTA ATT AAA GGG AAA AAT TAT
Ser Asn Tyr Ser Asp Cys Lys Val Arg Leu Ile Lys Gly Lys Asn Tyr
1210                              1215                        1220

TAT TTC GCA GCA CGC AAT AAT ATG GCA TTA GGG AAA TAC GTT GAT TTA
Tyr Phe Ala Ala Arg Asn Asn Met Ala Leu Gly Lys Tyr Val Asp Leu
1225                        1230                              1235                         1240

FIG. 3N.

GGT TTA GGT ATG AGG TAT GAC GTA TCT CGT ACA AAA GCT AAT GAA TCA
Gly Leu Gly Met Arg Tyr Asp Val Ser Arg Thr Lys Ala Asn Glu Ser
                    1245                              1250                              1255

ACT ATT AGT GTT GGT AAA TTT AAA AAT TTC TCT TGG AAT ACT GGT ATT
Thr Ile Ser Val Gly Lys Phe Lys Asn Phe Ser Trp Asn Thr Gly Ile
            1260                              1265                              1270

GTC ATA AAA CCA ACG GAA TGG CTT GAT CTT TCT TAT CGC CTT TCT ACT
Val Ile Lys Pro Thr Glu Trp Leu Asp Leu Ser Tyr Arg Leu Ser Thr
        1275                              1280                              1285

GGA TTT AGA AAT CCT AGT TTT GCT GAA ATG TAT GGT TGG CGG TAT GGT
Gly Phe Arg Asn Pro Ser Phe Ala Glu Met Tyr Gly Trp Arg Tyr Gly
    1290                              1295                              1300

GGC AAG GAT ACC GAT GTT TAT ATA GGT AAA TTT AAG CCT GAA ACA TCT
Gly Lys Asp Thr Asp Val Tyr Ile Gly Lys Phe Lys Pro Glu Thr Ser
1305                              1310                              1315                              1320

CGT AAC CAA GAG TTT GGT CTC GCT CTA AAA GGG GAT TTT GGT AAT ATT
Arg Asn Gln Glu Phe Gly Leu Ala Leu Lys Gly Asp Phe Gly Asn Ile
                1325                              1330                              1335

FIG. 30.

```
GAG ATC AGT CAT TTT AGT AAT GCT TAT CGA AAT CTT ATC GCC TTT GCT
Glu Ile Ser His Phe Ser Asn Ala Tyr Arg Asn Leu Ile Ala Phe Ala
1340                    1345                    1350

GAA GAA CTT AGT AAA AAT GGA ACT ACT GGA AAG GGC AAT TAT GGA TAT
Glu Glu Leu Ser Lys Asn Gly Thr Thr Gly Lys Gly Asn Tyr Gly Tyr
                1355                    1360                    1365

CAT AAT GCA CAA AAT GCA AAA TTA GTT GGC GTA AAT ATA ACT GCG CAA
His Asn Ala Gln Asn Ala Lys Leu Val Gly Val Asn Ile Thr Ala Gln
1370                    1375                    1380

TTA GAT TTT AAT GGT TTA TGG AAA CGT ATT CCC TAC GGT TGG TAT GCA
Leu Asp Phe Asn Gly Leu Trp Lys Arg Ile Pro Tyr Gly Trp Tyr Ala
1385                    1390                    1395                    1400

ACA TTT GCT TAT AAC CGA GTA AAA GTT AAA GAT CAA AAA ATC AAT GCT
Thr Phe Ala Tyr Asn Arg Val Lys Val Lys Asp Gln Lys Ile Asn Ala
                1405                    1410                    1415

GGT TTA GCT TCC GTA AGC AGT TAT TTA TTT GAT GCC ATT CAG CCC AGC
Gly Leu Ala Ser Val Ser Ser Tyr Leu Phe Asp Ala Ile Gln Pro Ser
                1420                    1425                    1430
```

FIG. 3P.

CGT TAT ATC ATT GGT TTA GGC TAT GAT CAT CCA AGT AAT ACT TGG GGA
Arg Tyr Ile Ile Gly Leu Gly Tyr Asp His Pro Ser Asn Thr Trp Gly
        1435                1440                1445

ATT AAG ACA ATG TTT ACT CAA TCA AAA GCA AAA TCT CAA AAT GAA TTG
Ile Lys Thr Met Phe Thr Gln Ser Lys Ala Lys Ser Gln Asn Glu Leu
        1450                1455                1460

CTA GGA AAA CGT GCA TTG GGT AAC AAT TCA AGG AAT GTA AAA TCA ACA
Leu Gly Lys Arg Ala Leu Gly Asn Asn Ser Arg Asn Val Lys Ser Thr
1465                1470                1475                1480

AGA AAA CTT ACT CGG GCA TGG CAT ATC TTA GAT GTA TCG GGT TAT TAC
Arg Lys Leu Thr Arg Ala Trp His Ile Leu Asp Val Ser Gly Tyr Tyr
        1485                1490                1495

ATG GTG AAT AGA AGT ATT TTG TTC CGA TTA GGA GTA TAT AAT TTA TTA
Met Val Asn Arg Ser Ile Leu Phe Arg Leu Gly Val Tyr Asn Leu Leu
        1500                1505                1510

AAC TAT CGC TAT GTC ACT TGG GAA GCG GTG CGT CAA ACA GCA CAA GGT
Asn Tyr Arg Tyr Val Thr Trp Glu Ala Val Arg Gln Thr Ala Gln Gly
        1515                1520                1525

FIG. 3Q.

GCG GTC AAT CAA CAT CAA AAT GTT GGT AAC TAT ACT CGC TAC GCA GCA
Ala Val Asn Gln His Gln Asn Val Gly Asn Tyr Thr Arg Tyr Ala Ala
1530                        1535                    1540

TCA GGA CGA AAC TAT ACC TTA ACA TTA GAA ATG AAA TTC TAA
Ser Gly Arg Asn Tyr Thr Leu Thr Leu Glu Met Lys Phe
1545                        1550                    1555

FIG. 4A.

GCCCAAGCTA CATTGGTTAA TGATAAGCCT ATAAATGATA AGAAAGAAAT TTGTTTTACG

CCATTTTTCA TATTTTATCC ATGAACTTAA AAAACTCTAA CTTGACATTA TTACAAAAAA

AGATCAATAA TGCGAATTAT TATCAATTTT GTATGAGTAT ATAATTCT ATG AAA TCT
                                                                                       Met Lys Ser
                                                                                              1

GTA CCT CTT ATC TCT GGT GGA CTT TCC TTT TTA CTA AGT GCT TGT AGC
Val Pro Leu Ile Ser Gly Gly Leu Ser Phe Leu Leu Ser Ala Cys Ser
 5                                10                          15

GGA GGG GGG TCT TTT GAT GTA GAT AAC GTC TCT AAT ACC CCC TCT TCT
Gly Gly Gly Ser Phe Asp Val Asp Asn Val Ser Asn Thr Pro Ser Ser
 20                             25                              30                        35

AAA CCA CGT TAT CAA GAC GAT ACC TCG AAT CAA AGA AAA AAA TCT AAT
Lys Pro Arg Tyr Gln Asp Asp Thr Ser Asn Gln Arg Lys Lys Ser Asn
                       40                              45                              50

TTG AAA AAG TTG TTC ATT CCT TCT TTA GGA GGA GGG ATG AAA TTG GTG
Leu Lys Lys Leu Phe Ile Pro Ser Leu Gly Gly Gly Met Lys Leu Val
                       55                              60                              65

FIG. 4B.

GCT CAG AAT CTT CGT GGT AAT AAA GAA CCT AGT TTC TTA AAT GAA GAT
Ala Gln Asn Leu Arg Gly Asn Lys Glu Pro Ser Phe Leu Asn Glu Asp
         70                  75                  80

GAC TAT ATA TCA TAT TTT TCC TCA CTT TCT ACG ATT GAA AAG GAT GTT
Asp Tyr Ile Ser Tyr Phe Ser Ser Leu Ser Thr Ile Glu Lys Asp Val
         85                  90                  95

AAA GAT AAC AAT AAA AAC GGG GCG CTT ATT GGC TCA ATA GAC GAG
Lys Asp Asn Asn Lys Asn Gly Ala Asp Leu Ile Gly Ser Ile Asp Glu
100                 105                 110                 115

CCT AGT ACA ACA AAT CCA CCC GAA AAG CAT GGA CAA AAA TAT GTA
Pro Ser Thr Thr Asn Pro Pro Glu Lys His His Gly Gln Lys Tyr Val
                120                 125                 130

TAT TCA GGG CTT TAT TAT ACT CCA TCG TGG AGT TTA AAC GAT TCT AAA
Tyr Ser Gly Leu Tyr Tyr Thr Pro Ser Trp Ser Leu Asn Asp Ser Lys
            135                 140                 145

AAC AAG TTT TAT TTA GGT TAC TAT GGA TAT GCG TTT TAT TAT GGT AAT
Asn Lys Phe Tyr Leu Gly Tyr Tyr Gly Tyr Ala Phe Tyr Tyr Gly Asn
        150                 155                 160

FIG. 4C.

```
AAA ACT GCA ACA AAC TTG CCA GTA AAC GGT GTA GCT AAA TAC AAA GGA
Lys Thr Ala Thr Asn Leu Pro Val Asn Gly Val Ala Lys Tyr Lys Gly
165                     170                     175

ACT TGG GAT TTC ATC ACT GCA ACT AAA AAT GGC AAA CGT TAT CCT TTG
Thr Trp Asp Phe Ile Thr Ala Thr Lys Asn Gly Lys Arg Tyr Pro Leu
        180                     185                     190                     195

TTA AGT AAT GGC AGT CAC GCT TAT TAT CGA CGT AGT GCA ATT CCA GAA
Leu Ser Asn Gly Ser His Ala Tyr Tyr Arg Arg Ser Ala Ile Pro Glu
                200                     205                     210

GAT ATT GAT TTA GAA AAT GAT TCA AAG AAT GGT GAT ATA GGC TTA ATA
Asp Ile Asp Leu Glu Asn Asp Ser Lys Asn Gly Asp Ile Gly Leu Ile
            215                     220                     225

AGT GAA TTT AGT GCA GAT TTT GGG ACT AAA AAA CTG ACA GGA CAA CTG
Ser Glu Phe Ser Ala Asp Phe Gly Thr Lys Lys Leu Thr Gly Gln Leu
        230                     235                     240

TCT TAC ACC AAA AGA AAA ACT AAT CAA CCA TAT GAA AAG AAA AAA
Ser Tyr Thr Lys Arg Lys Thr Asn Gln Pro Tyr Glu Lys Lys Lys
245                     250                     255
```

FIG. 4D.

```
CTC TAT GAT ATA GAT GCC GAT ATT TAT AGT AAT AGA TTC AGG GGT ACA
Leu Tyr Asp Ile Asp Ala Asp Ile Tyr Ser Asn Arg Phe Arg Gly Thr
260                 265                 270                 275

GTA AAG CCA ACC GAA AAA GAT TCT GAA GAA CAT CCC TTT ACC AGC GAG
Val Lys Pro Thr Glu Lys Asp Ser Glu Glu His Pro Phe Thr Ser Glu
                280                 285                 290

GGA ACA TTA GAA GGT GGT TTT TAT GGG CCT AAT GCT GAA GAA CTA GGG
Gly Thr Leu Glu Gly Gly Phe Tyr Gly Pro Asn Ala Glu Glu Leu Gly
            295                 300                 305

GGG AAA TTT TTA GCT ACG GAT AAC CGA GTT TTT GGG GTA TTT AGT GCC
Gly Lys Phe Leu Ala Thr Asp Asn Arg Val Phe Gly Val Phe Ser Ala
310                 315                 320

AAA GAA ACG GAA GAA ACA AAA AAG GAA GCG TTA TCC AAG GAA ACC TTA
Lys Glu Thr Glu Glu Thr Lys Lys Glu Ala Leu Ser Lys Glu Thr Leu
                325                 330                 335

ATT GAT GGC AAG CTA ATT ACT TTC TCT ACT AAA AAA ACC GAT GCA AAA
Ile Asp Gly Lys Leu Ile Thr Phe Ser Thr Lys Lys Thr Asp Ala Lys
340                 345                 350                 355
```

FIG. 4E.

ACC AAT GCA ACA ACC AGT ACC GCA GCT AAT ACA ACC GAT ACA ACC
Thr Asn Ala Thr Thr Ser Thr Ala Ala Asn Thr Thr Asp Thr Thr
              360                   365                   370

GCC AAT ACA ATA ACC GAT GAA AAA AAC TTT AAG ACG GAA GAT ATA TCA
Ala Asn Thr Ile Thr Asp Glu Lys Asn Phe Lys Thr Glu Asp Ile Ser
              375                   380                   385

AGT TTT GGT GAA GCT GAT TAT CTG TTA ATT GAC AAA TAT CCT ATT CCA
Ser Phe Gly Glu Ala Asp Tyr Leu Leu Ile Asp Lys Tyr Pro Ile Pro
              390                   395                   400

CTT TTA CCT GAT AAA AAT ACT AAT GAT TTC ATA AGT AGT AAG CAT CAT
Leu Leu Pro Asp Lys Asn Thr Asn Asp Phe Ile Ser Ser Lys His His
              405                   410                   415

ACT GTA GGA AAT AAA CGC TAT AAA GTG GAA GCA TGT TGC AGT AAT CTA
Thr Val Gly Asn Lys Arg Tyr Lys Val Glu Ala Cys Cys Ser Asn Leu
              420                   425                   430                   435

AGC TAT GTG AAA TTT GGT ATG TAT TAT GAA GAC CCA CTT AAA GAA AAA
Ser Tyr Val Lys Phe Gly Met Tyr Tyr Glu Asp Pro Leu Lys Glu Lys
              440                   445                   450

FIG. 4F.

GAA ACA GAA ACA GAA ACA GAA AAA GAC AAA GAA AAA GAA AAA
Glu Thr Glu Thr Glu Thr Glu Lys Asp Lys Glu Lys Glu Lys
455                             460                     465

GAA AAA GAC AAA GAA AAA GAA CAA ACG GCG GCA ACG AAC ACT
Glu Lys Asp Lys Glu Lys Gln Thr Ala Ala Thr Asn Thr
470                             475                     480

TAT TAT CAA TTC TTA TTA GGT CAC CGT ACT CCC AAG GAC GAC ATA CCT
Tyr Tyr Gln Phe Leu Leu Gly His Arg Thr Pro Lys Asp Asp Ile Pro
485                             490                     495

AAA ACA GGA AGT GCA AAA TAT CAT GGT AGT TGG TTT GGT TAT ATT ACT
Lys Thr Gly Ser Ala Lys Tyr His Gly Ser Trp Phe Gly Tyr Ile Thr
500                             505                     510                     515

GAC GGT AAG ACA TCT TAC TCC CCC AGT GGT GAT AAG AAA CGC GAT AAA
Asp Gly Lys Thr Ser Tyr Ser Pro Ser Gly Asp Lys Lys Arg Asp Lys
520                             525                     530

AAT GCT GTC GCC GAG TTT AAT GTT GAT TTT GCC GAG AAA AAG CTA ACA
Asn Ala Val Ala Glu Phe Asn Val Asp Phe Ala Glu Lys Lys Leu Thr
535                             540                     545

FIG. 4G.

GGC GAA TTA AAA CCA CAC GAT ACT GGA AAT CCC GTA TTT AGT ATT GAG
Gly Glu Leu Lys Arg His Asp Thr Gly Asn Pro Val Phe Ser Ile Glu
550                             555                         560

GCA AAC TTT AAT AAT AGT AGT AAT GCC TTC ACT GGT ACA GCA ACC GCA
Ala Asn Phe Asn Asn Ser Ser Asn Ala Phe Thr Gly Thr Ala Thr Ala
565                             570                         575

ACA AAT TTT GTA ATA GAT GGT AAA AAT AGT CAA AAT AAA AAT ACC CCA
Thr Asn Phe Val Ile Asp Gly Lys Asn Ser Gln Asn Lys Asn Thr Pro
580                             585                         590                 595

ATT AAT ATT ACA ACT AAA GTA AAC GGG GCA TTT TAT AAC GGA AAT TCT ACA GCT ACA
Ile Asn Ile Thr Thr Lys Val Asn Gly Ala Phe Tyr Asn Gly Asn Ser Thr Ala Thr
                600                             605                         610

TCT GAA TTA GGC GGT TAT TTC ACT TAT TTC ACT TAT TTC ACT TCA AAA AAT
Ser Glu Leu Gly Gly Tyr Phe Thr Tyr Phe Thr Tyr Gly Pro Lys Ala
615                             620                         625

AAT TCT GAA AGT TCC TCA ACC GTA TCT TCA TCC AAT TCA AAA AAT
Asn Ser Glu Ser Ser Ser Thr Val Ser Ser Ser Asn Ser Lys Asn
630                             635                         640

FIG. 4H.

GCA AGA GCT GCA GTT GTC TTT GGT GCG AGA CAA CAA GTA GAA ACA ACC
Ala Arg Ala Ala Val Val Phe Gly Ala Arg Gln Gln Val Glu Thr Thr
645                                      650                             655

AAA TAATGAATA CTAAAA ATG ACT AAA AAA CCC TAT TTT CGC CTA AGT
Lys                        Met Thr Lys Lys Pro Tyr Phe Arg Leu Ser
660                                665                              670

ATT ATT TCT TGT CTT TTA ATT TCA TGC TAT GTA AAA GCA GAA ACT CAA
Ile Ile Ser Cys Leu Leu Ile Ser Cys Tyr Val Lys Ala Glu Thr Gln
                675                              680                             685

AGT ATA AAA GAT ACA AAA GAA GCT ATA TCA TCT GAA GTG GAC ACT CAA
Ser Ile Lys Asp Thr Lys Glu Ala Ile Ser Ser Glu Val Asp Thr Gln
              690                              695                             700

AGT ACA GAA GAT TCA GAA TTA GAA ACT ATC TCA GTC ACT GCA GAA AAA
Ser Thr Glu Asp Ser Glu Leu Glu Thr Ile Ser Val Thr Ala Glu Lys
             705                              710                             715

ATA AGA GAT CGT AAA GAT AAT GAA GTA ACT GGA CTT GGC AAA ATT ATC
Ile Arg Asp Arg Lys Asp Asn Glu Val Thr Gly Leu Gly Lys Ile Ile
             720                              725                             730

FIG. 41.

AAA ACT AGT GAA AGT ATC AGC CGA GAA CAA GTA TTA AAT ATT CGT GAT
Lys Thr Ser Glu Ser Ile Ser Arg Glu Gln Val Leu Asn Ile Arg Asp
735                          740                          745                 750

CTA ACA CGC TAT GAT CCA GGG ATT TCA GTT GTA GAA CAA GGT CGC GGT
Leu Thr Arg Tyr Asp Pro Gly Ile Ser Val Val Glu Gln Gly Arg Gly
                755                          760                          765

GCA AGT TCT GGA TAT TCT ATT CGT GGT ATG GAC AGA AAT AGA GTT GCT
Ala Ser Ser Gly Tyr Ser Ile Arg Gly Met Asp Arg Asn Arg Val Ala
770                          775                          780

TTA TTA GTA GAT GGT TTA CCT CAA ACG CAA TCT TAT GTA CAA AGC
Leu Leu Val Asp Gly Leu Pro Gln Thr Gln Ser Tyr Val Val Gln Ser
        785                          790                          795

CCT TTA GTT GCT CGT TCA GGA TAT TCT GGC ACT GGT GCA ATT AAT GAA
Pro Leu Val Ala Arg Ser Gly Tyr Ser Gly Thr Gly Ala Ile Asn Glu
                800                          805                          810

ATT GAA TAT GAA AAT GTA AAG GCC GTC GAA ATA AGC AAG GGG AGT
Ile Glu Tyr Glu Asn Val Lys Ala Val Glu Ile Ser Lys Gly Ser
815                          820                          825                 830

FIG. 4J.

TCT TCT GAG TAT GGT AAT GGA GCA CTA GCT GGT TCT GTA ACA TTT CAA
Ser Ser Glu Tyr Gly Asn Gly Ala Leu Ala Gly Ser Val Thr Phe Gln
            835                     840                     845

AGC AAA TCA GCA GCC GAT ATC TTA GAA GGA GAC AAA TCA TGG GGA ATT
Ser Lys Ser Ala Ala Asp Ile Leu Glu Gly Asp Lys Ser Trp Gly Ile
            850                     855                     860

CAA ACT AAA AAT GCT TAT TCA AGC AAA AAT AAA GGC TTT ACC CAT TCT
Gln Thr Lys Asn Ala Tyr Ser Ser Lys Asn Lys Gly Phe Thr His Ser
            865                     870                     875

TTA GCT GTA GCA GGA AAA CAA GGT GGA TTT GAA GGG CTA GCC ATT TAC
Leu Ala Val Ala Gly Lys Gln Gly Gly Phe Glu Gly Leu Ala Ile Tyr
            880                     885                     890

ACT CAA CGA AAT TCA ATT GAA ACC CAA GTC CAT AAA GAT GCA TTA AAA
Thr Gln Arg Asn Ser Ile Glu Thr Gln Val His Lys Asp Ala Leu Lys
            895                     900                     905                     910

GGC GTA CAA AGT TAT GAT CGA TTA ATC GCC ACA ACA GAT AAA TCT TCA
Gly Val Gln Ser Tyr Asp Arg Leu Ile Ala Thr Thr Asp Lys Ser Ser
            915                     920                     925

FIG. 4K.

GGA TAC TTT GTG ATA CAA GGT GAG TGT CCA AAT GGT GAT GAC AAG TGT
Gly Tyr Phe Val Ile Gln Gly Glu Cys Pro Asn Gly Asp Asp Lys Cys
930                             935                         940

GCA GCC AAG CCA CCT GCG ACT TTA TCC ACC CAA AGC GAA ACC GTA AGC
Ala Ala Lys Pro Pro Ala Thr Leu Ser Thr Gln Ser Glu Thr Val Ser
945                             950                         955

GTT TCA GAT TAT ACG GGG GCT AAC CGT ATC AAA CCT AAT CCA ATG AAA
Val Ser Asp Tyr Thr Gly Ala Asn Arg Ile Lys Pro Asn Pro Met Lys
960                             965                         970

TAT GAA AGC CAG TCT TGG TTT TTA AGA GGA GGG TAT CAT TTT TCT GAA
Tyr Glu Ser Gln Ser Trp Phe Leu Arg Gly Gly Tyr His Phe Ser Glu
975                             980                         985                    990

CAA CAT TAT ATT GGT GGT ATT TTT GAA TTC ACA CAA CAA AAA TTT GAT
Gln His Tyr Ile Gly Gly Ile Phe Glu Phe Thr Gln Gln Lys Phe Asp
995                             1000                        1005

ATC CGT GAT ATG ACA TTT CCC GCT TAT TTA AGC CCA ACA GAA AGA CGG
Ile Arg Asp Met Thr Phe Pro Ala Tyr Leu Ser Pro Thr Glu Arg Arg
1010                            1015                        1020

FIG. 4L.

GAT GAT AGT AGT CGT TCT TTT TAT CCA ATG CAA GAT CAT GGT GCA TAT
Asp Asp Ser Ser Arg Ser Phe Tyr Pro Met Gln Asp His Gly Ala Tyr
                            1030                        1035

CAA CAT ATT GAG GAT GGC AGA GGC GTT AAA TAT GCA AGT GGG CTT TAT
Gln His Ile Glu Asp Gly Arg Gly Val Lys Tyr Ala Ser Gly Leu Tyr
1040                        1045                        1050

TTC GAT GAA CAC CAT AGA CAG CGT GTA GGT ATT GAA TAT ATT TAC
Phe Asp Glu His His Arg Gln Arg Val Gly Ile Glu Tyr Ile Tyr
1055                        1060                    1065        1070

GAA AAT AAG AAC AAA GCG GGC ATC ATT GAC AAA GCA GTG TTA AGT GCT
Glu Asn Lys Asn Lys Ala Gly Ile Ile Asp Lys Ala Val Leu Ser Ala
                        1075                        1080                1085

AAT CAA CAA AAC ATC ATA CTT GAC AGT TAT ATG CGA CAT ACG CAT TGC
Asn Gln Gln Asn Ile Ile Leu Asp Ser Tyr Met Arg His Thr His Cys
                    1090                        1095                    1100

AGT CTT TAT CCT AAT CCA AGT AAG AAT TGC CGC CCA ACA CTT GAT AAA
Ser Leu Tyr Pro Asn Pro Ser Lys Asn Cys Arg Pro Thr Leu Asp Lys
        1105                        1110                        1115

FIG. 4M.

CCT TAT TCA TAC TAT CGT TCT GAT AGA AAT GTT TAT AAA GAA AAA CAT
Pro Tyr Ser Tyr Tyr Arg Ser Asp Arg Asn Val Tyr Lys Glu Lys His
1120                     1125                    1130

AAT ATG TTG CAA TTG AAT TTA GAG AAA AAA ATT CAA CAA AAT TGG CTT
Asn Met Leu Gln Leu Asn Leu Glu Lys Lys Ile Gln Gln Asn Trp Leu
1135                     1140                    1145           1150

ACT CAT CAA ATT GTC TTC AAT CTT GGT TTT GAT GAC TTT ACT TCA GCG
Thr His Gln Ile Val Phe Asn Leu Gly Phe Asp Asp Phe Thr Ser Ala
                    1155                     1160                    1165

CTT CAG CAT AAA GAT TAT TTA ACT CGA CGT GTT ATC GCT ACG GCA GAT
Leu Gln His Lys Asp Tyr Leu Thr Arg Arg Val Ile Ala Thr Ala Asp
                    1170                     1175                    1180

AGT ATT CCA AGG AAA CCT GGT GAA ACT GGT GGG AAA CCA AGA AAT TTG
Ser Ile Pro Arg Lys Pro Gly Glu Thr Gly Lys Pro Arg Asn Leu
1185                     1190                    1195

CAA TCA CAA CCT TAC TTA TAC CCA AAA CCA GAG CCA TAT TTT GCA GGA
Gln Ser Gln Pro Tyr Leu Tyr Pro Lys Pro Glu Pro Tyr Phe Ala Gly
1200                     1205                    1210

FIG. 4N.

CAA GAT CAT TGT AAT TAT CAA GGT AGC TCC TCT AAT TAC AGA GAC TGT
Gln Asp His Cys Asn Tyr Gln Gly Ser Ser Ser Asn Tyr Arg Asp Cys
1215                        1220                   1225              1230

AAA GTG CGG TTA ATT AAA GGG AAA AAT TAT TAT TTC GCA GCA CGC AAT
Lys Val Arg Leu Ile Lys Gly Lys Asn Tyr Tyr Phe Ala Ala Arg Asn
        1235                        1240                   1245

AAT ATG GCA TTA GGG AAA TAC GTT GAT TTA GGT TTA GGT ATT CGG TAT
Asn Met Ala Leu Gly Lys Tyr Val Asp Leu Gly Leu Gly Ile Arg Tyr
1250                        1255                   1260

GAC GTA TCT CGT ACA AAA GCT AAT GAA TCA ACT ATT AGT GTT GGT AAA
Asp Val Ser Arg Thr Lys Ala Asn Glu Ser Thr Ile Ser Val Gly Lys
        1265                        1270                   1275

TTT AAA AAT TTC TCT TGG AAT ACT GGT ATT GTC ATA AAA CCA ACG GAA
Phe Lys Asn Phe Ser Trp Asn Thr Gly Ile Val Ile Lys Pro Thr Glu
1280                        1285                   1290

TGG CTT GAT CTT CTT TCT TAT CGC CTT TCT ACT GGA TTT AGA AAT CCT AGT
Trp Leu Asp Leu Ser Tyr Arg Leu Ser Thr Gly Phe Arg Asn Pro Ser
1295            1300                    1305                1310

FIG. 40.

```
TTT TCT GAA ATG TAT GGT TGG CGG TAT GGT GGC AAG AAT GAC GAG GTT
Phe Ser Glu Met Tyr Gly Trp Arg Tyr Gly Gly Lys Asn Asp Glu Val
1315                        1320                        1325

TAT GTA GGT AAA TTT AAG CCT GAA ACA TCT CGT AAC CAA GAG TTT GGT
Tyr Val Gly Lys Phe Lys Pro Glu Thr Ser Arg Asn Gln Glu Phe Gly
1330                        1335                        1340

CTC GCT CTA AAA GGG GAT TTT GGT AAT ATT GAG ATC AGT CAT TTT AGT
Leu Ala Leu Lys Gly Asp Phe Gly Asn Ile Glu Ile Ser His Phe Ser
1345                        1350                        1355

AAT GCT TAT CGA AAT CTT ATC GCC TTT GCT GAA GAA CTT AGT AAA AAT
Asn Ala Tyr Arg Asn Leu Ile Ala Phe Ala Glu Glu Leu Ser Lys Asn
1360                        1365                        1370

GGA ACT GAA AAG GGC AAT TAT GGA TAT CAT AAT GCA CAA AAT GCA AAA
Gly Thr Glu Lys Gly Asn Tyr Gly Tyr His Asn Ala Gln Asn Ala Lys
1375                        1380                        1385                        1390

TTA GTT GGC GTA AAT ATA ACT GCA CAA TTA GAT TTT AAT GGT TTA TGG
Leu Val Gly Val Asn Ile Thr Ala Gln Leu Asp Phe Asn Gly Leu Trp
1395                        1400                        1405
```

FIG. 4P.

AAA CGT ATT CCC TAC GGT TGG TAT TGC ACA TTT GCT TAT AAC CAA GTA
Lys Arg Ile Pro Tyr Gly Trp Tyr Ala Thr Phe Ala Tyr Asn Gln Val
                1410                          1415                    1420

AAA GTT AAA GAT CAA AAA ATC AAT GCT GGT TTA GCC TCC GTA AGC AGT
Lys Val Lys Asp Gln Lys Ile Asn Ala Gly Leu Ala Ser Val Ser Ser
             1425                          1430                  1435

TAT TTA TTT GAT GCC ATT CAG CCC AGC CGT TAT ATC ATT GGT TTA GGC
Tyr Leu Phe Asp Ala Ile Gln Pro Ser Arg Tyr Ile Ile Gly Leu Gly
             1440                          1445                     1450

TAT GAT CAT CCA AGT AAT ACT TGG GGA ATT AAT ACA ATG TTT ACT CAA
Tyr Asp His Pro Ser Asn Thr Trp Gly Ile Asn Thr Met Phe Thr Gln
             1455                          1460                    1465                1470

TCA AAA GCA AAA TCT CAA AAT GAA TTG CTA GGA AAA CGT GCA TTA GGT
Ser Lys Ala Lys Ser Gln Asn Glu Leu Leu Gly Lys Arg Ala Leu Gly
             1475                          1480                          1485

AAC AAT TCA AGG GAT GTA AAA AGA AAA TCA ACA AGA CTT ACT CGG GCA TGG
Asn Asn Ser Arg Asp Val Lys Arg Lys Ser Thr Arg Lys Leu Thr Arg Ala Trp
             1490                          1495                       1500

FIG. 4Q.

```
CAT ATC TTA GAT GTA TCG GGT TAT TAC ATG GCG AAT AAA AAT ATT ATG
His Ile Leu Asp Val Ser Gly Tyr Tyr Met Ala Asn Lys Asn Ile Met
            1505                           1510                       1515

CTT CGA TTA GGG ATA TAT AAT TTA TTC AAC TAT CGC TAT GTT ACT TGG
Leu Arg Leu Gly Ile Tyr Asn Leu Phe Asn Tyr Arg Tyr Val Thr Trp
            1520                           1525                       1530

GAA GCG GTG CGT CAA ACA GCA CAA GGT GCG GTC AAT CAA CAT CAA AAT
Glu Ala Val Arg Gln Thr Ala Gln Gly Ala Val Asn Gln His Gln Asn
1535                           1540                           1545                 1550

GTT GGT AGC TAT ACT CGC TAC GCA GCA TCA GGA CGA AAC TAT ACC TTA
Val Gly Ser Tyr Thr Arg Tyr Ala Ala Ser Gly Arg Asn Tyr Thr Leu
                  1555                           1560                       1565

ACA TTA GAA ATG AAA TTC TAAATTAAAA TGCGCCAGAT GGACTAGATA
Thr Leu Glu Met Lys Phe
       1570

TGCTATATCT ATACCTTACT GGGGCATCTT TTTCTGTTCT ATAATCTGCT TAAGTGAAAA

ACCAAACTTG GATTTTTTAC AAGATCTTTT CACACATTTA TTG
```

FIG. 5A.

ATTTGTTTA CGCCATTTT CATATTTAT CCATGAACTT AAAAAACTCT AACTTGACAT

TATTACAAAA AAAGATCAAT AATGCGAATT ATTATCAATT TTGTATGAGT ATATAATTCT

| ATG | AAA | TCT | GTA | CCT | CTT | ATC | TCT | GGT | GGA | CTT | TCC | TTT | TTA | CTA | AGT |
|---|---|---|---|---|---|---|---|---|---|---|---|---|---|---|---|
| Met | Lys | Ser | Val | Pro | Leu | Ile | Ser | Gly | Gly | Leu | Ser | Phe | Leu | Leu | Ser |
| 1 | | | | 5 | | | | | 10 | | | | | 15 | |

| GCT | TGT | AGC | GGA | GGG | GGG | TCT | TTT | GAT | GTA | GAT | AAC | GTC | TCT | AAT | ACC |
|---|---|---|---|---|---|---|---|---|---|---|---|---|---|---|---|
| Ala | Cys | Ser | Gly | Gly | Gly | Ser | Phe | Asp | Val | Asp | Asn | Val | Ser | Asn | Thr |
| | | | 20 | | | | | 25 | | | | | 30 | | |

| CCC | TCT | TCT | AAA | CCA | CGT | TAT | CAA | GAC | GAT | ACC | TCG | AAT | CAA | AGA | AAA |
|---|---|---|---|---|---|---|---|---|---|---|---|---|---|---|---|
| Pro | Ser | Ser | Lys | Pro | Arg | Tyr | Gln | Asp | Asp | Thr | Ser | Asn | Gln | Arg | Lys |
| | | | 35 | | | | | 40 | | | | | 45 | | |

| AAA | TCT | AAT | TTG | AAA | AAG | TTG | TTC | ATT | CCT | TCT | TTA | GGA | GGA | GGG | ATG |
|---|---|---|---|---|---|---|---|---|---|---|---|---|---|---|---|
| Lys | Ser | Asn | Leu | Lys | Lys | Leu | Phe | Ile | Pro | Ser | Leu | Gly | Gly | Gly | Met |
| | | | 50 | | | | | 55 | | | | | 60 | | |

| AAA | TTG | GTG | GCT | CAG | AAT | CTT | CGT | GGT | AAT | AAA | GAA | CCT | AGT | TTC | TTA |
|---|---|---|---|---|---|---|---|---|---|---|---|---|---|---|---|
| Lys | Leu | Val | Ala | Gln | Asn | Leu | Arg | Gly | Asn | Lys | Glu | Pro | Ser | Phe | Leu |
| | | | 65 | | | | | 70 | | | | | 75 | | 80 |

FIG. 5B.

```
AAT GAA GAT GAC TAT ATA TCA TAT TTT TCC TCA CTT TCT ACG ATT GAA
Asn Glu Asp Asp Tyr Ile Ser Tyr Phe Ser Ser Leu Ser Thr Ile Glu
 85                          90                          95

AAG GAT GTT AAA GAT AAC AAT AAA AAC GGG GCG GAC CTT ATT GGC TCA
Lys Asp Val Lys Asp Asn Asn Lys Asn Gly Ala Asp Leu Ile Gly Ser
                100                         105                         110

ATA GAC GAG CCT AGT ACA ACA AAT CCA CCC GAA AAG CAT CAT GGA CAA
Ile Asp Glu Pro Ser Thr Thr Asn Pro Pro Glu Lys His His Gly Gln
        115                         120                         125

AAA TAT GTA TAT TCA GGG CTT TAT TAT ACT CCA TCG TGG AGT TTA AAC
Lys Tyr Val Tyr Ser Gly Leu Tyr Tyr Thr Pro Ser Trp Ser Leu Asn
130                         135                         140

GAT TCT AAA AAC AAG TTT TAT TTA GGT TAC TAT GGA TAT GCG TTT TAT
Asp Ser Lys Asn Lys Phe Tyr Leu Gly Tyr Tyr Gly Tyr Ala Phe Tyr
145                         150                         155                 160

TAT GGT AAT AAA ACT GCA ACA AAC TTG CCA GTA AAC GGT GTA GCT AAA
Tyr Gly Asn Lys Thr Ala Thr Asn Leu Pro Val Asn Gly Val Ala Lys
            165                         170                         175
```

FIG. 5C.

```
TAC AAA GGA ACT TGG GAT TTC ATC ACT GCA ACT AAA AAT GGC AAA CGT
Tyr Lys Gly Thr Trp Asp Phe Ile Thr Ala Thr Lys Asn Gly Lys Arg
        180                     185                     190

TAT CCT TTG TTA AGT AAT GGC AGT CAC GCT TAT TAT CGA CGT AGT GCA
Tyr Pro Leu Leu Ser Asn Gly Ser His Ala Tyr Tyr Arg Arg Ser Ala
        195                     200                     205

ATT CCA GAA GAT ATT GAT TTA GAA AAT GAT TCA AAG AAT GGT GAT ATA
Ile Pro Glu Asp Ile Asp Leu Glu Asn Asp Ser Lys Asn Gly Asp Ile
        210                     215                     220

GGC TTA ATA AGT GAA TTT AGT GCA GAT TTT GGG ACT AAA AAA CTG ACA
Gly Leu Ile Ser Glu Phe Ser Ala Asp Phe Gly Thr Lys Lys Leu Thr
        225                     230                     235                     240

GGA CAA CTG TCT TAC ACC AAA AGA AAA ACT AAT AAT CAA CCA TAT GAA
Gly Gln Leu Ser Tyr Thr Lys Arg Lys Thr Asn Asn Gln Pro Tyr Glu
        245                     250                     255

AAG AAA AAA CTC TAT GAT ATA GAT GCC GAT ATT TAT AGT AAT AGA TTC
Lys Lys Lys Leu Tyr Asp Ile Asp Ala Asp Ile Tyr Ser Asn Arg Phe
        260                     265                     270
```

FIG. 5D.

AGG GGT ACA GTA AAG CCA ACC GAA AAA GAT TCT GAA GAA CAT CCC TTT
Arg Gly Thr Val Lys Pro Thr Glu Lys Asp Ser Glu Glu His Pro Phe
                    275                 280                 285

ACC AGC GAG GGA ACA TTA GAA GGT GGT TTT TAT GGG CCT AAT GCT GAA
Thr Ser Glu Gly Thr Leu Glu Gly Gly Phe Tyr Gly Pro Asn Ala Glu
                290                 295                 300

GAA CTA GGG GGG AAA TTT TTA GCT ACG GAT AAC CGA GTT TTT GGG GTA
Glu Leu Gly Gly Lys Phe Leu Ala Thr Asp Asn Arg Val Phe Gly Val
305                 310                 315                 320

TTT AGT GCC AAA GAA ACG GAA ACA AAA AAG GAA GCG TTA TCC AAG
Phe Ser Ala Lys Glu Thr Glu Thr Lys Lys Glu Ala Leu Ser Lys
                    325                 330                 335

GAA ACC TTA ATT GAT GGC AAG CTA ATT ACT TTC TCT ACT AAA AAA ACC
Glu Thr Leu Ile Asp Gly Lys Leu Ile Thr Phe Ser Thr Lys Lys Thr
                340                 345                 350

GAT GCA AAA ACC AAT GCA ACA ACC AGT ACC GCA GCT AAT ACA ACA ACC
Asp Ala Lys Thr Asn Ala Thr Thr Ser Thr Ala Ala Asn Thr Thr Thr
                    355                 360                 365

FIG. 5E.

GAT ACA ACC GCC AAT ACA ATA ACC GAT GAA AAA AAC TTT AAG ACG GAA
Asp Thr Thr Ala Asn Thr Ile Thr Asp Glu Lys Asn Phe Lys Thr Glu
370                          375                          380

GAT ATA TCA AGT TTT GGT GAA GCT GAT TAT CTG TTA ATT GAC AAA TAT
Asp Ile Ser Ser Phe Gly Glu Ala Asp Tyr Leu Leu Ile Asp Lys Tyr
385                          390                          395                  400

CCT ATT CCA CTT TTA CCT GAT AAA AAT ACT AAT GAT TTC ATA AGT AGT
Pro Ile Pro Leu Leu Pro Asp Lys Asn Thr Asn Asp Phe Ile Ser Ser
            405                          410                          415

AAG CAT CAT ACT GTA GGA AAT AAA CGC TAT AAA GTG GAA GCA TGT TGC
Lys His His Thr Val Gly Asn Lys Arg Tyr Lys Val Glu Ala Cys Cys
                    420                          425                     430

AGT AAT CTA AGC TAT GTG AAA TTT GGT ATG TAT TAT GAA GAC CCA CTT
Ser Asn Leu Ser Tyr Val Lys Phe Gly Met Tyr Tyr Glu Asp Pro Leu
            435                          440                         445

AAA GAA AAA GAA ACA GAA ACA GAA ACA GAA ACA GAA AAA GAC AAA GAA
Lys Glu Lys Glu Thr Glu Thr Glu Thr Glu Thr Glu Lys Asp Lys Glu
        450                          455                          460

FIG. 5F.

```
AAA GAA AAA GAA GAC AAA GAC AAA GAA AAA CAA ACG GCG GCA ACG
Lys Glu Lys Glu Asp Lys Asp Lys Glu Lys Gln Thr Ala Ala Thr
465                     470                    475                    480

ACC AAC ACT TAT TAT CAA TTC TTA TTA GGT CAC CGT ACT CCC AAG GAC
Thr Asn Thr Tyr Tyr Gln Phe Leu Leu Gly His Arg Thr Pro Lys Asp
                485                    490                    495

GAC ATA CCT AAA ACA GGA AGT GCA AAA TAT CAT GGT TAT CAT GGT
Asp Ile Pro Lys Thr Gly Ser Ala Lys Tyr His Gly Ser Trp Phe Gly
            500                    505                    510

TAT ATT ACT GAC GGT AAG ACA TCT TAC TCC CCC AGT GGT GAT AAG AAA
Tyr Ile Thr Asp Gly Lys Thr Ser Tyr Ser Pro Ser Gly Asp Lys Lys
        515                    520                    525

CGC GAT AAA AAT GCT GTC GCC GAG TTT AAT GTT GAT TTT GCC GAG AAA
Arg Asp Lys Asn Ala Val Ala Glu Phe Asn Val Asp Phe Ala Glu Lys
        530                    535                    540

AAG CTA ACA GGC GAA TTA AAA CGA CAC GAT ACT GGA AAT CCC GTA TTT
Lys Leu Thr Gly Glu Leu Lys Arg His Asp Thr Gly Asn Pro Val Phe
545                    550                    555                    560
```

FIG. 5G.

AGT ATT GAG GCA AAC TTT AAT AAT AGT AGT AAT GCC TTC ACT GGT ACA
Ser Ile Glu Ala Asn Phe Asn Asn Ser Ser Asn Ala Phe Thr Gly Thr
565                           570                           575

GCA ACC GCA ACA AAT TTT GTA ATA GAT GGT AAA AAT AGT CAA AAT AAA
Ala Thr Ala Thr Asn Phe Val Ile Asp Gly Lys Asn Ser Gln Asn Lys
580                           585                           590

AAT ACC CCA ATT AAT ATT ACA ACT AAA GTA AAC GGG GCA TTT TAT GGA
Asn Thr Pro Ile Asn Ile Thr Thr Lys Val Asn Gly Ala Phe Tyr Gly
595                           600                           605

CCT AAG GCT TCT GAA TTA GGC GGT TAT TTC ACT TAT AAC GGA AAT TCT
Pro Lys Ala Ser Glu Leu Gly Gly Tyr Phe Thr Tyr Asn Gly Asn Ser
610                           615                           620

ACA GCT ACA AAT TCT GAA AGT TCC TCA ACC GTA TCT TCA TCC AAT
Thr Ala Thr Asn Ser Glu Ser Ser Ser Thr Val Ser Ser Ser Asn
625                           630                           635                640

TCA AAA AAT GCA AGA GCT GCA GTT GTC TTT GGT GCG AGA CAA CAA GTA
Ser Lys Asn Ala Arg Ala Ala Val Val Phe Gly Ala Arg Gln Gln Val
645                           650                           655

FIG. 5H.

```
GAA ACA ACC AAA TAATGGAATA CTAAAAA ATG ACT AAA AAA CCC TAT TTT
Glu Thr Lys                         Met Thr Lys Lys Pro Tyr Phe
    660                                     665

CGC CTA AGT ATT ATT TCT TGT CTT TTA ATT TCA TGC TAT GTA AAA GCA
Arg Leu Ser Ile Ile Ser Cys Leu Leu Ile Ser Cys Tyr Val Lys Ala
        670                     675                     680

GAA ACT CAA AGT ATA AAA GAT ACA AAA GAA GCT ATA TCA TCT GAA GTG
Glu Thr Gln Ser Ile Lys Asp Thr Lys Glu Ala Ile Ser Ser Glu Val
        685                     690                     695

GAC ACT CAA AGT ACA GAA GAT TCA GAA TTA GAA ACT ATC TCA GTC ACT
Asp Thr Gln Ser Thr Glu Asp Ser Glu Leu Glu Thr Ile Ser Val Thr
    700                     705                     710         715

GCA GAA AAA ATA AGA GAT CGT AAA GAT AAT GAA GTA ACT GGA CTT GGC
Ala Glu Lys Ile Arg Asp Arg Lys Asp Asn Glu Val Thr Gly Leu Gly
        720                     725                     730

AAA ATT ATC AAA ACT AGT GAA AGT ATC AGC CGA GAA CAA GTA TTA AAT
Lys Ile Ile Lys Thr Ser Glu Ser Ile Ser Arg Glu Gln Val Leu Asn
        735                     740                     745
```

FIG. 51.

ATT CGT GAT CTA ACA CGC TAT GAT CCA GGG ATT TCA GTT GTA GAA CAA
Ile Arg Asp Leu Thr Arg Tyr Asp Pro Gly Ile Ser Val Val Glu Gln
    750                             755                     760

GGT CGC GGT GCA AGT TCT GGA TAT TCT ATT CGT GGT ATG GAC AGA AAT
Gly Arg Gly Ala Ser Ser Gly Tyr Ser Ile Arg Gly Met Asp Arg Asn
            765                     770                 775

AGA GTT GCT TTA TTA GTA GAT GGT TTA CCT CAA ACG CAA TCT TAT GTA
Arg Val Ala Leu Leu Val Asp Gly Leu Pro Gln Thr Gln Ser Tyr Val
780                     785                     790         795

GTG CAA AGC CCT TTA GTT GCT CGT TCA GGA TAT TCT GGC ACT GGT GCA
Val Gln Ser Pro Leu Val Ala Arg Ser Gly Tyr Ser Gly Thr Gly Ala
            800                     805                     810

ATT AAT GAA ATT GAA TAT GAA AAT GTA AAG GCC GTC GAA ATA AGC AAG
Ile Asn Glu Ile Glu Tyr Glu Asn Val Lys Ala Val Glu Ile Ser Lys
        815                     820                     825

GGG GGG AGT TCT TCT GAG TAT GGT AAT GGA GCA CTA GCT GGT TCT GTA
Gly Gly Ser Ser Ser Glu Tyr Gly Asn Gly Ala Leu Ala Gly Ser Val
    830                     835                         840

FIG. 5J.

ACA TTT CAA AGC AAA TCA GCA GCC GAT ATC TTA GAA GGA GAC AAA TCA
Thr Phe Gln Ser Lys Ser Ala Ala Asp Ile Leu Glu Gly Asp Lys Ser
845                          850                          855

TGG GGA ATT CAA ACT AAA AAT GCT TAT TCA AGC AAA AAT AAA GGC TTT
Trp Gly Ile Gln Thr Lys Asn Ala Tyr Ser Ser Lys Asn Lys Gly Phe
860                          865                          870                     875

ACC CAT TCT TTA GCT GTA GCA GGA AAA CAA GGT GGA TTT GAA GGG CTA
Thr His Ser Leu Ala Val Ala Gly Lys Gln Gly Gly Phe Glu Gly Leu
880                          885                          890

GCC ATT TAC ACT CAA CGA AAT TCA ATT GAA ACC CAA GTC CAT AAA GAT
Ala Ile Tyr Thr Gln Arg Asn Ser Ile Glu Thr Gln Val His Lys Asp
895                          900                          905

GCA TTA AAA GGC GTA CAA AGT TAT GAT CGA TTA ATC GCC ACA ACA GAT
Ala Leu Lys Gly Val Gln Ser Tyr Asp Arg Leu Ile Ala Thr Thr Asp
910                          915                          920

AAA TCT TCA GGA TAC TTT GTG ATA CAA GGT GAG TGT CCA AAT GGT GAT
Lys Ser Ser Gly Tyr Phe Val Ile Gln Gly Glu Cys Pro Asn Gly Asp
925                          930                          935

FIG. 5K.

GAC AAG TGT GCA GCC AAG CCA CCT GCG ACT TTA TCC ACC CAA AGC GAA
Asp Lys Cys Ala Ala Lys Pro Pro Ala Thr Leu Ser Thr Gln Ser Glu
940                         945                         950                         955

ACC GTA AGC GTT TCA GAT TAT ACG GGG GCT AAC CGT ATC AAA CCT AAT
Thr Val Ser Val Ser Asp Tyr Thr Gly Ala Asn Arg Ile Lys Pro Asn
             960                         965                         970

CCA ATG AAA TAT GAA AGC CAG TCT TGG TTT TTA AGA GGA GGG TAT CAT
Pro Met Lys Tyr Glu Ser Gln Ser Trp Phe Leu Arg Gly Gly Tyr His
975                         980                         985

TTT TCT GAA CAA CAT TAT ATT GGT GGT ATT TTT GAA TTC ACA CAA CAA
Phe Ser Glu Gln His Tyr Ile Gly Gly Ile Phe Glu Phe Thr Gln Gln
         990                         995                         1000

AAA TTT GAT ATC CGT GAT ATG ACA TTT CCC GCT TAT TTA AGC CCA ACA
Lys Phe Asp Ile Arg Asp Met Thr Phe Pro Ala Tyr Leu Ser Pro Thr
         1005                        1010                        1015

GAA AGA CGG GAT GAT AGT CGT TCT TTT TAT CCA ATG CAA GAT CAT
Glu Arg Arg Asp Asp Ser Arg Ser Phe Tyr Pro Met Gln Asp His
1020                        1025                        1030                 1035

FIG. 5L.

GGT GCA TAT CAA CAT ATT GAG GAT GGC AGA GGC GTT AAA TAT GCA AGT
Gly Ala Tyr Gln His Ile Glu Asp Gly Arg Gly Val Lys Tyr Ala Ser
               1040                    1045                1050

GGG CTT TAT TTC GAT GAA CAC CAT AGA AAA CAG CGT GTA GGT ATT GAA
Gly Leu Tyr Phe Asp Glu His His Arg Lys Gln Arg Val Gly Ile Glu
               1055                    1060                1065

TAT ATT TAC GAA AAT AAG AAC AAA GCG GGC ATC ATT GAC AAA GCA GTG
Tyr Ile Tyr Glu Asn Lys Asn Lys Ala Gly Ile Ile Asp Lys Ala Val
               1070                    1075                1080

TTA AGT GCT AAT CAA CAA AAC ATC ATA CTT GAC AGT TAT ATG CGA CAT
Leu Ser Ala Asn Gln Gln Asn Ile Ile Leu Asp Ser Tyr Met Arg His
               1085                    1090                1095

ACG CAT TGC AGT CTT TAT CCT AAT CCA AGT AAG AAT TGC CGC CCA ACA
Thr His Cys Ser Leu Tyr Pro Asn Pro Ser Lys Asn Cys Arg Pro Thr
               1100                    1105                1110                1115

CTT GAT AAA CCT TAT TCA TAC TAT CGT TCT GAT AGA AAT GTT TAT AAA
Leu Asp Lys Pro Tyr Ser Tyr Tyr Arg Ser Asp Arg Asn Val Tyr Lys
               1120                    1125                1130

FIG. 5M.

GAA AAA CAT AAT ATG TTG CAA TTG AAT TTA GAG AAA AAA ATT CAA CAA
Glu Lys His Asn Met Leu Gln Leu Asn Leu Glu Lys Lys Ile Gln Gln
                                 1135                    1145

AAT TGG CTT ACT CAT CAA ATT GTC TTC AAT CTT GGT TTT GAT GAC TTT
Asn Trp Leu Thr His Gln Ile Val Phe Asn Leu Gly Phe Asp Asp Phe
             1150                         1160

ACT TCA GCG CTT CAG CAT AAA GAT TAT TTA ACT CGA CGT GTT ATC GCT
Thr Ser Ala Leu Gln His Lys Asp Tyr Leu Thr Arg Arg Val Ile Ala
        1165                        1170                    1175

ACG GCA GAT AGT ATT CCA AGG AAA CCT GGT GAA ACT GGT AAA CCA AGA
Thr Ala Asp Ser Ile Pro Arg Lys Pro Gly Glu Thr Gly Lys Pro Arg
1180                             1185                   1190        1195

AAT GGT TTG CAA TCA CAA CCT TAC TTA TAC CCA AAA CCA GAG CCA TAT
Asn Gly Leu Gln Ser Gln Pro Tyr Leu Tyr Pro Lys Pro Glu Pro Tyr
                1200                         1205            1210

TTT GCA GGA CAA GAT CAT TGT AAT TAT CAA GGT AGC TCC TCT AAT TAC
Phe Ala Gly Gln Asp His Cys Asn Tyr Gln Gly Ser Ser Ser Asn Tyr
         1215                        1220                    1225

FIG. 5N.

```
AGA GAC TGT AAA GTG CGG TTA ATT AAA GGG AAA AAT TAT TTC GCA
Arg Asp Cys Lys Val Arg Leu Ile Lys Gly Lys Asn Tyr Phe Ala
        1230                    1235                   1240

GCA CGC AAT AAT ATG GCA TTA GGG AAA TAC GTT GAT TTA GGT TTA GGT
Ala Arg Asn Asn Met Ala Leu Gly Lys Tyr Val Asp Leu Gly Leu Gly
        1245                    1250                   1255

ATT CGG TAT GAC GTA TCT CGT ACA AAA GCT AAT GAA TCA ACT ATT AGT
Ile Arg Tyr Asp Val Ser Arg Thr Lys Ala Asn Glu Ser Thr Ile Ser
        1260                    1265                   1270        1275

GTT GGT AAA TTT AAA AAT TTC TCT TGG AAT ACT GGT ATT GTC ATA AAA
Val Gly Lys Phe Lys Asn Phe Ser Trp Asn Thr Gly Ile Val Ile Lys
        1280                    1285                   1290

CCA ACG GAA TGG CTT GAT CTT TCT TAT CGC CTT TCT ACT GGA TTT AGA
Pro Thr Glu Trp Leu Asp Leu Ser Tyr Arg Leu Ser Thr Gly Phe Arg
        1295                    1300                   1305

AAT CCT AGT TTT TCT GAA ATG TAT GGT TGG CGG TAT GGT GGC AAG AAT
Asn Pro Ser Phe Ser Glu Met Tyr Gly Trp Arg Tyr Gly Gly Lys Asn
        1310                    1315                   1320
```

FIG. 50.

```
GAC GAG GTT TAT GTA GGT AAA TTT AAG CCT GAA ACA TCT CGT AAC CAA
Asp Glu Val Tyr Val Gly Lys Phe Lys Pro Glu Thr Ser Arg Asn Gln
        1325                    1330                    1335

GAG TTT GGT CTC GCT CTA AAA GGG GAT TTT GGT AAT ATT GAG ATC AGT
Glu Phe Gly Leu Ala Leu Lys Gly Asp Phe Gly Asn Ile Glu Ile Ser
1340                    1345                    1350        1355

CAT TTT AGT AAT GCT TAT CGA AAT CTT ATC GCC TTT GCT GAA GAA CTT
His Phe Ser Asn Ala Tyr Arg Asn Leu Ile Ala Phe Ala Glu Glu Leu
                1360                    1365                1370

AGT AAA AAT GGA ACT GGA AAG GGC AAT TAT GGA TAT CAT AAT GCA CAA
Ser Lys Asn Gly Thr Gly Lys Gly Asn Tyr Gly Tyr His Asn Ala Gln
        1375                    1380                    1385

AAT GCA AAA TTA GTT GGC GTA AAT ACT GCA CAA TTA GAT TTT AAT
Asn Ala Lys Leu Val Gly Val Asn Ile Thr Ala Gln Leu Asp Phe Asn
        1390                    1395                    1400

GGT TTA TGG AAA CGT ATT CCC TAC GGT TGG TAT GCA ACA TTT GCT TAT
Gly Leu Trp Lys Arg Ile Pro Tyr Gly Trp Tyr Ala Thr Phe Ala Tyr
1405                    1410                    1415
```

FIG. 5P.

AAC CAA GTA AAA GAT CAA AAA ATC AAT GCT GGT TTA GCC TCC
Asn Gln Val Lys Asp Gln Lys Ile Asn Ala Gly Leu Ala Ser
1420              1425                    1430              1435

GTA AGC AGT TAT TTA TTT GAT GCC ATT CAG CCC AGC CGT TAT ATC ATT
Val Ser Ser Tyr Leu Phe Asp Ala Ile Gln Pro Ser Arg Tyr Ile Ile
              1440                    1445                    1450

GGT TTA GGC TAT GAT CAT CCA AGT AAT ACT TGG GGA ATT AAT ACA ATG
Gly Leu Gly Tyr Asp His Pro Ser Asn Thr Trp Gly Ile Asn Thr Met
                    1455                    1460                    1465

TTT ACT CAA TCA AAA GCA AAA TCT CAA AAT GAA TTG CTA GGA AAA CGT
Phe Thr Gln Ser Lys Ala Lys Ser Gln Asn Glu Leu Leu Gly Lys Arg
              1470                    1475                    1480

GCA TTA GGT AAC AAT TCA AGG GAT GTA AAA TCA ACA AGA AAA CTT ACT
Ala Leu Gly Asn Asn Ser Arg Asp Val Lys Ser Thr Arg Lys Leu Thr
                    1485                    1490                    1495

CGG GCA TGG CAT ATC TTA GAT GTA TCG GGT TAT TAC ATG GCG AAT AAA
Arg Ala Trp His Ile Leu Asp Val Ser Gly Tyr Tyr Met Ala Asn Lys
1500                    1505                    1510              1515

FIG. 5Q.

```
AAT ATT ATG CTT CGA TTA GGG ATA TAT AAT TTA TTC AAC TAT CGC TAT
Asn Ile Met Leu Arg Leu Gly Ile Tyr Asn Leu Phe Asn Tyr Arg Tyr
            1520                    1525                    1530

GTT ACT TGG GAA GCG GTG CGT CAA ACA GCA CAA GGT GCG GTC AAT CAA
Val Thr Trp Glu Ala Val Arg Gln Thr Ala Gln Gly Ala Val Asn Gln
            1535                    1540                    1545

CAT CAA AAT GTT GGT AGC TAT ACT CGC TAC GCA GCA TCA GGA CGA AAC
His Gln Asn Val Gly Ser Tyr Thr Arg Tyr Ala Ala Ser Gly Arg Asn
            1550                    1555                    1560

TAT ACC TTA ACA TTA GAA ATG AAA TTC TAAAATTAAAA TCCGCCAGAT
Tyr Thr Leu Thr Leu Glu Met Lys Phe
            1565                    1570

GGACTAGATA TGCTATATCT ATACCTTACT GGGCCATCTT TTTCTGTTCT ATAATCTGCT

TAAGTGAAAA ACCAAACTTG GATTTTTAC AAGATCTTTT CACACATTA TTGTAAAATC

TCCGACAATT TTGACCG
```

FIG. 6A.

AAAATTCGGT AATGATAACC CTATAAATGA TAAGAGAGAA AGTTGTTTA CGCCATTTTT

CATATTTTAT CCATGAACTT AAAAAATTCT AAGTTGACAT TATTACAAAA AAGAACAAT

AATGCGAATT ATTATCAATT TTGTATAAGT ATTAATTCT ATG AAA TCT GTA CCT
                                                                  Met Lys Ser Val Pro
                                                                     1          5

CTT ATC ACT GGT GGA CTT TCC TTT TTA CTA AGC GCT TGT AGC GGG GGA
Leu Ile Thr Gly Gly Leu Ser Phe Leu Leu Ser Ala Cys Ser Gly Gly
          10                        15                        20

GGT GGT TCT TTT GAT GTA GAT GAC GTC TCT AAT CCC TCC TCT AAA
Gly Gly Ser Phe Asp Val Asp Asp Val Ser Asn Pro Ser Ser Lys
          25                        30                        35

CCA CGT TAT CAA GAC GAT ACC TCG AAT CAA AGA ACA AAA TCT GAT TTG
Pro Arg Tyr Gln Asp Asp Thr Ser Asn Gln Arg Thr Lys Ser Asp Leu
          40                        45                        50

GAA AAG TTG TTC ATT CCT TCT TTA GGG GGA GGG ATG AAG TTA GTG GCT
Glu Lys Leu Phe Ile Pro Ser Leu Gly Gly Gly Met Lys Leu Val Ala
          55                        60                        65

FIG. 6B.

```
CAA AAT TTT ATT GGT GCT AGA GAA CCT AGT TTC TTA AAT GAA GAT GGC
Gln Asn Phe Ile Gly Ala Arg Glu Pro Ser Phe Leu Asn Glu Asp Gly
 70                      75                      80                  85

TAT ATG ATA TTT TCC TCA CTT TCT ACG ATT GAA GAG GAT GTT GAA AAA
Tyr Met Ile Phe Ser Ser Leu Ser Thr Ile Glu Glu Asp Val Glu Lys
                         90                      95                     100

GTT AAA AAT AAC AAT AAA AAC GGG GGG AGG CTT ATT GGC TCA ATT GAG
Val Lys Asn Asn Asn Lys Asn Gly Gly Arg Leu Ile Gly Ser Ile Glu
                        105                     110                     115

GAA CCT AAT GGA ACA TCA CAA AAT TCA AAT TCA CAA TAC GTT TAT
Glu Pro Asn Gly Thr Ser Gln Asn Ser Asn Ser Gln Tyr Val Tyr
                        120                     125                     130

TCT GGT TTG TAT TAT ATC GAT AGT TGG CGT GAT TAT AAG AAG GAA GAG
Ser Gly Leu Tyr Tyr Ile Asp Ser Trp Arg Asp Tyr Lys Lys Glu Glu
                        135                     140                     145

CAA AAA GCT TAT ACT GGC TAT TAT GCA TTT TAT TAT GGT AAT
Gln Lys Ala Tyr Thr Gly Tyr Tyr Ala Phe Tyr Tyr Gly Asn
    150                     155                     160            165
```

FIG. 6C.

GAA ACT GCA AAA AAC TTG CCA GTA AAA GGT GTA GCT AAA TAC AAA GGA
Glu Thr Ala Lys Asn Leu Pro Val Lys Gly Val Ala Lys Tyr Lys Gly
170                             175                     180

ACG TGG AAC TTC ATC ACT GCA ACT GAA AAT GGC AAA CGT TAT TCT TTG
Thr Trp Asn Phe Ile Thr Ala Thr Glu Asn Gly Lys Arg Tyr Ser Leu
        185                             190                 195

TTC AGT AAT TCT ATC GGT CAA GCT TAT TCC AGA CGC AGC GCT ATT TCA
Phe Ser Asn Ser Ile Gly Gln Ala Tyr Ser Arg Arg Ser Ala Ile Ser
            200                             205             210

GAA GAT ATC TAT AAT TTA GAA AAC GGT GAC GCG GGC TTA ATA AGT GAA
Glu Asp Ile Tyr Asn Leu Glu Asn Gly Asp Ala Gly Leu Ile Ser Glu
215                             220                     225

TTT AGT GTA GAT TTT GGT AAG AAA GAG CTC ACT GGA GAA CTT TAT TAT
Phe Ser Val Asp Phe Gly Lys Lys Glu Leu Thr Gly Glu Leu Tyr Tyr
230                         235                     240         245

AAT GAA AGG AAA ACA AGT GTT AAT GAA TCA CAA AAT ACA CAT AAA
Asn Glu Arg Lys Thr Ser Val Asn Glu Ser Gln Asn Thr His Lys
            250                             255             260

FIG. 6D.

CTC ACT CTA GAA GCT AAA GTG TAT AGC AAC CGA TTC AGA GGT AAA
Leu Tyr Thr Leu Glu Ala Lys Val Tyr Ser Asn Arg Phe Arg Gly Lys
265                         270                         275

GTA AAG CCA ACC AAA ACA AAG TCT GAA GAT CAT CCC TTT ACC AGC GAG
Val Lys Pro Thr Lys Thr Lys Ser Glu Asp His Pro Phe Thr Ser Glu
        280                         285                         290

GGA ACA TTA GAA GGT GGT TTT TAT GGG CCT AAT GCT GAA GAA CTA GGG
Gly Thr Leu Glu Gly Gly Phe Tyr Gly Pro Asn Ala Glu Glu Leu Gly
295                         300                         305

GGA AAG TTT TTA GCT AAC GAC GAA AAA GTT TTT GGG GTA TTT AGT GCC
Gly Lys Phe Leu Ala Asn Asp Glu Lys Val Phe Gly Val Phe Ser Ala
310                         315                         320                         325

AAA GAA GAC CCA CAA AAC CCA GAA AAC CAA TTA TCC ACA GAA ACC
Lys Glu Asp Pro Gln Asn Pro Glu Asn Gln Lys Leu Ser Thr Glu Thr
        330                         335                         340

TTA ATT GAT GGC AAG CTA ATT ACT TTT AAA AGA ACT GAT GCA ACA ACC
Leu Ile Asp Gly Lys Leu Ile Thr Phe Lys Arg Thr Asp Ala Thr Thr
345                         350                         355

FIG. 6E.

```
AAT GCA ACA ACC GAT GCA AAA ACC AGT GCA ACA ACC GAT GCA ACC AGT
Asn Ala Thr Thr Asp Ala Lys Thr Ser Ala Thr Thr Asp Ala Thr Ser
        360                 365                 370

ACA ACA GCC AAT AAA AAA ACC GAT GCA GAA AAC TTT AAG ACG GAA GAT
Thr Thr Ala Asn Lys Lys Thr Asp Ala Glu Asn Phe Lys Thr Glu Asp
        375                 380                 385

ATA CCA AGT TTT GGT GAA GCT GAT TAC CTT TTA ATT GGC AAT CAG CCT
Ile Pro Ser Phe Gly Glu Ala Asp Tyr Leu Leu Ile Gly Asn Gln Pro
        390                 395                 400                 405

ATT CCT CTT TTA CCT GAA AAA AAT ACT GAT GAT TTC ATA AGT AGT AAG
Ile Pro Leu Leu Pro Glu Lys Asn Thr Asp Asp Phe Ile Ser Ser Lys
        410                 415                 420

CAC CAT ACG GTA GGA GGT AAA ACC TAT AAA GTA GAA GCA TGT TGC AAG
His His Thr Val Gly Gly Lys Thr Tyr Lys Val Glu Ala Cys Cys Lys
        425                 430                 435

AAT CTA AGC TAT GTG AAA TTT GGT ATG TAT GAG GAT AAA GAT AAG
Asn Leu Ser Tyr Val Lys Phe Gly Met Tyr Glu Asp Lys Asp Lys
        440                 445                 450
```

FIG.6F.

GAC AAC AAA AAT GAA ACA GAC AAA GAA AAA GGC AAA GAA AAA CCA ACG
Asp Asn Lys Asn Glu Thr Asp Lys Glu Lys Gly Lys Glu Lys Pro Thr
455                          460                      465

ACG ACA ACA TCT ATC AAC ACT TAT CAA TTC TTA TTA GGT CTC CGT
Thr Thr Thr Ser Ile Asn Thr Tyr Tyr Gln Phe Leu Leu Gly Leu Arg
470                          475                      480                      485

ACT CCC AAG GAC GAA ATA CCT AAA GAA GGA AGT GCA AAA TAT CAT GGT
Thr Pro Lys Asp Glu Ile Pro Lys Glu Gly Ser Ala Lys Tyr His Gly
490                          495                      500

AAT TGG TTT GGT TAT ATT AGT GAT GGC GAG ACA TCT TAC TCC GCC AGT
Asn Trp Phe Gly Tyr Ile Ser Asp Gly Glu Thr Ser Tyr Ser Ala Ser
505                          510                      515

GGT GAT AAG GAA CGC AGT AAA AAT GCT GTC GCC GAG TTT GAT GTA AGT
Gly Asp Lys Glu Arg Ser Lys Asn Ala Val Ala Glu Phe Asp Val Ser
520                          525                      530

TTT GCC AAT AAA ACA TTA ACA GGC GAA TTA ACA CGA CAC GAT AAT GGA
Phe Ala Asn Lys Thr Leu Thr Gly Glu Leu Lys Arg His Asp Asn Gly
535                          540                      545

FIG. 6G.

```
AAT ACC GTA TTT AAA ATT AAT GCA GAA TTA AAT GGT AGT AAT GAC TTC
Asn Thr Val Phe Lys Ile Asn Ala Glu Leu Asn Gly Ser Asn Asp Phe
550                     555                     560                     565

ACT GGT ACA GCA ACC GCA ACA AAT TTT GTA ATA GAT GGT AAC AAT AGT
Thr Gly Thr Ala Thr Ala Thr Asn Phe Val Ile Asp Gly Asn Asn Ser
                570                     575                     580

CAA ACT TCA AAT GCC AAA ATT AAT ATT ACA ACT AAA GTA AAT GGG GCA
Gln Thr Ser Asn Ala Lys Ile Asn Ile Thr Thr Lys Val Asn Gly Ala
            585                     590                     595

TTT TAT GGA CCT AAG GCT TCT GAA TTA GGA GGG TAT TTC ACC TAT AAC
Phe Tyr Gly Pro Lys Ala Ser Glu Leu Gly Gly Tyr Phe Thr Tyr Asn
        600                     605                     610

GGA AAA AAT CCT ACA GCT ACA AAT TCT GAA AGT TCC TCA ACC GTA CCT
Gly Lys Asn Pro Thr Ala Thr Asn Ser Glu Ser Ser Thr Val Pro
    615                     620                     625

TCA CCA CCC AAT TCA CCA AAT GCA AGC GCT GCA GTT GTC TTT GGT GCT
Ser Pro Pro Asn Ser Pro Asn Ala Ser Ala Ala Val Val Phe Gly Ala
630                     635                     640                     645
```

FIG. 6H.

```
AAA AAA CAA GTA GAA ACA ACC AAC AAG TAAAAACAAC CAAGTAATGG
Lys Lys Gln Val Glu Thr Thr Asn Lys
            650

AATACTAAAA ATG ACT AAA AAA CCC TAT TTT CGC CTA AGT ATT ATT TCT
           Met Thr Lys Lys Pro Tyr Phe Arg Leu Ser Ile Ile Ser
               655                 660                 665

TGT CTT TTA ATT TCA TGC TAT GTA AAA GCA GAA ACT CAA AGT ATA AAA
Cys Leu Leu Ile Ser Cys Tyr Val Lys Ala Glu Thr Gln Ser Ile Lys
            670                 675                 680

GAT ACA AAA GAA GCT ATA TCA TCT GAA GTG GAC ACT CAA AGT ACA GAA
Asp Thr Lys Glu Ala Ile Ser Ser Glu Val Asp Thr Gln Ser Thr Glu
        685                 690                 695

GAT TCA GAA TTA GAA ACT ATC TCA GTC ACT GCA GAA AAA ATA AGA GAT
Asp Ser Glu Leu Glu Thr Ile Ser Val Thr Ala Glu Lys Ile Arg Asp
        700                 705                 710             715

CGT AAA GAT AAT GAA GTA ACT GGA CTT GGC AAA ATT ATC AAA ACT AGT
Arg Lys Asp Asn Glu Val Thr Gly Leu Gly Lys Ile Ile Lys Thr Ser
        720                 725                 730
```

FIG.61.

GAA AGT ATC AGC CGA GAA CAA GTA TTA AAT ATT CGT GAT CTA ACA CGC
Glu Ser Ile Ser Arg Glu Gln Val Leu Asn Ile Arg Asp Leu Thr Arg
            735                 740                 745

TAT GAT CCA GGC ATT TCA GTT GTA GAA CAA GGC CGT GGT GCA AGT TCT
Tyr Asp Pro Gly Ile Ser Val Val Glu Gln Gly Arg Gly Ala Ser Ser
            750                 755                 760

GGA TAT TCT ATT CGT GGT ATG GAC AGA AAT AGA GTT GCT TTA TTA GTA
Gly Tyr Ser Ile Arg Gly Met Asp Arg Asn Arg Val Ala Leu Leu Val
            765                 770                 775

GAT GGT TTA CCT CAA ACG CAA TCT TAT GTA GTG CAA AGC CCT TTA GTT
Asp Gly Leu Pro Gln Thr Gln Ser Tyr Val Val Gln Ser Pro Leu Val
            780                 785                 790                 795

GCT CGT TCA GGA TAT TCT GGC ACT GGT GCA ATT AAT GAA ATT GAA TAT
Ala Arg Ser Gly Tyr Ser Gly Thr Gly Ala Ile Asn Glu Ile Glu Tyr
            800                 805                 810

GAA AAT GTA AAG GCC GTC GAA ATA AGC AAG GGG GGA AGT TCT TCT GAG
Glu Asn Val Lys Ala Val Glu Ile Ser Lys Gly Gly Ser Ser Ser Glu
            815                 820                 825

FIG. 6J.

TAT GGT AAT GGA GCA CTA GCT GGT TCT GTA ACA TTT CAA AGC AAA TCA
Tyr Gly Asn Gly Ala Leu Ala Gly Ser Val Thr Phe Gln Ser Lys Ser
              830                     835                     840

GCA GCC GAT ATC TTA GAA GGA GAC AAA TCA TGG GGA ATT CAA ACT AAA
Ala Ala Asp Ile Leu Glu Gly Asp Lys Ser Trp Gly Ile Gln Thr Lys
              845                     850                     855

AAT GCT TAT TCA AGC AAA AAT AAA GGC TTT ACC CAT TCT TTA GCT GTA
Asn Ala Tyr Ser Ser Lys Asn Lys Gly Phe Thr His Ser Leu Ala Val
              860                     865                     870                875

GCT GGA AAA CAA GGG GGA TTT GAC GGG GTC GCC ATT TAT ACT CAA CGA
Ala Gly Lys Gln Gly Gly Phe Asp Gly Val Ala Ile Tyr Thr Gln Arg
              880                     885                     890

AAT TCA ATT GAA ACC CAA GTC CAT AAA GAT GCA TTA AAA GGC GTA CAA
Asn Ser Ile Glu Thr Gln Val His Lys Asp Ala Leu Lys Gly Val Gln
              895                     900                     905

AGT TAT CAT CGA TTA ATC GCC AAA CCA GAG GAT CAA TCT GCA TAC TTT
Ser Tyr His Arg Leu Ile Ala Lys Pro Glu Asp Gln Ser Ala Tyr Phe
              910                     915                     920

FIG. 6K.

GTG ATG CAA GAT GAG TGT CCA AAG CCA GAT GAT TAT AAC AGT TGT TTA
Val Met Gln Asp Glu Cys Pro Lys Pro Asp Asp Tyr Asn Ser Cys Leu
925                         930                         935

CCT TTC GCC AAA CGA CCT GCG ATT TTA TCC TCC CAA AGA GAA ACC GTA
Pro Phe Ala Lys Arg Pro Ala Ile Leu Ser Ser Gln Arg Glu Thr Val
940                         945                         950                         955

AGC GTT TCA GAT TAT ACG GGG GCT AAC CGT ATC AAA CCT AAT CCA ATG
Ser Val Ser Asp Tyr Thr Gly Ala Asn Arg Ile Lys Pro Asn Pro Met
960                         965                         970

AAA TAT GAA AGC CAG TCT TGG TTT TTA AGA GGA GGG TAT CAT TTT TCT
Lys Tyr Glu Ser Gln Ser Trp Phe Leu Arg Gly Gly Tyr His Phe Ser
975                         980                         985

GAA CAA CAT TAT ATT GGT GGT ATT TTT GAA TTC ACA CAA CAA AAA TTT
Glu Gln His Tyr Ile Gly Gly Ile Phe Glu Phe Thr Gln Gln Lys Phe
990                         995                         1000

GAT ATC CGT GAT ATG ACA TTT CCC GCT TAT TTA AGA TCA ACA GAA AAA
Asp Ile Arg Asp Met Thr Phe Pro Ala Tyr Leu Arg Ser Thr Glu Lys
1005                        1010                        1015

FIG. 6L.

CGG GAT GAT AGC AGT GGC TCT TTT TAT CCA AAG CAA GAT TAT GGT GCA
Arg Asp Asp Ser Ser Gly Ser Phe Tyr Pro Lys Gln Asp Tyr Gly Ala
1020                        1025                    1030              1035

TAT CAA CGT ATT GAG GAT GGC CGA GGC GTT AAC TAT GCA AGT GGG CTT
Tyr Gln Arg Ile Glu Asp Gly Arg Gly Val Asn Tyr Ala Ser Gly Leu
            1040                        1045                    1050

TAT TTC GAT GAA CAC CAT AGA AAA CAG CGT GTA GGT ATT GAA TAT ATT
Tyr Phe Asp Glu His His Arg Lys Gln Arg Val Gly Ile Glu Tyr Ile
                  1055                        1060                1065

TAC GAA AAT AAG AAC AAA GCG GGC ATC ATT GAC AAA GCA GTG TTA AGT
Tyr Glu Asn Lys Asn Lys Ala Gly Ile Ile Asp Lys Ala Val Leu Ser
        1070                        1075                    1080

GCT AAT CAA CAA AAC ATC ATA CTT GAC AGT TAT ATG CAA CAT ACG CAT
Ala Asn Gln Gln Asn Ile Ile Leu Asp Ser Tyr Met Gln His Thr His
                    1085                        1090                1095

TGC AGT CTT TAT CCT AAT CCA AGT AAG AAT TGC CGC CCA ACA CGT GAT
Cys Ser Leu Tyr Pro Asn Pro Ser Lys Asn Cys Arg Pro Thr Arg Asp
1100                        1105                    1110              1115

FIG. 6M.

AAA CCT TAT TCA TAC TAT CAT TCT GAT AGA AAT GTT TAT AAA GAA AAA
Lys Pro Tyr Ser Tyr Tyr His Ser Asp Arg Asn Val Tyr Lys Glu Lys
                    1120                1125                1130

CAT AAT ATG TTG CAA TTG AAT TTA GAG AAA AAA ATT CAA CAA AAT TGG
His Asn Met Leu Gln Leu Asn Leu Glu Lys Lys Ile Gln Gln Asn Trp
            1135                1140                1145

CTT ACT CAT CAA ATT GTC TTC AAT CTT GGT TTT GAT GAC TTT ACT TCA
Leu Thr His Gln Ile Val Phe Asn Leu Gly Phe Asp Asp Phe Thr Ser
                1150                1155                1160

GCG CTT CAG CAT AAA GAT TAT TTA ACT CGA CGT GTT ACC GCT ACG GCA
Ala Leu Gln His Lys Asp Tyr Leu Thr Arg Arg Val Thr Ala Thr Ala
        1165                1170                1175

AAG AGT ATT TCA GAG AAA GCT AAT GAA ACA AGA AGA AAT GGT TAC AAA
Lys Ser Ile Ser Glu Lys Ala Asn Glu Thr Arg Arg Asn Gly Tyr Lys
                    1180                1185                1190                1195

AAA CAA CCT TAC TTA TAC CCA AAA CCA ACA GTA GGT TTT GTA GTA CAA
Lys Gln Pro Tyr Leu Tyr Pro Lys Pro Thr Val Gly Phe Val Val Gln
                1200                1205                1210

FIG. 6N.

GAT CAT TGT GAT TAT AAA GGT AAC TCC TCT AAT TAC AGA GAC TGT AAA
Asp His Cys Asp Tyr Lys Gly Asn Ser Ser Asn Tyr Arg Asp Cys Lys
1215                         1220                         1225

GTG CGG TTA ATT AAA GGG AAA AAT TAT TTC GCA GCA CGC AAT AAT
Val Arg Leu Ile Lys Gly Lys Asn Tyr Tyr Phe Ala Ala Arg Asn Asn
1230                         1235                         1240

ATG GCA TTA GGG AAA TAC GTT GAT TTA GGT TTA ATT CGG TAT GAC
Met Ala Leu Gly Lys Tyr Val Asp Leu Gly Leu Ile Arg Tyr Asp
1245                         1250                         1255

GTA TCT CGC ACA AAA GCT AAT GAA TCA ACT ATT AGT GTT GGT AAA TTT
Val Ser Arg Thr Lys Ala Asn Glu Ser Thr Ile Ser Val Gly Lys Phe
1260                         1265                         1270                         1275

AAA AAT TTC TCT TGG AAT ACT GGT ATT GTC ATA AAA CCA ACG GAA TGG
Lys Asn Phe Ser Trp Asn Thr Gly Ile Val Ile Lys Pro Thr Glu Trp
1280                         1285                         1290

CTT GAT CTT TCT TAT CGC CTT TCT ACT GGA TTT AGA AAT CCT AGT TTT
Leu Asp Leu Ser Tyr Arg Leu Ser Thr Gly Phe Arg Asn Pro Ser Phe
1295                         1300                         1305

FIG. 60.

GCT GAA ATG TAT GGT TGG CGG TAT GGC AAT AAT AGC GAG GTT TAT
Ala Glu Met Tyr Gly Trp Arg Tyr Gly Gly Asn Asn Ser Glu Val Tyr
1310                            1315                           1320

GTA GGT AAA TTT AAG CCT GAA ACA TCT CGT AAC CAA GAG TTT GGT CTC
Val Gly Lys Phe Lys Pro Glu Thr Ser Arg Asn Gln Glu Phe Gly Leu
1325                            1330                           1335

GCT CTA AAA GGG GAT TTT GGT AAT ATT GAG ATC AGT CAT TTT AGT AAT
Ala Leu Lys Gly Asp Phe Gly Asn Ile Glu Ile Ser His Phe Ser Asn
1340                            1345                      1350                   1355

GCT TAT CGA AAT CTT ATC GCC TTT GCT GAA GAA CTT AAT AAA AAT GGA
Ala Tyr Arg Asn Leu Ile Ala Phe Ala Glu Glu Leu Asn Lys Asn Gly
1360                            1365                           1370

ACT GGA AAG GCC AAT TAT GGA TAT CAT AAT GCA CAA AAT GCA AAA TTA
Thr Gly Lys Ala Asn Tyr Gly Tyr His Asn Ala Gln Asn Ala Lys Leu
1375                            1380                           1385

GTT GGC GTA AAT ATA ACT GCG CAA TTA GAT TTT AAT GGT TTA TGG AAA
Val Gly Val Asn Ile Thr Ala Gln Leu Asp Phe Asn Gly Leu Trp Lys
1390                            1395                           1400

FIG. 6P.

```
CGT ATT CCC TAC GGT TGG TAT GCA ACA TTT GCT TAT AAC CGA GTA AAA
Arg Ile Pro Tyr Gly Trp Tyr Ala Thr Phe Ala Tyr Asn Arg Val Lys
1405                         1410                        1415

GTT AAA GAT CAA AAA ATC AAT GCT GGT TTG GCC TCC GTA AGC AGT TAT
Val Lys Asp Gln Lys Ile Asn Ala Gly Leu Ala Ser Val Ser Ser Tyr
1420                         1425                        1430                        1435

TTA TTT GAT GCC ATT CAG CCC AGC CGT TAT ATC ATT GGT TTA GGC TAT
Leu Phe Asp Ala Ile Gln Pro Ser Arg Tyr Ile Ile Gly Leu Gly Tyr
              1440                        1445                        1450

GAT CAT CCA AGT AAT ACT TGG GGA ATT AAT ACA ATG TTT ACT CAA TCA
Asp His Pro Ser Asn Thr Trp Gly Ile Asn Thr Met Phe Thr Gln Ser
1455                        1460                        1465

AAA GCA AAA TCT CAA AAT GAA TTG CTA GGA AAA CGT GCA TTG GGT AAC
Lys Ala Lys Ser Gln Asn Glu Leu Leu Gly Lys Arg Ala Leu Gly Asn
              1470                        1475                        1480

AAT TCA AGG GAT GTA AAA TCA ACA AGA AAA CTT ACT CGG GCA TGG CAT
Asn Ser Arg Asp Val Lys Ser Thr Arg Lys Leu Thr Arg Ala Trp His
1485                        1490                        1495
```

FIG. 6Q.

```
ATC TTA GAT GTA TCG GGT TAT TAC ATG GCG AAT AAA AAT ATT ATG CTT
Ile Leu Asp Val Ser Gly Tyr Tyr Met Ala Asn Lys Asn Ile Met Leu
1500                     1505                    1510               1515

CGA TTA GGG ATA TAT AAT TTA TTC AAC TAT CGC TAT GTT ACT TGG GAA
Arg Leu Gly Ile Tyr Asn Leu Phe Asn Tyr Arg Tyr Val Thr Trp Glu
                    1520                     1525                  1530

GCG GTG CGT CAA ACA GCA CAA GGT GCG GTC AAT CAA CAT CAA AAT GTT
Ala Val Arg Gln Thr Ala Gln Gly Ala Val Asn Gln His Gln Asn Val
               1535                     1540                  1545

GGT AGC TAT ACT CGC TAC GCA TCA GGA CGA AAC TAT ACC TTA ACA
Gly Ser Tyr Thr Arg Tyr Ala Ala Ser Gly Arg Asn Tyr Thr Leu Thr
          1550                     1555                  1560

TTA GAA ATG AAA TTCTAAATTA AAATGCGCCA GATGGACTAG ACATGCTATA
Leu Glu Met Lys
     1565

TCTATACCTT ACTGGGGCAT CTTTTTCTGT TCTATAATCT GGTTAAGTGA AAAACCAAAC

TTGGATTTTT TAGAAGATCT TTCCACGCAT TTATTGTAAA ATCTCCGACA ATTTTTACCG

CACTTTTCTC TATTACAAAA ACAATAAGGA TCCTTTTGTG AATCTCTCA
```

FIG. 7A.

```
CAACATCTGC CCAAGCTATA TTCGTTAATG ATAAGCCTAT TAATGATAAG CCTATTAATG

ATAAGAAAGA AATTTGTTTT ACGCCATTTT TCATATTTTA TCCATGAACT TAAAAAATTC

TAAGTTGACA TTATTACAAA AAAAGAACAA TAATGCGAAT TATTATCAAT TTTGTATAAG

AATATAATTC T ATG AAA TCT GTA CCT CTT ATC TCT GGT GGA CTT TCC TTT
          Met Lys Ser Val Pro Leu Ile Ser Gly Gly Leu Ser Phe
            1                   5                          10

TTA TTA AGT GCT TGT AGC GGA GGA GGG TCT TTT GAT GTA GAT AAC GTC
Leu Leu Ser Ala Cys Ser Gly Gly Gly Ser Phe Asp Val Asp Asn Val
         15                  20                  25

TCT AAT CCC TCC TCT TCT AAA CCA CGT TAT CAA GAC GAT ACC TCG AAT
Ser Asn Pro Ser Ser Ser Lys Pro Arg Tyr Gln Asp Asp Thr Ser Asn
     30                  35                  40                  45

CAA AGA ACA AAA TCT GAT TTG CAA AAG TTG TCC ATT CCT TCT TTA GGG
Gln Arg Thr Lys Ser Asp Leu Gln Lys Leu Ser Ile Pro Ser Leu Gly
         50                      55                      60
```

FIG. 7B.

GGA GGG ATG AAG TTA GTG GCT CAG AAT CTT CTT GGT AAG AAA GAA CCT
Gly Gly Met Lys Leu Val Ala Gln Asn Leu Leu Gly Lys Lys Glu Pro
        65                      70                      75

AGT CTC TTA AAT AAT GAA GAT GGC TAT ATG ATA TTT TCC TCA CTT TCT
Ser Leu Leu Asn Asn Glu Asp Gly Tyr Met Ile Phe Ser Ser Leu Ser
        80                      85                      90

ACG ATT GAA GAG GAT GTT ACA AAA GAA AAT AAA TCT CAG GAA CCC ACT
Thr Ile Glu Glu Asp Val Thr Lys Glu Asn Lys Ser Gln Glu Pro Thr
        95                      100                     105

ATT GGC TCA ATA GAC GAG CCT AGC AAA ACA AAT TCA CCC CAA AAT CAT
Ile Gly Ser Ile Asp Glu Pro Ser Lys Thr Asn Ser Pro Gln Asn His
110                     115                     120             125

CAT GGC AAT ATG TAT ATT CGG GTC TTT ATT ATA TTC AAT CGT GGC GTA
His Gly Asn Met Tyr Ile Arg Val Phe Ile Ile Phe Asn Arg Gly Val
        130                     135                     140

ATT CCT CAA ATG GCA AGT TTT ATT CAG GTT ACT ATG GAT ATG CGT ATT
Ile Pro Gln Met Ala Ser Phe Ile Gln Val Thr Met Asp Met Arg Ile
        145                     150                     155

FIG. 7C.

ACT TTG GCA AGC AAA CAG CCA CTA CAT TAC CTG TAGATGGGA AGCAACGTAT
Thr Leu Ala Ser Lys Gln Pro Leu His Tyr Leu
              160                         165

AAAGGAACTT GGCACTTCAT CACCGCAACT GAAAATGGCA AAAAGTATTC TTTGTTCAGT

AATGATAGCG GTCAAGCTTA TCGCAGACGT AGTGCAATTC CAGAAGATAT TGATTTAGAA

AAAAATGATT CAACTAATGG TGACAAGGGC TTAATAAGTG AATTTAGTGT CAATTTTGT

ACAAAAAAGC TCACTGGAAA ACTTTATTAT AATGAAAGAG AAACAGAACT TAATAAATCA

AAAGATAGAA AACATACACT CTACAATCTA GAAGCTGAAG TGTATAGTAA CCGATTCAGG

GGTACAGTAA AGCCAACCGA AAAAGATTCT ACAGATCATC CCTTTACCAG CGAGGAACA

TTAGAAGGTG GTTTTTATGG GCCTAAAGGT GAAGAACTAG GAGGAAAGTT TTTAGCTGGC

GATAAAAAAG TTTTTGGGGT ATTTAGTGCC AAAGAAACGG AAGAAACAAA AAAGAAAGCG

TTATCCAAGG AAACCTTAAT TGATGGCAAG CTAACTACTT TTAAAACAAC CAATGCAACA

ACCAATGCAA CAGCCAATGC AACAACCAGT ACAACAGCCA GTACAACAAC CGATGCAGAA

FIG.7D.

AACTTTACGA CGAAAGATAT ACCAAGTTTT GGTGAAGCTG ATTACCTTTT AATTGATAAT

TACCCTGTTC CTCTTTTACC TGAGAGTGGT GATTTCATAA GTAGTAAGCA CCATACTGTA

GGAAAGAAAA CCTATCAAGT AGAAGCATGT TGCAGTAATC TAAGCTATGT GAAATTTGGT

ATGTTTTATG AAGACCCACT TAAAGAAGAA AAAGACAAAG AAAAAGAAGA AGACAAAGAA

AAACAAACGG CGGCAACGAC CAACACTTAT TATCAATTCT TATTAGGTCT CCGTACTGCC

AGTTCTGAAA TTCCTAAAAT GGGAAACGTG GAATATGCGG GTAATTGGTT TGGTTATATT

AGTGATGGCA CGACATCTTA CTCCCCCAGT GGTGATAAGG AACGCAATAA AAATGCTCCC

GCCGATTTTA ATGTTGATTT TGTCAATAAA AAGCTAACAG GCACATTAAA ACGACACGAT

AATGGAAATA CCGTATTTAG TATTGAGGCA AACTTTAACA GTGGGAATGA CTTCACTGGT

AAAGCAACCG CAAAAGATTT AGTAATAGAT GGTAAAAGTA CACAAGCCAC ATCTAAAGTC

AATTCACCG CAACAGTAAA AGGGGCATTT TATGGACCTG ATGCTTCTGA ATTAGGCGGT

TATTTCACCT ATAACGGAAA AAATCCTACA GCTACAAATT CCCCAACCGT ATCTTCACCA

FIG. 7E.

TCCAATTCAG CAAATGCTCG TGCTGCCGTT GTGTTTGGAG CTAAAAAACA AGTAGACACA
ACCAACAAGT AGAAAAAACC AAATAATGGA ATACTAAAA ATG ACT AAA AAA CCC
                                                                                               Met Thr Lys Lys Pro
                                                                                               170

TAT TTT CGC CTA AGT ATT ATT TCT TGT CTT TTA ATT TCA TGC TAT GTA
Tyr Phe Arg Leu Ser Ile Ile Ser Cys Leu Leu Ile Ser Cys Tyr Val
175                                  180                              185

AAA GCA GAA ACT CAA AGT ATA AAA GAT ACA AAA GAA GCT ATA TCA TCT
Lys Ala Glu Thr Gln Ser Ile Lys Asp Thr Lys Glu Ala Ile Ser Ser
190                                  195                              200                205

GAA GTG GAC ACT CAA AGT ACA GAA GAT TCA GAA TTA GAA ACT ATC TCA
Glu Val Asp Thr Gln Ser Thr Glu Asp Ser Glu Leu Glu Thr Ile Ser
                    210                              215                              220

GTC ACT GCA GAA AAA ATA AGA GAT CGT AAA GAT AAT GAA GTA ACT GGA
Val Thr Ala Glu Lys Ile Arg Asp Arg Lys Asp Asn Glu Val Thr Gly
                    225                              230                              235

CTT GGC AAA ATT ATA AAA ACG AGT GAA AGT ATC AGC CGA GAA CAA GTA
Leu Gly Lys Ile Ile Lys Thr Ser Glu Ser Ile Ser Arg Glu Gln Val
                    240                              245                              250

FIG. 7F.

```
TTA AAT ATT CGT GAT CTA ACA CGC TAT GAT CCA GGC ATT TCA GTT GTA
Leu Asn Ile Arg Asp Leu Thr Arg Tyr Asp Pro Gly Ile Ser Val Val
255                         260                         265

GAA CAA GGT CGC GGT GCA AGT TCT GGA TAT TCT ATT CGT GGT ATG GAC
Glu Gln Gly Arg Gly Ala Ser Ser Gly Tyr Ser Ile Arg Gly Met Asp
270                         275                         280                         285

AGA AAT AGA GTT GCT TTA TTA GAT GGT TTA CCT CAA ACG CAA TCT
Arg Asn Arg Val Ala Leu Leu Val Asp Gly Leu Pro Gln Thr Gln Ser
290                         295                         300

TAT GTA GTG CAA AGC CCT TTA GTT GCT CGT TCA GA TAT TCT GGC ACT
Tyr Val Val Gln Ser Pro Leu Val Ala Arg Ser Gly Tyr Ser Gly Thr
305                         310                         315

GGT GCA ATT AAT GAA ATT GAA TAT GAA AAT GTA AAG GCC GTC GAA ATA
Gly Ala Ile Asn Glu Ile Glu Tyr Glu Asn Val Lys Ala Val Glu Ile
320                         325                         330

AGC AAG GGG GGG AGT TCT TCT GAG TAT GGT AAT GGA GCA CTA GCT GGT
Ser Lys Gly Gly Ser Ser Ser Glu Tyr Gly Asn Gly Ala Leu Ala Gly
335                         340                         345
```

FIG. 7G.

TCT GTA ACA TTT CAA AGC AAA TCC GCA GCC GAT ATC TTA GAA GGA GAC
Ser Val Thr Phe Gln Ser Lys Ser Ala Ala Asp Ile Leu Glu Gly Asp
350                          355                         360                         365

AAA TCA TGG GGA ATT CAA ACT AAA AAT GCT TAT TCA AGC AAA AAT AAA
Lys Ser Trp Gly Ile Gln Thr Lys Asn Ala Tyr Ser Ser Lys Asn Lys
                370                         375                         380

GGC TTT ACC CAT TCT TTA GCT GTA GCA GGA AAA CAA GGT GGA TTT GAA
Gly Phe Thr His Ser Leu Ala Val Ala Gly Lys Gln Gly Gly Phe Glu
        385                         390                         395

GGG GTC GCC ATT TAC ACT CAA CGA AAT TCG GAG GAA ACC CAA GTC CAT
Gly Val Ala Ile Tyr Thr Gln Arg Asn Ser Glu Glu Thr Gln Val His
400                         405                         410

AAA GAT GCA TTA AAA GGC GTA CAA AGT TAT GAG CGA TTC ATC GCC ACA
Lys Asp Ala Leu Lys Gly Val Gln Ser Tyr Glu Arg Phe Ile Ala Thr
            415                         420                         425

ACA GAT AAA TCT TCA GGA TAC TTT GTG ATA CAA GGT GAG TGT CCA AAT
Thr Asp Lys Ser Ser Gly Tyr Phe Val Ile Gln Gly Glu Cys Pro Asn
430                         435                         440                         445

FIG. 7H.

```
GGT GAT GAC AAG TGT GCA GCC AAA CCA CCT GCA AAG TTA TCC CCC CAA
Gly Asp Asp Lys Cys Ala Ala Lys Pro Pro Ala Lys Leu Ser Pro Gln
                    450                     455                 460

AGC GAA ACC GTA AGC GTT TCA GAT TAT ACG GGG GCT AAC CGT ATC AAA
Ser Glu Thr Val Ser Val Ser Asp Tyr Thr Gly Ala Asn Arg Ile Lys
                    465                     470                 475

CCT AAT CCA ATG AAA TAT GAA AGC CAG TCT TGG TTT TTA AGA GGA GGG
Pro Asn Pro Met Lys Tyr Glu Ser Gln Ser Trp Phe Leu Arg Gly Gly
                    480                     485                 490

TAT CAT TTT TCT GAA CAA CAC TAT ATT GGT GGT ATT TTT GAA TTC ACA
Tyr His Phe Ser Glu Gln His Tyr Ile Gly Gly Ile Phe Glu Phe Thr
                    495                     500                 505

CAA CAA AAA TTT GAT ATC CGT GAT ATG ACA TTT CCC GCT TAT TTA AGA
Gln Gln Lys Phe Asp Ile Arg Asp Met Thr Phe Pro Ala Tyr Leu Arg
                    510                     515                 520                 525

TCA ACA GAA AAA CGG GAT GAT AGA ACT GGC CCT TTT TAT CCA AAG CAA
Ser Thr Glu Lys Arg Asp Asp Arg Thr Gly Pro Phe Tyr Pro Lys Gln
                    530                     535                 540
```

FIG. 71.

GAT TAT GGT GCA TAT CAA CGT ATT GAG GAT GGC CGA GGC GTT AAC TAT
Asp Tyr Gly Ala Tyr Gln Arg Ile Glu Asp Gly Arg Gly Val Asn Tyr
545                               550                               555

GCA AGT GGG CTT TAT TTC GAT GAA CAC CAT AGA AAA CAG CGT GTA GGT
Ala Ser Gly Leu Tyr Phe Asp Glu His His Arg Lys Gln Arg Val Gly
560                               565                               570

ATT GAA TAT ATT TAC GAA AAT AAG AAC AAA GCG GGC ATC ATT GAC AAA
Ile Glu Tyr Ile Tyr Glu Asn Lys Asn Lys Ala Gly Ile Ile Asp Lys
575                               580                               585

GCA GTG TTA AGT GCT AAT CAA CAA AAC ATC ATA CTT GAC AGT TAT ATG
Ala Val Leu Ser Ala Asn Gln Gln Asn Ile Ile Leu Asp Ser Tyr Met
590                               595                               600                               605

CGA CAT ACG CAT TGC AGT CTT TAT CCT AAT CCA AGT AAG AAT TGC CGC
Arg His Thr His Cys Ser Leu Tyr Pro Asn Pro Ser Lys Asn Cys Arg
610                               615                               620

CCG ACA CTT GAT AAA CCT TAT TCA TAC TAT CGT TCT GAT AGA AAT GTT
Pro Thr Leu Asp Lys Pro Tyr Ser Tyr Tyr Arg Ser Asp Arg Asn Val
625                               630                               635

FIG. 7J.

TAT AAA GAA AAA CAT AAT ATG TTG CAA TTG AAT TTA GAG AAA AAA ATT
Tyr Lys Glu Lys His Asn Met Leu Gln Leu Asn Leu Glu Lys Lys Ile
640                          645                          650

CAA CAA AAT TGG CTT ACT CAT CAA ATT GTC TTC AAT CTT GGT TTT GAT
Gln Gln Asn Trp Leu Thr His Gln Ile Val Phe Asn Leu Gly Phe Asp
655                          660                          665

GAC TTT ACT TCA GCG CTT CAG CAT AAA GAT TAT TTA ACT CGA CGT GTT
Asp Phe Thr Ser Ala Leu Gln His Lys Asp Tyr Leu Thr Arg Arg Val
670                          675                          680                     685

ACC GCT ACG GCA AAT ATT ATT TCA GGG ACA GTT GCT GGT AAA CGA AGA
Thr Ala Thr Ala Asn Ile Ile Ser Gly Thr Val Ala Gly Lys Arg Arg
                             690                          695                     700

AAT GGT TAC GAA AAA CAA CCT TAC TTA TAC TCA AAA CCA AAA GTA GAT
Asn Gly Tyr Glu Lys Gln Pro Tyr Leu Tyr Ser Lys Pro Lys Val Asp
                 705                          710                     715

TTT GTA GGA CAA GAT CAT TGT AAT TAT AAA GGT AGC TCC TCT AAT TAC
Phe Val Gly Gln Asp His Cys Asn Tyr Lys Gly Ser Ser Ser Asn Tyr
720                          725                          730

FIG. 7K.

```
AGC GAC TGT AAA GTG CGG TTA ATT AAA GGG AAA AAT TAT TAT TTC GCA
Ser Asp Cys Lys Val Arg Leu Ile Lys Gly Lys Asn Tyr Tyr Phe Ala
        735                 740                 745

GCA CGC AAT AAT ATG GCA TTA GGG AAA TAC ATT GAT TTA GGT TTA GGT
Ala Arg Asn Asn Met Ala Leu Gly Lys Tyr Ile Asp Leu Gly Leu Gly
        750                 755                 760             765

ATT CGG TAT GAC GTA TCT CGT ACA AAA GCT AAT GAA TCA ACT ATT AGT
Ile Arg Tyr Asp Val Ser Arg Thr Lys Ala Asn Glu Ser Thr Ile Ser
        770                 775                 780

GTT GGT AAA TTT AAA AAT TTC TCT TGG AAT ACT GGT ATT GTC ATA AAA
Val Gly Lys Phe Lys Asn Phe Ser Trp Asn Thr Gly Ile Val Ile Lys
        785                 790                 795

CCA ACG GAA TGG CTT GAT CTT TCT TAT CGC CTT TCT ACT GGA TTT AGA
Pro Thr Glu Trp Leu Asp Leu Ser Tyr Arg Leu Ser Thr Gly Phe Arg
        800                 805                 810

AAT CCT AGT TTT GCT GAA ATG TAT GGT TGG CGG TAT GGT GGC AAT AAT
Asn Pro Ser Phe Ala Glu Met Tyr Gly Trp Arg Tyr Gly Gly Asn Asn
        815                 820                 825
```

FIG. 7L.

```
AGC GAT GTT TAT GTA GGT AAA TTT AAG CCT GAA ACA TCT CGT AAC CAA
Ser Asp Val Tyr Val Gly Lys Phe Lys Pro Glu Thr Ser Arg Asn Gln
830                 835                 840                 845

GAG TTT GGT CTC GCT CTA AAA GGG GAT TTT GGT AAT ATT GAG ATC AGT
Glu Phe Gly Leu Ala Leu Lys Gly Asp Phe Gly Asn Ile Glu Ile Ser
    850                 855                 860

CAT TTT AGT AAT GCT TAT CGA AAT CTT ATC GCC TTT GCT GAA GAA CTT
His Phe Ser Asn Ala Tyr Arg Asn Leu Ile Ala Phe Ala Glu Glu Leu
865                 870                 875

AGT AAA AAT GGA ACT ACT GGA AAG GGC AAT TAT GGA TAT CAT AAT GCA
Ser Lys Asn Gly Thr Thr Gly Lys Gly Asn Tyr Gly Tyr His Asn Ala
    880                 885                 890

CAA AAT GCA AAA TTA GTT GGC GTA AAT GGT GTA AAT ATA ACT GCG CAA TTA GAT TTT
Gln Asn Ala Lys Leu Val Gly Val Asn Ile Thr Ala Gln Leu Asp Phe
895                 900                 905

AAT GGT TTA TGG AAA CGT ATT CCC TAC GGT TGG TAT GCA ACA TTT GCT
Asn Gly Leu Trp Lys Arg Ile Pro Tyr Gly Trp Tyr Ala Thr Phe Ala
910                 915                 920                 925
```

FIG. 7M.

TAT AAC CGA GTA AAA GTT AAA GAT CAA AAA ATC AAT GCT GGT TTG GCC
Tyr Asn Arg Val Lys Val Lys Asp Gln Lys Ile Asn Ala Gly Leu Ala
930                         935                         940

TCC GTA AGC AGT TAT TTA TTT GAT GCC ATT CAG CCC AGC CGT TAT ATC
Ser Val Ser Ser Tyr Leu Phe Asp Ala Ile Gln Pro Ser Arg Tyr Ile
945                         950                         955

ATT GGT TTA GGC TAT GAT CAT CCA AGT AAT ACT TGG GGA ATT AAT ACA
Ile Gly Leu Gly Tyr Asp His Pro Ser Asn Thr Trp Gly Ile Asn Thr
960                         965                         970

ATG TTT ACT CAA TCA AAA GCA AAA TCT CAA AAT GAA TTG CTA GGA CAA
Met Phe Thr Gln Ser Lys Ala Lys Ser Gln Asn Glu Leu Leu Gly Gln
975                         980                         985

CGT GCA TTG GGT AAC AAT TCA AGG AAT GTA AAA TCA ACA AGA AAA CTT
Arg Ala Leu Gly Asn Asn Ser Arg Asn Val Lys Ser Thr Arg Lys Leu
990                         995                         1000                        1005

ACT CGG GCA TGG CAT ATC TTA GAT GTA TCG GGT TAT TAC ATG GCG AAT
Thr Arg Ala Trp His Ile Leu Asp Val Ser Gly Tyr Tyr Met Ala Asn
1010                        1015                        1020

FIG. 7N.

AAA AAT ATT ATG CTT CGA TTA GGG ATA TAT AAT TTA TTC AAC TAT CGC
Lys Asn Ile Met Leu Arg Leu Gly Ile Tyr Asn Leu Phe Asn Tyr Arg
1025                          1030                          1035

TAT GTT ACT TGG GAA GCG GTG CGT CAA ACA GCA CAA GGT GCG GTC AAT
Tyr Val Thr Trp Glu Ala Val Arg Gln Thr Ala Gln Gly Ala Val Asn
1040                          1045                          1050

CAA CAT CAA AAT GTT GGT AGC TAT ACT CGC TAC GCA GCA TCA GGA CGA
Gln His Gln Asn Val Gly Ser Tyr Thr Arg Tyr Ala Ala Ser Gly Arg
1055                          1060                          1065

AAC TAT ACC TTA ACA TTA GAA ATG AAA TTC TAAATTAAAA TGCGCCAGAT
Asn Tyr Thr Leu Thr Leu Glu Met Lys Phe
1070                          1075

GGACTAGATA TGCTATATCT ATACCTTACT GGGGCATCTT TTTCTGTTCT ATAATCTGCT

TAAGTGAAAA ACCAAACTTG GATTTTTTAC AAGATCTTTT CACGCATTTA TTGTAAAATC

TCCGACAATT TTTACCGCAC TTTTCTCTAT TACAAAAACA ATAAGGATCC TTTTGTTGACT

CTTCTCAATCT TTGGCAAGTT GCTGTTACAA CTTCAGATCA AGTTTCAGCC AGCGATCTTA

GGCACTTGGG TTCCGCC

FIG. 8A.

```
AT ATG AAA TCT GTA CCT CTT ATC TCT GGT GGA CTT TCC TTT TTA TTA
   Met Lys Ser Val Pro Leu Ile Ser Gly Gly Leu Ser Phe Leu Leu
   1               5                  10                   15

AGT GCT TGT AGC GGG GGA GGT GGT TCT TTT GAT GTA GAT GAC GTC TCT
Ser Ala Cys Ser Gly Gly Gly Gly Ser Phe Asp Val Asp Asp Val Ser
                20                  25                  30

AAT CCC TCC TCT TCT AAA CCA CGT TAT CAA GAC GAT ACT TCA AGT TCA
Asn Pro Ser Ser Ser Lys Pro Arg Tyr Gln Asp Asp Thr Ser Ser Ser
                35                  40                  45

AGA ACA AAA TCT AAA TTG GAA AAT TTG TCC ATT CCT TCT TTA GGG GGA
Arg Thr Lys Ser Lys Leu Glu Asn Leu Ser Ile Pro Ser Leu Gly Gly
                50                  55                  60

GGG ATG AAG TTA GTG GCT CAG AAT CTT CGT GAT AGG ACA AAA CCT AGT
Gly Met Lys Leu Val Ala Gln Asn Leu Arg Asp Arg Thr Lys Pro Ser
        65                  70                  75

CTC TTA AAT GAA GAT GAC TAT ATG ATA TTT TCC TCA CTT TCA ACG ATT
Leu Leu Asn Glu Asp Asp Tyr Met Ile Phe Ser Ser Leu Ser Thr Ile
        80                  85                  90              95
```

FIG. 8B.

AAA GCT GAT GTT GAA AAA GAA AAT AAA CAC TAT ACA AGT CCA GTT GGC
Lys Ala Asp Val Glu Lys Glu Asn Lys His Tyr Thr Ser Pro Val Gly
            100                 105                 110

TCA ATA GAC GAG CCT AGT ACA ACA AAT CCA AAA GAA AAT GAT CAT GGA
Ser Ile Asp Glu Pro Ser Thr Thr Asn Pro Lys Glu Asn Asp His Gly
        115                 120                 125

CAA AGA TAT GTA TAT TCA GGA CTT TAT TAT TAT ATT CCA TCG TGG AAT TTA
Gln Arg Tyr Val Tyr Ser Gly Leu Tyr Tyr Tyr Ile Pro Ser Trp Asn Leu
            130                 135                 140

AAC GAT CTT AAA AAT AAC AAG TAT TAT TAT TCT GGT TAC TAT GGA TAT
Asn Asp Leu Lys Asn Asn Lys Tyr Tyr Tyr Ser Gly Tyr Tyr Gly Tyr
        145                 150                 155

GCG TAT TAC TTT GGC AAG CAA ACA GCC ACT ACA TTA CCT GTA AAT GGC
Ala Tyr Tyr Phe Gly Lys Gln Thr Ala Thr Thr Leu Pro Val Asn Gly
            160                 165                 170                 175

AAA GTA ACG TAT AAA GGA ACT TTC ATC ACC GCA GCT GAA AAT
Lys Val Thr Tyr Lys Gly Thr Trp Ser Phe Ile Thr Ala Ala Glu Asn
        180                 185                 190

FIG. 8C.

```
GGC AAA AGG TAT CCT TTG TTA AGT AAT GGC AGT CAA GCT TAT TTT CGA
Gly Lys Arg Tyr Pro Leu Leu Ser Asn Gly Ser Gln Ala Tyr Phe Arg
195                              200                         205

CGT AGT GCA ATT CCA GAA GAT ATT GAT TTA GAA GTT AAA AAT GAT GAG
Arg Ser Ala Ile Pro Glu Asp Ile Asp Leu Glu Val Lys Asn Asp Glu
210                              215                         220

AAT AGA GAA AAA GGG CTA GTG AGT GAA TTT AGT GCA GAT TTT GGG ACT
Asn Arg Glu Lys Gly Leu Val Ser Glu Phe Ser Ala Asp Phe Gly Thr
225                              230                         235

AAA AAA CTG ACA GGA GGA CTG TTT TAC ACC AAA AGA CAA ACT CAT ATT
Lys Lys Leu Thr Gly Gly Leu Phe Tyr Thr Lys Arg Gln Thr His Ile
240                              245                         250                         255

CAA AAC CAT GAA AAG AAA CTC TAT GAT ATA GAT GCC CAT ATT TAT
Gln Asn His Glu Lys Lys Leu Tyr Asp Ile Asp Ala His Ile Tyr
260                              265                         270

AGT AAT AGA TTC AGA GGT AAA GTA AAT CCT ACC CAA AAA GAT TCT AAA
Ser Asn Arg Phe Arg Gly Lys Val Asn Pro Thr Gln Lys Asp Ser Lys
275                              280                         285
```

FIG. 8D.

```
GAA CAT CCC TTT ACC AGC GAG GGA ACA TTA GAA GGT GGT TTT TAC GGG
Glu His Pro Phe Thr Ser Glu Gly Thr Leu Glu Gly Gly Phe Tyr Gly
        290                     295                     300

CCT GAA GGT CAA GAA TTA GGA GGA AAG TTT TTA GCT GGC GAC AAA AAA
Pro Glu Gly Gln Glu Leu Gly Gly Lys Phe Leu Ala Gly Asp Lys Lys
        305                     310                     315

GTT TTT GGG GTA TTT AGT GCC AAA GGA ACG GAA AAC AAA AAA TTA
Val Phe Gly Val Phe Ser Ala Lys Gly Thr Glu Asn Lys Lys Leu
        320                 325                 330         335

CCC AAA GAA ACC TTA ATT GAT GGC AAG CTA ACT ACT TTC TCT ACT AAA
Pro Lys Glu Thr Leu Ile Asp Gly Lys Leu Thr Thr Phe Ser Thr Lys
        340                     345                     350

ACA ACC GAT GCA AAA ACC AAT GCA ACA GCC AAT GCA ACA ACC AGT ACC
Thr Thr Asp Ala Lys Thr Asn Ala Thr Ala Asn Ala Thr Thr Ser Thr
        355                     360                     365

GCA GCC AAT ACA ACA ACC GAT ACA ACA GCC AAT ACA ATA ACC GAT GCA
Ala Ala Asn Thr Thr Thr Asp Thr Thr Ala Asn Thr Ile Thr Asp Ala
        370                     375                     380
```

FIG. 8E.

GAA AAC TTT AAG ACG AAA GAT ATA TCA AGT TTT GGT GAA GCT GAT TAC
Glu Asn Phe Lys Thr Lys Asp Ile Ser Ser Phe Gly Glu Ala Asp Tyr
    385                 390                 395

CTT TTA ATT GAT AAT TAC CCT GTT CCT CTT TTA CCT GAG AGT GGT GAT
Leu Leu Ile Asp Asn Tyr Pro Val Pro Leu Leu Pro Glu Ser Gly Asp
400                 405                 410                 415

TTC ATA AGT AGT AAG CAC CAT ACT GTA GGA AAG AAA ACC TAT CAA GTA
Phe Ile Ser Ser Lys His His Thr Val Gly Lys Lys Thr Tyr Gln Val
            420                 425                 430

AAA GCA TGT TGC AGT AAT CTA AGC TAT GTG AAA TTT GGT ATG TAT TAT
Lys Ala Cys Cys Ser Asn Leu Ser Tyr Val Lys Phe Gly Met Tyr Tyr
        435                 440                 445

GAA GTC CCA CCT AAA GAA GAA GAC AAA GAA AAA AAA GAA AAA
Glu Val Pro Pro Lys Glu Glu Asp Lys Glu Lys Lys Glu Lys
    450                 455                 460

GAA AAA GAA CAA GCG ACA AAT CTA TCG AAC ACT TAT TAT CAA TTC
Glu Lys Glu Lys Gln Ala Thr Asn Leu Ser Asn Thr Tyr Tyr Gln Phe
465                 470                 475

FIG. 8F.

```
TTA GGT CTC CGT ACT CCC AGT TCT GAA ATT CCT AAA GGA GGA AGT
Leu Gly Leu Arg Thr Pro Ser Ser Glu Ile Pro Lys Gly Gly Ser
480             485                 490                 495

GCA AAA TAT CTC GGT AGT TGG TTT GGT TAT CTC AGC GAT GGT TCA ACA
Ala Lys Tyr Leu Gly Ser Trp Phe Gly Tyr Leu Ser Asp Gly Ser Thr
        500                 505                 510

TCT TAC TCC CCC AGT GGT GAT AAG AAA CGC GAG AAC AAT GCT CTC GCC
Ser Tyr Ser Pro Ser Gly Asp Lys Lys Arg Glu Asn Asn Ala Leu Ala
            515                 520                 525

GAG TTT AAT GTA AAT TTT GTC GAT AAA ACA TTA AAA GGC CAA TTA ATA
Glu Phe Asn Val Asn Phe Val Asp Lys Thr Leu Lys Gly Gln Leu Ile
                530                 535                 540

CGA CAC GAT AAT CAA AAT ACC GTT TTT ACA ATT GAT GCA ACC TTT AAA
Arg His Asp Asn Gln Asn Thr Val Phe Thr Ile Asp Ala Thr Phe Lys
        545                 550                 555

GGT GGT AAG AAT AAC TTC ACT GGT ACA GCA ACC GCA AAC AAT GTA GCG
Gly Gly Lys Asn Asn Phe Thr Gly Thr Ala Thr Ala Asn Asn Val Ala
    560                 565                 570                 575
```

FIG. 8G.

```
ATT GAT CCC CAA AGT ACA CAA GGC ACA TCT AAC GTC AAT TTC ACG GCA
Ile Asp Pro Gln Ser Thr Gln Gly Thr Ser Asn Val Asn Phe Thr Ala
        580                 585                 590

ACA GTA AAT GGG GCA TTT TAT GGG CCG AAC GCT ACA GAA TTA GGC GGT
Thr Val Asn Gly Ala Phe Tyr Gly Pro Asn Ala Thr Glu Leu Gly Gly
        595                 600                 605

TAT TTC ACC TAT AAC GGA AAT CCT ACA GAT AAA AGT TCC TCA ACC GTA
Tyr Phe Thr Tyr Asn Gly Asn Pro Thr Asp Lys Ser Ser Ser Thr Val
        610                 615                 620

CCT TCA TCA TCC AAT TCA AAA AAT GCA AGA GCT GCA GTT GTC TTT GGT
Pro Ser Ser Asn Ser Lys Asn Ala Arg Ala Ala Val Val Phe Gly
        625                 630                 635

GCG AGA CAA CAA GTA GAA ACA ACC AAA TAATGGAATA CTAAAAATGA
Ala Arg Gln Gln Val Glu Thr Thr Lys
        640                 645

CTAAAAAAGC TTCTAGAAGC CGAATTC
```

FIG. 9A.

GAATTCGGCT TGGATCCAT ATG AAA TCT GTA CCT CTT ATC TCT GGT GGA CTT
                     Met Lys Ser Val Pro Leu Ile Ser Gly Gly Leu
                      1               5                      10

TCC TTT TTA CTA AGT GCT TGT AGC GGA GGG GGG TCT TTT GAT GTA GAT
Ser Phe Leu Leu Ser Ala Cys Ser Gly Gly Gly Ser Phe Asp Val Asp
                 15                  20                      25

AAC GTC TCT AAT CCA TCC TCT TCT AAA CCA CGT TAT CAA GAC GAT ACT
Asn Val Ser Asn Pro Ser Ser Ser Lys Pro Arg Tyr Gln Asp Asp Thr
            30                  35                      40

TCA AGT TCA AGA ACA AAA TCT AAT TTG AAA AAG TTG TCC ATT CCT TCT
Ser Ser Arg Thr Lys Ser Asn Leu Lys Lys Leu Ser Ile Pro Ser
        45                  50                  55

TTA GGG GGA GGG ATG AAG TTA GTG GCT CAG AAT CTT AGT GAT AAG AAC
Leu Gly Gly Gly Met Lys Leu Val Ala Gln Asn Leu Ser Asp Lys Asn
        60                  65                  70              75

AAA CCT AGT CTC TTA AAT GAA GAT GAC TAT ATA TCA TAT TTT TCC TCA
Lys Pro Ser Leu Leu Asn Glu Asp Asp Tyr Ile Ser Tyr Phe Ser Ser
            80                  85                      90

FIG. 9B.

```
CTT TCT ACA ATT CAA GAT GAT GTT AAA AAA GAA AAT AAA CGC CAT ACA
Leu Ser Thr Ile Gln Asp Asp Val Lys Lys Glu Asn Lys Arg His Thr
         95                  100                 105

AAT CCA GTT GGC TCA ATA GAC GAG CCT AAC GCA ACA AAT CCA CCC GAA
Asn Pro Val Gly Ser Ile Asp Glu Pro Asn Ala Thr Asn Pro Pro Glu
        110                  115                 120

AAG CAT CAT GGA CAA AGA TAT GTA TAT TCA GGG CTT TAT TAT ATT CCA
Lys His His Gly Gln Arg Tyr Val Tyr Ser Gly Leu Tyr Tyr Ile Pro
        125                  130                 135

TCG TGG AGT CAT TCC TCA AAT GGC AAG CTT TAT TTA GGT TAC TAT GGA
Ser Trp Ser His Ser Ser Asn Gly Lys Leu Tyr Leu Gly Tyr Tyr Gly
        140                  145                 150                 155

TAT GCG TTT TAT TAT TAT AAA GGA AAT ACT GCA ACA AAC TTG CCA GTA AGC
Tyr Ala Phe Tyr Tyr Tyr Lys Gly Asn Thr Ala Thr Asn Leu Pro Val Ser
        160                  165                 170

GGC ATA GCT AAA TAC AAA GGA ACT TGG GAT TTT ATT ACT GCA ACT AAA
Gly Ile Ala Lys Tyr Lys Gly Thr Trp Asp Phe Ile Thr Ala Thr Lys
        175                  180                 185
```

FIG. 9C.

```
AAT GGC CAA CGT TAT TCT TTA TTT GGT AGC GCT TTT GGA GCT TAT AAT
Asn Gly Gln Arg Tyr Ser Leu Phe Gly Ser Ala Phe Gly Ala Tyr Asn
            190                 195                 200

AGA CGC AGT GCT ATT TCA GAA GAT AAT TTA GAA AAT AAT CTA
Arg Arg Ser Ala Ile Ser Glu Asp Asn Leu Glu Asn Asn Leu
            205                 210             215

AAG AAT GGT GCG GGA TTA ACT AGT GAA TTT ACT GTC AAT TTT GGT ACG
Lys Asn Gly Ala Gly Leu Thr Ser Glu Phe Thr Val Asn Phe Gly Thr
            220                 225                 230             235

AAA AAG CTC ACT GGA AAA CTT TAT TAT AAT GAA AGG GAA ACA AAT CTT
Lys Lys Leu Thr Gly Lys Leu Tyr Tyr Asn Glu Arg Glu Thr Asn Leu
            240                 245                 250

AAT AAA TTA CAA AAG AGA AAA CAT GAA CTC TAT GAT ATA GAT GCC GAT
Asn Lys Leu Gln Lys Arg Lys His Glu Leu Tyr Asp Ile Asp Ala Asp
            255                 260                 265

ATT TAT AGT AAT AGA TTC AGA GGT AAA GTA AAG CCA ACA ACC CAA AAA
Ile Tyr Ser Asn Arg Phe Arg Gly Lys Val Lys Pro Thr Thr Gln Lys
270                 275                 280
```

FIG.9D.

GAT TCT CAA GAA CAT CCC TTT ACC AGC GAG GGA ACA TTA GAA GGT GGT
Asp Ser Gln Glu His Pro Phe Thr Ser Glu Gly Thr Leu Glu Gly Gly
285                         290                         295

TTT TAT GGG CCT AAC GGT GAA GAA TTA GGA GGA AAG TTT TTA GCT GGC
Phe Tyr Gly Pro Asn Gly Glu Glu Leu Gly Gly Lys Phe Leu Ala Gly
300                         305                         310                 315

GAT AAC CGA GTT TTT GGG GTA TTT AGT GCC AAA GAA GAA ACA AAA
Asp Asn Arg Val Phe Gly Val Phe Ser Ala Lys Glu Glu Thr Lys
320                         325                         330

GAC AAA AAA TTA TCC AGA GAA ACC TTA ATT GAT GGC AAG CTA ATT ACT
Asp Lys Lys Leu Ser Arg Glu Thr Leu Ile Asp Gly Lys Leu Ile Thr
335                         340                         345

TTT AAA AGA ACT GAT GCA ACA ACC AAT ACA GCA AAT GCA AAA ACC
Phe Lys Arg Thr Asp Ala Thr Thr Asn Thr Ala Ala Asn Ala Lys Thr
350                         355                         360

GAT GAA AAA AAC TTT ACG ACG AAA GAT ATA CCA AGT TTT GGT GAA GCT
Asp Glu Lys Asn Phe Thr Thr Lys Asp Ile Pro Ser Phe Gly Glu Ala
365                         370                         375

FIG. 9E.

```
GAT TAC CTT TTA ATT GAT AAT TAC CCT GTT CCT CTT TTC CCT GAA GAA
Asp Tyr Leu Leu Ile Asp Asn Tyr Pro Val Pro Leu Phe Pro Glu Glu
380                     385                 390                 395

AAT ACT AAT GAT TTC ATA ACT AGT AGG CAC CAT AAG GTA GGA GAT AAA
Asn Thr Asn Asp Phe Ile Thr Ser Arg His His Lys Val Gly Asp Lys
                400                 405                 410

ACC TAT AAA GTA GAA GCA TGT TGC AAG AAT CTA AGC TAT GTG AAA TTT
Thr Tyr Lys Val Glu Ala Cys Cys Lys Asn Leu Ser Tyr Val Lys Phe
        415                 420                 425

GGT ATG TAT TAT GAA GAC CCA TTA AAT GGA GAA AAT GGC AAA GAA AAA
Gly Met Tyr Tyr Glu Asp Pro Leu Asn Gly Glu Asn Gly Lys Glu Lys
430                 435                 440

GAA AAA GAA AAA GAC AAA GAA AAA CAA GCG ACA ACA TCT ATC
Glu Lys Glu Lys Asp Lys Glu Lys Gln Ala Thr Thr Ser Ile
    445                 450                 455

AAG ACT TAT TAT CAA TTC TTA GGT CAC CGT ACT GCC AAG GCC GAC
Lys Thr Tyr Tyr Gln Phe Leu Gly His Arg Thr Ala Lys Ala Asp
460                 465                 470                 475
```

FIG. 9F.

ATA CCT GCA ACG GGA AAC GTG AAA TAT CGC GGT AAT TGG TTT GGT TAT
Ile Pro Ala Thr Gly Asn Val Lys Tyr Arg Gly Asn Trp Phe Gly Tyr
        480                     485                     490

ATT GGT GAT GAC AAG ACA TCT TAC TCC ACT ACT GGA GAT AAA AAT GCT
Ile Gly Asp Asp Lys Thr Ser Tyr Ser Thr Thr Gly Asp Lys Asn Ala
        495                     500                     505

GTC GCC GAG TTT GAT GTA AAT TTT GCC GAT AAA ACA TTA ACA GGC ACA
Val Ala Glu Phe Asp Val Asn Phe Ala Asp Lys Thr Leu Thr Gly Thr
        510                     515                     520

TTA AAA CGA CAC GAT AAT GGA AAT CCC GTA TTT ACA ATT AAT GCA AGC
Leu Lys Arg His Asp Asn Gly Asn Pro Val Phe Thr Ile Asn Ala Ser
        525                     530                     535

TTT CAA AGT GGT AAG AAT GAC TTC ACT GGT ACA GCA ACC GCA AAC AAT
Phe Gln Ser Gly Lys Asn Asp Phe Thr Gly Thr Ala Thr Ala Asn Asn
        540                     545                     550                     555

GTA GCG ATT GAT CCC CAA AAT ACA CAA ACC ACA TCT AGA GTC AAT TTC
Val Ala Ile Asp Pro Gln Asn Thr Gln Thr Thr Ser Arg Val Asn Phe
        560                     565                     570

FIG. 9G.

ACG GCA ACA GTA AAC GGG GCA TTT TAT GGA CCT AAG GCT ACA GAA TTA
Thr Ala Thr Val Asn Gly Ala Phe Tyr Gly Pro Lys Ala Thr Glu Leu
    575                     580                     585

GGC GGT TAT TTC ACT TAT AAC GGA AAC AAT CCT ACA GAT AAA AAT TCC
Gly Gly Tyr Phe Thr Tyr Asn Gly Asn Asn Pro Thr Asp Lys Asn Ser
    590                     595                     600

TCA ACC GTT TCA CCA TCC AAT TCA GCA AAT GCT AAT GCT CGT GCT GTT GTG
Ser Thr Val Ser Pro Ser Asn Ser Ala Asn Ala Arg Ala Ala Val Val
    605                     610                     615

TTT GGC GCT AAA AAA CAA GTA GAA ACA ACC AAC AAG TAAAAACAAC
Phe Gly Ala Lys Lys Gln Val Glu Thr Thr Asn Lys
    620                     625                     630

CAAGTAATGG AATACTAAAA ATGACTAAAA AAGCTTCTAG AAAGCCGAAT TC

FIG. 10A.

```
ATG AAA TCT GTA CCT CTT ATC TCT GGT GGA CTT TCC CTT TTA AGT
Met Lys Ser Val Pro Leu Ile Ser Gly Gly Leu Ser Leu Leu Ser
 1                   5                  10                  15

GCT TGT AGC GGG GGA GGT GGT TCT TTT GAT GTA GAT GAC GTC TCT AAT
Ala Cys Ser Gly Gly Gly Gly Ser Phe Asp Val Asp Asp Val Ser Asn
              20                  25                  30

CCC TCC TCT TCT AAA CCA CGT TAT CAA GAC GAT ACC TCG AGT CAA AGA
Pro Ser Ser Ser Lys Pro Arg Tyr Gln Asp Asp Thr Ser Ser Gln Arg
         35                  40                  45

ACA AAA TCT AAT TTG GAA AAG TTG TCC ATT CCT TCT TTA GGA GGA GGG
Thr Lys Ser Asn Leu Glu Lys Leu Ser Ile Pro Ser Leu Gly Gly Gly
     50                  55                  60

ATG AAA TTG GTG GCT CAG AAT CTG AGT GGT AAT AAA GAA CCT AGT TTC
Met Lys Leu Val Ala Gln Asn Leu Ser Gly Asn Lys Glu Pro Ser Phe
 65                  70                  75                  80

TTA AAT GGA AAT GAC TAT ATG ATA TTT TCC TCA CGT TCT ACG ATT AAA
Leu Asn Gly Asn Asp Tyr Met Ile Phe Ser Ser Arg Ser Thr Ile Lys
             85                  90                  95
```

FIG. 10B.

GAT GAT GTT GAA AAT AAC AAT ACA AAC GGG GAC TAT ATT GGC TCA
Asp Asp Val Glu Asn Asn Thr Asn Gly Gly Asp Tyr Ile Gly Ser
              100                         105                        110

ATA GAC GAG CCT AGT ACA ACA AAT CCA CTC GAA AAG CAT CAT GGA CAA
Ile Asp Glu Pro Ser Thr Thr Asn Pro Leu Glu Lys His His Gly Gln
              115                         120                        125

AGG TAT GTA TAT TCA GGG CTT TAT TAT TAT ATT CAA TCG TGG AGT CTA AGA
Arg Tyr Val Tyr Ser Gly Leu Tyr Tyr Tyr Ile Gln Ser Trp Ser Leu Arg
              130                         135                        140

GAT TTA CCA AAG AAG TTT TAT TCA GGT TAC TAT GGA TAT GCG TAT TAC
Asp Leu Pro Lys Lys Phe Tyr Ser Gly Tyr Tyr Gly Tyr Ala Tyr Tyr
              145                         150                        155                        160

TTT GGC AAG GAA ACA ACA GCC ACT ACA TTA CCT GTA AAT GGC GAA GCA ACG
Phe Gly Lys Glu Thr Thr Ala Thr Thr Leu Pro Val Asn Gly Glu Ala Thr
              165                         170                        175

TAT AAA GGA ACT TGG GAT TTC ATC ACT AGA AAT GCC AAA AGT
Tyr Lys Gly Thr Trp Asp Phe Ile Thr Ala Thr Arg Asn Gly Lys Ser
              180                         185                        190

FIG. 10C.

TAT TCT TTG TTA AGT AAT AAC CGA CAA GCT TAT TCC AAA CGT AGT GCA
Tyr Ser Leu Leu Ser Asn Asn Arg Gln Ala Tyr Ser Lys Arg Ser Ala
195                     200                     205

ATT CCA GAA GAC ATT GAT TTA GAA AAT GAT CCA AAG AAT GGT GAG ACG
Ile Pro Glu Asp Ile Asp Leu Glu Asn Asp Pro Lys Asn Gly Glu Thr
210                     215                     220

AGA TTA ACT AGT GAA TTT ACT GTG AAT TTT GGT ACG AAA AAG CTC ACA
Arg Leu Thr Ser Glu Phe Thr Val Asn Phe Gly Thr Lys Lys Leu Thr
225                     230                     235                     240

GGT GGA CTT TAT TAC CAT TTA CGT AAA ACA AAT GCT AAT GAA AAC CAA
Gly Gly Leu Tyr Tyr His Leu Arg Lys Thr Asn Ala Asn Glu Asn Gln
245                     250                     255

AAT AGA AAA CAT AAA CTC TAC AAT CTA GAA GCT GAT GTG TAT AGC AAC
Asn Arg Lys His Lys Leu Tyr Asn Leu Glu Ala Asp Val Tyr Ser Asn
260                     265                     270

CGA TTC AGA GGT AAA GTA AAG CCA ACC AAA GAG TCT TCT GAA GAA CAT
Arg Phe Arg Gly Lys Val Lys Pro Thr Lys Glu Ser Ser Glu Glu His
275                     280                     285

FIG. 10D.

```
CCC TTT ACC AGC GAG GGA ACA TTA GAA GGT GGT TTT TAT GGG CCT AAT
Pro Phe Thr Ser Glu Gly Thr Leu Glu Gly Gly Phe Tyr Gly Pro Asn
290                     295                     300

GCT GAA GAA CTA GGG GGA AAA TTT TTA GCT AGC GAT AAA AAA GTT TTT
Ala Glu Glu Leu Gly Gly Lys Phe Leu Ala Ser Asp Lys Lys Val Phe
305                     310                     315                 320

GGG GTA TTT AGT GCC AAA GAA CAG CAA GAA ACG GAA GAA AAC AAA AAA
Gly Val Phe Ser Ala Lys Glu Gln Gln Glu Thr Glu Glu Asn Lys Lys
            325                     330                     335

TTA CTC AAA GAA ACC TTA ATT GAT GGC AAG CTA ACT ACT TTC TCT ACT
Leu Leu Lys Glu Thr Leu Ile Asp Gly Lys Leu Thr Thr Phe Ser Thr
340                     345                     350

AAA AAA ACC AAT GCA ACA ACC GAT GCA ACA ACC AGT ACA ACA ACC AGT
Lys Lys Thr Asn Ala Thr Thr Asp Ala Thr Thr Ser Thr Thr Thr Ser
355                     360                     365

ACA GCA ACC AAT GCA ACA GCC GAT GCA GAA AAC TTT ACG ACA AAA GAT
Thr Ala Thr Asn Ala Thr Ala Asp Ala Glu Asn Phe Thr Thr Lys Asp
            370                     375                     380
```

FIG. 10E.

ATA TCA AGT TTT GGT GAA GCT GAT TAT CTT TTA ATT GAT AAT TAC CCT
Ile Ser Ser Phe Gly Glu Ala Asp Tyr Leu Leu Ile Asp Asn Tyr Pro
385                         390                         395                         400

GTT CCT CTT TTA CCT GAA AAT ACT AAT GAT TTC ATA AGC AGT AAG CAC
Val Pro Leu Leu Pro Glu Asn Thr Asn Asp Phe Ile Ser Ser Lys His
            405                         410                         415

CAT GAG GTA GGA GGT AAA CAC TAT AAA GTG GAA GCA TGT TGC AAG AAT
His Glu Val Gly Gly Lys His Tyr Lys Val Glu Ala Cys Cys Lys Asn
420                         425                         430

CTA AGC TAT GTG AAA TTT GGT ATA TAT GAG GAT AAT GAG AAG AAC
Leu Ser Tyr Val Lys Phe Gly Ile Tyr Tyr Glu Asp Asn Glu Lys Asn
            435                         440                         445

ACC AAA ATT GAA ACA GAA CAA TAC CAC CAA TTT TTG TTA GGT CTC CGT
Thr Lys Ile Glu Thr Glu Gln Tyr His Gln Phe Leu Leu Gly Leu Arg
450                         455                         460

ACT CCC AGT TCT CAA ATT CCT GCA ACG GGA AAC GTG AAA TAT CGC GGT
Thr Pro Ser Ser Gln Ile Pro Ala Thr Gly Asn Val Lys Tyr Arg Gly
465                         470                         475                         480

FIG.10F.

AGT TGG TTT GGT TAT ATT GGT GAT GAC AAG ACA TCT TAC TCC ACT ACT
Ser Trp Phe Gly Tyr Ile Gly Asp Asp Lys Thr Ser Tyr Ser Thr Thr
            485                 490                 495

GGA GAT AAA AAT GCT CTC GCC GAG TTT GAT GTA AAT TTT ACC GAT AAA
Gly Asp Lys Asn Ala Leu Ala Glu Phe Asp Val Asn Phe Thr Asp Lys
            500                 505                 510

AAG CTA ACA GGC GAA TTA AAA CGA GCC GAT AAT CAA AAT ACC GTA TTT
Lys Leu Thr Gly Glu Leu Lys Arg Ala Asp Asn Gln Asn Thr Val Phe
            515                 520                 525

AGA ATT AAT GCA GAC TTT AAA AAT GAT AAT GAT GCC TTC AAA GGT ACA
Arg Ile Asn Ala Asp Phe Lys Asn Asp Asn Asp Ala Phe Lys Gly Thr
            530                 535                 540

GCA ACC GCA GAA AAT TTT GTA ATA GAT GGT AAC AAT AGT CAA ACT GGA
Ala Thr Ala Glu Asn Phe Val Ile Asp Gly Asn Asn Ser Gln Thr Gly
            545                 550                 555                 560

AAT ACC CAA ATT AAT ATT AAA ACT GAA GTA AAT GGG GCA TTT TAT GGT
Asn Thr Gln Ile Asn Ile Lys Thr Glu Val Asn Gly Ala Phe Tyr Gly
            565                 570                 575

FIG. 10 G.

CCG AAC GCT ACA GAA TTA GGC GGT TAT TTC ACT TAT AAC GGA AAA AAT
Pro Asn Ala Thr Glu Leu Gly Gly Tyr Phe Thr Tyr Asn Gly Lys Asn
         580                      585                     590

CCT ACA GAT AAA AAT TCT GAA AGT TCC TCA ACC GTA CCT TCA CCA CCC
Pro Thr Asp Lys Asn Ser Glu Ser Ser Ser Thr Val Pro Ser Pro Pro
         595                      600                     605

AAT TCA CCA AAT GCA AGA GCT GCA GTT GTC TTT GGT GCT AAA AAA CAA
Asn Ser Pro Asn Ala Arg Ala Ala Val Val Phe Gly Ala Lys Lys Gln
         610                      615                     620

GTA GAA AAA AAC AAC AAG TAAAAACAAC CAAGTAATGG AATACTAAAA
Val Glu Lys Asn Asn Lys
         625          630

ATGACTAAAA AAGCTTCTAG AAGCCGAATT C

FIG.11A.

```
ATG AAA TCT GTA CCT CTT ATC TCT GGT GGA CTT TCC TTT TTA CTA AGT
Met Lys Ser Val Pro Leu Ile Ser Gly Gly Leu Ser Phe Leu Leu Ser
 1               5                  10                 15

GCT TGT AGC GGA GGG GGG TCT TTT GAT GTA GAT AAC GTC TCT AAT ACC
Ala Cys Ser Gly Gly Gly Ser Phe Asp Val Asp Asn Val Ser Asn Thr
            20                  25                  30

CCC TCT TCT AAA CCA CGT TAT CAA GAC GAT ACC TCG AAT CAA AGA ACA
Pro Ser Ser Lys Pro Arg Tyr Gln Asp Asp Thr Ser Asn Gln Arg Thr
        35                  40                  45

AAA TCT AAA TTG GAA AAG TTG TCC ATT CCT TCT TTA GGA GGA GGG ATG
Lys Ser Lys Leu Glu Lys Leu Ser Ile Pro Ser Leu Gly Gly Gly Met
    50                  55                  60

AAG TTA GTT GTG CAA AAT TTT GCT GGT GCT AAA GAA CCT AGT TTC TTA
Lys Leu Val Val Gln Asn Phe Ala Gly Ala Lys Glu Pro Ser Phe Leu
65                  70                  75                  80

AAT GAA AAT GAC TAT ATA TCA TAT TTT TCC TCA CTT TCT ATG ATT AAA
Asn Glu Asn Asp Tyr Ile Ser Tyr Phe Ser Ser Leu Ser Met Ile Lys
                85                  90                  95
```

FIG.11B.

GAT GAT GTT GAA AAT AAC AAT AAA AAT AAG GAT ACT CCA ATT GGC TCA
Asp Asp Val Glu Asn Asn Asn Lys Asn Lys Asp Thr Pro Ile Gly Ser
            100                     105                     110

ATA GAC GAG CCT AGA GCA CCA AAT TCA AAC GAA AAT CAT CAA AAT CAT
Ile Asp Glu Pro Arg Ala Pro Asn Ser Asn Glu Asn His Gln Asn His
            115                     120                     125

CAT GGA CAG CAA TAT GTA TAT TCG GGT CTT TAT TAT ATT CCA TCG TGG
His Gly Gln Tyr Val Tyr Ser Gly Leu Tyr Tyr Ile Pro Ser Trp
            130                     135                     140

CGT CTA ATA AAT TTA CCA AAT AAG TTT TAT TCA GGT TAC TAT GGA TAT
Arg Leu Ile Asn Leu Pro Asn Lys Phe Tyr Ser Gly Tyr Tyr Gly Tyr
        145                     150                     155                 160

GCC TAT TAC TTT GGC AAG CAA ACT GCC ACT ACA TTA CCT GTA AAT GGC
Ala Tyr Tyr Phe Gly Lys Gln Thr Ala Thr Thr Leu Pro Val Asn Gly
            165                     170                     175

GAA GCA ACG TAT AAA GGA ACT TGG AGC TTC ATC ACC GCA ACT GAA AGA
Glu Ala Thr Tyr Lys Gly Thr Trp Ser Phe Ile Thr Ala Thr Glu Arg
            180                     185                     190

FIG. 11C.

```
GGC AAA AAT TAT TCT TTG TTC AAT AAT AGA GGT CAA GCT TAT TCT CGA
Gly Lys Asn Tyr Ser Leu Phe Asn Asn Arg Gly Gln Ala Tyr Ser Arg
    195                     200                     205

CGT AGT GCT ACT CCA GGA GAT ATT GAT TTA GAA AAC GGT GAC GCA GGC
Arg Ser Ala Thr Pro Gly Asp Ile Asp Leu Glu Asn Gly Asp Ala Gly
    210                     215                     220

TTA ACA AGT GAA TTT ACT GTC AAT TTT GGT ACA AAA AAG CTC ACT GGA
Leu Thr Ser Glu Phe Thr Val Asn Phe Gly Thr Lys Lys Leu Thr Gly
225                     230                     235             240

GAA CCT TAT TAT AAT GAA AGG GAA ACA AAT CTT AAT CAA TCA AAA GAT
Glu Pro Tyr Tyr Asn Glu Arg Glu Thr Asn Leu Asn Gln Ser Lys Asp
            245                     250                     255

AGA AAA CAT AAA CTC TAC GAT CTA GAA GCT GAT GTG TAT AGC AAC CGA
Arg Lys His Lys Leu Tyr Asp Leu Glu Ala Asp Val Tyr Ser Asn Arg
                260                     265                     270

TTC AGA GGT ACA GTA AAG CCA ACC AAA AAG GAG TCT TCT GAA GAA CAT
Phe Arg Gly Thr Val Lys Pro Thr Lys Lys Glu Ser Ser Glu Glu His
    275                     280                     285
```

FIG.11D.

CCC TTT ACC AGC GAG GGA ACA TTA GAA GGT GGT TTT TAT GGG CCT AAT
Pro Phe Thr Ser Glu Gly Thr Leu Glu Gly Gly Phe Tyr Gly Pro Asn
290                          295                          300

GCT GAA GAA CTA GGG GGA AAA TTT TTA GCT AGC GAT AAA AAA GTT TTT
Ala Glu Glu Leu Gly Gly Lys Phe Leu Ala Ser Asp Lys Lys Val Phe
305                          310                          315                 320

GGG GTA TTT AGT GCC AAA GAA GAA GAA GAG CTG AAA CCA AAA TTA CCC AAA
Gly Val Phe Ser Ala Lys Glu Glu Glu Glu Lys Pro Lys Leu Pro Lys
                             325                          330                 335

GAA ACC TTA ATT GAT GGC AAG CTA ACT TTC TCT AAA ACA ACC GAT
Glu Thr Leu Ile Asp Gly Lys Leu Thr Thr Phe Ser Lys Thr Thr Asp
                             340                          345                 350

ACA ACA ACC AAT AAA ACA ACC AGT GCA AAA ACC AAT ACA GAA AAC TTT
Thr Thr Thr Asn Lys Thr Thr Ser Ala Lys Thr Asn Thr Glu Asn Phe
355                          360                          365

ACG ACA AAA GAT ATA CCA AGT TTT GGT GAA GCT GAT TAT CTT TTA ATT
Thr Thr Lys Asp Ile Pro Ser Phe Gly Glu Ala Asp Tyr Leu Leu Ile
370                          375                          380

FIG. 11E.

GAT AAT TAC CCT ATT CCG CTT TTA CCT GAG AGT GGT GAT TTC ATA AGT
Asp Asn Tyr Pro Ile Pro Leu Leu Pro Glu Ser Gly Asp Phe Ile Ser
385                     390                     395                 400

AGT AAG CAC CAT GAG GTA GGA GGT AAA CGC TAT AAA GTG GAA GCA TGT
Ser Lys His His Glu Val Gly Gly Lys Arg Tyr Lys Val Glu Ala Cys
        405                     410                     415

TGC AAG AAT CTA TGC TAT GTG AAA TTT GGT ATG TAT TAT GAG GAT AAA
Cys Lys Asn Leu Cys Tyr Val Lys Phe Gly Met Tyr Tyr Glu Asp Lys
        420                     425                     430

GAG AAC AAC AAA AAT GAA GAC AAA GAA AAA GAA AAA CAA ACG ACA
Glu Asn Asn Lys Asn Glu Thr Asp Lys Lys Glu Lys Gln Thr Thr
        435                     440                     445

ACA TCT ATC AAG ACT TAT TAT CAA TTC TTA GGT CTC CGG ACT CCC
Thr Ser Ile Lys Thr Tyr Tyr Gln Phe Leu Leu Gly Leu Arg Thr Pro
        450                     455                     460

AGT TCT GAA ATT CCT AAA ATG GGA AAC GTG ACA TAT CGC GGT AGT TGG
Ser Ser Glu Ile Pro Lys Met Gly Asn Val Thr Tyr Arg Gly Ser Trp
465                     470                     475                 480

FIG. 11F.

TTT GGT TAT ATT GGT GAT GAC AAG ACA TCT TAC TCC GCT ACA GGA GAT
Phe Gly Tyr Ile Gly Asp Asp Lys Thr Ser Tyr Ser Ala Thr Gly Asp
            485                     490                     495

AAA CGA CAA GAT AAA AAT GCT CCC GCC GAG TTT AAT GCT GAT TTT AAC
Lys Arg Gln Asp Lys Asn Ala Pro Ala Glu Phe Asn Ala Asp Phe Asn
            500                     505                     510

AAT AAA AAG CTA ACA GGC ACA TCA AAA CGA CAC GAT AAT CAA AAT CCC
Asn Lys Lys Leu Thr Gly Thr Ser Lys Arg His Asp Asn Gln Asn Pro
            515                     520                     525

GTG TTT AAC ATT AAG GCA ACC TTT CAA AAT GGT CGG AAT GAC TTT GAA
Val Phe Asn Ile Lys Ala Thr Phe Gln Asn Gly Arg Asn Asp Phe Glu
            530                     535                     540

GGT ACA GCA ACC GCA GAA AAT TTT GTA ATA GAT GGT AAA GAT AGT CAA
Gly Thr Ala Thr Ala Glu Asn Phe Val Ile Asp Gly Lys Asp Ser Gln
            545                     550                     555                     560

GGA AAT ACC CCA ATT AAT ATT ACA ACT AAA GTA AAC GGG GCA TTT TAT
Gly Asn Thr Pro Ile Asn Ile Thr Thr Lys Val Asn Gly Ala Phe Tyr
            565                     570                     575

FIG.11G.

```
GGA CCT GAT GCT TCT GAA TTA GGC GGT TAT TTC ACC TAT AAC GGA AAA
Gly Pro Asp Ala Ser Glu Leu Gly Gly Tyr Phe Thr Tyr Asn Gly Lys
        580                     585                     590

GAC ACT ATA ACT AAA AAT ACT GAA AGT TCC TCA ACC GTA CCT TCA CCA
Asp Thr Ile Thr Lys Asn Thr Glu Ser Ser Ser Thr Val Pro Ser Pro
        595                     600                     605

CCC AAT TCA CCA AAT GCA AGA GCT GCA GTT GTG TTT GGA GCT AAA AAA
Pro Asn Ser Pro Asn Ala Arg Ala Ala Val Val Phe Gly Ala Lys Lys
        610                     615                     620

CAA GTA GAA ACA ACC AAC AAG TAGAAAAAAA CAAATAATGG AATACTAAAA
Gln Val Glu Thr Thr Asn Lys
        625                 630

ATGACTAAAA AAGCTTCTAG AAAGCCGAAT TC
```

FIG. 12A.

```
TCTAACTTGA CATTATTACA AAAAAAGATC AATAATGCGA ATTATTATCA ATTTGTATG
AGTATATAAT TCTATGAAAT CTGTACCTCT TATCTCTGGT TCTAACTTGA CATTATTACA
AAAAAGATC AATAATGCGA ATTATTATCA ATTTGTATG AGTATATAAT TCTATGAAAT
CTGTACCTCT TATCTCTGGT TCTAAGTTGA CATTATTACA AAAAAGAAC AATAATGCGA
ATTATTATCA ATTTGTATA AGTATTAATT CTATGAAATC AAAAAGAAC AATAATGCGA
TCTAAGTTGA CATTATTACA AAAAAGAAC AATAATGCGA ATTATTATCA ATTTGTATA
AGAATATAAT TCTATGAAAT CTGTACCTCT TATCTCTGGT GGATCCATAT GAAATCTGTA
CCTCTTATCT CTGT
```

FIG.12B.

GTAGAAACAA CCAAATAATG GAATACTAAA AATGACTAAA AAACCCTATT TTCGCCTAAG
T

GTAGAAACAA CCAAATAATG GAATACTAAA AATGACTAAA AAACCCTATT TTCGCCTAAG
T

GTAGAAACAA CCAAGTAATG GAATACTAAA AATGACTAAA AAACCCTATT TTCGCCTAAG
T

GTAGAAACAA CCAACAAGTA AAAACAACCA AGTAATGGAA TACTAAAAAT GACTAAAAAA
CCCTATTTTC GCCTAAGT

GTAGAAACAA CCAAATAATG GAATACTAAA AATGACTAAA AAA

GTAGAAACAA CCAACAAGTA AAAACAACCA AGTAATGGAA TACTAAAAAT GACTAAAAAA

GTAGAAAAAA ACAACTAGTA AAAACAACCA AGTAATGGAA TACTAAAAAT GACTAAAAAA

GTAGAAACAA CCAACAAGTA GAAAAAAACA AATAATGGAA TACTAAAAAT GACTAAAAAA

TCTAGAAGCT TTTTTAGTCA TTTTTAGTAT TCCAT

FIG.14A.

Comparison of TBP1 amino acid sequences

```
MTKKPYFRLSIISCLLISCYVKAETQSIKDTKEAISSEVDTQSTEDSELETISVTAEKIRDRKDNEVTGLGKIIKTSESISREQVLNIRDLTRYDPGISV    EAGAN
................................................................................................    DL63
................................................................V.............................     PAK
..QQQHL...N.L-..SLMTALPVYAENTQAEQAQEKQ-------D..Q.K.K.QKT.R...........LV.S.DTL.K.........A.          SB33
..QQQHL...N.L-..SLMTALP.YAENTQAGQAQEKQ-------D..Q.K.K.QKT.R...........LV..ADTL.K...D                 B16B6
................................................................................................    M982
..QQQHL...N.L-..SLMTALP.YAENTQAGQAQEKQ-------D..Q.K.K.QKT.R...........LV..ADTL.K...D.........A.      FA19

VEQGRGASSGYSIRGMDRNRVALLVDGLPQTQSYVVQSPLVARSGYSGTGAINEIEYENVKAVEISKGGSSEYGNCALAGSVTFQSKSAADILEGDKSW    EAGAN
................................................................................................    DL63
................................................................................................    PAK
............K...S.T...VS.I...TA.AA.GGTRTAGSS....................SN............A..T.T...IGEG.Q.      SB33
............K...S.T....A.I...TA.AA.GGTRTAGSS.........................SN.V.Q.S..........A..T.T.D.VIGEGRQ.   B16B6
................................................................................................    M982
............K...S.T....A.I...TA.AA.GGTRTAGSS.........................SN.V.Q.S..........A..T.T.D.VIGEGRQ.   FA19

GIQTKNAYSSKNKGFTHSLAVAGKQGGFEGLAIYTQRNSIETQVHKDALKGVQSYDRLIATTDKSSGYFVIQG-----ECPNGDDK--CAA--KPPATLS    EAGAN
............V...H.....................F....EDQ.A...M.D------..LD.Y..--.KTSP.R......                DL63
..........D.V.....................................H...KPEDQ.A...M.D------...KP..YNS.LPFA.R..I..     PAK
..............V......E............E.F...........FN..VLDE..KE.GSQYRFIVEE..H.YAA--..KNKL.ED.SVK      SB33
...S.T...G.DHAL.Q...L.RS..A.A.L..K.RGR.IHA....G.....FN..VLDE..KE.GSQYRFIVEE..H.YAA--..KNKL.ED.SVK    B16B6
...S.T...G..R.L.Q.I.L..RI..A.A.L.H.K.RGG.IRA.E..GR...FN..VLVE..----SSEYAYFIVED..EGKNYET-.KSKP.KDVVGK   M982
...S.T...G..R.L.Q.I.L..RI..A.A.L.H.K.RGG.IRA.EA.GR...FN..APVD.----GSKYAYFIVEE..K..GHEK-.K.NP.KDVVGE   FA19
```

FIG. 14B.

```
TQSETVSVSDYTGANRIKPNPMKYESQSWFLRGGYHFSE-QHYIGGIFEFTQQKFDIRDMTFPAYLSPTERRDDSSRSFYPMQDHGAYQHIEDGR----     EAGAN
..R.....................................-................................R..DK.LQ..P...K.Y....G....---     DL63
.S.R....................................-..............................................Y......----     PAK
........................................-................................RS..K....G....K.Y....R.---     SB33
P.......................................-................................RS..K...RTGP...K.Y....R.---     B16B6
DERK...TQ.....S..LLA..LE.G......LF.P.W.LDN-R...V.AVL.R......T...T.....V....FTSEDYVP----GSLKGLGKYSGDNKAE.LFVQG  M982
DERQ...TR....P..FLAD.LS.....R..LF.P.FR.ENKRR............L.H...T...T.....V..F.TKAVFDAN.KQAGSLPGNGKYAGNHKY.GLFTNG  FA19
DERQ...TR.....P..FLAD.LS.....R..LF.P.FR.ENKRR...........L.H...T...T.....V..F.TKAVFDANQKQAGSLPGNGKYAGNHKY.GLFTSG

------GVKYASGLYFDEHHRKQRVGIEYIYENKNKAGIIDKAVLSANQQNIILDSYMRHTHCSLYPNPSKNCRPTLDKPYSYRSDRNVYKEKHNMLQL    EAGAN
.............................................................................H......................     DL63
.............................................................................H......................     PAK
----..N.................................Q............................................................     SB33
----..N................................................................................................     B16B6
EGSTLQ.IG.GT.VFY..R.T.N.Y.V..V.H.AD.DTWA.Y.R..YDR.G.D.NRLQQ......HDGSD-.....DGN.....F.K....MI.E.SR.LF.A   M982
ENGALV.AE.GT.VFY..T.T.S.Y.L..V.T.AD.DTWA.Y.R..YDR.G.D.NHFQQ.....ADGSD-.Y...SA...F....K....VI.G.S.RL..A   FA19
ENNAPV.AE.GT.VFY..T.T.S.Y.L..V.T.AD.DTWA.Y.R..YDR.G.D.NHFQQ.....ADG.-.Y...SA...F....K....VI.G.S.KL..A

NLEKKIQQNWLTHQIVFNLGFDDFTSALQHKDYLTRRVIATADSIPRKPGETGKPRNGLQSQ-PYLYPKPEPYFAGQDHCNYQGSSNYRDCKVRLIKGK   EAGAN
.............A...............................S..SE.R..A--R......S-......T.KAEIV.G.L....K.....S.......     DL63
.................................................T...K..SE.AN..--R...YKK.-.....TVG.VV....D.K.N.......     PAK
.............................................................................S..KVG.V....S..KVG.V.---     SB33
...................T...NI.SGTVA--..R....YEK.-.....S..KVG.V....S........                                  B16B6
VFK.AFDTAKIR..NLSI...Y.R.K.Q.S.S..YLQNAVQAY.L.TP.KPPFP---.SKDN-..RVSIGKTTVNTSPI.RFGNNT--.Y..TP.N.G.N     M982
AFK.SFDTAKIR..NLSV....R.D.N.R.Q..YYQHANRAYS.KTPPKTANP----.DK.K-..WVSIGGGNVVTGQI.LFGNNT--.Y..TP.S.N..     FA19
AFK.SFDTAKIR..NLSV...Y.R.G.N.R.Q..YYQSANRAYSLKTPPQNNGK.TSPNGREKN..WVSIGRGNVVTRQI.LFGNNT--.Y..TP.S.N..

NYYFAARNMALGKYVDLGLGIRYDVSRTKANESTISVGKFKNFSWNTGIVIKPTEMLDLSYRLSTGFRNPSFSEMYGMRYGGKNDEVVGKFKPETSRN    EAGAN
.....................M................................................A.............DTD.I.........     DL63
........................................................................A..........N.S.............     PAK
```

FIG. 14C.

```
                        I.......................A.............................  SB33
G..A.VQD.VR..RMA.V.A.....YRS.HSEDKSV.T.THR.L..A.V.L.FT.M..T.A......A.---ESLKTLDL...K.F.  B16B6
G..A.V.D.VR..RMA.V.A.L...YRS.HSDDGSV.T.THRTL..A...L..AD...T..A....L..A......S.---VQSKAV.ID.K.F.  M982
S..A.V.D.VR..RMA.V.A.L...YRS.HSDDGSV.T.THRTL..A..L..AD...T..A....L..A......S.---.KIKAV.ID.K.F.  FA19

QEFGLALKGDFGNIEISHFSNAYRNLIAFAEELSKNG-TGKGNY--GYHNAQNAKLVGVNITAQLDFNGLWKRIPYGWYATFAYNQVKVKDQKINAGLAS  EAGAN
.........................................T..--..........................................R.........  DL63
.........................................................................................R.........  PAK
.........................................T..--..........................................R.........  SB33
R.A.IVF..........L.A.Y.N....D....GY.TRTQNGQTSASGDP..R......RIA.I..LGKI.WH.V.GGL.D.L.S.L....RI....AD.R.DRTF  B16B6
R.A.IVF..........L.A.W.N....D..VRGY.AQIKNGKEEAKGDPA.L....S.RIT.I..LGKI.W..V.DKL.E....S.......R.H.R.I.KR.DRTD  M982
K.A.IVF..........L.A.W.N....D..VRGY.AQIKDGKEQVKGNPA.L....S.RIT.I..LGKI.W..V.DKL.E....S.......R.R.R.I.KR.DRTD  FA19

VSSYLFDAIQPSRYIIGLGYDHPSNTWGINTMFTQSKAKSQNELLGKRALGNNSRD-VKSTRKLTRAWHILDVSGYYMANKNIMLRLGIYNLFNYRYVTW  EAGAN
............................................................................V.RS.LF..V..L..........  DL63
.........................................................-..........................................  PAK
.........................................................-..........................................  SB33
.T......VL........DGI......Y..........VD....SQ..L.GNANAK.AASRR..P.YVT......NIK.HLT..A.V....L........  B16B6
IQ.H....VV....Q.EGK..V.G.L.Y......EIT....S...L.GNSRNT.A.ARR..P.Y.V......TIK.HFT..A.V...L........  M982
IQ.H....VV.S..Q.EGK..V.G.L.Y......EIT....S...L.GNSRNT.A.ARR..P.Y.V......TVK.HFT..A.V...L.H......  FA19

EAVRQTAQGAVNQHQNVGSYTRYAASGRNYTLTLEMKF*  EAGAN
.....................N................*  DL63
.......................................*  PAK
.......................................*  SB33
.N.......G......K...V.N....P.....FS.....*  B16B6
.N.......G....G.K...V.N....P.....FS.....*  M982
.N.......A......K...V.N....P.....FS.....*  FA19
```

FIG. 15A.

Comparison of TNP2 amino acid sequences

```
MKSVPLISGLSFLLSACSGGG-SFDVDNVSNTPS--SKPRYQDDTS----NQRKKS-NLKKLFIPSLGGMKLVAQNLRGNREPSFLNEDDYISYFSS         EAGAN
..........................................--......SS.T..-K.E.S............A.L.FDRNK..L.....S.M-I...   DL63
.....T....................................--......    .-.D.E..............    FI.AR.......G.M-I...   PAK
..........................G......D...PS..--........SS.T...-K.EN.S.............DRTK..L.......M-I...   SB12
..........................G......D...PS..--........SS.T...                    .FDRNK..L............   SB19
..........................      ..D...PS..--........SS.T....                                          SB29
.........L................G......D...PS..--........S..T...-..E.S............S........GN..M-I...      SB30
..........................................--........T....-K.E.S..............V.FA.A.......N.....     SB32
MNNPLVNQAAMVLPV.......L...G.....L.S.ETVQDMH...K.E.EK.Q-PES.QDV.E.SGAAYGFAVKLPRRNAHF.PKYKFKHKP.GSM.WKKLQ-R   B16B6
MNNPLVNQAAMVLPV.......L...G.....L.S.DT-EAPRPA.K...VS.EKPQA.KD----QG-GYGFAMRLKRRN--WYPGAEESEVK...S.WEATGLP   M982
MNNPLVNQAAMVLPV.......L...G.....L.S.DT-EAPRPA.K...VP.KKPEARKD----QG-GYGFAMRFKRRNQHPSANPKEDEVK.KN..WEATGLP   FA19
MHFKLNPYALAFTSL..-V.......KG.....LED.RPNKTTGVSKEEYK.VETAKKEKEQ-----..GE.ME.A..YVV.V--------.VSSF.NKKVDI--   AP205
MHFKLNPYALAFTSL..-V.......KG.....LED.RPNQTAKAEKATTSYQDEETKKKT.--EE.D..ME.A..YET----..I..R..A.KTETGEKRNREV--   AP37

L-------------STIEKDVK---DNNKNGADLIGSIDEPSTTNPPEK---HHGQF-----------YVYSGLYYTPSWSLNDSKN-KF----------YLGYYGYAFY   EAGAN
R---------..E..---ND.Q..EHP.D..VD.RAP.SN.N---R.........IQ...R.LP.K...-..S........Y..                         DL63
.----------..E..EKVKN......GR....E..NG.SQNSN---S--E---------ID..RDYKKEEQ.A...-..T........                   PAK
.----------...KA..EK--E..HYTSPV............K.N----D...R-----------I..N..L..N.Y---..Y.S........Y..           SB12
.----------....QD...K--E..RHTNPV.........NA........R-----------I....HSSNGKL---........                      SB29
R----------....KD..E--N..T..G.Y..........L.---R-----------IQ...R.LPK-...-........S.......Y..                SB30
.--------..M.KD..E---N...KDTP......RAP.SN.NHQN...Q----------I...R.INLP.-...-........S.......Y..             SB32
GEPNSFSERDE--L..KRG------SSE-...E.KW.DG--------QSRVVGYTNFT..R..YV.LNK-NNI.I..NIV--LFGPDG..Y.K.KEPS           B16B6
TKPKELPKRQK.V...VETDGDSDIYSSPY.TR.NHQNGSAGNGVN---QPKNQATGHENFQ.....WF.KHAA.EK.FS.K.I--KSGDDG.IF.H.EKPS       M982
TEPKKLPLKQQ.V.SEVETNGNSKMYTSPY.SQDA.SSH--ANGAN---QPKNEVTDYKKFK.....WF.KHAK.EVKNE.GLVSAKRGDDG.IF.H.DKPS       FA19
----------.D..VITNGNL.DVPYK.NSSKYNYPDI................KTKDSSLQ..R..YVIDGEH.GSNE--------.VY.                 AP205
----------VELSED.IT.LYQESVEIIPH.DELNGKTTSNDVYHS----.DSKRLDKNRDLK..R..YV.DG.FNEIRRNDSG.HVFKQGID-----..VY.     AP37
```

FIG. 15B.

```
YGNKTATNLPVNGVAKYKGTWDFITATKNGKRYPLLSNGS---HAYYRRSAIPEDIDLENDSKNGDI-GLISEFSADFGTKKLTGQLSYTKRKT------N      EAGAN
F..T..SA...G...T......S.....AE...N.E..R.SGGG-Q..S....T......DRKT-----..T....TVN......G.Y.NL.E.DAN----K      DL63
...E...K....K........N......E.....S.F.SIG--Q..S......S..YNLENGDA-----------..V...K.E..E.Y.NE...SVN---E      PAK
F.KQ...T....KVT......S.....AE..............---Q..F...............VKNDENREK..V..............G.F....Q---H      SB12
.........S.I.........................Q..S.FGSAF---G..N........S......NLENNLKNGA-....T.......TVN......K.Y.NE.E.------N      SB29
F.KE...T......E.T..........R...S.S.S....NR--Q..SK.................P...ETR-.T...TVN........G.Y.HL...NAN----E      SB30
F.KQ...T......E.T..........S.....ER..N.S.FN.RG---Q..S...T.G..............A-..T...TVN..........EPY.NE.E.N----L      SB32
KELP-SEKITYK.TWD.VTDAMEKQRFEGL.--GSAAGGFKSGALSALEEGVLRNQAEAS--SGHT.F-.MT..EV..SD.TIK.T.YRNN.I.QNNSENKQ      B16B6
RQLPASGKVIYK..WHFVTDTKKGQDFREIIQPSKKQGDRYSGFSGDGSEEYSNKNESTLKDDHEGY-.FT.NLEV..N.....K.IRNNASLNNNTNNDK      M982
RQLPASEAVIYK..WHFVTDTKQGQKFNDILETSKGQGDKYSGFSGDDEGETSNRT.SNLND.HEGY-.FT.N.KV..NN.....K.IRNNKVINTAASDG-      FA19
K..SP.KE....QLLT.T.S..TSNANLNNEEGRPNYLN---DD..TKFIGKRVGLVSG.A.PAKH-KYT.Q.EV..A..M..KJ.-D.E.........      AP205
L.VTPSKE..KGK.IS......VSNINLEREIDGKDTSGDGKNVSATSITETVNR.HKVGE.L..N-EVKGVAHSSEFAVDFDNKKLTGSLYRNGYINRNK      AP37

NQ--PYEKKLYDIDADIYSNRFRGTVKPTEKD-SEEHPFTSEGT-LEGGFYGPNAEELGGKFLATNDRVFGVFSAKETEETKKEA-LSKETLIDGLITFFS      EAGAN
S.--NRTH-....LE.VH......K.....K.ES.............EGQ.........H.KK.L......QQ..SENKK.P................T..K      DL63
S.--NTTH-.....TLE.KV.....K....KTK-..D................N.EK.............DPQNPENQK..T................K      PAK
I.--NH.........H.........K.N.Q..-K..............EGQ...........G.KK.........G...N.---.P..............T...      SB12
.NKLQKR.HE................K.....TQKD.Q...............G.................G........-.....DKK-...R............K      SB29
.--NR.H..NLE..V.........K.....KES-...........................................-...QQ..EENKK.L......T......      SB30
..-SKDR.H...LE..V.........K.ES-..........................................-......S.KK............-..P.---.T......      SB32
IK--TTRYTIQATLHGNRFKGKALAAD.GATNG-.--..........I.DSDS.......KG..A.....SN..K.AA..G..QKDKKDG.NAAGPA.E---      B16B6
HT--TQYYSLDAQ.TGNRFNGTATA.D.KENET-KL-..........V.DSSS.S...F..QG....FR..SD.QK.AV.G..TKDKLENG.AA.GS.GAAASGGAAG      M982
YT--TEYYSLDATLRGNRF.GKAIA.D..NTGGTKL-..........VFDSSS.S...F..QG....FR..SD.GK.AV.G..TKDSTANGNAPAASSG----      FA19
IY--TV----NA..RGNRFTGAATASD.NKG.GE.YNF-.SADSQS........K...MA..V.N.KSL.A..................-...........      AP205
A.-----.VT.R.S.E....AG......KA.A-..AGD---.IFTDSNY.........K...MA..FTNNKSL.A..A.................-......      AP37

TKKTDAKT-----NATTSTAANTTTDTTANTITDEKNFKTEDISSFGEADYLLIDKY--------------------------PIPLLPDKNTNDFI      EAGAN
.TNAT.NATT--D....T.S.K....T.ATANTE..T.K..P.L..........N.................................V..F.--ESG...      DL63
RTDATTNATT--D.K..ATTDA.S-......KK..AE........P.............GNQ----------------------------.E..D......      PAK
..T..........NATA..........AE......K..............................N-------------------------------ESG...      SB12
```

FIG. 15C.

```
                                                                                           SB29
...........T----------------------A..AK........T.K..P................N.------------------ SB30
...N.T.----D.........------...S.ATNATA,AE..T.K................................------V..-E SB32
...........------KTTD...NK.TSAK.NTE..T.K..P................N.-------------------------ESG. B16B6
----------..VID.YRI.GEEFKKEQIDSFGDVKKLLVD.VELS..PSEGNKAA--------------FQHEIE-------------- M982
.S----SENS--KL..VLD.VEL.LNDKKIKNLDNFSNAAQLVVD.IMIP..PKDSESGNTQADKGKNGGTEFTRKFEHTPESDKKDAQAGTQTNGAQTASN FA19
PGAATMPSET--RL..VLD.VEL.PDGKEIKNLDNFSNATRLVVD.IMIP..PT--ESGNGQADKGKNGGTDFTYETTYTPESDKKDTKAQTGAGGMQTASG AP205
----------------HNGSNVN.VRIIDASKI.LT..SISELNN..D.SV.I...-------------------------GKKIKLAGSG.T AP37
-----------SENG--ET..E------RIIDA.KI.LTQ.NAKELNN..D.SV.I..-------------------------GQKI.LAGVN.K

SSKHHTVGNKR--YKVEACCSNLSYVKFGMYYEDPLKEKETETETEKDKEKEKEKDKDKEKQTAATTNTYQFLLGHRTPKDDIPK--TGSAKYHGSWFG EAGAN
......K.T--Q.........A.P..--E.K.K.KD...............ATTSIK......L....SSE.....--E........N.... DL63
......G.T--..........----------KDKDN.NETDKEKGKEKPT.TTSI.............L.....E.....--E........N.... PAK
......K.T--.Q.K................----------KE.E.....ATNLS.............L.....SSE.....--G........L.... SB12
T.R..K.D.T--.........K.........------................E.................ATTSIK.........A.A...A--...NV..R.N... SB29
....E..G.H--.........K.........------...I.............................------N..N.KIE.EQ.H......L....SSQ.A--...NV..R..... SB30
....E..G....--.......K..C......------...................................------KENNKN.T..E.....TTSIK........L....SSE.....--M.NVT.R..... SB32
---QNGVKAT.-----V........D.MS..KLSKEN-.--------------------------------DDM..Q.V...VS.VAARTEAN...R.T.Y. B16B6
TAGDTNGKT.T-- E..V......N.L.Y..LTRKNS.--------------SAMQAGGNSSQADAKTEQVEQSM..Q.E..DEKE..--TDQNVV.R...Y. M982
TAGVNGGQVGTKT...QV.......N.L.Y.LLTREN-----------NNSVMQAVKNSS.AD.K.KQIE.SMFLQGERT.ENKIPQEQGIV.L.F.Y. FA19
NKHTIEING.T--MVAV........E.M...QLW------------QQAEGGKPENNSL..Q.E..AT.KM..--G.NY..I.T.D- AP205
N..TVEING.T--MVAV........E.M...QLW------------Q..EGKQQVKDNSL..Q.E..AT.KM.A--G.NY..V.T.D- AP37

YITDGKTSYSPSGDKKRDKNAVAEFNVDFAEKKLTGELKRHDTG-NPVFSIEANFNNSSNAFTGTATATN--FVIDGKNSQNKNTPINITTKVNGAFYCPKA EAGAN
..S...E.....A....E.S.........N.....T..........Q-......K.N.T.QSGK.D........KD--LA.....T.GTSKVNFTA.- DL63
..S...E.....A....E.S.........D.S..N.T..............------.........N..TS.AK................ PAK
.LS..S................EN..L.....N.VD.T.KGQ.I....NQ--T..T.D.T.KGGK.N........N..--VA..PQSTQGTSNVNFTA.-........N. SB12
...G.D......TT....------.......D.N..D.T.......N.--.......T.N.S..QSGK.D........N.--VA..PQ.T.TTSRVNFTA.- SB29
...G.D......TT....------L....D.N.TD..........A.NQ--T..R.N.D.K.ND...K......E.--......N...TG..Q..K.E........N. SB30
...G.D......AT....RQ....P....A..NN.....TS......NQ--......N.K.T.Q.GR.D.E......E.--...........D.G-.........D. SB32
```

..AN.-..W.GEASNQEGG.-R...D...ST..IS.T.TAK.RT-S.A.T.T.MIKD--.G.S.V.KTGENG.AL.PQ.TG.SHYTHI-EAT.S.G...KN.
H.AN.-..W.GNASD.EGG.-R...T.N..D..I..K.TAENRQ-AQT.T..GMIQG--.G.E...KTAESG.DL.Q..TTRTPKAYITDA..K.G......
R.AN.-..W.GKASNAT.G.-R.K.T.N.DR.EI..T.TAENRS-EAT.T.D.MIEG--.G.K...KTG.DG.AP.QN..TVTHKVHIANAE.Q.G.....N.
AQVSKENNWVATA.DD.KSGYRT..D...GN.N.S.K.LFDKN.V....TVD.KIDG--.G...K.KTSDEG.AL.SGS.RYE.VKF.DVA-.S.G....T.
ALVSKG.NWIAEA.NN.ESGYRT..D.N.SD..VN.K.-FDKG.V....TVD.TI.G--.G.I.S.KTSDSG.AL.AGS..HG.AVFSDI-...G......T.

SELGGYFTYNGN-STATNSESSTVSSSSNSKNARAAVVFGAR-QQVETT-K*       EAGAN
T.............-----NPTDKN....EK..........KK...........    DL63
..............KNP........P.PP..P..S........KK.........N.* PAK
T.............----PTDK....P................-..........-.* SB12
T.............-----NPTDKN....P.-..A........KK.........N.* SB29
T.............KNP.DK......P.PP..P..........KK-...KNN.*    SB30
.............KDTITK.T.....P.PP..P..........KK-........N.* SB32
I.M..S.SFP..APEGKQE-----------K.S......KR..LVQ*           B16B6
E...W.A.P.DKQ.EKAT-----AT..DGNSASS.T.....KR..PVQ*         M982
E...W.A.P..EQ.KNA------.E.GNGNSASS.T.....KR.KLVK*         FA19
A....Q.HHKSENGSVGA--------------.........K-...KK*         AP205
G....Q.HHKSDNGSVGA--------------.........K-R.I.K*         AP37
```

FIG. 19. Oligonucleotides to expresss TBP2 with no signal sequence.

Nde I                                      Ear I
TATGTGTTCTGGTGGTTCTTTCGACGTTGACAACGTTCTAACACTCCCTCTTCT
ACACAAGACCACCAAGAAAGCTGCAACTGTTGCAAAGATTGTGAGGAGAAGATTT

ATG start codon is enderlined
TGT cysteinr of mature protein is double underlined

FIG. 20A.

Sequence of oligonucleotide pairs (A, B, C and D) for constructing TBP1 and TBP2 expression plasmids Oligonucleotide pair A (Seq. ID 86 and 87) to join the T7 promoter and Eagan TBP1 gene Nde I
TA<u>T</u>GAAACTCAAAGTATAAAAGATACAAAAGAAGCTATATCATCTGAAGT...
   ACTTTGAGTTTCATATTTTCTATGTTTTCTTCGATATAGTAGACTTCA...

Pst I
...GGACACTCAAAGTACAGAAGATTCAGAATTAGAAACTATCTCAGTCACTGCA
...CCTGTGAGTTTCATGTCTTCTAAGTCTTAATCTTTGATAGAGTCAGTG

Oligonucleotide pair B (Seq. ID 88 and 89) to join the T7 promoter and Eagan TBP2 genes throught the E. coli lpp leader Nde I
TA<u>T</u>GAAAGCTACTAAACTGGTTCTGGGTGCTGTGTTATCCTGGGTTCCACTCTG....
   ACTTTCGATGATTTGACCAAGACCCACGACAATAGGACCCAAGGTGAGAC....

Ear I
...CTGGCTGGT<u>TGT</u>AGCGGAGGTGGTTGTTTGATGTAGATAACGTCTCTAATACCCCCTCTTCT
...GACCCACCAACATCGCCTCCACCAACAAACTACATCTATTGCAGAGATTATGGGGGAGAAGATTT

FIG.20B.

Oligonucleotide pair C (Seq. ID 90 and 91) to join the T7 promoter and Eagan TBP2 genes throught the *E. coli* r1p B leader

```
Nde I
TATGCGATATCTGGCAACATTGTTGTTATCTCTGGCGGTGTTAATCACCGCTG...
  ACGCTATAGACCGTTGTAACAACAATAGAGACCGCCACAATTAGTGGCGAC...
                                                                     Ear I
                        ...GTTGTAGCGGAGGTGGTTCTTTTGATGTAGATAACGTCTCTAATACCCCCTCTTCT
                         ...CAACATCGCCTCCACCAAGAAAACTACATCTATTGCAGAGATTATGGGGGAGAAGATTT
```

Oligonucleotide pair D (Seq. ID 92 and 93) to join the T7 promoter and Eagan TBP2 genes throught the *E. coli* pal leader

```
Nde I
TATGCAACTGAACAAAGTGCTGAAAGGGCTGATGATTGCTCTGCCTGTTATGGCAA...
  ACGTTGACTTGTTTCACGACTTTCCCGACTACTAACGAGACGGACAATACCGTT...
                                                                     Ear I
                      ...TTGCTGGTTGTAGCGGAGGTGGTTCTTTTGATGTAGATAACGTCTCTAATACCCCCTCTTCT
                  ... AACGACCAACATCGCCTCCTACCAAGAAAACTACATCTATTGCAGAGATTATGGGGGAGAAGATTT
```

ATG start codons are underlined
TGT coding for Cys of lipoproteins are double underlined
TGT may be replaced by TCC coding for Ser to secrete non-lipoprotein
Kinetics of Antibody Response to TBP1/TBP2 in Mice

NUCLEIC ACIDS ENCODING TRANSFERRIN RECEPTORS

REFERENCE TO RELATED APPLICATION

This application is a continuation-in-part of copending U.S. patent application Ser. No. 08/175,116, filed Dec. 29, 1993, now abandoned, which itself is a continuation-in-part of copending U.S. patent application Ser. No. 08/148,968 filed Nov. 8, 1993, now abandoned.

FIELD OF INVENTION

The present invention is related to the molecular cloning of genes encoding transferrin receptor and in particular to the cloning of transferrin receptor genes from Haemophilus influenzae.

BACKGROUND OF THE INVENTION

Encapsulated Haemophilus influenzae type b strains are the major cause of bacterial meningitis and other invasive infections in young children. However, the non-encapsulated or non-typable H. influenzae (NTHi) are responsible for a wide range of human diseases including otitis media, epiglottitis, pneumonia, and tracheobronchitis. Vaccines based upon H. influenzae type b capsular polysaccharide conjugated to diphtheria toxoid (Berkowitz et al., 1987. Throughout this application, various references are referred to in parenthesis to more fully describe the state of the art to which this invention pertains. Full bibliographic information for each citation is found at the end of the specification, immediately preceding the claims. The disclosures of these references are hereby incorporated by reference into the present disclosure), tetanus toxoid (Classon et al., 1989 and U.S. Pat. No. 4,496,538), or Neisseria meningitidis membrane protein (Black et al., 1991) have been effective in reducing H. influenzae type b-induced meningitis, but not NTHi-induced disease Bluestone, 1982).

Otitis media is the most common illness of early childhood with 60–70% of all children of less than 2 years of age experiencing between one and three ear infections. Chronic otitis media is responsible for hearing, speech and cognitive impairments in children. H. influenzae infections account for about 30%; of the cases of acute otitis media and about 60% of chronic otitis media. In the United States alone, treatment of otitis media costs between 1 and 2 billion dollars per year for antibiotics and surgical procedures such as tonsillectomies, adenoidectomies and insertion of tympanostomy tubes. Furthermore, many of the causative organisms of otitis media are becoming resistant to antibiotic treatment. An effective prophylactic vaccine against otitis media is thus desirable. Non-typable strains of H. influenzae are also important pathogens responsible for pneumonia in the elderly and other individuals who are particularly susceptible to respiratory infections. There is thus a need for antigens from H. influenzae which are useful as components in immunogenic preparations that provide protection against the many serotypes of H. influenzae.

Iron is an essential nutrient for the growth of many bacteria. Several human pathogens, such as H. influenzae, Branhamella catarrhalis, N. meningitidis, N. gonorrhoeae and non-pathogenic commensal Neisseria strains, can utilize human transferrin as an iron source (Schryvers, 1988; Schryvers and Lee, 1989; Mickelsen and Sparling, 1981). The bacterial transferrin receptor (TfR) is composed of two chains, Tbp1 and Tbp2. In strains of H. influenzae, the molecular weight of Tbp1 is approximately 100,000, whereas the molecular weight of Tbp2 is variable, ranging from 60,000 to 90,000, depending upon the strain (Schryvers and Gray-Owen, 1992; Holland et al., 1992). Expression of H. influenzae transferrin receptor is thought to be iron-and/or hemin-regulated (Morton et al., 1993) and a putative fur-binding site (Braun and Hantke, 1991) has been identified upstream of tbp2. This sequence is found in the promoter region of genes which are negatively regulated by iron, including N. meningitidis TfR (Legrain et al., 1993). The promoter is followed by the tbp2 and tbp1 genes, an arrangement found in other bacterial TfR operons (Legrain et al, 1993; Wilton et al., 1993). Antibodies which block the access of the transferrin receptor to its iron source may prevent bacterial growth. In addition, antibodies against TfR that are opsonizing or bactericidal may also provide protection by alternative mechanisms. Thus, the transferrin receptor, fragments thereof, its constituent chains, or peptides derived therefrom are vaccine candidates to protect against H. influenzae disease. Mice immunized with N. meningitidis TfR proteins in Freund's adjuvant were protected from homologous challenge and the anti-TfR antisera were bactericidal and protective in a passive transfer assay (Danve et al., 1993). Pigs immunized with recombinant A. pleuropneumoniae Tbp2 were protected against homologous challenge but not heterologous challenge (Rossi-Campos et al., 1992). These data indicate the efficacy of TfR-based vaccines in protection from disease. It would be desirable to provide the sequence of the DNA molecule that encodes transferrin receptor and peptides corresponding to portions of the transferrin receptor and vectors containing such sequences for diagnosis, immunization and the generation of diagnostic and immunological reagents.

Poliovirus is an enterovirus, a genus of the family Picornaviridae. There are three distinct serotypes of the virus, and multiple strains within each serotype. Virulent strains are causative agents of paralytic poliomyelitis. Attenuated strains, which have reduced potential to cause paralytic disease, and inactivated virulent strains, are used as vaccines. Infection with the virus induces long-lasting, protective, mucosal immunity. Inoculation with inactivated poliovirus vaccines can also induce a mucosal immune response.

The structure of poliovirus is known, and is highly conserved among strains and serotypes. The structures of several other picornaviruses (viruses belonging to genera of the family Picornaviridae) have also been determined, and have been shown to be closely related to the structure of poliovirus. It is possible to express foreign epitopes on the capsid of polioviruses (Murdin et al, 1992) and this work has been extended to other picornaviruses. Epitopes which have been expressed are usually short, well defined, contiguous epitopes, and most have been expressed within poliovirus neutralisation antigenic site I (NAgI) or the equivalent site on other picornaviruses. This site includes the loop linking beta strands B and C (the BC loop) of poliovirus capsid protein VP1. The BC loop of VP1 is a surface-exposed loop of nine amino acids which can be replaced and extended with at least twenty-five heterologous amino acids (Murdin et al, 1991). Hybrid or chimeric polioviruses expressing transferrin receptor epitopes, which grow to a high titre and are immunogenic, would be useful as vaccines and as tools for the generation of immunological reagents.

SUMMARY OF THE INVENTION

The present invention is directed towards the provision of purified and isolated nucleic acid molecules encoding a transferrin receptor of a strain of Haemophilus or a fragment or an analog of the transferrin receptor protein. The nucleic acid molecules provided herein are useful for the specific detection of strains of Haemophilus, and for diagnosis of infection by Haemophilus. The purified and isolated nucleic acid molecules provided herein, such as DNA, are also useful for expressing the TfR genes by recombinant DNA means for providing, in an economical manner, purified and isolated transferrin receptor subunits, fragments or analogs thereof. The transferrin receptor, subunits or fragments thereof or analogs thereof, as well as nucleic acid molecules encoding the same and vectors containing such nucleic acid molecules, are useful in immunogenic compositions against diseases caused by Haemophilus, the diagnosis of infection by Haemophilus and as tools for the generation of immunological reagents. Monoclonal antibodies or mono-specific antisera (antibodies) raised against the transferrin receptor protein produced in accordance with aspects of the present invention are useful for the diagnosis of infection by Haemophilus, the specific detection of Haemophilus (in for example in vitro and in vivo assays) and for the treatment of diseases caused by Haemophilus.

Peptides corresponding to portions of the transferrin receptor or analogs thereof are useful immunogenic compositions against disease caused by Haemophilus, the diagnosis of infection by Haemophilus and as tools for the generation of immunological reagents. Monoclonal antibodies or antisera raised against these peptides, produced in accordance with aspects of the present invention, are useful for the diagnosis of infection by Haemophilus, the specific detection of Haemophilus (in, for example, in vitro and in vivo assays) and for use in passive immunization as a treatment of disease caused by Haemophilus.

In accordance with one aspect of the present invention, there is provided a purified and isolated nucleic acid molecule encoding a transferrin receptor protein of a strain of Haemophilus, more particularly, a strain of H. influenzae, specifically a strain of H. influenzae type b, such as H. influenzae type b strain DL63, Eagan or MinnA, or a non-typable strain of H. influenzae, such as H. influenzae strain PAK 12085, SB33, SB12, SB29, SB30 or SB32, or a fragment or an analog of the transferrin receptor protein.

In one preferred embodiment of the invention, the nucleic acid molecule may encode only the Tbp1 protein of the Haemophilus strain or only the Tbp2 protein of the Haemophilus strain. In another preferred embodiment of the invention, the nucleic acid may encode a fragment of the transferrin receptor protein of a strain of Haemophilus having a conserved amino acid sequence which is conserved among bacteria that produce transferrin receptor protein. Such conserved amino acid sequence may have an amino acid sequence contained within the amino acid sequence of the peptides shown in Tables 2 and 3 below for Haemophilus influenzae type b strain Eagan as well as corresponding peptides of other strains of Haemophilus influenzae.

In another aspect of the present invention, there is provided a purified and isolated nucleic acid molecule having a DNA sequence selected from the group consisting of (a) any one of the DNA sequences set out in FIGS. 3, 4, 5, 6, 7, 8, 9, 10 or 11 (SEQ ID NOS: 1, 2, 3, 4, 105, 108, 110, 112, 114) or the complementary DNA sequence of any one of said sequences; (b) a DNA sequence encoding one of the amino acid sequences set out in FIGS. 3, 4, 5, 6, 7, 8, 9, 10 or 11 (SEQ ID NOS: 5, 6, 7, 8, 9, 10, 11, 12, 106, 107, 109, 111, 113, 115) or the complementary DNA sequence thereto; and (c) a DNA sequence which hybridizes under stringent conditions to any one of the DNA sequences defined in (a) or (b). The DNA sequence defined in (c) preferably has at least about 90% sequence identity with any one of the DNA sequences defined in (a) and (b).

In an additional aspect, the present invention includes a vector adapted for transformation of a host, comprising a nucleic acid molecule as provided herein. The vector may be one having the characteristics of plasmid DS-712-1-3 having ATCC accession number 75603 or plasmid JB-1042-7-6 having ATCC accession number 75607.

The plasmids may be adapted for expression of the encoded transferrin receptor, fragments or analogs thereof, in a heterologous or homologous host, in either a lipidated or non-lipidated form. Accordingly, a further aspect of the present invention provides an expression vector adapted for transformation of a host comprising a nucleic acid molecule as provided herein and expression means operatively coupled to the nucleic acid molecule for expression by the host of the transferrin receptor protein or the fragment or analog of the transferrin receptor protein. In specific embodiments of this aspect of the invention, the nucleic acid molecule may encode substantially all the transferrin receptor protein, only the Tbp1 protein or only the Tbp2 protein of the Haemophilus strain. The expression means may include a nucleic acid portion encoding a leader sequence for secretion from the host of the transferrin receptor protein or the fragment or the analog of the transferrin receptor protein. The expression means also may include a nucleic acid portion encoding a lipidation signal for expression from the host of a lipidated form of the transferrin receptor protein or the fragment or the analog of the transferrin receptor protein. The expression plasmid may have the identifying characteristics of plasmid JB-1468-29, JB-1600-1 or JB-1424-2-8. The host may be selected from, for example, *Escherichia coli*, Bacillus, Haemophilus, fungi, yeast or baculovirus and Semliki Forest virus expression systems may be used.

In an additional aspect of the invention, there is provided a transformed host containing an expression vector as provided herein. Such host may selected from JB-1476-2-1, JB-1437-4-1 and JB-1607-1-1. The invention further includes a recombinant transferrin receptor protein or fragment or analog thereof producible by the transformed host.

As described in more detail below, there has been produced Tbp1 and Tbp2 protein receptors separate from each other. Further aspects of the present invention, therefore, provide an isolated and purified Tbp1 protein of a strain of Haemophilus free from the Tbp2 protein of the Haemophilus strain and an isolated and purified Tbp2 protein of a strain of Haemophilus free from the Tbp1 protein of the Haemophilus strain. The Haemophilus strain may be H. influenzae type b or a non-typable strain of H. influenzae.

The present invention further provides synthetic peptides corresponding to portions of the transferrin receptor. Accordingly, in a further aspect of the invention, there is provided a synthetic peptide having no less than six amino acids and no more than 150 amino acids and containing an amino acid sequence corresponding to a portion only of a transferrin receptor protein of a strain of bacteria or of an analog the transferrin receptor protein. The bacterial strain preferably is a Haemophilus strain, particularly a H. influenzae strain, specifically a strain of H. influenzae type b or a non-typable strain of H. influenzae.

The peptides provided herein may comprise an amino acid sequence which is conserved among bacteria that produces transferrin receptor protein, including strains of Haemophilus. The peptide may include an amino acid sequence LEGGFYGP (SEQ ID NO: 74) or LEGGFYG (SEQ ID NO: 85). The peptides provided herein may have an amino acid sequence selected from those presented in Table 2 or 3 below for the Eagan strain of H. influenzae type b and corresponding amino acid sequences for other strains of H. influenzae.

In accordance with another aspect of the invention, an immunogenic composition is provided which comprises at least one active component selected from at least one nucleic acid molecule as provided herein, at least one recombinant protein as provided herein, at least one of the purified and isolated Tbp1 or Tbp2 proteins, as provided herein, at least one synthetic peptide, as provided herein, and a live vector, as provided herein, and a pharmaceutically acceptable carrier therefor or vector therefor. The at least one active component produces an immune response when administered to a host.

The immunogenic compositions provided herein may be formulated as a vaccine for in vivo administration to protect against diseases caused by bacterial pathogens that produce transferrin receptors. For such purpose, the compositions may be formulated as a microparticle, capsule or liposome preparation. Alternatively, the compositions may be provided in combination with a targeting molecule for delivery to specific cells of the immune system or to mucosal surfaces. The immunogenic composition may comprise a plurality of active components to provide protection against disease caused by a plurality of species of transferrin receptor producing bacteria. The immunogenic compositions may further comprise an adjuvant.

In accordance with another aspect of the invention, there is provided a method for inducing protection against infection or disease caused by Haemophilus or other bacteria that produce transferrin receptor protein, comprising the step of administering to a susceptible host, such as a human, an effective amount of the immunogenic composition as recited above.

In accordance with another aspect of the invention, an antiserum or antibody specific for the recombinant protein, the isolated and purified Tbp1 protein or Tbp2 protein, synthetic peptide or the immunogenic composition, is provided.

In a further aspect, there is provided a live vector for delivery of transferrin receptor to a host, comprising a vector containing the nucleic acid molecule as described above. The vector may be selected from Salmonella, BCG, adenovirus, poxvirus, vaccinia and poliovirus. The vector may specifically be poliovirus and the nucleic acid molecule may code for a fragment of transferrin receptor having an amino acid sequence of LEGGFYGP (SEQ ID NO: 74) or LEGGFYG (SEQ ID NO: 85). The present invention further includes a plasmid vector having the identifying characteristics of pT7TBP2A, pT7TBP2B, pT7TBP2C or pT7TBP2D (ATCC designation Nos. 75931, 75932, 75933, 75934).

An additional aspect of the invention provides a strain of Haemophilus that does not produce transferrin receptor protein. Such strain may comprise a gene encoding transferrin receptor which is functionally disabled, such as by insertional mutagenesis. The Haemophilus strain may be one that has been attenuated and the attenuated strain may comprise the vector for delivery of transferrin receptor.

As mentioned above, one aspect of the invention provides novel Tbp1 or Tbp2 protein of a strain of Haemophilus, preferably a strain of Haemophilus influenzae, which is isolated and purified and free from the other. A yet further aspect of the present invention provides a method for producing such proteins. Accordingly, in this yet further aspect, the present invention provides a method of producing an isolated and purified Tbp1 or Tbp2 protein of a strain of Haemophilus, comprising the steps of (a) providing a recombinant host expressing, in inclusion bodies, Tbp1 or Tbp2 protein, but not both; (b) growing the host to provide a cell mass; (c) disrupting the cell mass to provide a cell lysate; (d) fractionating the cell lysate to provide a first supernatant and a first pellet, the first supernatant comprising substantially a large proportion of soluble host proteins; (e) separating the first supernatant from the first pellet; (f) selectively extracting the first pellet to remove substantially all soluble host proteins and host membrane proteins therefrom to provide a second supernatant and an extracted pellet containing the inclusion bodies; (g) separating the second supernatant from the extracted pellet; (h) solubilizing the extracted pellet to provide a solubilized extract; and (i) fractionating the solubilized extract to provide a Tbp1 or Tbp2 protein containing fraction.

The cell lysate may be fractionated to provide the first supernatant and first pellet may be effected by at least one detergent extraction.

The solubilized extract may be fractionated by gel filtration to provide the Tbp1 or Tbp2 protein containing fraction, which may be subsequently dialyzed to remove at least the detergent and provide a further purified solution of Tbp1 or Tbp2 protein.

BRIEF DESCRIPTION OF DRAWINGS

The present invention will be further understood from the following description with reference to the drawings, in which:

FIGS. 3A to 3Q show the nucleotide sequences of the transferrin receptor genes (SEQ ID NO: 1) and their deduced amino acid sequences (SEQ ID NO: 5-Tbp1 and SEQ ID NO: 6-Tbp2) from H. influenzae type b, strain DL63. The underlined amino acid sequences correspond to peptides of Tbp1 identified by amino acid sequencing. The putative signal sequences are indicated by double overlining and correspond to residues 1 to 17 for Tbp1 and 1 to 25 for Tbp2.

FIGS. 4A to Q show the nucleotide sequences of the transferrin receptor genes (SEQ ID NO: 2) and their deduced amino acid sequences (SEQ ID NO: 7-Tbp1 and SEQ ID NO: 8-Tbp2) from H. influenzae type b strain Eagan. Putative −35, −10 and ribosomal binding site sequences are overlined.

FIGS. 5A to 5Q show the nucleotide sequences of the transferrin receptor genes (SEQ ID NO: 3) and their deduced amino acid sequences (SEQ ID NO: 9-Tbp1 and SEQ ID NO: 10-Tbp2) from H. influenzae type b strain MinnA. Putative −35, −10 and ribosomal binding site sequences are overlined.

FIGS. 6A to Q show the nucleotide sequences of the transferrin receptor genes (SEQ ID NO: 4) and their deduced amino acid sequences (SEQ ID NO. 11-Tbp1 and SEQ ID NO. 12-Tbp2) from the non-typable H. influenzae strain PAK 12085. Putative −35, −10 and ribosomal binding site sequences are overlined.

FIGS. 7A to 7N show the nucleotide sequences of the transferrin receptor genes (SEQ ID NO: 105) and their deduced amino acid sequences (SEQ ID NO. 106-Tbp1 and SEQ ID NO. 107-Tbp2) from the non-typable H. influenzae strain SB33.

FIGS. 8A to 8G show the nucleotide sequence of the Tbp2 gene (SEQ ID NO: 108) and the deduced amino acid sequence (SEQ ID NO: 109-Tbp2) from non-typable strain H. influenzae strain SB12.

FIGS. 9A to 9G show the nucleotide sequence of the Tbp2 gene (SEQ ID NO: 110) and the deduced amino acid sequence (SEQ ID NO: 111-Tbp2) from non-typable strain H. influenzae strain SB29.

FIGS. 10A to 10G show the nucleotide sequence of the Tbp2 gene (SEQ ID NO: 112) and the deduced amino acid sequence (SEQ ID NO: 113-Tbp2) from non-typable strain H. influenzae strain SB30.

FIGS. 11A to 11G show the nucleotide sequence of the Tbp2 gene (SEQ ID NO: 114) and the deduced amino acid sequence (SEQ ID NO: 115-Tbp2) from non-typable strain H. influenzae strain SB32.

FIG. 12A shows the nucleotide sequences of the promoter regions and 5'-end of the tbp2 genes from H. influenzae strains Eagan (SEQ ID NO: 116), MinnA (SEQ ID NO: 117), PAK 12085 (SEQ ID NO: 118) and SB33 (SEQ ID NO: 119). The coding strand primer used to amplify tbp2 genes by PCR is underlined (SEQ ID NO: 120).

FIG. 12B shows the nucleotide sequence of the intergenic region and 5'-end of the tbp1 genes from H. influenzae strains Eagan (SEQ ID NO: 121), MinnA (SEQ ID NO: 122), DL63 (SEQ ID NO: 123), PAK 12085 (SEQ ID NO: 124), SB12 (SEQ ID NO: 125), SB29 (SEQ ID NO: 126), SB30 (SEQ ID NO: 127), and SB32 (SEQ ID NO: 128). The non-coding strand primer used to amplify the tbp2 genes by PCR is underlined (SEQ ID NO: 129).

FIGS. 14A to 14C show a comparison of the amino acid sequences of Tbp1 from H. influenzae strains Eagan, DL63, PAK 12085 and SB33 (SEQ ID NOS: 7, 5, 11 and 106), N. meningitidis strains B16B6 and M982 (SEQ ID NOS: 94 and 95), and N. gonorrhoeae strain FA19 (SEQ ID NO: 96).

FIGS. 15A to 15D show a comparison of the amino acid sequence of Tbp2 from H. influenzae strains Eagan, DL63, PAK 12085, SB12, SB29, SB30 and SB32 (SEQ ID NOS: 8, 6, 12, 109, 110, 112, 114), N. meningitidis strains B16B6 and M982 (SEQ ID NOS: 97 and 98), N. gonorrhoeae strain FA19, and Actinobacillus pleuropneumoniae strains AP205 and AP37 (SEQ ID NOS: 99 and 100).

FIGS. 16A' and 16A" show the predicted secondary structure of H. influenzae Tbp1 protein.

FIG. 19 shows the oligonucleotide pairs (SEQ ID NOS: 130, 131) used to construct plasmid JB-1424-2-8.

FIGS. 20A and 20B show the sequence of oligonucleotide pairs A (SEQ ID NOS: 86, 87), B (SEQ ID NOS: 88, 89), C (SEQ ID NOS: 90, 91) and D (SEQ ID NOS: 92, 93) for constructing Tbp1 and Tbp2 expression plasmids.

Figure 1A:
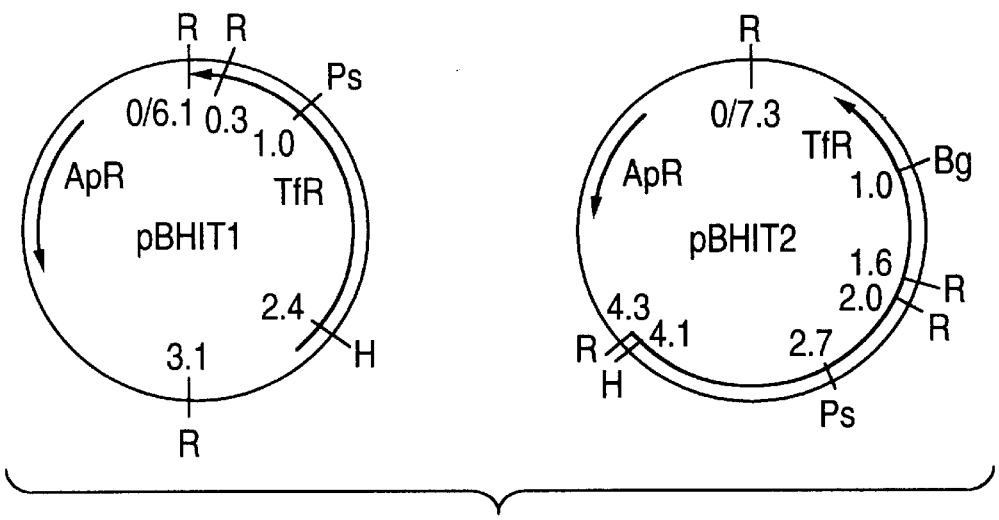
FIG. 1A shows the restriction map of two plasmid clones (pBHT1 and pBHT2) of the transferrin receptor operon of Haemophilus influenzae type b strain DL63.

Furthermore, the amino acid sequences of the transferrin receptor from a range of bacterial pathogens (H. influenzae type b, non-typable H. influenzae, Neisseria meningitidis, Neisseria gonorrhoeae and Actinobacillus (Haemophilus) pleuropneumoniae) were compared as shown in FIGS. 14 and 15. This analysis revealed regions of Tbp1 and Tbp2 which are conserved between all of these bacteria. Some of such conserved sequences are contained in peptides in Tables 2 and 3. In particular the sequences DNEVTGLGK (SEQ ID: 43), EQVLNIRDLTRYDPGI (SEQ ID NO: 44), EQVLNIRDLTRYDPGISVVEQG RGASSGYSIRGMD (SEQ ID NO: 45), GAINEIEYENVKAVEISKG (SEQ ID NO: 46) and GALAGSV (SEQ ID NO: 47) are conserved in Tbp1 (Table 1 and FIG. 14). Particular conserved sequences in Tbp2 include LEGGFYGP (SEQ ID NO: 74), CSGGGSFD (SEQ ID NO: 75), YVYSGL (SEQ ID NO: 76), CCSNLSYVKFG (SEQ ID NO: 77), FLLGHRT (SEQ ID NO: 78), EFNVOF (SEQ ID NO: 79), NAFTGTA (SEQ ID NO: 80), VNGAFYG (SEQ ID NO: 81), ELGGYF (SEQ ID NO: 82), VVFGAR (SEQ ID NO: 83) and VVFGAK (SEQ ID NO: 84) (Table 2 and FIG. 15).

The discovery of conserved sequences within the transferrin receptor of a range of bacterial pathogens allows the selection of a minimal number of antigens having particular amino acid sequences (including in the form of synthetic peptides) to immunize against the disease caused by pathogens that have transferrin receptors. Such bacteria in addition to those recited above include other species of Neisseria, such as Neisseria gonorrhoeae, and Branhamella, including Branhamella catarrhalis. Such conserved amino acid sequences among many bacterial pathogens permits the generation of TfR specific antibodies, including monoclonal antibodies, that recognize most if not all transferrin receptors. Antiserum was raised against peptides corresponding to conserved portions of the transferrin receptor. This antiserum recognized the transferrin receptor in Branhamella catarrhalis. Such antisera are useful for the detection and neutralization of most if not all bacteria that produce TfR protein and are also useful for passive immunization against the diseases caused by such pathogens. Diagnostic assays and kits using such conserved amino acid sequences are useful to detect many if not all bacteria that produce transferrin receptor.

Epitopes containing the afore-mentioned amino acid sequences can be delivered to cells of the immune system by the use of synthetic peptides containing such sequences, or by the use of live vectors expressing such sequences, or by the direct administration of nucleic acid molecules encoding the amino acid sequence.

Some peptides containing conserved amino acid sequences within the Tbp1 proteins of H. influenzae type b strains Eagan, MinnA, DL63 and the nontypable strain PAK 12085 are shown in Table 2. Antibodies to some of these peptides were raised in guinea pigs (Table 4). Peptides containing conserved amino acid sequences within the Tbp2 proteins of H. influenzae type b strains Eagan, Minn A, DL63 and the nontypable strain PAK 12085 are shown in Table 3. Antibodies to some of these peptides were raised in guinea pigs (Table 4).

Figure 17:
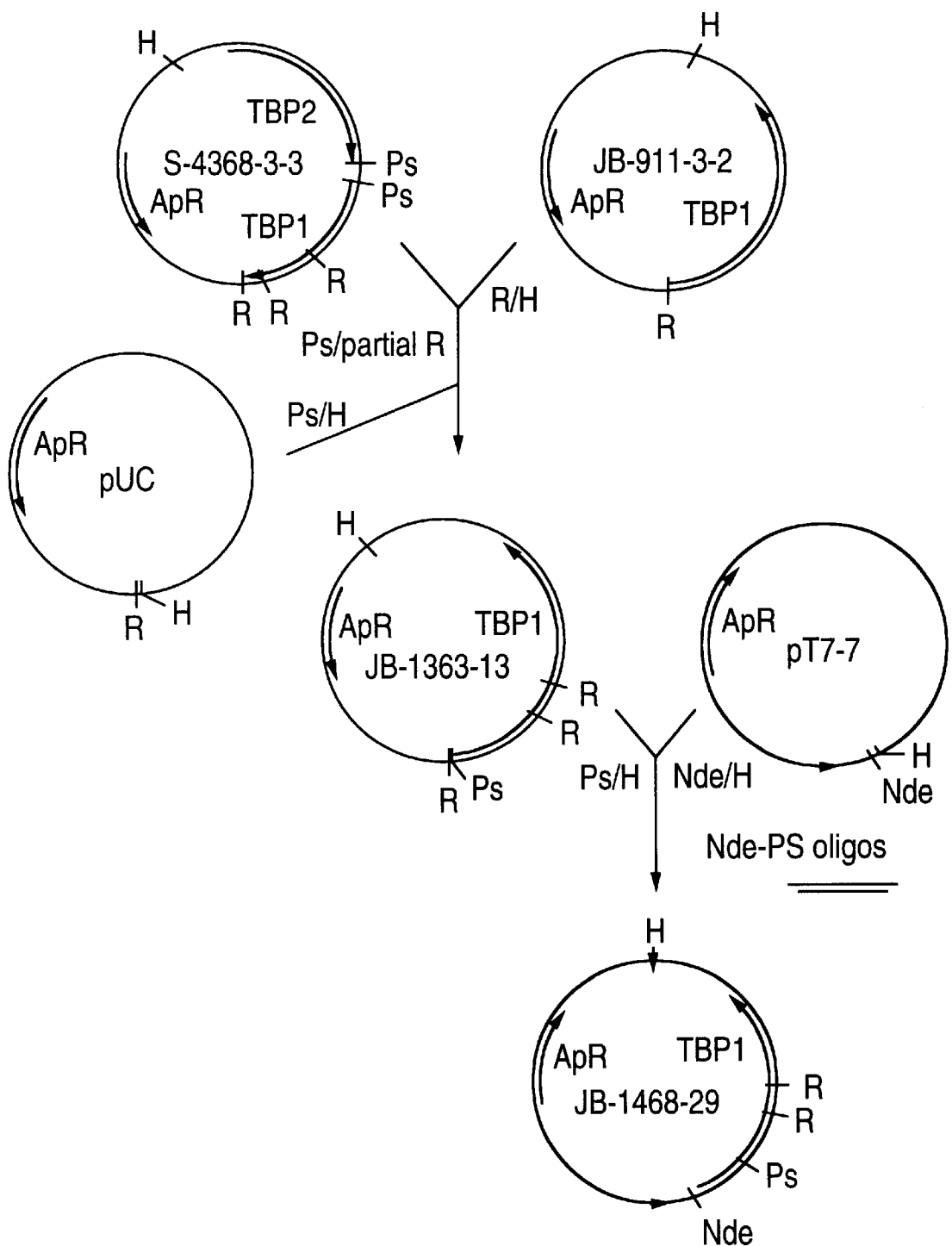
FIG. 17 shows the construction scheme of plasmid JB-1468-29 which expresses H. influenzae type b Eagan Tbp1 from E. coli.
Figure 22:
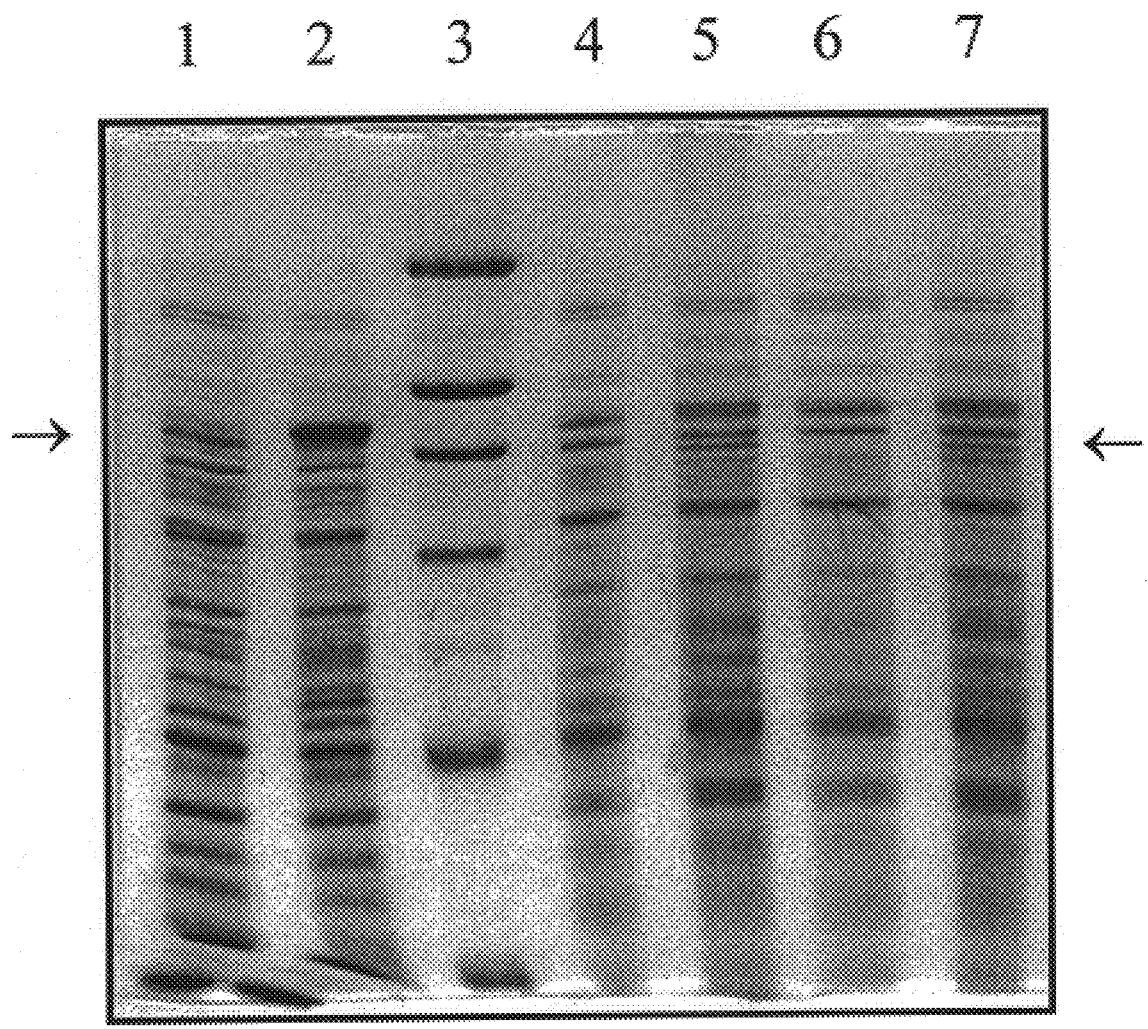
FIG. 22 shows SDS-PAGE gels of products from the expression of Haemophilus type b Eagan Tbp1 protein, Eagan Tbp2 protein, and non-typable H. influenzaea SB12 Tbp2 protein from E. coli. Lane 1, JB-1476-2-1 (T7/Eagan Tbp1) at $t_o$; lane 2, JB-1476-2-1 at t=4 h induction; lane 3, molecular weight markers of 200 kDa, 116 kDa, 97.4 kDa, 66 kDa, 45 kDa and 31 kDa; lane 4, JB-1437-4-1 (T7/Eagan Tbp2) at $t_o$; lane 5, JB-1437-4-1 at t=4 h induction; lane 6, JB-1607-1-1 (T7/SB12 Tbp2) at $t_o$; lane 7, JB-1607-1-1 at t=4 h induction.

The coding sequences of the Tbp1 and Tbp2 genes may be cloned into appropriate expression vectors to produce recombinant proteins. Recombinant Tbp1 and Tbp2 were expressed from E. coli using the T7 expression system. The tbp1 gene encoding the mature Eagan Tbp1 protein was cloned in-frame behind the T7 promoter generating plasmid JB-1468-29, as shown in FIG. 17. When introduced into BL21/DE3 cells and induced with IPTG or lactose, Eagan Tbp1 protein was expressed as shown in FIG. 22.

Figure 18:
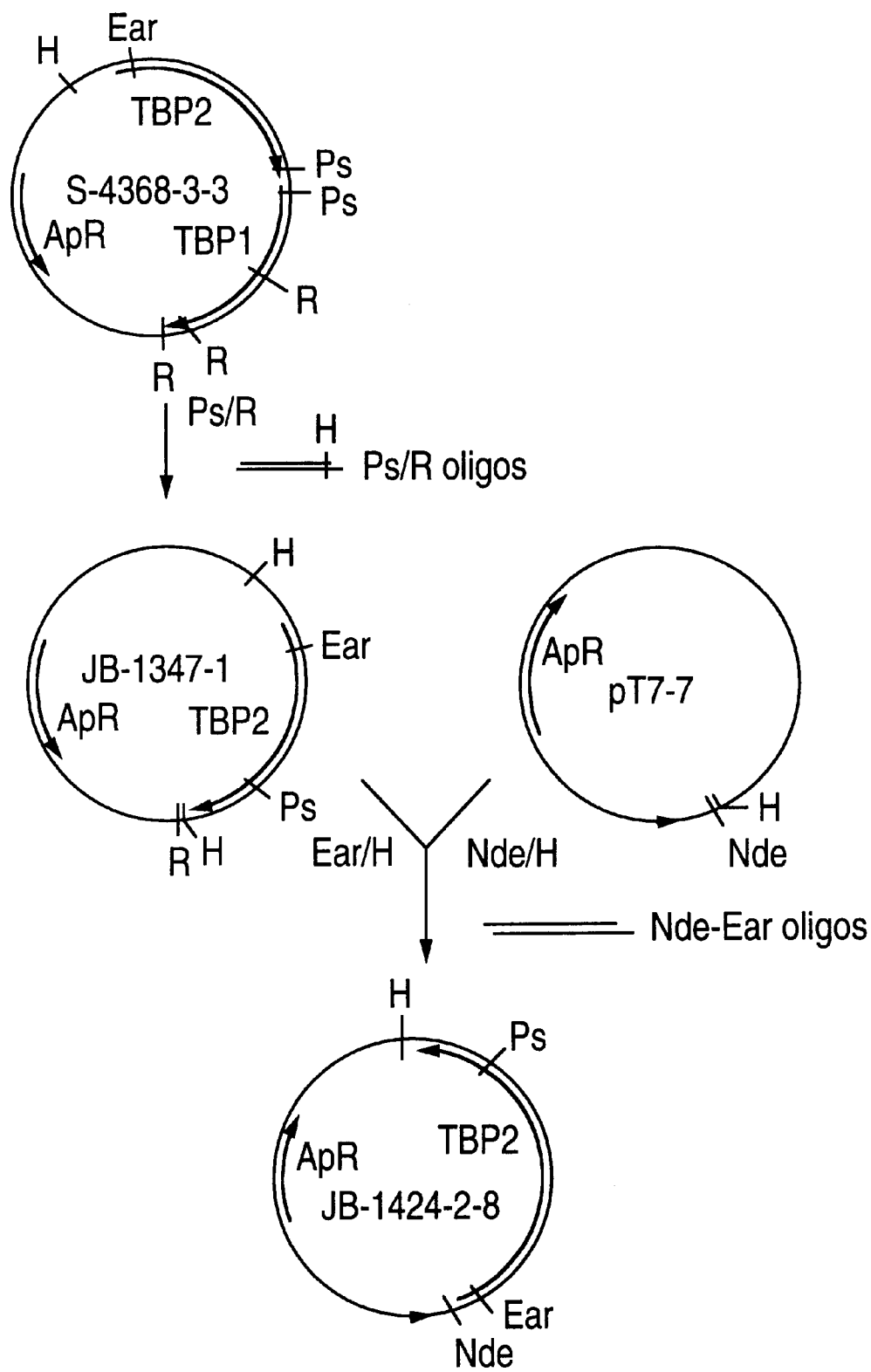
FIG. 18 shows the construction scheme of plasmid JB-1424-2-8 which expresses H. influenzae type b Eagan Tbp2 from E. coli.

The tbp2 gene encoding the mature Tbp2 protein was cloned in-frame behind the T7 promotor generating plasmid JB-1424-2-8 as shown in FIG. 18. When introduced into E. coli cells and induced as above, Tbp2 protein was expressed as shown in FIG. 22.

Figure 21:
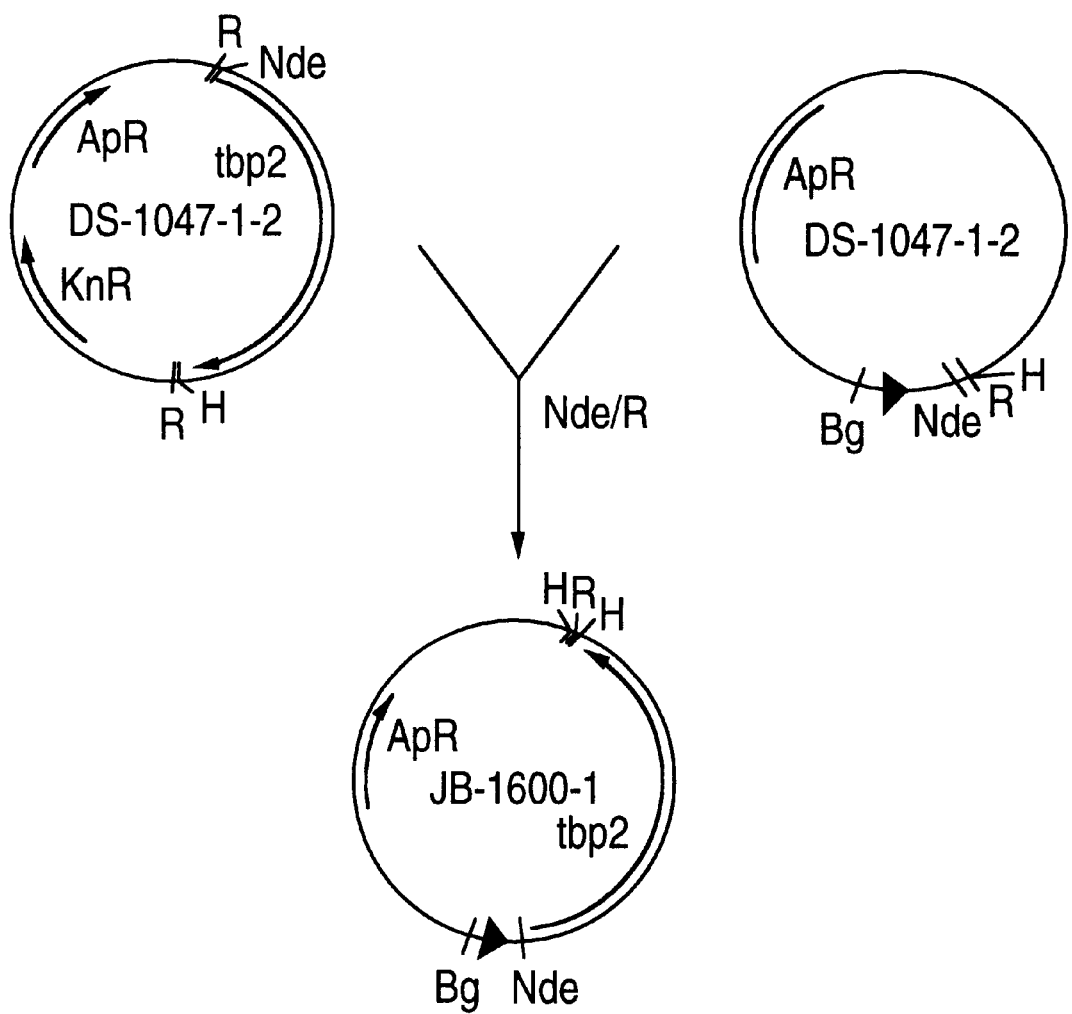
FIG. 21 shows the construction scheme of plasmid JB-1600-1 which expresses H. influenzae strain SB12 Tbp2 from E. coli.

The tbp2 gene from strain NTHi SB12 was amplified by PCR. The resultant amplified DNA contains the authentic H. influenzae Tbp2 signal sequence before the mature protein. The SB12 tbp2 gene encoding the signal sequence and the mature protein was cloned into the pT7-7 expression system as shown in FIG. 21. When the resultant plasmid (JB-1600-1) was introduced into E. coli BL21/DE3 cells and induced, SB12 Tbp2 was expressed, as shown in FIG. 22.

Figure 23:
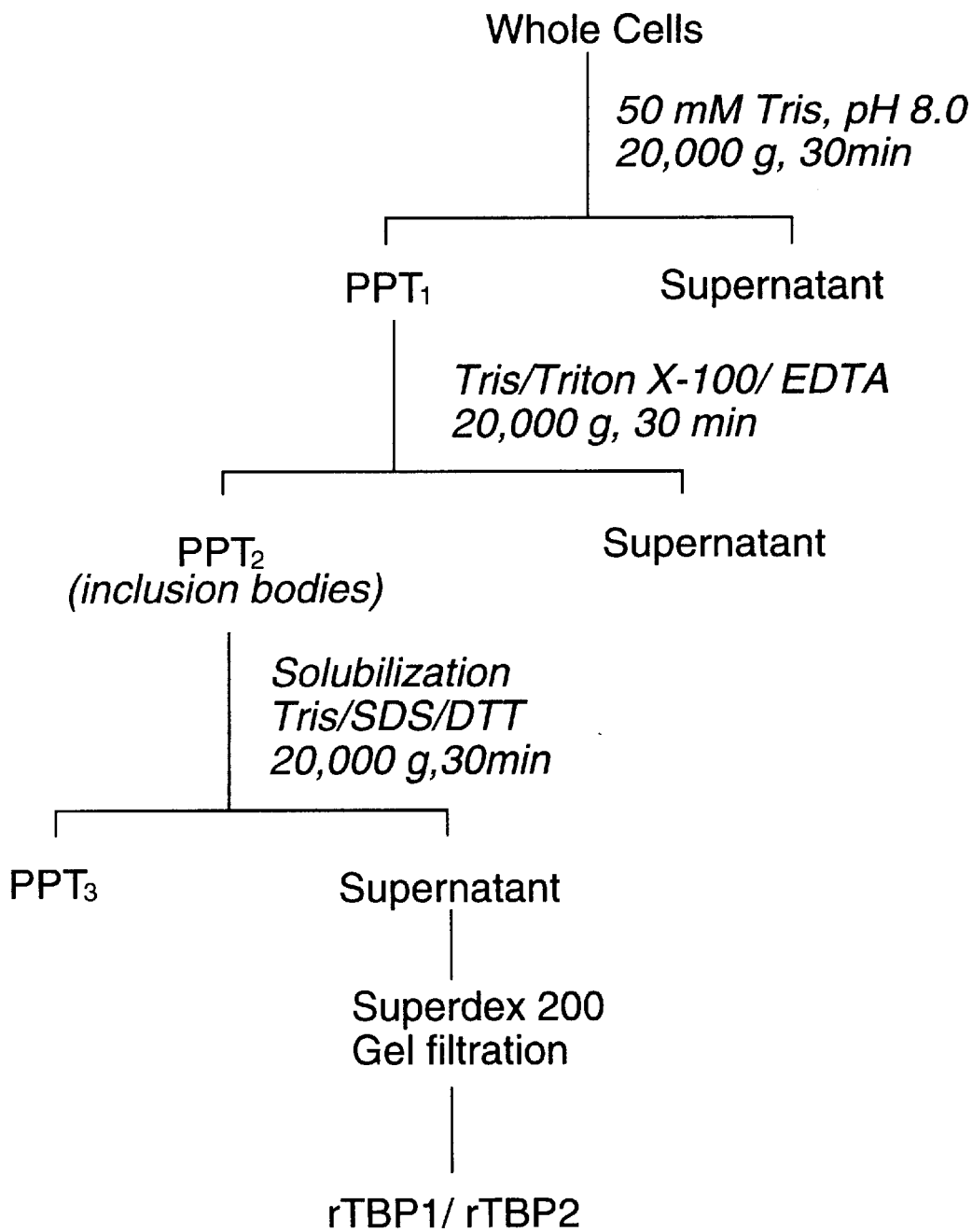
FIG. 23 shows a purification scheme for recombinant Tbp1 and Tbp2 expressed from E. coli.
Figure 24:
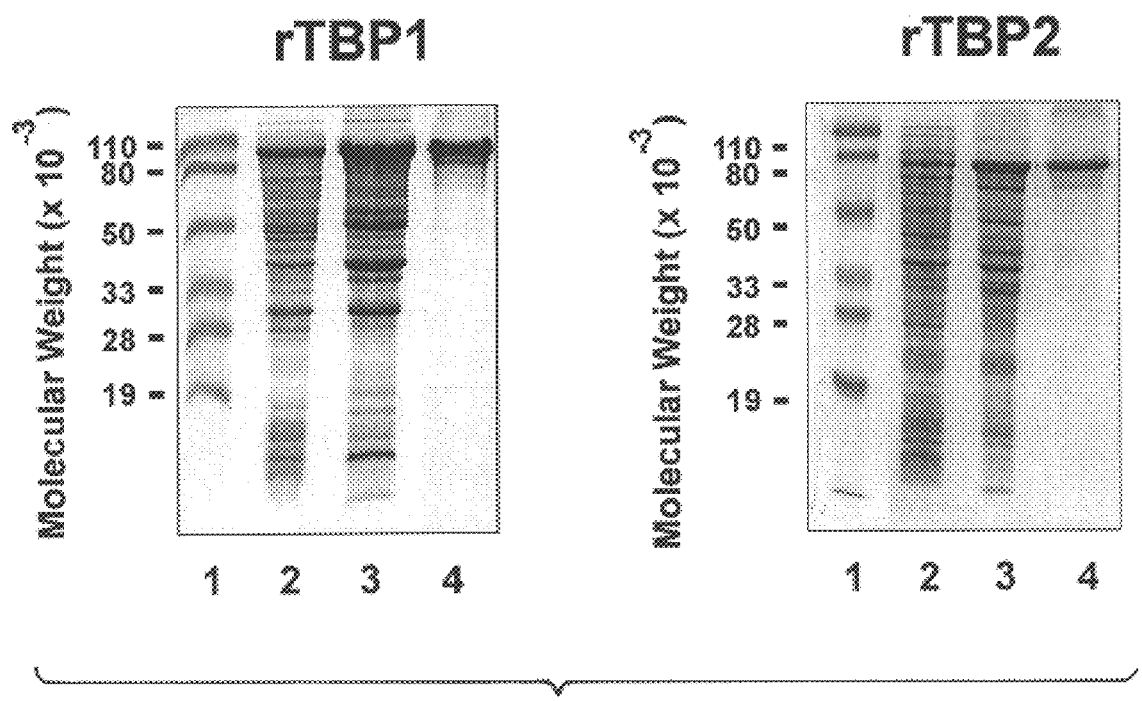
FIG. 24 comprising panels A and B, shows an analysis of the purity of recombinant Tbp1 (Panel A) and Tbp2 (Panel B) purified by the scheme of FIG. 23. Lane 1 contains molecular weight size markers (106, 80, 49.5, 32.5, 27.5 and 18.5 kDa), Lane 2 is E. Coli whole cell lysate. Lane 3 is solubilized inclusion bodies. Lane 4 is purified Tbp1 or Tbp2.
Figure 25A:
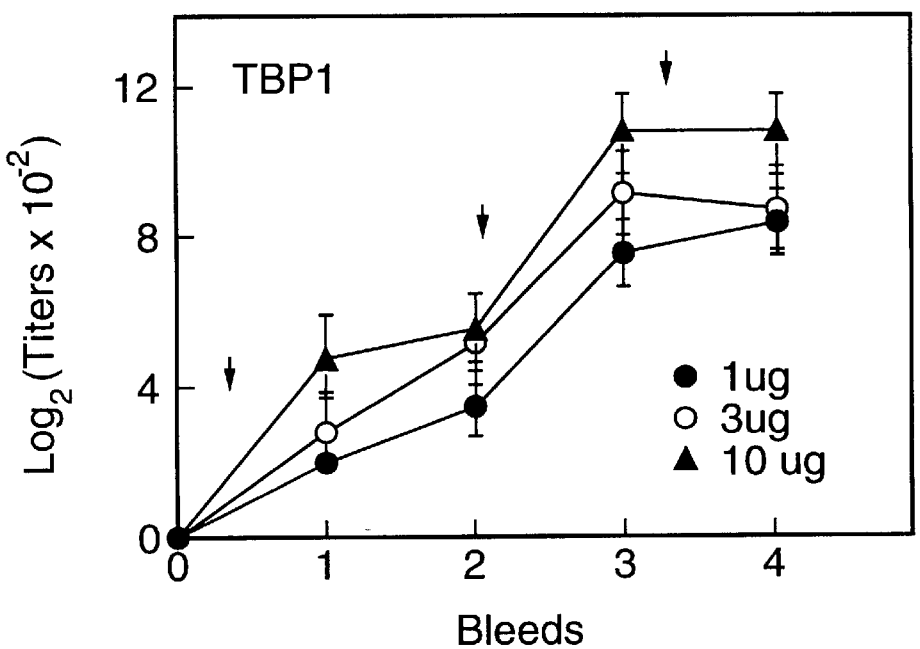
FIGS. 25A and 25B show the immunogenicity of rTbp1 (upper panel) and rTbp2 (lower panel) in mice.
Figure 25B:
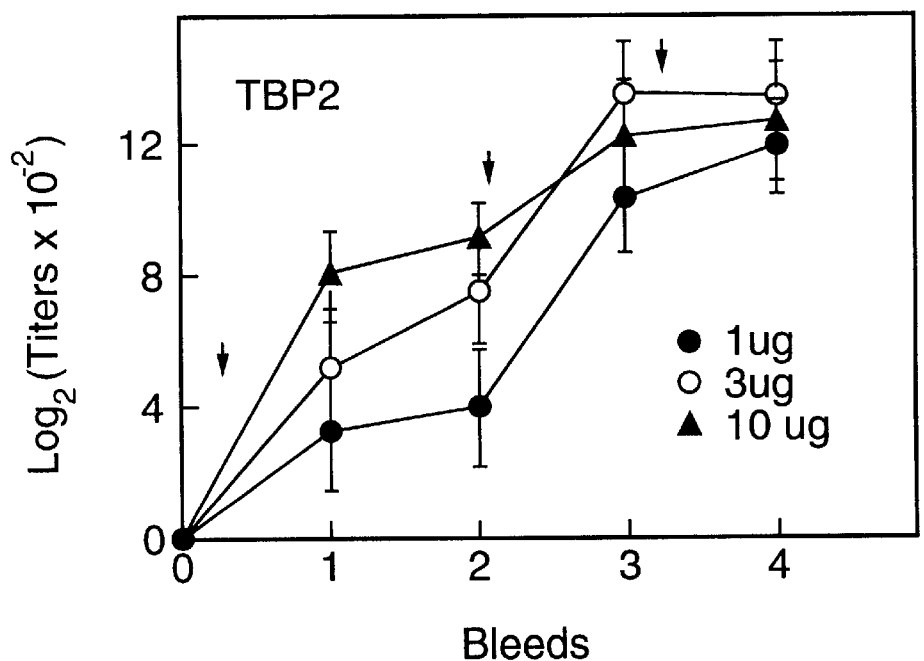

Recombinant proteins Tbp1 and Tbp2 produced in E. coli as inclusion bodies were purified by the scheme shown in FIG. 23. The purified proteins were at least about 70% pure as shown in FIG. 24. Immunogenicity studies were performed in mice with the purified recombinant Tbp1 and Tbp2 proteins. Both proteins elicited a good immune response in mice at 3–10 μg doses (FIG. 25).

Figure 26:
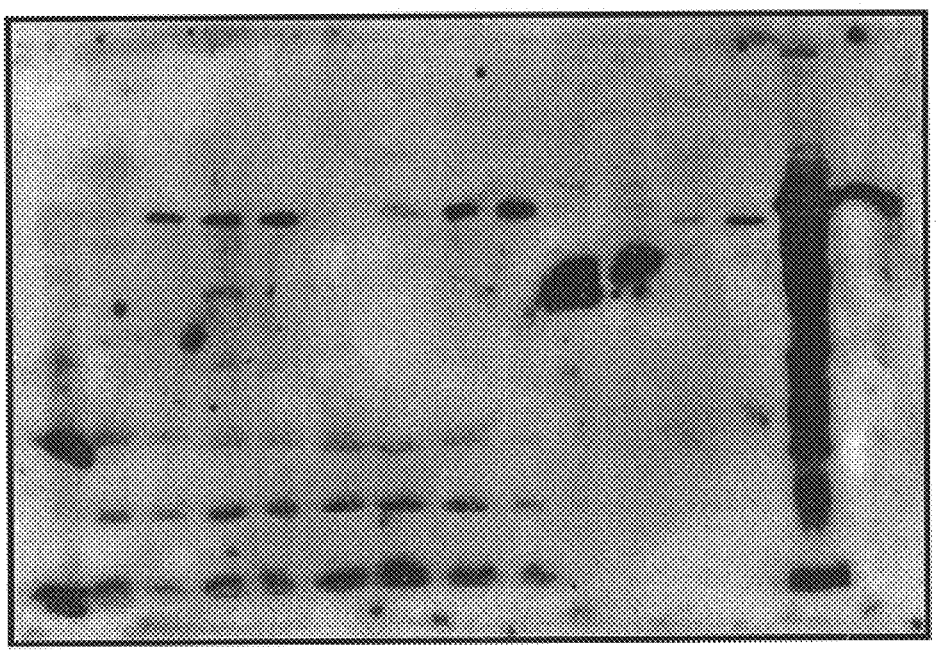
FIG. 26 shows the reactivity of anti-Eagan rTbp1 antisera with various H. influenzae strains on a Western blot. Lane 1, BL21/DE3; lane 2, SB12−EDDA; lane 3, SB12+EDDA; lane 4, SB29−EDDA; lane 5, SB29+EDDA; lane 6, SB33−EDDA; lane 7, SB33+EDDA; lane 8, Eagan−EDDA; lane 9, Eagan+EDDA; lane 10, B. catarrhalis 4223−EDDA; lane 11, B. catarrhalis 4223+EDDA; lane 12, N. meningitidis 608−EDDA; lane 13, N. meningitidis 608+EDDA; lane 14, induced JB-1476-2-1 expressing recombinant Eagan Tbp1; lane 15, molecular weight markers. Specific ~95 kDa bands reacted with the anti-Tbp1 antisera in lanes 3, 4, 5, 7, 8 and 9, corresponding to H. influenzae strains SB12, SB29, SB33 and Eagan; ~110 kDa bands in lanes 10 and 11, corresponding to B. catarrhalis strain 4223; and ~80 kDa bands in lanes 12 and 13, corresponding to N. meningitidis 608.
Figure 27:
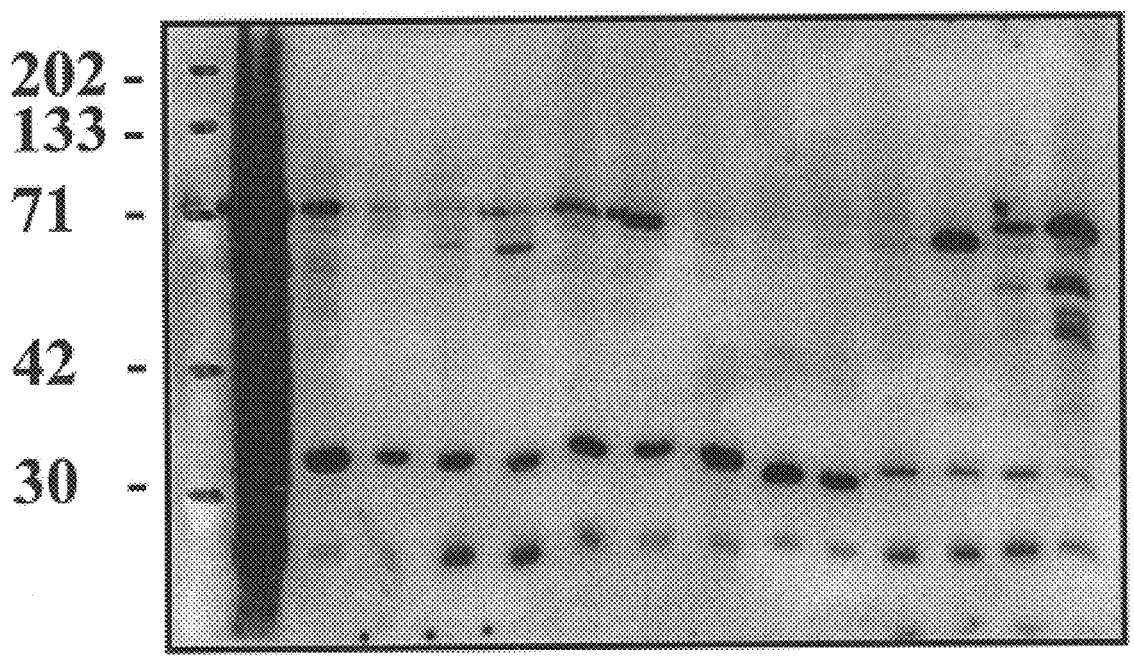
FIG. 27 shows the reactivity of anti-Eagan rTbp2 antisera with various H. influenzae strains on a Western blots. Lane 1, molecular weight markers; lane 2, induced JB-1437-4-1 expressing recombinant Eagan Tbp2; lane 3, SB12−EDDA; lane 4, SB12+EDDA; lane 5, SB29−EDDA; lane 6, SB29+EDDA; lane 7, SB30−EDDA; lane 8, SB30+EDDA; lane 9, SB32−EDDA; lane 10, SB33−EDDA; lane 11, SB33+EDDA; lane 12, PAK−EDDA; lane 13, PAK+EDDA; lane 14, Eagan−EDDA; lane 15, Eagan+EDDA. Specific bands of 60–70 kDa were reactive with the anti-Tbp2 antisera in lanes, 3, 6, 7, 8, 13, 14 and 15, i.e. strains SB12, SB29, SB30, PAK and Eagan.

Antisera raised to recombinant Tbp1 or Tbp2 derived from one H. influenzae strain are cross-reactive with other strains, making these potentially useful diagnostic reagents (FIGS. 26 and 27).

Figure 28:
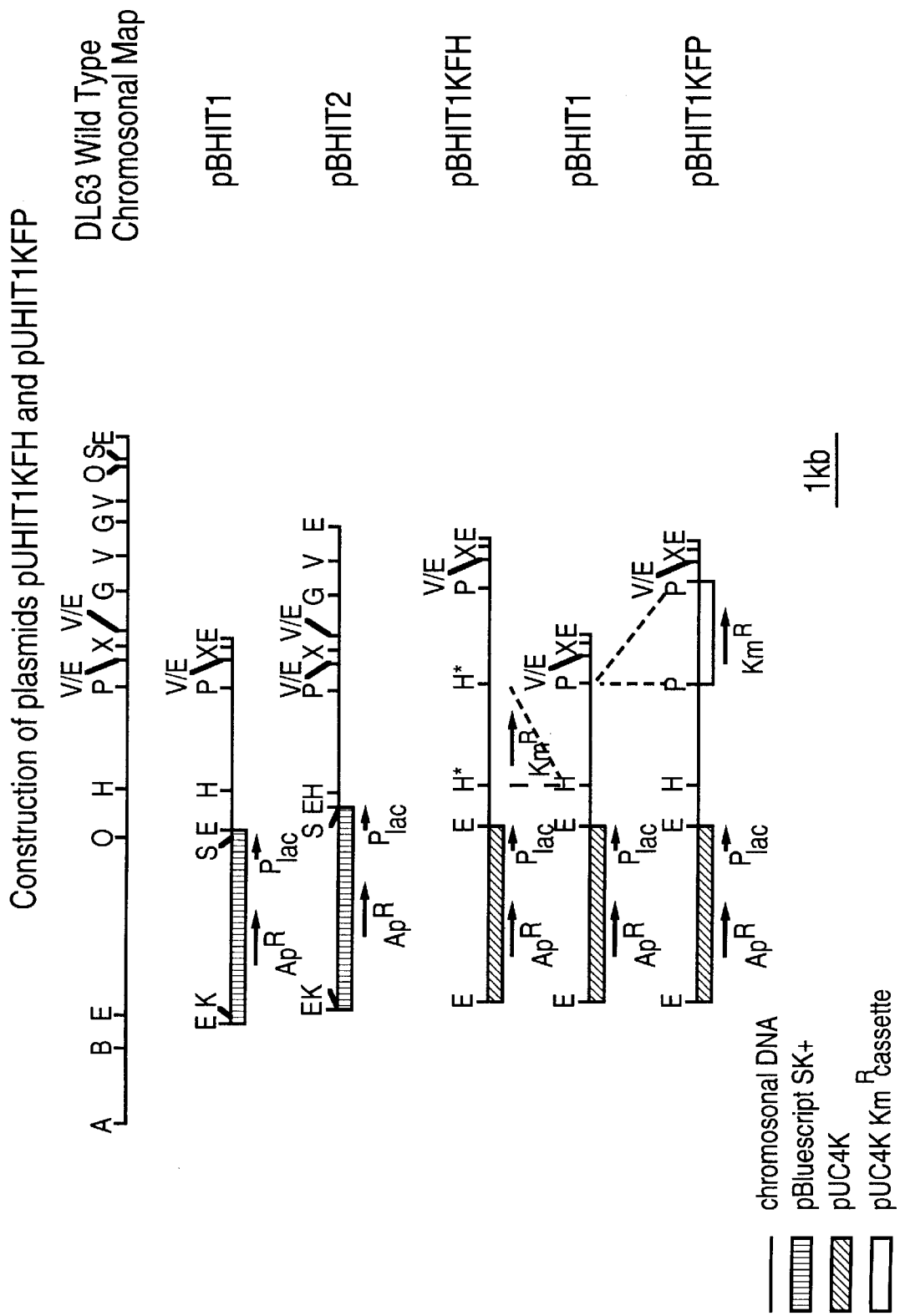
FIG. 28 shows the construction of plasmids pUHIT1KFH and pUHIT1KFP used to generate strains of H. influenzae that do not produce transferrin receptor.

Plasmids pUHIT1KFH and pUHITKFP shown in FIG. 28, contain a selectable antibiotic resistance marker cloned within the transferrin receptor operon and were constructed to insertionally inactivate the transferrin receptor operon. These plasmids were used to transform Haemophilus to generate strains that do not produce transferrin receptor Tbp1 and/or Tbp2 as described in Example 19. Such strains are useful as negative controls (since they do not produce TfR) in in vitro and in vivo detection and diagnostic embodiments. Such strains are also expected to be attenuated for in vivo growth and are useful as live vaccines to provide protection against diseases caused by Haemophilus.

Figure 29:
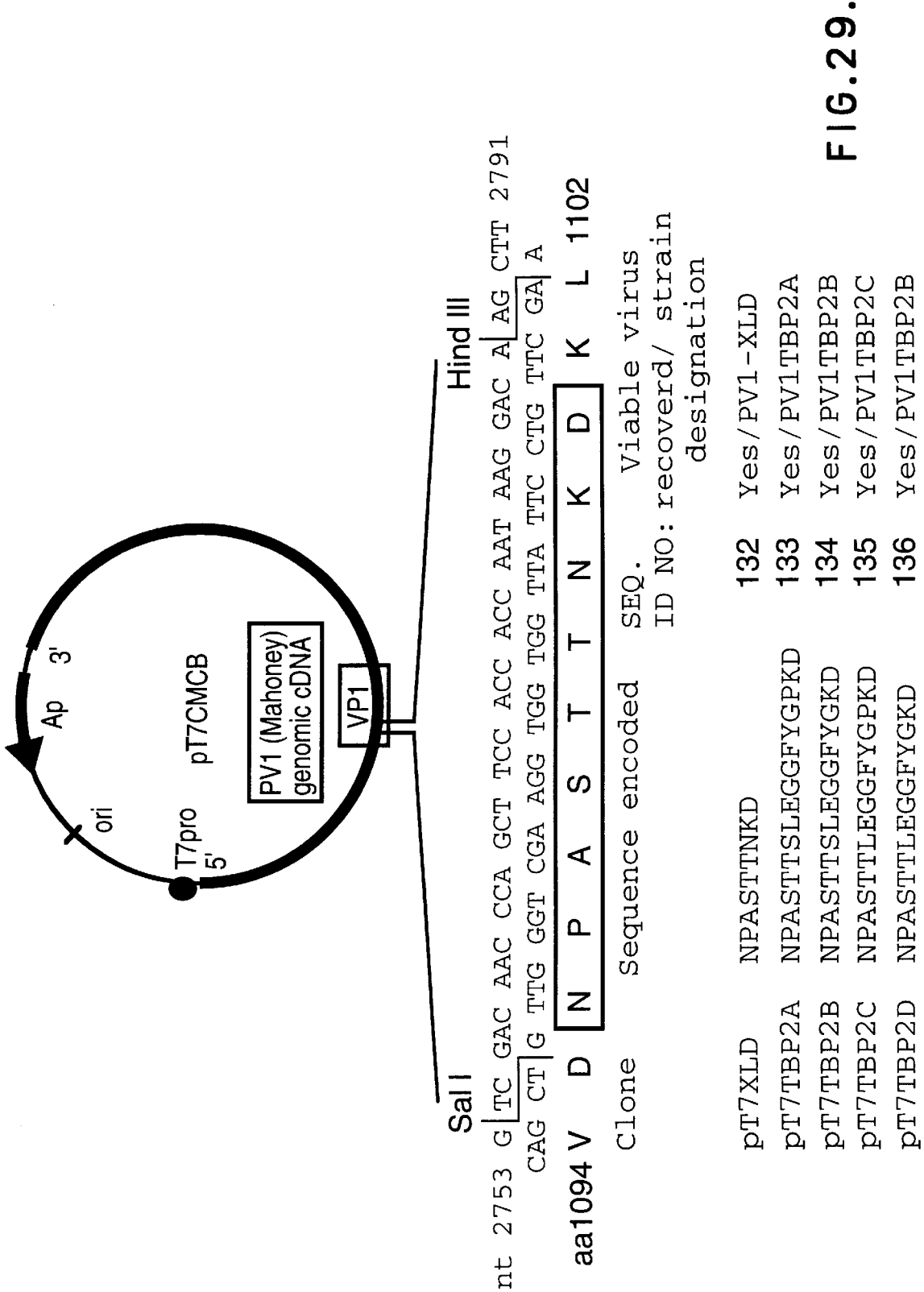
FIG. 29 shows the construction of plasmids encoding chimeric polioviruses expressing an epitope derived from transferrin receptor protein that is conserved among bacteria that produ and partial clones of the TfR genes of H. influenzae Eagan termed S-4368-3-3 and JB-901-5-3 were obtained. Thus, referring to FIGS. 1B and 2, there is illustrated according to further aspects of the present invention, plasmid clones S-4368-3-3 and JB-901-5-3 encoding Tbp1 and Tbp2 from H. influenzae type b strain Eagan. The DNA sequences of the Tbp1 and Tbp2 genes (SEQ ID NO: 2) from H. influenzae type b strain Eagan and their deduced amino acid sequences (SEQ ID NOS: 7 and 8) are sh similarities to Tbp1 and Tbp2 from Haemophilus species. Thus, a minimal number of transferrin receptor, analogs, fragments, and/or peptides, may be used to immunize against many or all strains of Haemophilus and other bacterial pathogens that produce transferrin receptor.

As discussed above, epitopes of transferrin receptor proteins can be delivered to cells of the immune system by the use of live vectors expressing such amino acid sequences and the live vector may be poliovirus. Referring to FIG. 29 there is illustrated the construction of hybrid polioviruses expressing an epitope of transferrin receptor protein including the conserved epitope from Tbp2 LEGGFYGP (SEQ ID NO: 74). Such viruses were recognized by antibodies raised against a peptide incorporating the amino acid sequence LEGGFYGP (SEQ ID NO: 74) (Table 5) indicating that the viruses expressed this sequence in an antigenically recognisable form. PV1TBP2A and PV1TBP2B were also neutralized by rabbit antisera raised against H. influenzae strain DL63 tbp2, indicating that at least these two viruses expressed the sequence in a form recognisable to antibodies raised against the protein. All viruses were neutralisable by anti-PVl sera, indicating that the changes in polio neutralization antigenic site I had not significantly affected other antigenic sites on the viruses. Furthermore, rabbit antiserum produced by immunization with poliovirus chimera PV1TBP2A or PV1TBP2B recognized a peptide incorporating the amino acid sequence LEGGFYGP (SEQ ID NO: 74). This indicates that the sequences expressed by PV1TB2A and PV1TBP2B are immunogenic and elicit antibodies capable of recognizing the same sequence in the context of a synthetic peptide.

Figure 30:
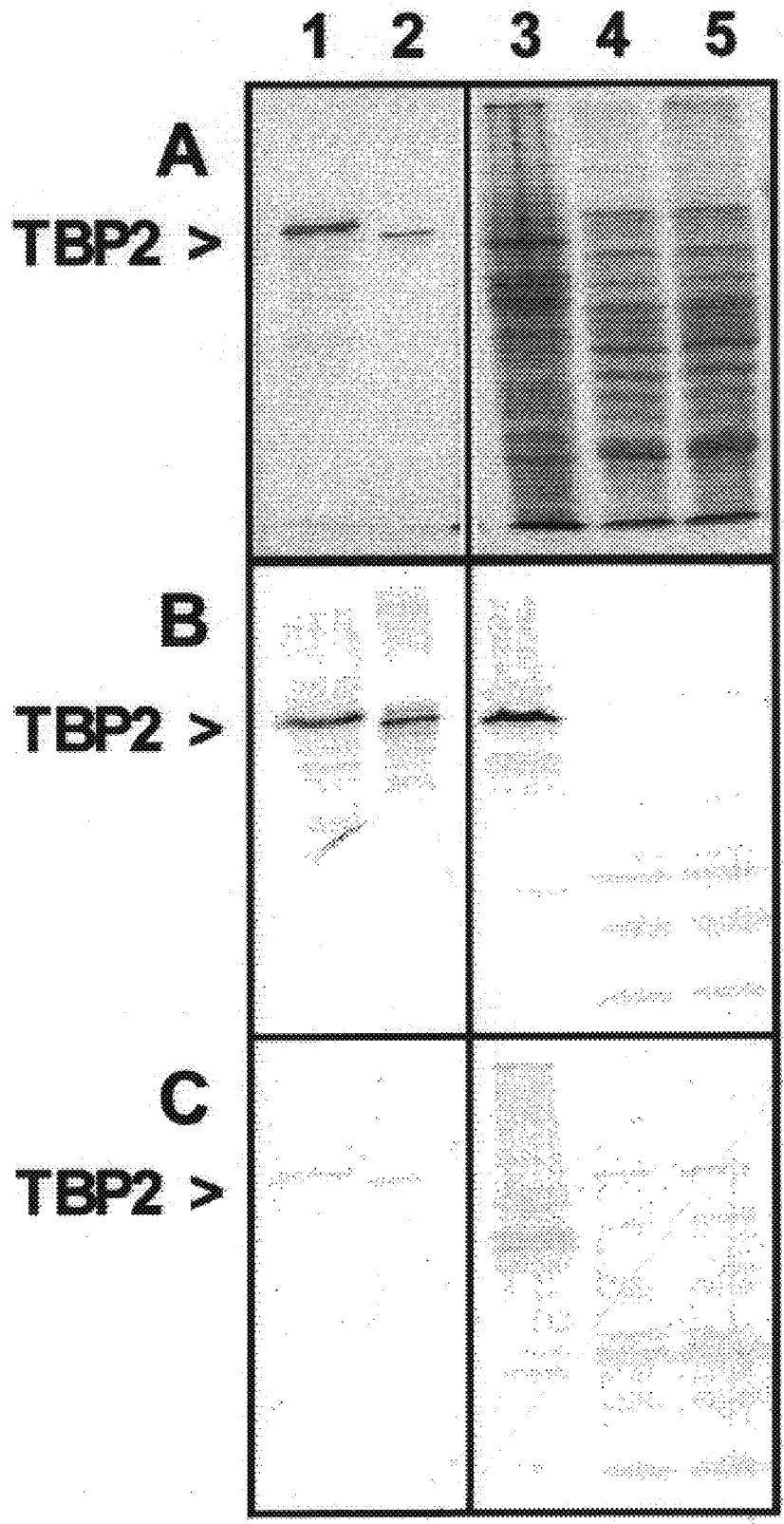

Referring to FIG. 30, panel A shows an SDS PAGE gel showing purified recombinant tbp2 from H. influenzae strain SB12 expressed in E. coli (lane 1), tbp2 from Branhamella catarrhalis strain 4223 (lane 2), a whole cell lysate of iron-limited B. catarrhalis strain 4223 (lane 3), a whole cell lysate of iron-limited E. coli JM109 (lane 4), and a whole cell lysate of E. coli JM109 grown under non-iron limited conditions (lane 5). Panel B shows results of a Western blot of a replicate gel using a pool of sera from rabbits immunized with PV1TBP2A. There was a strong reaction with the purified transferrin-binding proteins in lanes 1 and 2, and with a similar sized band in lane 3. There was no significant reaction with any E. coli proteins (lanes 4 and 5). Panel C shows the results for a pool of prebleed sera from the same rabbits, which displayed minimal specific reactivity. These results show that PV1TBP2A is able to induce antisera specific for transferrin binding proteins from H. influenzae and B. catarrhalis, and that the antisera can distinguish B. catarrhalis from E. coli, which does not express an equivalent protein.

The purified and isolated DNA molecules comprising at least a portion coding for a transferrin receptor of a species of Haemophilus typified by the embodiments described herein are advantageous as:

nucleic acid probes for the specific identification of Haemophilus strains in vitro or in vivo.

the products encoded by the DNA molecules are useful as diagnostic reagents, antigens for the production of Haemophilus-specific antisera, for vaccination against the diseases caused by species of Haemophilus and (for example) detecting infection by Haemophilus.

peptides corresponding to portions of the transferrin receptor as typified by the embodiments described herein are advantageous as diagnostic reagents, antigens for the production of Haemophilus-specific antisera, for vaccination against the diseases caused by species of Haemophilus and (for example) for detecting infection by Haemophilus.

The transferrin receptor encoded by the nucleic acid molecules of the present invention, fragments and analogs thereof, and peptides containing sequences corresponding to portions of the transferrin receptor that are conserved between various isolates of Haemophilus and other bacteria that produce transferrin receptor, are useful in diagnosis of and immunization against diseases caused by any bacterial strain that produces transferrin receptor. In particular, peptides containing the sequences LEGGFYGP are conserved in the transferrin receptor proteins of many bacterial pathogens that produce transferrin receptor and are appropriate for diagnosis of and immunization against diseases caused by bacteria that produce transferrin receptor. Such bacteria include but are not limited to species of Haemophilus, Neisseria (including N. meningitidis and N. gonorrhoeae) and Branhamella (including B. catarrhalis).

It is clearly apparent to one skilled in the art, that the various embodiments of the present invention have many applications in the fields of vaccination, diagnosis, treatment of, for example, Haemophilus infections, and infections with other bacterial pathogens that produce transferrin receptor and the generation of immunological reagents. A further non-limiting discussion of such uses is further presented below.

1. Vaccine Preparation and Use

Immunogenic compositions, suitable to be used as vaccines, may be prepared from immunogenic transferrin receptor, analogs and fragments thereof and/or peptides as disclosed herein. The vaccine elicits an immune response which produces antibodies, including anti-transferrin receptor antibodies and antibodies that are opsonizing or bactericidal. Should the vaccinated subject be challenged by Haemophilus or other bacteria that produce a transferrin receptor, the antibodies bind to the transferrin receptor and thereby prevent access of the bacteria to an iron source which is required for viability. Furthermore, opsonizing or bactericidal anti-TfR antibodies may also provide protection by alternative mechanisms.

Vaccines containing peptides are generally well known in the art, as exemplified by U.S. Pat. Nos. 4,601,903; 4,599,231; 4,599,230; and 4,596,792; all of which references are incorporated herein by reference. Immunogenic compositions including vaccines may be prepared as injectables, as liquid solutions or emulsions. The transferrin receptor, analogs and fragments thereof and/or peptides may be mixed with pharmaceutically acceptable excipients which are compatible with the transferrin receptor, fragments analogs or peptides. Such excipients may include, water, saline, dextrose, glycerol, ethanol, and combinations thereof. The immunogenic compositions and vaccines may further contain auxiliary substances such as wetting or emulsifying agents, pH buffering agents, or adjuvants to enhance the effectiveness of the vaccines. Immunogenic compositions and vaccines may be administered parenterally, by injection subcutaneously or intramuscularly. Alternatively, the immunogenic compositions formed according to the present invention, may be formulated and delivered in a manner to evoke an immune response at mucosal surfaces. Thus, the immunogenic composition may be administered to mucosal surfaces by, for example, the nasal or oral (intragastric) routes. The immunogenic composition may be provided in combination with a targeting molecule for delivery to specific cells of the immune system or to mucosal surfaces. Some such targeting molecules include strain B12 and fragments of bacterial toxins, as described in WO 92/17167 (Biotech Australia Pty. Ltd.), and monoclonal antibodies, as described in U.S. Pat. No. 5,194,254 (Barber et al). Alternatively, other modes of administration including suppositories and oral formulations may be desirable. For suppositories, binders and carriers may include, for example, polyalkalene glycols or triglycerides. Oral formulations may include normally employed incipients such as, for example, pharmaceutical grades of saccharine, cellulose and magnesium carbonate. These compositions take the form of solutions, suspensions, tablets, pills, capsules, sustained release formulations or powders and contain 10–95% of the transferrin receptor, fragment analogs and/or peptides.

The vaccines are administered in a manner compatible with the dosage formulation, and in such amount as will be therapeutically effective, protective and immunogenic. The quantity to be administered depends on the subject to be treated, including, for example, the capacity of the individual's immune system to synthesize antibodies, and if needed, to produce a cell-mediated immune response. Precise amounts of active ingredient required to be administered depend on the judgment of the practitioner. However, suitable dosage ranges are readily determinable by one skilled in the art and may be of the order of micrograms of the transferrin receptor, analogs and fragments thereof and/or peptides. Suitable regimes for initial administration and booster doses are also variable, but may include an initial administration followed by subsequent administrations. The dosage of the vaccine may also depend on the route of administration and will vary according to the size of the host.

The nucleic acid molecules encoding the transferrin receptor of the present invention may also be used directly for immunization by administration of the DNA directly, for example by injection for genetic immunization or by constructing a live vector such as Salmonella, BCG, adenovirus, poxvirus, vaccinia or poliovirus. A discussion of some live vectors that have been used to carry heterologous antigens to the immune system are discussed in for example O'Hagan (1992). Processes for the direct injection of DNA into test subjects for genetic immunization are described in, for example, Ulmer et al., 1993.

The use of peptides in vivo may first require their chemical modification since the peptides themselves may not have a sufficiently long serum and/or tissue half-life and/or sufficient immunogenicity. Such chemically modified peptides are referred to herein as "peptide analogs". The term "peptide analog" extends to any functional chemical equivalent of a peptide characterized by its increased stability and/or efficacy and immunogenicity in vivo or in vitro in respect of the practice of the invention. The term "peptide analog" is also used herein to extend to any amino acid derivative of the peptides as described herein. Peptide analogs contemplated herein are produced by procedures that include, but are not limited to, modifications to side chains, incorporation of unnatural amino acids and/or their derivatives during peptide synthesis and the use of cross-linkers and other methods which impose conformational constraint on the peptides or their analogs.

Examples of side chain modifications contemplated by the present invention include modification of amino groups such as by reductive alkylation by reaction with an aldehyde followed by reduction with $NaBH_4$; amidation with methylacetimidate; acetylation with acetic anhydride; carbamylation of amino groups with cyanate; trinitrobenzylation of amino groups with 2, 4, 6, trinitrobenzene sulfonic acid (TNBS); alkylation of amino groups with succinic anhydride and tetrahydrophthalic anhydride; and pyridoxylation of lysine with pyridoxal-5'-phosphate followed by reduction with $NaBH_4$.

The guanidino group of arginine residues may be modified by the formation of heterocyclic condensation products with reagents such as 2,3-butanedione, phenylglyoxal and glyoxal.

The carboxyl group may be modified by carbodiimide activation via o-acylisourea formation followed by subsequent derivatisation, for example, to a corresponding amide.

Sulfhydryl groups may be modified by methods such as carboxymethylation with iodoacetic acid or iodoacetamide; performic acid oxidation to cysteic acid; formation of mixed disulphides with other thiol compounds; reaction with maleimide; maleic anhydride or other substituted maleimide; formation of mercurial derivatives using 4-chloromercuribenzoate, 4-chloromercuriphenylsulfonic acid, phenylmercury chloride, 2-chloromercuric-4-nitrophenol and other mercurials; carbamylation with cyanate at alkaline pH.

Tryptophan residues may be modified by, for example, oxidation with N-bromosuccinimide or alkylation of the indole ring with 2-hydroxy-5-nitrobenzyl bromide or sulphonyl halides. Tryosine residues may be altered by nitration with tetranitromethane to form a 3-nitrotyrosine derivative.

Modification of the imidazole ring of a histidine residue may be accomplished by alkylation with iodoacetic acid derivatives or N-carbethoxylation with diethylpyrocarbonate.

Examples of incorporating unnatural amino acids and derivatives during peptide synthesis include, but are not limited to, use of norleucine, 4-amino butyric acid, 4-amino-3-hydroxy-5-phenylpentanoic acid, 6-aminohexanoic acid-, t-butylglycine, norvaline, phenylglycine, ornithine, sarcosine, 4-amino-3-hydroxy-6-methylheptanoic acid, 2-thienyl alanine and/or D-isomers of amino acids.

Immunogenicity can be significantly improved if the antigens are co-administered with adjuvants, commonly used as an 0.05 to 1.0 percent solution in phosphate-buffered saline. Adjuvants enhance the immunogenicity of an antigen but are not necessarily immunogenic themselves. Adjuvants may act by retaining the antigen locally near the site of administration to produce a depot effect facilitating a slow, sustained release of antigen to cells of the immune system. Adjuvants can also attract cells of the immune system to an antigen depot and stimulate such cells to elicit immune responses.

Immunostimulatory agents or adjuvants have been used for many years to improve the host immune responses to, for example, vaccines. Intrinsic adjuvants, such as lipopolysaccharides, normally are the components of the killed or attenuated bacteria used as vaccines. Extrinsic adjuvants are immunomodulators which are typically non-covalently linked to antigens and are formulated to enhance the host immune responses. Thus, adjuvants have been identified that enhance the immune response to antigens delivered parenterally. Some of these adjuvants are toxic, however, and can cause undesirable side-effects, making them unsuitable for use in humans and many animals. Indeed, only aluminum hydroxide and aluminim phosphate (collectively commonly referred to as alum) are routinely used as adjuvants in human and veterinary vaccines. The efficacy of alum in increasing antibody responses to diptheria and tetanus toxoids is will established and, more recently, a HBsAg vaccine has been adjuvanted with alum. While the usefulness of alum is well established for some applications, it has limitations. For example, alum is ineffective for influenza vaccination and inconsistently elicits a cell mediated immune response. The antibodies elicited by alum-adjuvanted antigens are mainly of the IgG1 isotype in the mouse, which may not be optimal for protection by some vaccinal agents.

A wide range of extrinsic adjuvants can provoke potent immune responses to antigens. These include saponins complexed to membrane protein antigens (immune stimulating complexes), pluronic polymers with mineral oil, killed mycobacteria and mineral oil, Freund's complete adjuvant, bacterial products, such as muramyl dipeptide (MDP) and lipopolysaccharide (LPS), as well as lipid A, and liposomes.

To efficiently induce humoral immune responses (HIR) and cell-mediated immunity (CMI), immunogens are emulsified in adjuvants. Many adjuvants are toxic, inducing granulomas, acute and chronic inflammations (Freund's complete adjuvant, FCA), cytolysis (saponins and pluronic polymers) and pyrogenicity, arthritis and anterior uveitis (LPS and MDP). Although FCA is an excellent adjuvant and widely used in research, it is not licensed for use in human or veterinary vaccines because of its toxicity.

Desirable characteristics of ideal adjuvants include:
(1) lack of toxicity;
(2) ability to stimulate a long-lasting immune response;
(3) simplicity of manufacture and stability in long-term storage;
(4) ability to elicit both CMI and HIR to antigens administered by various routes, if required;
(5) synergy with other adjuvants;

(6) capability of selectively interacting with populations of antigen presenting cells (APC);

(7) ability to specifically elicit appropriate $T_H1$ or $T_H2$ cell-specific immune responses; and (8) ability to selectively increase appropriate antibody isotype levels (for example, IgA) against antigens.

U.S. Pat. No. 4,855,283 granted to Lockhoff et al on Aug. 8, 1989 which is incorporated herein by reference thereto teaches glycolipid analogues including N-glycosylamides, N-glycosylureas and N-glycosylcarbamates, each of which is substituted in the sugar residue by an amino acid, as immuno-modulators or adjuvants. Thus, Lockhoff et al. 1991 reported that N-glycolipid analogs displaying structural similarities to the naturally-occurring glycolipids, such as glycosphingolipids and glycoglycerolipids, are capable of eliciting strong immune responses in both herpes simplex virus vaccine and pseudorabies virus vaccine. Some glycolipids have been synthesized from long chain-alkylamines and fatty acids that are linked directly with the sugars through the anomeric carbon atom, to mimic the functions of the naturally occurring lipid residues.

U.S. Pat. No. 4,258,029 granted to Moloney, assigned to the assignee hereof and incorporated herein by reference thereto, teaches that octadecyl tyrosine hydrochloride (OTH) functions as an adjuvant when complexed with tetanus toxoid and formalin inactivated type I, II and III poliomyelitis virus vaccine. Also, Nixon-George et al. 1990, reported that octadecyl esters of aromatic amino acids complexed with a recombinant hepatitis B surface antigen, enhanced the host immune responses against hepatitis B virus.

Lipidation of synthetic peptides has also been used to increase their immunogenicity. Thus, Wiesmuller 1989, describes a peptide with a sequence homologous to a foot-and-mouth disease viral protein coupled to an adjuvant tripalmityl-s-glyceryl-cysteinylserylserine, being a synthetic analogue of the N-terminal part of the lipoprotein from Gram negative bacteria. Furthermore, Deres et al. 1989, reported in vivo priming of virus-specific cytotoxic T lymphocytes with synthetic lipopeptide vaccine which comprised of modified synthetic peptides derived from influenza virus nucleoprotein by linkage to a lipopeptide, N-palmityl-s-[2,3-bis(palmitylxy)-(2RS)-propyl-[R]-cysteine (TPC).

2. Immunoassays

The transferrin receptor, analogs and fragments thereof and/or peptides of the present invention are useful as immunogens, as antigens in immunoassays including enzyme-linked immunosorbent assays (ELISA), RIAs and other non-enzyme linked antibody binding assays or procedures known in the art for the detection of anti-bacterial, Haemophilus, TfR and/or peptide antibodies. In ELISA assays, the transferrin receptor, analogs, fragments and/or peptides corresponding to portions of TfR protein are immobilized onto a selected surface, for example a surface capable of binding proteins or peptides such as the wells of a polystyrene microtiter plate. After washing to remove incompletely adsorbed transferrin receptor, analogs, fragments and/or peptides, a nonspecific protein such as a solution of bovine serum albumin (BSA) or casein that is known to be antigenically neutral with regard to the test sample may be bound to the selected surface. This allows for blocking of nonspecific adsorption sites on the immobilizing surface and thus reduces the background caused by nonspecific bindings of antisera onto the surface. Preferably, the selected peptides are from the conserved regions of Table 2 or Table 3 to enhance the cross-species detection unless one particular bacterial species is to be detected. In that event, a polypeptide is selected which is unique to the TfR of that particular species. Normally, the peptides are in the range of 12 residues and up and preferably 14 to 30 residues. It is understood however, that a mixture of peptides may be used either as an immunogen in a vaccine or as a diagnostic agent. There may be circumstances where a mixture of peptides from the conserved regions and/or from the non-conserved regions are used to provide cross-species protection and/or diagnosis. In this instance, the mixture of peptide immunogens is commonly referred to as a "cocktail" preparation for use as a vaccine or diagnostic agent.

The immobilizing surface is then contacted with a sample such as clinical or biological materials to be tested in a manner conducive to immune complex (antigen/antibody) formation. This may include diluting the sample with diluents such as BSA, bovine gamma globulin (BGG) and/or phosphate buffered saline (PBS)/Tween. The sample is then allowed to incubate for from 2 to 4 hours, at temperatures such as of the order of 25° to 37° C. Following incubation, the sample-contacted surface is washed to remove non-immunocomplexed material. The washing procedure may include washing with a solution such as PBS/Tween, or a borate buffer.

Following formation of specific immunocomplexes between the test sample and the bound transferrin receptor, analogs, fragments and/or peptides, and subsequent washing, the occurrence, and even amount, of immunocomplex formation may be determined by subjecting the immunocomplex to a second antibody having specificity for the first antibody. If the test sample is of human origin, the second antibody is an antibody having specificity for human immunoglobulins and in general IgG. To provide detecting means, the second antibody may have an associated activity such as an enzymatic activity that will generate, for example, a color development upon incubating with an appropriate chromogenic substrate. Quantification may then achieved by measuring the degree of color generation using, for example, a visible spectra spectrophotometer.

3. Use of Sequences as Hybridization Probes

The nucleotide sequences of the present invention, comprising the sequence of the transferrin receptor gene, now allow for the identification and cloning of the transferrin receptor genes from any species of Haemophilus and other bacteria that have transferrin receptor genes.

The nucleotide sequences comprising the sequence of the transferrin receptor genes of the present invention are useful for their ability to selectively form duplex molecules with complementary stretches of other TfR genes. Depending on the application, a variety of hybridization conditions may be employed to achieve varying degrees of selectivity of the probe toward the other TfR genes. For a high degree of selectivity, relatively stringent conditions are used to form the duplexes, such as low salt and/or high temperature conditions, such as provided by 0.02M to 0.15M NaCl at temperatures of between about 50° C. to 70° C. For some applications, less stringent hyrbridization conditions are required such as 0.15M to 0.9M salt, at temperatures ranging from between about 20° C. to 55° C. Hybridization conditions can also be rendered more stringent by the addition of increasing amounts of formamide, to destabilize the hybrid duplex. Thus, particular hybridization conditions can be readily manipulated, and will generally be a method of choice depending on the desired results. In general, convenient hybridization temperatures in the presence of 50% formamide are: 42° C. for a probe which is 95 to 100% homologous to the target fragment, 37° C. for 90 to 95% homology and 32° C. for 85 to 90% homology.

In a clinical diagnostic embodiment, the nucleic acid sequences of the TfR genes of the present invention may be used in combination with an appropriate means, such as a label, for determining hybridization. A wide variety of appropriate indicator means are known in the art, including radioactive, enzymatic or other ligands, such as avidin/biotin, which are capable of providing a detectable signal. In some diagnostic embodiments, an enzyme tag such as urease, alkaline phosphatase or peroxidase, instead of a radioactive tag may be used. In the case of enzyme tags, colorimetric indicator substrates are known which can be employed to provide a means visible to the human eye or spectrophotometrically, to identify specific hybridization with samples containing TfR gene sequences.

The nucleic acid sequences of TfR genes of the present invention are useful as hybridization probes in solution hybridizations and in embodiments employing solid-phase procedures. In embodiments involving solid-phase procedures, the test DNA (or RNA) from samples, such as clinical samples, including exudates, body fluids (e.g., serum, amniotic fluid, middle ear effusion, sputum, bronchoalveolar lavage fluid) or even tissues, is adsorbed or otherwise affixed to a selected matrix or surface. The fixed, single-stranded nucleic acid is then subjected to specific hybridization with selected probes comprising the nucleic acid sequences of the TfR genes or fragments thereof of the present invention under desired conditions. The selected conditions will depend on the particular circumstances based on the particular criteria required depending on, for example, the G+C contents, type of target nucleic acid, source of nucleic acid, size of hybridization probe etc. Following washing of the hybridization surface so as to remove non-specifically bound probe molecules, specific hybridization is detected, or even quantified, by means of the label. As with the selection of peptides, it is preferred to select nucleic acid sequence portions which are conserved among species of Haemophilus, such as nucleic acid sequences encoding the conserved peptide sequence of FIGS. 8, 9, 13 and 14 and particularly listed in Tables 2 and 3. The selected probe may be at least 18 bp and may be in the range of 30 bp to 90 bp long.

4. Expression of the Transferrin Receptor Genes

Plasmid vectors containing replicon and control sequences which are derived from species compatible with the host cell may be used for the expression of the transferrin receptor genes in expression systems. The vector ordinarily carries a replication site, as well as marking sequences which are capable of providing phenotypic selection in transformed cells. For example, *E. coli* may be transformed using pBR322 which contains genes for ampicillin and tetracycline resistance and thus provides easy means for identifying transformed cells. The pBR322 plasmid, or other microbial plasmid or phage must also contain, or be modified to contain, promoters which can be used by the host cell for expression of its own proteins.

In addition, phage vectors containing replicon and control sequences that are compatible with the host can be used as a transforming vector in connection with these hosts. For example, the phage in lambda GEM™-11 may be utilized in making recombinant phage vectors which can be used to transform host cells, such as *E. coli* LE392.

Promoters commonly used in recombinant DNA construction include the β-lactamase (penicillinase) and lactose promoter systems (Chang et al., 1978: Itakura et al., 1977 Goeddel et al., 1979; Goeddel et al., 1980) and other microbial promoters such as the T7 promoter system (U.S. Pat. No. 4,952,496). Details concerning the nucleotide sequences of promoters are known, enabling a skilled worker to ligate them functionally with genes. The particular promoter used will generally be a matter of choice depending upon the desired results. Hosts that are appropriate for expression of the transferrin receptor genes, fragment analogs or variants thereof include *E. coli*, Bacillus species, Haemophilus, fungi, yeast or the baculovirus expression system may be used.

In accordance with this invention, it is preferred to make the protein by recombinant methods, particularly when the naturally occurring TfR protein as purified from a culture of a species of Haemophilus may include trace amounts of toxic materials or other contaminants. This problem can be avoided by using recombinantly produced TfR protein in heterologous systems which can be isolated from the host in a manner to minimize comtaminants in the purified material. Particularly desirable hosts for expression in this regard include Gram positive bacteria which do not have LPS and are therefore endotoxin free. Such hosts include species of Bacillus and may be particularly useful for the production of non-pyrogenic transferrin receptor, fragments or analogs thereof. Furthermore, recombinant methods of production permit the manufacture of Tbp1 or Tbp2 or fragments thereof separate from one another which is distinct from the normal combined proteins present in Haemophilus.

Biological Deposits

Certain plasmids that contain at least a portion coding for a transferrin receptor from strains of Haemophilus influenzae that are described and referred to herein have been deposited with the American Type Culture Collection (ATCC) located at Rockville, Md. U.S.A. pursuant to the Budapest Treaty and prior to the filing of this application. Samples of the deposited plasmids will become available to the public upon grant of a patent based upon this United States patent application. The invention described and claimed herein is not to be limited in scope by plasmids deposited, since the deposited embodiment is intended only as an illustration of the invention. Any equivalent or similar plasmids that encode similar or equivalent antigens as described in this application are within the scope of the invention.

Deposit Summary

| Clone | ATCC Designation | Date Deposited |
|---|---|---|
| DS-712-1-3 | 75603 | November 4, 1993 |
| JB-1042-7-6 | 75607 | November 4, 1993 |
| JB-1424-2-8 | 75937 | October 27, 1994 |
| JB-1600-1 | 75935 | October 27, 1994 |
| JB-1468-29 | 75936 | October 27, 1994 |
| pT7TBP2A | 75931 | October 27, 1994 |
| pT7TBP2B | 75932 | October 27, 1994 |
| pT7TBP2C | 75933 | October 27, 1994 |
| pT7TBP2D | 75934 | October 27, 1994 |

Strains of Haemophilus

Hib strain Eagan is available from Connaught Laboratories Limited, 1755 Steeles Ave. W., Willowdale, Ontario, Canada M2R 3T4.

Hib strain MinnA was obtained from the collection of Dr. Robert Munson, Department of Microbiology and Immunology, Washington University School of Medicine, Children's Hospital, St. Louis, Mo. 63110.

Hib strain DL63 was obtained from the collection of Dr. Eric Hansen, Department of Microbiology, University of Texas Southwestern Medical Center, 5323 Harry Hines Boulevard, Dallas, Tex. 75235-9048.

PAK 12085 was obtained from the collection of Dr. Robert Munson (supra).

SB12, 29, 30, 32 and 33 were obtained from the collection of Dr. Stephen Barenkamp, Department of Pediatrics, School of Medicine, Saint Louis University Medical Centre, St. Louis, Mo. 63104.

EXAMPLES

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitations.

Methods of molecular genetics, protein biochemistry, immunology and fermentation technology used but not explicitly described in this disclosure and these Examples are amply reported in the scientific literature and are well within the ability of those skilled in the art.

Example 1

This Example illustrates the preparation of chromosomal DNA from H. influenzae strains DL63, Eagan, MinnA, and PAK 12085, and SB33.

H. influenzae strains were grown on Mueller-Hinton agar or in brain heart infusion broth as described by Harkness et al 1992.

A. Chromosomal DNA extraction from Haemophilus influenzae type b DL63

Chromosomal DNA was prepared as follows. Two hundred and fifty ml of culture were pelleted by centrifugation at 8,000 rpm in a Beckman J14 rotor for 15 minutes. The pellet was washed with 200 ml of 50 mM Tris-HCl, pH 8.0, centrifuged as before, resuspended in 12.5 ml of 50 mM Tris-HCl, 50 mM EDTA, pH 8.0, and frozen at −20° C. Then 1.25 ml of a 10 mg/ml lysozyme solution in 0.25M Tris-HCl, pH 8.0, was added to the frozen cell pellet. The pellet was thawed and incubated on ice for 45 minutes. Next, 2.5 ml of a solution of 1 mg/ml proteinase K in 0.5% SDS, 0.4M EDTA, 50 mM Tris-HCl, pH 7.5 was added and the mixture incubated at 50° C. for 1 hour with occasional mixing. The lysate was extracted once with 15 ml of Tris-buffered phenol, then 1.5 ml of 3M sodium acetate and 30 ml of ethanol were added to precipitate the DNA. The DNA was spooled on a glass rod, then dissolved in 12.5 ml of 50 mM Tris-HCl, 1 mM EDTA, pH 7.5 containing 0.2 mg/ml RNAse A by rocking overnight. The sample was extracted once with an equal volume of chloroform, precipitated, and spooled as above. The DNA was dissolved in 2 ml of 50 mM Tris-HCl, 1 mM EDTA, pH 7.5 and stored at 4° C.

B. Chromosomal DNA extraction from Haemophilus influenzae type b Eagan

Fifty ml of culture were pelleted by centrifugation, the pellet resuspended in 25 ml of TE (10 mM Tris, 1 mM EDTA, pH 7.5), and 2×5 ml aliquots used for chromosomal DNA preparation. To each aliquot was added 0.6 ml of 10% sarkosyl and 0.15 ml of 20 mg/ml proteinase K and the samples incubated at 37° C. for 1 hour. The lysate was extracted once with Tris-saturated phenol and three times with chloroform:isoamyl alcohol (24:1). The aqueous phases were pooled for a final volume of 7 ml. Then 0.7 ml of 3M sodium acetate (pH 5.2) and 4.3 ml of isopropanol were added to precipitate the DNA which was spooled, rinsed with 70% ethanol, dried, and resuspended in 1 ml of water.

C. Chromosomal DNA extraction from Haemophilus influenzae Eagan, MinnA, PAK 12085 and SB33

Cells were pelleted from 50 ml of culture by centrifugation at 5000 rpm for 15–20 minutes, at 4° C. The cell pellet was resuspended in 10 ml of TE (10 mM Tris-HCl, 1 mM EDTA, pH 7.5), pronase and SDS were added to final concentrations of 500 µg/ml and 1%, respectively. The sample was incubated at 37° C. for 4 hours until a clear lysate was obtained. The lysate was extracted once with Tris-saturated phenol, once with Tris-saturated phenol/chloroform (1:1), and once with chloroform. The final aqueous phase was dialysed for 24 hours against 2×500 ml of 1M NaCl at 4° C., changing the buffer once, and for 24 hours against 2×500 ml of TE at 4° C., changing the buffer once. The final dialysate was aliquotted for use.

Example 2

This Example illustrates the preparation of chromosomal libraries.

A. H. influenzae DL63-λZAP library

100 µg of H. influenzae DL63 chromosomal DNA in TE was mechanically sheared in a 1 ml syringe with a 25 gauge needle. The sheared DNA was made blunt-ended by adding water to a final volume of 405 µl, 45 µl of 10× S-1 nuclease buffer (2M NaCl, 500 mM NaOAc, pH 4.5, 10 mM $ZnSO_4$, 5% glycerol), and 1.7 µl of S1 nuclease at 100 U/µl and incubating at 37° C. for 15 min. The sample was extracted once with phenol/chloroform and once with chloroform and 1 ml of ethanol was added to precipitate the DNA. The sample was incubated on ice for 10 min or at −20° C. overnight and the DNA was harvested by centrifugation in a microfuge for 30 minutes. The DNA was washed with 70% ethanol and dried. The Eco RI sites in the DNA sequence were methylated using standard procedures. To this methylated DNA was added 5 µl of 100 mM $MgCl_2$, 8 µl of dNTP mix (2.5 mM each of dATP, dCTP, dGTP, and dTTP), and 4 µl of 5 U/µl Klenow. The mixture was incubated at 12° C. for 30 minutes. 450 µl of STE (0.1M NaCl, 10 mM Tris-HCl, 1 mM EDTA, pH 8.0) were added, and the mixture extracted once with phenol/chloroform, and once with chloroform, before adding 1 ml of ethanol to precipitate the DNA. The sample was incubated on ice for 10 min or at −20° C. overnight. The DNA was harvested by centrifugation in a microfuge for 30 minutes, washed with 70% ethanol and dried.

The DNA was resuspended in 7 µl of TE and to the solution was added 14 µl of phosphorylated Eco RI linkers (200 ng/µl), 3 µl of 10× ligation buffer, 3 µl of 10 mM ATP, and 3 µl of T4 DNA ligase (4 U/µl). The sample was incubated at 4° C. overnight, then incubated at 68° C. for 10 minutes to inactivate the ligase. To the mixture was added 218 µl of $H_2O$, 45 µl of 10× Universal buffer, and 7 µl of Eco RI at 30 U/µl. After incubation at 37° C. for 1.5 hours, 1.5 µl of 0.5M EDTA was added, and the mixture placed on ice.

The DNA was size fractionated on a sucrose gradient, pooling fractions containing DNA of 6–10 kb. The pooled DNA was ethanol precipitated and resuspended in 5 µl of TE buffer. 200 ng of insert DNA was ligated for 2–3 days at 4° C. with 1 µg of ZAP II vector in a final volume of 5 µl. The ligation mixture was packaged using Gigapack II Gold (Stratagene) and plated on E. coli SURE cells on NZY plates. The library was titrated, amplified, and stored at 4° C. under 0.3% chloroform.

B. H. influenzae Eagan-pUC library

Chromosomal DNA prepared from H. influenzae Eagan by the method in Example 1C was digested with Sau3A I for 2, 5, and 10 minutes and samples electrophoresed on a preparative agarose gel. Gel slices which included DNA fragments between 3–10 kb in length were excised and the DNA extracted by the standard freeze-thaw procedure. Plasmid DNA from pUC 8:2 (pUC 8 with additional Bgl II and Xba I restriction enzyme sites in the multiple cloning site) was digested with BamH I and Bgl II, and dephosphorylated with calf alkaline phosphatase (CAP). The fragments of H. influenzae Eagan DNA were ligated into pUC and the mixture used to transform E. coli JM109 cells.

C. H. influenzae Eagan-λZAP library

Chromosomal DNA from H. influenzae Eagan prepared as in Example 1B was digested with Eco RI and size fractionated on a preparative agarose gel. Gel slices corresponding to DNA fragments of 7–23 kb were excised and DNA was electroeluted overnight in dialysis tubing containing 3 ml of TAE (40 mM Tris-acetate, 1 mM EDTA) at 14V. The DNA was precipitated twice and resuspended in water before being ligated overnight with Eco RI digested λZAP II DNA. The ligation mixture was packaged using the Gigapack II packaging kit (Stratagene) and plated on E. coli XL1-Blue cells. The library was titrated, amplified, and stored at 4° C. under 0.3% chloroform.

D. EMBL3 libraries

H. influenzae MinnA chromosomal DNA (10 µg) was prepared as in Example 1C and digested with Sau3A I (40 units) for 2, 4, and 6 minutes then size-fractionated on a 10–30% sucrose gradient in TNE buffer (20 mM Tris-HCl, 5 mM NaCl, 1 mM EDTA, pH 8). Fractions containing DNA fragments greater than 5 kb were pooled and precipitated. In a second experiment, chromosomal DNA (2.6 µg) was digested with Sau3A I (4 units) for 1, 2, and 3 minutes and size-fractionated by preparative agarose gel electrophoresis. Gel slices containing DNA fragments of 10–20 kb were excised and DNA extracted by a standard freeze/thaw technique. The size- fractionated DNA from the two experiments was pooled for ligation with BamH I arms of EMBL3 (Promega). The ligation mixture was packaged using the Gigapack II packaging kit and plated on E. coli LE392 cells. The library was titrated, then amplified and stored at 4° C. under 0.3% chloroform.

Chromosomal DNA from H. influenzae PAK 12085 or SB33 prepared as in Example 1C was digested with Sau3A I (0.5 units/10 µg DNA) at 37° C. for 15 minutes and size-fractionated by agarose gel electrophoresis. Gel slices corresponding to DNA fragments of 15–23 kb were excised and DNA was electroeluted overnight in dialysis tubing containing 3 ml of TAE at 14V. The DNA was precipitated twice and resuspended in water before overnight ligation with EMBL3 BamH I arms (Promega). The ligation mixture was packaged using the Lambda in vitro packaging kit (Amersham) according to the manufacturer's instructions and plated onto E. coli NM539 cells. The library was titrated, then amplified, and stored at 4° C. in the presence of 0.3% chloroform.

Example 3

This Example illustrates screening of the libraries.

A. H. influenzae DL63-λZAP expression library

Tbp1 and Tbp2 proteins were affinity purified on solid phase human transferrin (hTf). Briefly, a 20 ml hTf-Sepharose column was prepared according to the manufacturer's protocol for coupling protein ligands to CNBr-activated Sepharose (Sigma). The resulting matrix was washed with 3 column volumes of 50 mM Tris-HCl, 1M NaCl, 6M guanidine-HCl, pH 8.0 to remove non-covalently bound hTf. The column was then equilibrated with 50 mM Tris-HCl, pH 8.0 and bound hTf was iron loaded using 1 ml of 10 mg/ml $FeCl_3$ in buffer containing 100 mM each of sodium citrate and sodium bicarbonate, pH 8.6, followed by 2 column volumes of 50 mM Tris-HCl, 1M NaCl, pH 8.0. Total bacterial membranes (300 mg total protein) were prepared from H. influenzae strain DL63 grown on iron deficient media as described previously (Schryvers et al., 1989). Membranes were diluted to 2 mg/ml in 50 mM Tris-HCl, 1M NaCl, pH 8.0 and solubilized by the addition of EDTA to 15 mM and Sarkosyl NL97 to 1.5%. After centrifugation at 40,000×g for 1 hour, the supernatant was applied to the hTf column and the column washed with 10 column volumes of 50 mM Tris-HCl, 1M NaCl, 10 mM EDTA, 0.5% Sarkosyl, pH 8.0. The receptor proteins were eluted using 2M GnHCl in the same buffer and the eluted fractions were dialysed extensively against 25 mM ammonium bicarbonate buffer (5 buffer changes), lyophilized, and stored at −20° C. Isolated proteins were used to generate transferrin receptor-specific antisera in New Zealand White rabbits using standard techniques. Briefly, rabbits were immunized 3 times subcutaneously, at intervals of two weeks, using complete Freund's adjuvant for the first injection and incomplete Freund's adjuvant for subsequent injections.

Figure 2:
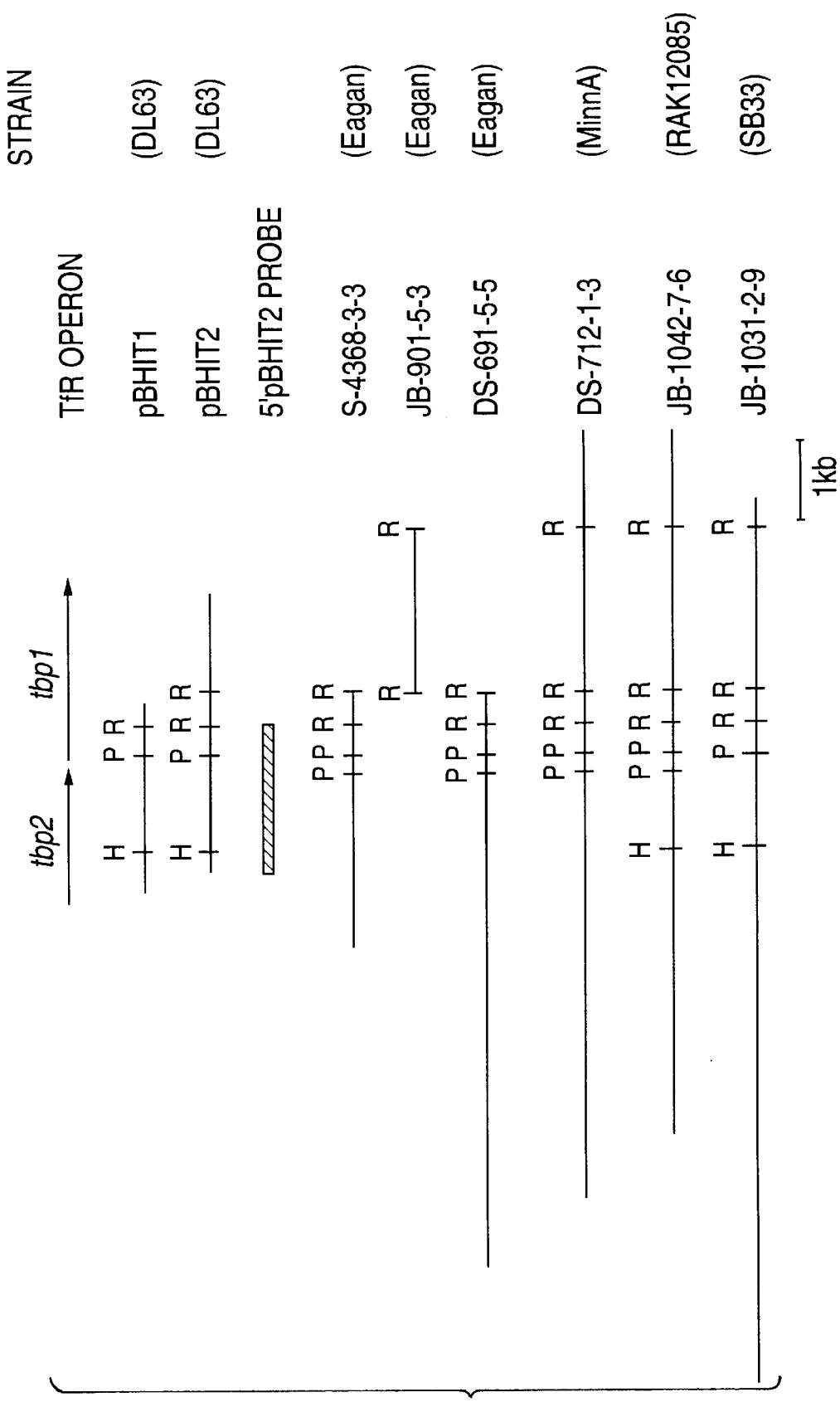
FIG. 2 illustrates the organization and restriction maps of the cloned Tbp1 and Tbp2 genes of identified strains and the genetic organization of the TfR operon with two genes (tbp1 and tbp2) in tandem forming an operon under the transcriptional regulation of a single promoter and also depicts the 3.0 kb DNA fragment of pBHIT2 used to probe libraries for TfR genes from the Haemophilus strains.

The DL63 λZAP library was plated on E. coli SURE cells and plaques were transferred onto nitrocellulose membranes which had been pre-soaked in 10 mM IPTG to induce expression from the pBluescript lacZ promoter. Filters were blocked using 0.5% skim milk in 50 mM Tris-HCl, 150 mM NaCl, pH 7.5, prior to being probed with the polyclonal anti-TfR antisera and horse radish peroxidase-conjugated goat anti-rabbit IgG. Plaques were purified by 3 rounds of screening and recombinant pBluescript plasmids (pBHIT1 and pBHIT2; FIGS. 1A and 2) were recovered by the in vivo excision procedure (Short et al., 1988).

B. Eagan, MinnA, and PAK 12085 non-expression libraries (i) Screening of H. influenzae Eagan-pUC library.

Figure 1B:
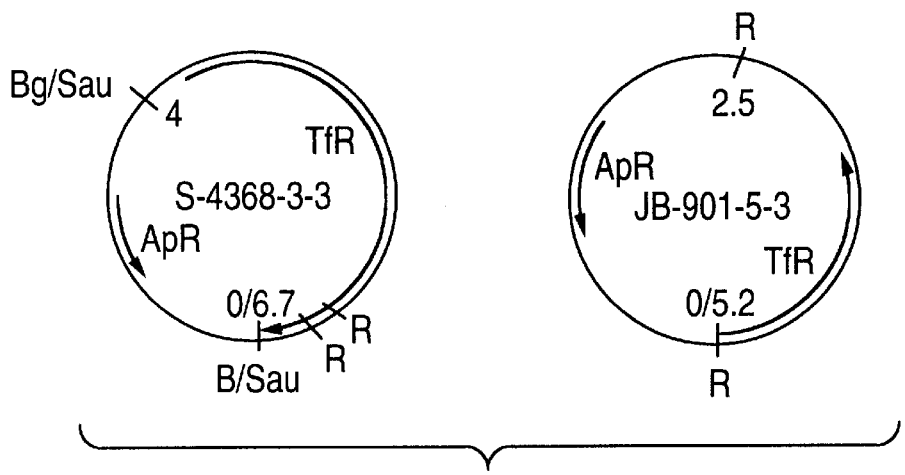
FIG. 1B shows the restriction map of clones S-4368-3-3 and JB-901-5-3 containing TfR genes from H. influenzae type b strain Eagan.

Colony lifts onto nitrocellulose were performed using standard techniques and the filters were probed with the 5'pBHIT2 probe of the transferrin receptor gene illustrated in FIG. 2. The probe was labelled with digoxigenin (dig, Boehringer Mannheim) following the manufacturer's specifications. Several putative clones were dot blotted onto nitrocellulose and submitted to second round screening using the same 5'pBHIT2 probe. Second round putatives were analysed by restriction enzyme mapping and clone S-4368-3-3 (FIG. 1B, FIG. 2) was selected for sequence analysis.

(ii) Screening H. influenzae Eagan-λZAP library

The phage library was plated using standard techniques on XLI Blue cells (Stratagene) using LB plates and a 0.7% agarose overlay layer. Plaques were lifted onto nitrocellulose using standard protocols and the filters were baked at 80° C., for 2 hours, under vacuum, to fix the DNA. The 5'pBHIT2 probe of the transferrin receptor gene (FIG. 2) was labelled with digoxigenin and the filters were pre-hybridized for 4 hours at 42° C., then hybridized with the labelled probe at 42° C., overnight. The filters were washed at 68° C. and after autoradiography, several plaques were selected for second round screening. In vivo excision of phagemid DNA from second round putatives was performed according to protocols provided with the λZAP system (Promega). Four clones with identical ~2.5 kb Eco RI inserts were obtained of which JB-901-5-3 in FIG. B, FIG. 2 is an example. Putative plaques were also amplified and phage DNA was purified from 500 ml of culture. Insert DNA was excised by digestion with Xba I and was cloned into pUC 8:2 (pUC 8 containing additional Bgl II and Xba I sites in its multiple cloning site) which had been digested with Xba I and dephosphorylated. Clone JB-911-3-2 (FIG. 17) contains the 3'-half of the H. influenzae Eagan TfR operon.

(iii) Screening EMBL 3 libraries

Figures 1C, 1D:
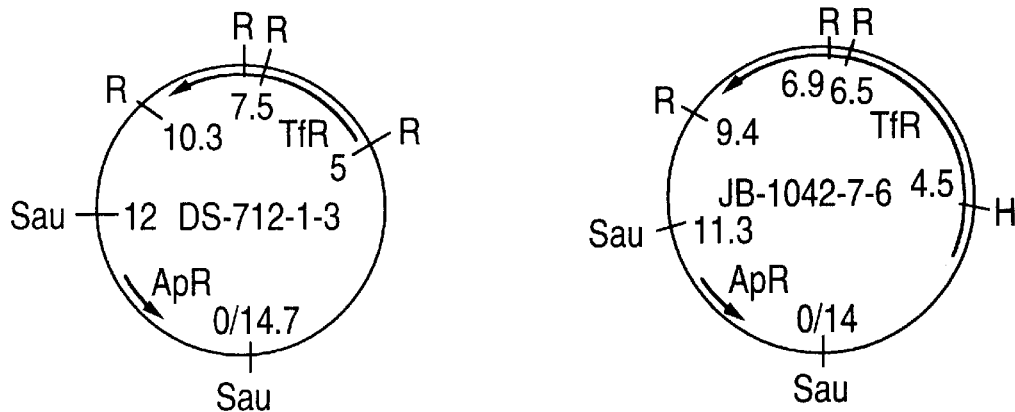
FIG. 1C shows the restriction map of clone DS-712-1-3 containing the transferrin receptor gene from H. influenzae type b strain MinnA.
FIG. 1D shows the restriction map of clone JB-1042-7-6 containing the transferrin receptor gene from the non-typable H. influenzae strain PAK 12085.

The H. influenzae MinnA library was plated onto LE392 cells on NZCYM plates using 0.7% top agarose in NZCYM as overlay. Plaque lifts onto nitrocellulose filters were performed following standard procedures, and filters were processed and probed with the 5'pBHIT2 probe (FIG. 2) labelled with digoxigenin. Putative plaques were plated and submitted to second and third rounds of screening using the same procedures. Phage DNA was prepared from 500 ml of culture using standard techniques, the insert DNA excised by Sal I digestion, and cloned into pUC to generate clone DS-712-1-3 (FIGS. 1C and 2).

The H. influenzae PAK 12085 library was plated on LE392 cells on NZCYM plates using 0.7% agarose in NZCYM as overlay. Plaques were lifted onto nitrocellulose and filters were processed and probed with the digoxigenin-labelled 5'pBHIT2 probe (FIG. 2). Putative plaques were plated and subjected to a second round of screening using the same procedures. Phage DNA was prepared from 500 ml cultures by standard techniques, the DNA insert was excised by digestion with Sal I, and cloned into pUC to generate clone JB-1042-7-6 (FIGS. 1D and 2).

The H. influenzae SB33 library was plated on LE392 cells on NZCYM plates using 0.7% agarose in NZCYM as overlay. Plaques were lifted onto nitrocellulose and filters were processed and probed with the digoxigenin-labelled 5'pBHIT2 probe (FIG. 2). Putative plaques were plated and subjected to a second round of screening using the same procedures. Phage DNA was prepared from 500 ml cultures by standard techniques, the DNA insert was excised by digestion with Sal I, and cloned into pUC to generate clone JB-1031-2-9 (FIG. 2).

Example 4

This Example illustrates the sequencing of the Tbp1 and Tbp2 genes of the TfR operon.

Plasmid DNA from clones pBHIT 1, pBHIT 2, S-4368-3-3, JB-901-5-3, DS-712-1-3, JB-1042-7-6 and JB-1031-2-9 was prepared using standard techniques. Oligonucleotide sequencing primers of 17–25 bases in length were synthesized on the ABI model 380B DNA Synthesizer and purified by chromatography using OPC cartridges obtained from Applied Biosystems Inc., and used in accordance with the manufacturers recommendations. Samples were sequenced using the ABI model 370A DNA Sequencer and dye terminator chemistry according to manufacturers' protocols. The sequence of the TfR operon from strain DL63 is illustrated in FIG. 3, that of strain Eagan in FIG. 4, that of strain MinnA in FIG. 5, that of PAK 12085 in FIG. 6 and that of SB33 in FIG. 7.

Example 5

This Example illustrates the PCR amplification of the tbp2 genes from non-typable H. influenzae strains SB12, SB29, SB30, and SB32.

Figure 13:
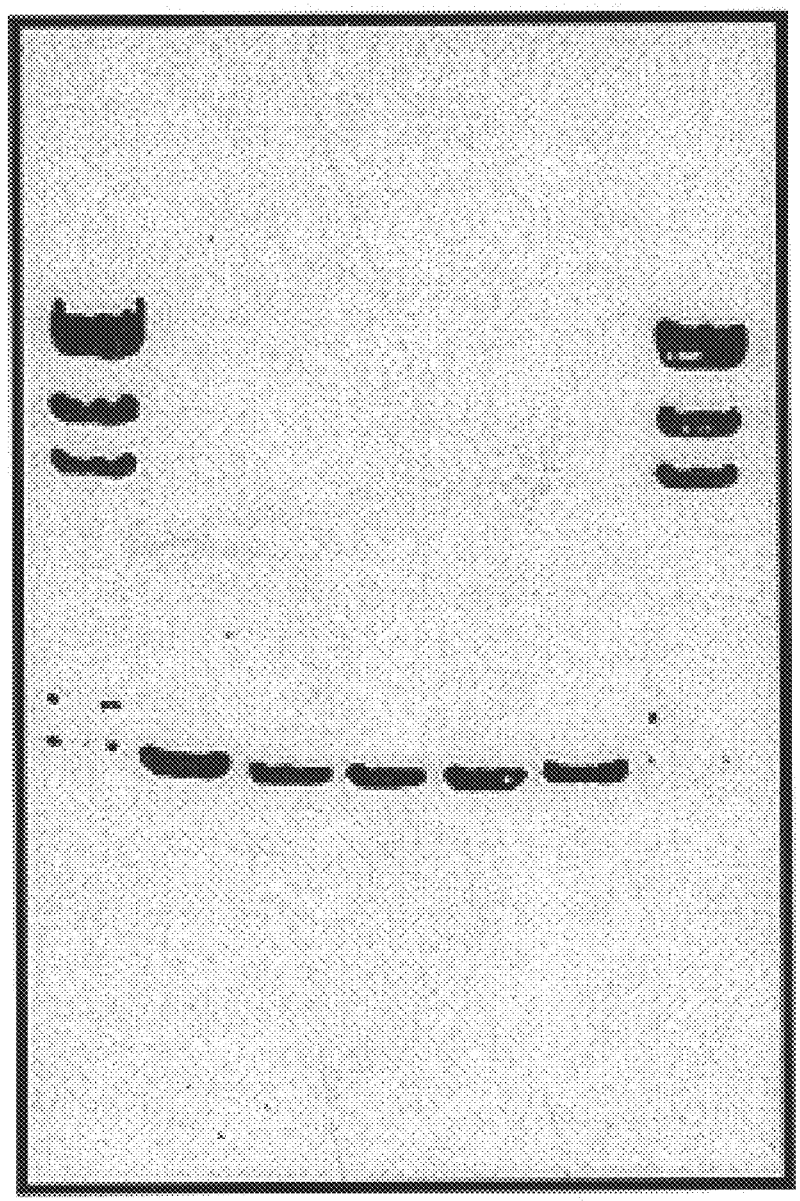
FIG. 13 shows the agarose gel analysis of PCR amplified tbp2 genes from non-typable H. influenzae strains SB12, SB29, SB30, SB32 and SB33. Lane 1 is SB33, lane 2 is SB12, lane 3 is SB29, lane 4 is SB30, lane 5 is SB32.

Chromosomal DNA from non-typable H. influenzae strains SB12, SB29, SB30, and SB32 was prepared as described above. The TfR genes are arranged as an operon with tbp2 followed by tbp1 (see FIGS. 12A (SEQ ID NOS: 116, 117, 118, 1999) and 12B (SEQ ID NOS: 121, 122, 123, 124, 125, 126, 127, 128). Oligonucleotides were synthesized to the 5'-end of the tbp2 and the reverse complement of the 5'-end of the tbp1 coding sequences. The primers were: GGATCCATATGAAATCTGT ACCTCTTATCTCTGGT (SEQ ID NO: 120) corresponding to MKSVPLISGS (SEQ ID NO: 147) from the leader sequence of Tbp2 and TCTAGAAGCTTTTTTAGTCATTTTTAGTATTCCAT (SEQ ID NO: 137) which is the reverse complement of the leader sequence MTKK (SEQ ID NO: 138) of Tbp1 and a part of the intergenic sequence (FIGS. 12A and 12B). PCR amplification was performed in buffer containing 10 mM Tris/HCl pH 8.3, 50 mM potassium chloride and 1.5 mM magnesium chloride. Each 100 µl reaction mixture contained 5 ng of chromosomal DNA, 1 µg of each primer, 5 units amplitaq DNA polymerase (Perkin Elmer Cetus) and 0.4 mM dNTPs (Perkin Elmer Cetus). The cycling conditions were 25 cycles of 94° C. for 1.0 min, 45° C. for 2.0 min and 72° C. for 1.5 min. Specific 2 kb fragments were amplified for each sample (FIG. 13). SB33 DNA was used as a positive control (Lane 1). Chromosomal DNA used for amplification of the Tbp2 gene were lane 1, SB33; lane 2, SB12; lane 3, SB29; lane 4, SB30; and lane 5, SB32. The fragments were cloned into the TA cloning vector (Invitrogen) and their nucleotide sequences determined. The nucleic acid sequences of Tbp2 from strains SB12 (SEQ ID NO: 108), SB29 (SEQ ID NO: 110), SB30 (SEQ ID NO: 112) and SB32 (SEQ ID NO: 114) are shown in FIGS. 8, 9 10 and 11 respectively.

Example 6

This Example illustrates the comparison of the amino acid sequences of transferrin the identification of potentially exposed epitopes of transferrin receptor proteins by secondary structure analysis.

Referring to FIG. 14, there is shown a comparison of the amino acid sequence of Tbp1 from H. influenzae type b Eagan, DL63, non-typable H. influenzae strains PAK 12085 and SB33, N. meningitidis strains B16B6 and M982 (Legrain et al., 1993) and N. gonorrhoeae FA19 (Cornelissen et al., 1992). This analysis revealed regions of Tbp1 which are conserved among all these bacteria.

Referring to FIG. 15, there is shown a comparison of the amino acid sequence of Tbp2 from H. influenzae type b strains Eagan, DL63, non-typable H. influenzae PAK 12085, SB12, SB29, SB30 and SB32, N. meningitidis strains B16B6 and M982, N. gonorrhoeae FA19 and Actinobacillus (Haemophilus) pleuropneumoniae (Gerlach et al., 1992) 205 and 37. This analysis revealed regions of Tbp2 which are conserved among all these bacteria.

Figure 16B:
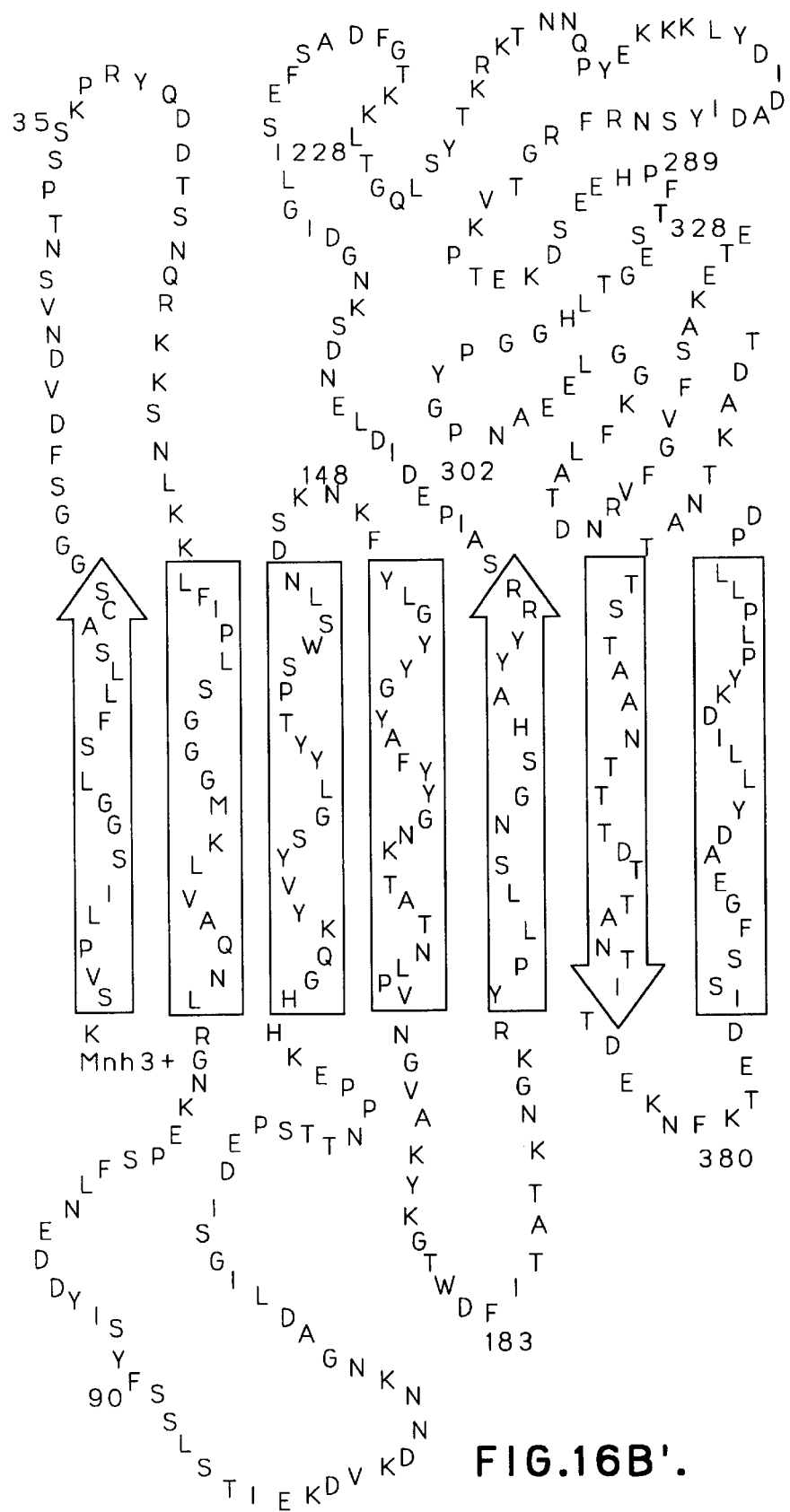
FIGS. 16B' and 16B" show the predicted secondary structure of H. influenzae Tbp2 protein.

Protein secondary structure analyses were performed using the Chou and Fasman algorithms (1978) and hydrophilicity/hydrophobicity plots were performed using the Hopp algorithm (1986). The values were derived from the averages of heptapeptide windows and are plotted at the midpoint of each fragment. FIG. 16A illustrates the predicted secondary structure of Tbp1 from H. influenzae type b Eagan and FIG. 16B illustrates the predicted secondary structure of Tbp2 from H. influenzae type b Eagan. The predicted secondary structures depicted in FIGS. 16A and 16B were arrived at using the procedures described above. However, the inventors have not yet been able to verify that the secondary structure is accurately depicted by these Figures.

Conserved epitopes of Tbp1 and Tbp2 proteins from several different bacteria were identified by sequence alignment as shown in FIGS. 14 and 15 respectively. Some such conserved epitopes include:

| TBP1 | DNEVTGLGK | SEQ ID NO:43 |
| TBP1 | EQVLNIRLTRYDPGI | SEQ ID NO:44 |
| TBP1 | GAINEIEYENVKAVEISKG | SEQ ID NO:45 |
| TBP1 | GALAGSV | SEQ ID NO:46 |
| TBP2 | LEGGFYGP | SEQ ID NO:74 |
| TBP2 | CSGGGSFD | SEQ ID NO:75 |
| TBP2 | YVYSGL | SEQ ID NO:76 |
| TBP2 | CCSNLSYVKFG | SEQ ID NO:77 |
| TBP2 | FLLGHRT | SEQ ID NO:78 |
| TBP2 | EFNVDF | SEQ ID NO:79 |
| TBP2 | NAFTGTA | SEQ ID NO:80 |
| TBP2 | VNGAFYG | SEQ ID NO:81 |
| TBP2 | LEGGYF | SEQ ID NO:82 |
| TBP2 | VVFGAR | SEQ ID NO:83 |

Furthermore, in combination with the predicted secondary structures, four conserved exposed epitopes were identified on Tbp1 and two were identified on Tbp2. These are:

| Tbp1 | DNEVTGLGK | SEQ ID NO:43 |
| Tbp1 | EQVLN/DIRDLTRYD | SEQ ID NOS:139 and 140 |
| Tbp1 | GAINEIEYENVKAVEISK | SEQ ID NO:141 |
| Tbp1 | GI/VYNLF/LNYRYVTWE | SEQ ID NOS:142 and 143 |
| Tbp2 | cS/LGGG(G)SFD | SEQ ID NOS:75, 144 and 145 |
| Tbp2 | LE/SGGFY/FGP | SEQ ID NOS:74 and 146 |

Proteins, polypeptides or peptides containing the aforementioned conserved amino acid sequences are particularly useful as detecting means in diagnostic embodiments and as immunogens to detect or protect from diseases caused by bacteria that produce transferrin receptor protein. For immunization, the particularly indicated amino acid sequences may be presented to the immune system as proteins or peptides or a live delivery vehicle, such as Salmonella, BCG, adenovirus, poxvirus, vaccinia or poliovirus may be used.

Example 7

This Example illustrates the construction of plasmid JB-1468-29 which expresses Eagan Tbp1 from *E. coli*.

Plasmids S-4368-3-3 (FIGS. 1B and 2) and JB-911-3-2 (FIG. 17) contain the 5'- and 3'- parts of the Eagan tbp1 gene, respectively. FIG. 17 illustrates the construction scheme for plasmid JB-1468-29. The oligonucleotide sequences used in the construction of JB-1468-29 are shown in FIG. 20, (SEQ ID NOS: 86 and 87). Plasmid JB-1468-29 was introduced into *E. coli* strain BL21/DE3 by electroporation to generate strain JB-1476-2-1.

JB-1476-2-1 was grown in YT medium and induced with IPTG following standard protocols. For preparation of Tbp1 for immunogenicity and other studies, strain JB-1476-2-1 was grown overnight in NZCYM media containing 3% glucose. A 1:40 inoculum was added to fresh NZCYM media without glucose, and the culture grown to $A_{578}$=0.3. Lactose was added to 1% and the culture was induced for 4 hours. SDS-PAGE analysis of whole cell lysates of JB-1476-2-1 is shown in FIG. 22. Lane 1, JB-1476-2-1 (T7/Eagan Tbp1) at $t_o$; lane 2, JB-1476-2-1 at t=4 h induction; lane 3, molecular weight markers of 200 kDa, 116 kDa, 97.4 kDa, 66 kDa, 45 kDa and 31 kDa; lane 4, JB-1437-4-1 (T7/Eagan Tbp2) at $t_o$,; lane 5, JB-1437-4-1 at t=4 h induction; lane 6, JB-1607-1-1 (T7/SB12 Tbp2) at $t_o$; lane 7, JB-1607-1-1 at t=4 h induction.

Example 8

This Example illustrates the construction of plasmid JB-1424-2-8 which expresses Eagan Tbp2 from *E. coli*.

Referring to FIG. 18, there is shown plasmid S-4368-3-3 which contains the entire tbp2 gene from H. influenzae type b Eagan. FIG. 18 illustrates plasmid JB-1424-2-8 and FIG. 19 shows the oligonucleotides used. Plasmid JB-1424-2-8 was introduced into *E. coli* strain BL21/DE3 by electroporation to generate *E. coli* strain JB-1437-4-1. Upon induction with IPTG or lactose, Tbp2 was expressed by *E. coli* JB-1437-4-1 as shown in FIG. 22. Lane 1, JB-1476-2-1 (T7/Eagan Tbp1) at $t_o$; lane 2, JB-1476-2-1 at t=4 h induction; lane 3, molecular weight markers of 200 kDa, 116 kDa, 97.4 kDa, 66 kDa, 45 kDa and 31 kDa; lane 4, JB-1437-4-1 (T7/Eagan Tbp2) at $t_o$; lane 5, JB-1437-4-1 at t=4 h induction; lane 6, JB-1607-1-1 (T7/SB12 Tbp2) at $t_o$; lane 7, JB-1607-1-1 at t=4 h induction.

Example 9

This Example illustrates the construction of plasmids which encode a lipoprotein leader sequence before the Tbp2 sequence.

Oligonucleotides used for the construction of plasmids with lipoprotein leader sequences derived from *E. coli* lpp (SEQ ID NOS: 88 and 89), rlpB (SEQ ID NOS: 90 and 91), and pal (SEQ ID NOS: 92 and 93) preceeding Tbp2 are shown in FIG. 20. Plasmids constructed and corresponding strains generated are illustrated in Table 1 below.

Example 10

This Example illustrates the construction of plasmid JB-1600-1 which expresses SB12 Tbp2 from *E. coli*.

Plasmid DS-1047-1-2 (FIG. 21) contains the PCR-amplified SB12 tbp2 gene. The tbp2 gene was excised as a Nde I to EcoR I restriction fragment and inserted into the pT7-7 expression vector to generate plasmid JB-1600-1. Electroporation into BL21/DE3 cells yielded *E. coli* strain JB-1607-1-1 which expresses SB12 Tbp2. Upon induction with IPTG or lactose, SB12 Tbp2 was expressed, as shown in FIG. 22. Lane 1, JB-1476-2-1 (T7/Eagan Tbp1) at $t_o$; lane 2, JB-1476-2-1 at t=4 h induction; lane 3, molecular weight markers of 200 kDa, 116 kDa, 97.4 kDa, 66 kDa, 45 kDa and 31 kDa; lane 4, JB-1437-4-1 (T7/Eagan Tbp2) at $t_o$; lane 5, JB-1437-4-1 at t=4 h induction; lane 6, JB-1607-1-1 (T7/SB12 Tbp2) at $t_o$; lane 7, JB-1607-1-1 at t=4 h induction.

Example 11

This Example illustrates the extraction and purification of Tbp1 and Tbp2.

The purification scheme for Tbp1 and Tbp2 is shown in FIG. 23. Both recombinant proteins are expressed as inclusion bodies in *E. coli* and the purification schemes are identical. Cells from a 500 ml culture, prepared as described in Example 7 for Tbp1 and in Example 8 for Tbp2, were resuspended in 50 ml of 50 mM Tris-HCl, pH 8.0, and disrupted by sonication (3×10 min, 70% duty circle). The extract was centrifuged at 20,000×g for 30 min and the resultant supernatant which contained >95% of the soluble *E. coli* proteins was discarded.

The remaining pellet (FIG. 23, $PPT_1$) was further extracted in 50 ml of 50 mM Tris, pH 8.0 containing 0.5% Triton X-100 and 10 mM EDTA. After centrifugation at 20,000×g for 30 min, the supernatant containing residual soluble proteins and the majority of the membrane proteins, was discarded. The resultant pellet (FIG. 23, $PPT_2$) obtained after the above extraction, contained the inclusion bodies. The Tbp1 and Tbp2 proteins were solubilized in 50 mM Tris, pH 8.0, containing 0.1 SDS and 5 mM DTT. After centrifugation, the resultant supernatant was further purified on a Superdex 200 gel filtration column equilibrated in 50 mM Tris, pH 8.0, containing 0.1% SDS and 5 mM DTT. The fractions were analysed by SDS PAGE and those containing purified Tbp1 or Tbp2 were dialysed overnight at 4° C. against 50 mM Tris, pH 8.0 and then centrifuged at 20,000×g for 30 min. The protein remained soluble under these conditions and the purified Tbp1 and Tbp2 were stored at −20° C.

The SDS-PAGE analysis of the purification process is shown in FIG. 24. Lanes 1, prestained molecular weight protein markers (106, 80, 49.5, 32.5, 27.5, 18.5 kDa); lanes 2, E. coli whole cell lysates; lanes 3, solubilized inclusion bodies; lanes 4, purified Tbp1 or Tbp2.

Example 12

This Example illustrates immunogenicity studies of recombinant Tbp1 and Tbp2 in mice.

Groups of five Balb/c mice were injected subcutaneously (s.c.) on days 1, 29 and 43 with purified rTbp1 or rTbp2 (1 µg to 10 µg), prepared as described in Example 11, in the presence of $AlPO_4$ (1.5 mg per dose). Blood samples were taken on days 14, 28, 42 and 56 for analysis of the anti-rTbp1 and anti-rTbp2 antibody titers by EIA. The results of the immunogenicity studies are illustrated in FIG. 25.

Example 13

This Example illustrates the development of EIAs for determination of anti-rTbp1 and anti-rTbp2 antibodies in mouse sera.

Anti-rTbp1 and anti-rTbp2 antibody titres were determined essentially as described by Panezutti et al. (1993). Microtiter wells were coated with 0.5 µg of rTbp1 or rTbp2, prepared as described in Example 11, for 16 h at room temperature, then blocked with 0.1% (w/v) BSA in PBS. The sera were serially diluted, added to the wells, then incubated for one hour at room temperature. Affinity-purified $F(ab')_2$ fragments of goat anti-mouse IgG (Fc specific) antibody conjugated to horseradish peroxidase were used as second antibody. The reactions were developed using tetramethyl-benzidine ($TMB/H_2O_2$) and the absorbance was measured at 450 nm (using 540 nm as a reference wavelength) in a Flow Multiskan MCC microplate reader. The reactive titer of an antiserum was defined as the reciprocal of the dilution consistently showing a two-fold increase in absorbance over that obtained with the pre-immune serum sample.

Example 14

This Example illustrates the cross-reactivity of anti-Tbp1 antisera, produced by immunization with recombinant Eagan Tbp1, with various strains of H. influenzae.

Whole cell lysates of H. influenzae strains grown in BHI media supplemented with NAD and heme (Harkness et al., 1992)±EDDA were separated by SDS PAGE gel, transferred to nitrocellulose membrane, and probed with guinea pig anti-Tbp1 antisera raised to purified recombinant Eagan Tbp1 (FIG. 26). Lane 1, BL21/DE3; lane 2, SB12−EDDA; lane 3, SB12+EDDA; lane 4, SB29−EDDA; lane 5, SB29+EDDA; lane 6, SB33−EDDA; lane 7, SB33+EDDA; lane 8, Eagan−EDDA; lane 9, Eagan+EDDA; lane 10, B. catarrhalis 4223−EDDA; lane 11, B. catarrhalis 4223+EDDA; lane 12, N. meningitidis 608−EDDA; lane 13, N. meningitidis 608+EDDA; lane 14, induced JB-1476-2-1 expressing recombinant Eagan Tbp1; lane 5, molecular weight markers. Specific ~95 kDa bands reacted with the anti-Tbp1 antisera in lanes 3, 4, 5, 7, 8 and 9, corresponding H. influenzae strains SB12, SB29, SB33 and Eagan; ~110 kDa bands in lanes 10 and 11, corresponding B. catarrhalis strain 4223; and ~80 kDa bands in lanes 12 and 13, corresponding to N. meningitidis 608.

Example 15

This Example illustrates the cross-reactivity of anti-Tbp2 antisera, produced by immunization with recombinant Eagan Tbp2, with various strains of H. influenzae.

Whole cell lysates of H. influenzae strains grown in BHI media supplemented with NAD and heme (Harkness et al., 1992)±EDDA were separated on an SDS PAGE gel, transferred to nitrocellulose membrane, and probed with guinea pig anti-Tbp2 antisera raised to purified recombinant Eagan Tbp2 (FIG. 27). Lane 1, molecular weight markers; lane 2, induced JB-1437-4-1 expressing recombinant Eagan Tbp2; lane 3, SB12−EDDA; lane 4, SB12+EDDA; lane 5, SB29−EDDA; lane 6, SB29+EDDA; lane 7, SB30−EDDA; lane 8, SB30+EDDA; lane 9, SB32−EDDA; lane 10, SB33−EDDA; lane 11, SB33+EDDA; lane 12, PAK−EDDA; lane 13, PAK+EDDA; lane 14, Eagan−EDDA; lane 15, Eagan+EDDA. Specific bands of about 60–70 kDa were reactive with the anti-Tbp2 antisera in lanes 3, 6, 7, 8, 13, 14 and 15, corresponding to Haemophilus strains SB12, SB29, SB30, PAK and Eagan.

Example 16

This Example illustrates the synthesis of synthetic peptides corresponding to conserved regions in Tbp2 and Tbp1.

The deduced amino acid sequences of Tbp1 and Tbp2 were compared as shown in FIGS. 14 and 15 respectively. This comparison identified regions of amino acid sequence conservation within the transferrin receptor described above and, as shown in Tables 2 and 3, peptides were synthesized containing a portion of the transferrin receptor. Such synthesis may be effected by expression in a suitable host of recombinant vectors containing nucleic acid encoding said peptides or by standard peptide synthesis.

Briefly, peptides were synthesized using an ABI 430A peptide synthesizer and optimized t-Boc chemistry using the conditions recommended by the manufacturer, and peptides were cleaved from the resin using hydrofluoric acid (HF). The peptides were purified by reverse-phase high performance liquid chromatography (RP-HPLC) on a Vydac C4 semi-preparative column (1×30 cm) using a 15 to 55% acetonitrile gradient in 0.1% trifluoryl acetic acid (TFA) developed over 40 minutes at a flow rate of 2 ml/minute. All synthetic peptides used in biochemical and immunological studies were >95% pure as judged by analytical HPLC. Amino acid composition analyses were performed on a Waters Pico-Tag system and were in good agreement with the theoretical compositions.

Example 17

This Example illustrates the immunogenicity of synthetic peptides in test animals.

Guinea pigs were immunized intramuscularly with 100 µg of peptide, prepared as described in Example 16, emulsified in Freund's complete adjuvant on day 0 followed by boosters on days +14 and +28 using the same amount of peptide emulsified in Freund's incomplete adjuvant. Sera samples were obtained on day 42+ and antibody titres determined by enzyme-linked immunosorbent assay (ELISA). Briefly, microtiter wells (Nunc-Immunoplate, Nunc, Denmark) were coated with 500 ng of any one particular peptide in 50 μL of coating buffer (15 mM Na$_2$CO$_3$, 35 mM NaHCO$_3$, pH 9.6) for 16 hours at room temperature. The plates were then blocked with 0.1% (w/v) BSA in phosphate buffer saline (PBS) for 30 minutes at room temperature. The antisera were serially diluted, added to the wells and incubated for 1 hour at room temperature. After removal of the antisera, the plates were washed five times with PBS containing 0.1% (w/v) Tween-20 and 0.1% (w/v) BSA. F(ab')$_2$ from goat anti-guinea pig IgG antibodies conjugated to horseradish peroxidase (Jackson ImmunoResearch Labs Inc., Pennysylvania) were diluted (1/8,000) with washing buffer, and added onto the microtiter plates. After 1 hour of incubation at room temperature, the plates were washed five times with the washing buffer. The plates were developed using the substrate tetramethylbenzidine (TMB) in H$_2$O$_2$ (ADI, Toronto), the reaction was stopped with 1N H$_2$SO$_4$ and the optical density was measured at 450 nm using a Titretek Multiskan II (Flow Labs., Virginia). Two irrelevant peptides of 32 amino acid residues were included as negative controls in these ELISAs. Assays were performed in triplicate, and the reactive titer of each antiserum was defined as the dilution consistently showing a 2-fold increase in absorbance value over those obtained from the negative controls. The antisera raised in guinea pigs were monospecific for the peptide used for immunization. The titres of the sera obtained following immunization are shown in Table 4.

Peptides of the present invention comprise single copies of any of those shown in Tables 2 and 3 or peptides containing multiple copies of analogs thereof. A peptide may further comprise multiples of different peptides selected from those shown in Tables 2 and 3 or analogs thereof and include suitable carrier molecules. It is preferred that the peptides from conserved regions be used to develop antibodies because an immuno- or other type of binding assay can then be used to detect several species of Haemophilus. Tables 2 and 3 therefore set out several other conserved regions of transferrin receptor to identify other peptides which would be useful in diagnosis, immunization and medical treatment.

Example 18

This Example describes the ability of antiserum raised against peptides corresponding to conserved portions of transferrin receptor to recognize the transferrin receptor of Branhamella catarrhalis.

Guinea pigs were immunized with peptide, corresponding to conserved portions of transferrin receptor, and antisera obtained are described in Example 17. A whole-cell extract of Branhamella catarrhalis was immunoblotted with the peptide-specific antiserum which specifically recognized the transferrin receptor from this bacterium. Anti-peptide antiserum from a guinea pig immunized with the Tbp2 N-terminal peptide and peptide TBP2-25 specifically recognized Tbp2 protein from Branhamella catarrhalis and recombinant Tbp2 expressed by plasmid clone pBHIT2 in E. coli. Clone pBHIT2 expresses a truncated version of Tbp2 starting at amino acid 80. (i.e. NKKFYSG SEQ ID NO: 105). Therefore, the Tbp2 protein from pBHIT2 can only be recognized by antibodies raised against the second epitope LEGGFYGP (TBP2-25). This analysis shows that peptides corresponding to conserved sequences between transferrin receptor are useful in detecting most, if not all, bacteria that produce transferrin receptor and as components in immunogenic compositions, including vaccines to produce an immune response against transferrin receptor and protect against diseases caused by such bacteria.

The sera from these rabbits were tested by ELISA against a peptide incorporating the sequence LEGGFYGP (SEQ ID NO: 74) or against H. influenzae strain DL63, Tbp2. ELISA plates were coated with the peptide or the protein then blocked with 5% skim milk. Serial two-fold dilutions of sera in phosphate buffered saline, 0.05% tween-20, and 1 dried milk were incubated on the plates for two hours at 37° C., following which the plates were washed five times in phosphate buffered saline with 0.05% tween-20. Washed plates were probed with a horse-radish peroxidase (HRPO)-conjugated donkey anti-rabbit IgG for 30 minutes at room temperature, then washed five times in phosphate buffered saline with 0.05% tween-20. HRPO-substrate was added to all wells for 30 minutes at room temperature in the dark, then color developemnt was halted by the addition of 50 ul 1M sulphuric acid. Color was measured by determining absorbance at 450 nm.

Example 19

This Example illustrates the generation of H. influenzae strains that do not produce transferrin receptor.

A 2.55 Eco RI fragment of the insert from pBHIT1 was subcloned into the Eco RI site of pUC4K, resulting in removal of the Tn903 kanamycin resistance (kan) cassette from this vector (pUHIT1; FIG. 28). This subcloning step facilitated the subsequent insertion of either a HincII or PstI pUC4K fragment containing the kan cassette into the Hind III or Pst I sites of pUHIT1 as both are unique sites in this construction to produce pUHIT1KFH and pUHIT1KFP, FIG. 28. Following digestion with Eco RI to remove the interrupted gene sequences, the constructs were introduced into the H. influenzae wild type genome by transformation using M-IV media as described previously (Barcak et al., 1991) and transformants were selected on BHINH agar containing 20 μg/ml kanamycin.

Example 20

This Example illustrates the construction of polioviruses expressing an epitope of a transferrin receptor.

A cDNA clone of bases 1175 to 2956 of the poliovirus type 1, Mahoney strain (PV1-M) genome was cut with restriction enzymes Sau I and Hind III. These enzymes excise a fragment containing bases 2754 to 2786, which encodes PV1-M amino acids 1094 to 1102, as shown in FIG. 29. In this application, we use the four-digit code for poliovirus amino-acids; for example, 1095 is amino acid 95 of capsid protein VP1. New hybrid cDNA clones encoding both poliovirus and transferrin receptor amino-acid sequences were constructed by replacing the excised fragment with synthetic oligonucleotides coding for amino acids from H. influenzae Tbp2. The new hybrid cDNA clones were cut with restriction enzymes Nhe I and SnaB I, which excise a hybrid fragment, including the transferrin receptor DNA sequences, from poliovirus base 2471 to 2956. A cDNA clone, for example pT7XLD or pT7CMCB, of the entire genome of PV1-M was cut with Nhe I and SnaBI to excise a fragment from poliovirus base 2471 to 2956. This was then replaced with a hybrid fragment including the transferrin receptor DNA sequences to produce a hybrid cDNA clone of the genome of PV1-M with bases 2754 to 2786 replaced by bases encoding a hybrid BC loop including transferrin receptor amino acids, as shown in FIG. 29.

The plasmid pT7XLD and clones derived from pT7XLD, such as pT7CMCB, contain a promoter sequence for the enzyme T7 RNA polymerase at the 5' end of the PV1-M cDNA. RNA transcripts of the PV1-M cDNA, including any bases encoding transferrin receptor amino acids, were prepared using T7 RNA polymerase as described by van der Werf et al. Transfection of Vero cells with these RNA transcripts produced four viable hybrid viruses, designated PV1TBP2A, PV1TBP2B, PV1TBP2C and PV1TBP2D. Transfection with transcripts of pT7CMCB yielded a transfection-derived wild-type poliovirus designated PV1XLD (FIG. 29).

The antigenic characteristics of PV1TBP2A, PV1TBP2B, PV1TBP2C and PV1TBP2D are shown in Table 5. All were neutralized by guinea-pig antisera raised against a peptide incorporating the sequence LEGGFYGP (SEQ ID NO: 74), indicating that the viruses expressed this sequence in an antigenically recognisable form. To produce the antisera female guinea pigs were immunized 1M with a 500 ul volume containing 200 ug peptide formulated in aluminum phosphate (3 mg/ml). Animals were immunized on days 1, 14, 28 and 42 and bled on days 0, 28, 42 and 56. Sera were from the day 56 bleed. PV1TBP2A and PV1TBP2B were also neutralized by rabbit antisera raised against H. influenzae strain DL63 Tbp2, indicating that at least these two viruses expressed the sequence in a form recognisable to antibodies raised against the protein. All viruses were neutralisable by anti-PV1 sera, indicating that the changes in polio neutralization antigenic site I had not significantly affected other antigenic sites on the viruses.

Example 21

This Example illustrates the use of poliovirus hybrids to induce high titer antisera against Tbp2.

Rabbits were inoculated with CsCl-purified PV1TBP2A (rabbits #40, 41, 42). Note that, although the viruses used were live, poliovirus does not replicate in rabbits and that any response observed is effectively the response to an inactivated antigen. On day 1, rabbits were inoculated with 1 ug of virus in Freund's complete adjuvant subcutaneously on the back, and, on day 14, the rabbits were boosted with 1 ug of virus in Freund's incomplete adjuvant inoculated subcutaneously on the back. The rabbits were bled on day 0 (prebleed) and on day 27. The dose of virus per inoculation was $2.5 \times 10^8$ pfu, which was determined from $A_{260}$ values to be approximately $3.0 \times 10^{11}$ virions. This equivalent to 0.5 pmol of virus or 30 pmol of the LEGGFYG (SEQ ID NO: 74) epitope, since each virion expresses 60 copies of the epitope.

SUMMARY OF THE DISCLOSURE

In summary of this disclosure, the present invention provides purified and isolated DNA molecules containing transferrin receptor genes, the sequences of these transferrin receptor genes and the derived amino acid sequences thereof. The invention also provides peptides corresponding to portions of the transferrin receptor. The genes, DNA sequences, recombinant proteins and peptides are useful for diagnosis, immunization and the generation of diagnostic and immunological reagents. Vaccines based upon expressed recombinant Tbp1 and/or Tbp2, portions thereof, or peptides derived from the provided sequences can be prepared for prevention of diseases caused by bacterial pathogens that produce transferrin receptor. Modifications are possible within the scope of this invention.

TABLE 1

| leader | 1st residue | plasmid | strain |
| --- | --- | --- | --- |
| E. coli lpp | Cys | JB-1360-1R-10 | JB-1407-1-1 |
| E. coli lpp | Ser | JB-1366-1R-7 | JB-1407-3-1 |
| E. coli pal | Cys | JB-1360-3-10 | JB-1407-2-1 |
| E. coli pal | Ser | JB-1366-3R-5 | JB-1407-4-4 |
| E. coli rlpB | Cys | JB-1399-1 | JB-1437-1-1 |
| E. coli rlpB | Ser | JB-1378-7 | JB-1407-5-1 |

TABLE 2

PREDICTED ANTIGENIC Tbp1 PEPTIDES

| PEPTIDE | RESIDUES[1] | SEQUENCES | SEQ ID NO: |
| --- | --- | --- | --- |
| TBP1-N | 1–36 | AETQSIYLTKEAISSEVDTQSTEDSELETISVTAEK | 13 |
| TBP1-2 | 31–66 | SVTAEKVRDRYLNEVTGLGKIIKTSESISREQVLNI | 14 |
| TBP1-3 | 59–94 | SREQVLNIRDLTRYDPGISVVEQGRGASSGYSIRGM | 15 |
| TBP1-4 | 88–123 | GYSIRGMDRNRVALLVDGLPQTQSYVVQSPLVARSG | 16 |
| TBP1-5 | 117–152 | PLVARSGYGTGAINEIEYENVKAVEISKGGSSSEYG | 17 |
| TBP1-6 | 147–182 | SSSEYGNGALAGSVTFQSKSAADILEGDKSWGIQTK | 18 |
| TBP1-7 | 179–214 | GIQTKNAYSSKNKGFTHSLAVAGKQGGFEGVAIYTH | 19 |
| TBP1-8 | 208–243 | GVAIYTHRNSIETQVHKDALKGVQSYDRFIATTEDQ | 20 |
| TBP1-9 | 236–271 | IATTEDQSAYFVMQDECLDGYDKCKTSPKRPATLST | 21 |
| TBP1-10 | 266–301 | PATLSTQRETVSVSDYTGANRIKPNPMKYESQSWFL | 22 |
| TBP1-11 | 293–328 | YESQSWFLRGGYHFSEQHYIGGIFEFTQQKFDIRDM | 23 |
| TBP1-12 | 322–357 | KFDIRDMTFPAYLRPTEDKDLQSRPFYPKQDYGAYQ | 24 |
| TBP1-13 | 352–387 | DYGAYQHIGDGRGVKYASGLYFDEHHRKQRVGIEYI | 25 |
| TBP1-14 | 383–418 | GIEYIYENKNKAGIIDKAVLSANQQNIILDSYMRHT | 26 |
| TBP1-15 | 412–447 | DSYMRHTHCSLYPNPSKNCRPTLDKPYSYYHSDRNV | 27 |
| TBP1-16 | 443–478 | SDRNVYKEKHNMLQLNLEKKIQQNWLTHQIAFNLGF | 28 |
| TBP1-17 | 469–504 | THQIAFNLGFDDFTSALQHKDYLTRRVIATASSISE | 29 |
| TBP1-M | 498–534 | TASSISEKRGEARRNGLQSSPYLYPTPKAELVGGDLC | 30 |
| TBP1-19 | 528–563 | LVGGDLCNYQGKSSNYSDCKVRLIKGKNYYFAARNN | 31 |
| TBP1-20 | 558–593 | FAARNNMALGKYVDLGLGMRYDVSRTKANESTISVG | 32 |
| TBP1-21 | 588–623 | STISVGKFKNFSWNTGIVIKPTEWLDLSYRLSTGFR | 33 |
| TBP1-22 | 618–653 | LSTGFRNPSFAEMYGWRYGGKDTDVYIGKFKPETSR | 34 |
| TBP1-23 | 648–663 | KPETSRNQEFGLALKGDFGNIEISHFSNAYRNLIAF | 35 |
| TBP1-24 | 677–712 | YNNLIAFAEELSKNGTTGKGNYGYHNAQNAKLVGVN | 36 |
| TBP1-25 | 706–741 | AKLVGVNITAQLDFNGLWKRIPYGWYATFAYNRVKV | 37 |

TABLE 2-continued

PREDICTED ANTIGENIC Tbp1 PEPTIDES

| PEPTIDE | RESIDUES[1] | SEQUENCES | SEQ ID NO: |
|---|---|---|---|
| TBP1-26 | 735–770 | AYNRVKVKDQKINAGLASVSSYLFDAIQPSRYIIGL | 38 |
| TBP1-27 | 764–799 | SRYIIGLDYDHPSNTWGIKTMFTQSKAKSQNELLGK | 39 |
| TBP1-28 | 794–829 | NELLGKRALGNNSRNVKSTRKLTRAWHILDVSGYYM | 40 |
| TBP1-29 | 825–854 | SGYYMVNRSILFRLGVYNLLNYRYVTWEAV | 41 |
| TBP1-30 | 843–865 | LLNYRYVTWEAVRQTAQGAEFDI | 42 |
| TBP1-31 | 42–50 | DNEVTGLGK | 43 |
| TBP1-32 | 61–76 | EQVLNIRDLTRYDPGI | 44 |
| TBP1-33 | 61–95 | EQVLNIRDLTRYDPGISVVEQGRGASSGYSIRGMD | 45 |
| TBP1-34 | 128–146 | GAINEIEYENVKAVEISKG | 46 |
| TBP1-35 | 155–161 | GALAGSV | 47 |
| TBP1-1 | 1–14 | AETQSIKDTKEAISC[2] | 48 |

1. Residue number from the sequence of Tbp1 of H. influenzae type b strain Eagan (as shown in FIG. 8).
2. Cysteine added to facilitate coupling to a carrier protein, for example KLH.

TABLE 3

PREDICTED CONSERVED ANTIGENIC Tbp2 PEPTIDES

| PEPTIDE | RESIDUES[1] | SEQUENCES | SEQ ID NO: |
|---|---|---|---|
| TBP2-1 | 18–31 | CSGGGSFDVDNVSN | 49 |
| TBP2-2 | 231–261 | LEGGFYGPKGEELGFRFLAGDKKVFGVFSAK | 50 |
| TBP2-3 | 358–380 | TVGKKTYQVEACCSNLSYVKFGM | 51 |
| TBP2-4 | 527–549 | ATVKGAFYGPKASELGGYFTYNG | 52 |
| TBP2-5 | 1–36 | MKLAALNLFDRNKPSLLNEDSYMIFSSRSTIEEDV | 53 |
| TBP2-6 | 29–64 | STIEEDVKNDNQNGEHPIDSIVDPRAPNSNENRHG | 54 |
| TBP2-7 | 57–92 | SNENRHGQKYVYSGLYYIQSWSLRDLPNKKFYSGY | 55 |
| TBP2-8 | 85–120 | KKFYSGYYGYAYYFGNTTASALPVGGVATYKGTWS | 56 |
| TBP2-9 | 113–148 | TYKGTWSFITAAENGKNYELLRNSGGGQAYSRRSA | 57 |
| TBP2-10 | 141–176 | AYSRRSATPEDIDLDRKTGLTSEFTVNFGTKKLTG | 58 |
| TBP2-11 | 169–204 | GTKKLTGGLYYNLRETDANKSQNRTHKLYDLEADV | 59 |
| TBP2-12 | 197–232 | YDLEADVHSNRFRGKVKPTKKESSEEHPFTSEGTL | 60 |
| TBP2-13 | 225–260 | FTSEGTLEGGFYGPEGQELGGKFLAHDKKVLGVFS | 61 |
| TBP2-14 | 253–268 | KVLGVFSAKEQQETSENKKLPKETLIDGKLTTFKT | 62 |
| TBP2-15 | 281–316 | KLTTFKTTNATANATTDATTSTTASTKTDTTTNAT | 63 |
| TBP2-16 | 309–344 | DTTTNATANTENFTTKDIPSLGEADYLLIDNYPVP | 64 |
| TBP2-17 | 337–372 | IDNYPVPLFPESGDFISSKHHTVGKKTYQVEACCS | 65 |
| TBP2-M | 360–406 | CSNLSYVKFGMYYEAPPKEEEKEKEKDKDKEKEKQA | 66 |
| TBP2-19 | 393–428 | KEKDKDKEKEKQAITSIKTYYQFLLGLRTPSSEIP | 67 |
| TBP2-20 | 421–456 | TPSSEIPKEGSAKYHGNWFGYISDGETSYSASGDK | 68 |
| TBP2-21 | 449–484 | YSASGDKERSKNAVAEFNNNFAEKTLTGELKRHDT | 69 |
| TBP2-22 | 477–512 | ELKRHDTQNPVFKINATFQSGKNDFTGTATAKDLA | 70 |
| TBP2-23 | 505–540 | ATAKDLAIDGKNTQGTSKVNFTATVNGAFYGPHAT | 71 |
| TBP2-24 | 533–559 | FYGPHATELGGYFTYNGNNPTDKNSS | 72 |
| TBP2-C | 553–581 | CPTDKNSSSNSEKARAAVVFGAKKQQVETTK | 73 |
| TBP2-25 | 231–238 | LEGGFYGP | 74 |
| TBP2-26 | 18–25 | CSGGGSFD | 75 |
| TBP2-27 | 130–134 | YVYSGL | 76 |
| TBP2-28 | 345–355 | CCSNLSYVKFG | 77 |
| TBP2-29 | 401–407 | FLLGHRT | 78 |
| TBP2-30 | 450–456 | EFNVDF | 79 |
| TBP2-31 | 485–491 | NAFTGTA | 80 |
| TBP2-32 | 516–522 | VNGAFYG | 81 |
| TBP2-33 | 527–532 | ELGGYF | 82 |
| TBP2-34 | 562–566 | VVFGAR | 83 |
| TBP2-35 | 562–568 | WFGAK | 84 |
| TBP2-36 | 231–238 | LEGGFYG | 85 |

1. Residue number from the sequence of Tbp2 of H. influenzae type B Eagan strain (as shown in FIG. 9).

TABLE 4

Guinea pig antibody responses to Tbp1 and Tbp2 peptides

| PEPTIDE | SEQ ID | SEQUENCES | TITRE |
|---|---|---|---|
| TBP1-N | 13 | AETQSIKDTKEAISSEVDTQSTEDSELETISVTAEK | 500 |
| TBP1-M | 30 | TASSISEKRGEARRNGLQSSPYLYPTPKAELVGGDLC | 1562500 |
| TBP1-1 | 46 | AETQSIKDTKEAISC | <100 |
| TBP2-1 | 49 | CSGGGSFDVDNVSN | 2500 |
| TBP2-2 | 50 | LEGGFYGPKGEELGFRFLAGDKKVFGVFSAK | 12500 |
| TBP2-3 | 51 | TVGKKTYQVEACCSNLSYVKFGM | 62500 |
| TBP2-4 | 52 | ATVKGAFYGPKASELGGYFTYNG | <100 |
| TBP2-M | 66 | CSNLSYVKFGMYYEAPPKEEEKEKEKDKDKEKEKQA | 62500 |
| TBP2-C | 73 | CPTDKNSSSNSEKARAAWFGAKKQQVETTK | 312500 |

TABLE 5

Neutralizing activity of anti-Tbp2 and anti-peptide sera against polio/Tbp2 hybrid viruses

| | Neutralizing Titre v. Virus[b] | | | | |
|---|---|---|---|---|---|
| Sera[a] | PV1TBP2A | PV1TBP2B | PV1TBP2C | PV1TBP2D | PV1XLD |
| Rb @PV1 | >40,9600 | 25,844 | 20,480 | 16,763 | >40,960 |
| Rb 516 D0 | <4 | <4 | <4 | <4 | <4 |
| Rb 516 D42 | 40 | 20 | <4 | <4 | <4 |
| GP561, 562 D0 pool | <4 | <4 | <4 | <4 | <4 |
| GP 561 D56 | >2048 | >2048 | >2048 | 1164 | <4 |
| GP S62 D56 | >2048 | >2048 | 25 | 10 | <4 |
| GP558, 559, 560 D56 pool | <4 | <4 | <4 | <4 | <4 |

[a]Rb @PV1 is pool of rabbit immune sera raised against PV1XLD. Rabbit 516 was immunised with three successive 3 μg dses of recombinant *H. influenzae* DL63 transferrin binding protein 2 on days 1, 14 and 28. Serum was collected on days 0 (D0) and 42 (D42). Guinea-pigs were immunized with four successive doses of 200 μg of peptide on days 1, 14, 28 and 42. Sera were collected on day 0 (D0)and day 56 (D56). Guinea-Pigs 561 and 562 received a peptide containing the sequence LEGGFYGP (SEQ ID NO:74). Guinea-pigs 558, 559 and 556 received a control peptide with an unrelated sequence.
[b]Titre is the inverse dilution of serum giving a 50% endpoint in a virus neutralization assay versus 100 $TCID_{50}$ of virus.

TABLE 6

Peptide-specific IgG titres of rabbits immunised with PV1TBP2A or PV1TBP2B

| | PEPTIDE-SPECIFIC IgG TITRES[a] | |
|---|---|---|
| RABBIT (ANTIGEN) | PREBLEED | DAY 27 |
| 40 (PV1TBP2A) | <20 | 640 |
| 41 (PV1TBP2A) | <20 | 640 |
| 42 (PV1TBP2A) | <20 | 2560 |
| 43 (PV1TBP2B) | <20 | 160 |
| 44 (PV1TBP2B) | <20 | 1280 |
| 45 (PV1TBP2B) | <20 | 1280 |
| 10 (PV1 Mahoney) | | <20[b] |
| 11 (PV1 Mahoney) | | <20 |

[a]Titres are the reciprocal of the greatest dilution of sera giving an $A_{450}$ of at least twice the background value. The background value was the mean $A_{450}$ of wells assayed in the absence of rabbit sera.
[b]Titres for rabbits 10 and 11 refer to sera taken on day 42 after three immunisations with PV1 Mahoney. Rabbits 10 and 11 were immunised as rabbits 40 to 45, except that an additional booster dose was administered on day 28.

LIST OF REFERENCES

Barcak et al., (1991) Methods Enzymol. 204: 321–342.
Berkowitz et al., (1987) J. Pediatr. 110:509.
Black et al., (1991) Pediatr. Infect. Dis. J. 10:97.
Bluestone, N. (1982) Engl. J. Med. 306:1399.
Chang et al., (1978) Nature 375:615.
Chou, et: al., (1978). Annual Reviews of Biochemistry 47, 251–276.
Claesson et al., (1989) J. Pediatr. 114:97.
Cornelissen et al., (1992) J. Bacteriol. 174:5788
Danve, et al., (1993). Vaccine 11, 1214–1220.
Deres et al., (1989) Nature 342:651.
Gerlach, et al., (1992) Infect. Immun. 608:325
Goeddel et al., (1979) Nature 281:544.
Goeddel et al., (1980) Nucl. Acids Res. 8:4057
Harkness et al., (1992) J. Bacteriol. 174:2425.
Holland et al., (1992) Infect. Immun. 60:2986.
Hopp, T. P. (1986) Journal of Immunological Methods 88, 1–18.
Itakura et al., (1977) Science 198:1056.
Jarosik et al., (1994). Infection and Immunity 62, 2470–2477.
Legrain et al., (1993). Gene 130:73
Lockhoff et al., (1991) Chem. Int. Ed. Engl. 30:1611.
Mickelsen and Sparling, (1981) Infect. Immun. 33:555.
Morton et al., (1993) Infection and Immunity 61, 4033–4037.
Murdin et al., (1992) J. Gen. Viral 73: 607.
Murdin et al., (1991) Microbial Pathogenesis 10:27.
Nixon-George et al., (1990) J. Immunol. 14:4798.
Ogunnariwo, and Schryvers, (1992) Avian Dis. 36:655.

O'Hagan (1992) Clin Pharmokinet. 22:1.
Panezutti et al., (1993) Infection and Immunity 61, 1867–1872.
Roosi-Campos et al., (1992) Vaccine 10, 512–518.
Schryvers, (1988) Molec. Microbiol. 2:467.
Schryvers and Lee, (1989) Can. J. Microbiol. 35:409.
Schryvers and Gray-Owen, (1992) J. Infect. Dis. 165 suppl 1:S103.
Schryvers (1989) Med. Microbiol. 29:121.
Short et al., (1988) Nucl. Acids Res. 16:7583.
Ulmer et al., (1993) Curr. Opinion Invest. Drugs. 2 (9): 983–989.
Van der Werf et al., (1986) Proc. Natl. Acad. Sci. 83: 2330.
Weismuller et al., (1989) Vaccine 8:29.
Wilton et al., (1993) FEMS Microbiology Letters 107, 59–66.
U.S. Pat. No. 4,855,283
U.S. Pat. No. 4,258,029
U.S. Pat. No. 4,496,538
U.S. Pat. No. 4,599,230
U.S. Pat. No. 4,599,231
U.S. Pat. No. 4,601,903
U.S. Pat. No. 5,141,743
U.S. Pat. No. 4,596,792
U.S. Pat. No. 4,952,496
U.S. Pat. No. 5,194,254
WO 92/17167

SEQUENCE LISTING (1) GENERAL INFORMATION:

(iii) NUMBER OF SEQUENCES: 147

(2) INFORMATION FOR SEQ ID NO:1:

(i) SEQUENCE CHARACTERISTICS:
      (A) LENGTH: 4699 base pairs
      (B) TYPE: nucleic acid
      (C) STRANDEDNESS: double
      (D) TOPOLOGY: linear (ix) FEATURE:
      (A) NAME/KEY: CDS
      (B) LOCATION: join(10..1940, 1957..4696)

(xi) SEQUENCE DESCRIPTION: SEQ ID NO:1:

```
TATAACTCA ATG AAA TCT GTA CCT CTT ATC TCT GGT GGA CTT TCC TTT        48
          Met Lys Ser Val Pro Leu Ile Ser Gly Gly Leu Ser Phe
            1               5                  10

TTA CTA AGT GCT TGT AGC GGA GGG GGG TCT TTT GAT GTA GAT AAC GTC       96
Leu Leu Ser Ala Cys Ser Gly Gly Gly Ser Phe Asp Val Asp Asn Val
        15                  20                  25

TCT AAT ACC CCC TCT TCT AAA CCA CGT TAT CAA GAC GAT ACT TCA AGT      144
Ser Asn Thr Pro Ser Ser Lys Pro Arg Tyr Gln Asp Asp Thr Ser Ser
 30                  35                  40                  45

TCA AGA ACA AAA TCT AAA TTG GAA AAG TTG TCC ATT CCT TCT TTA GGG      192
Ser Arg Thr Lys Ser Lys Leu Glu Lys Leu Ser Ile Pro Ser Leu Gly
                 50                  55                  60

GGA GGG ATG AAG TTA GCG GCT CTG AAT CTT TTT GAT AGG AAC AAA CCT      240
Gly Gly Met Lys Leu Ala Ala Leu Asn Leu Phe Asp Arg Asn Lys Pro
             65                  70                  75

AGT CTC TTA AAT GAA GAT AGC TAT ATG ATA TTT TCC TCA CGT TCT ACG      288
Ser Leu Leu Asn Glu Asp Ser Tyr Met Ile Phe Ser Ser Arg Ser Thr
         80                  85                  90

ATT GAA GAG GAT GTT AAA AAT GAC AAT CAA AAC GGC GAG CAC CCT ATT      336
Ile Glu Glu Asp Val Lys Asn Asp Asn Gln Asn Gly Glu His Pro Ile
     95                 100                 105

GAC TCA ATA GTC GAT CCT AGA GCA CCA AAT TCA AAC GAA AAT CGT CAT      384
Asp Ser Ile Val Asp Pro Arg Ala Pro Asn Ser Asn Glu Asn Arg His
110                 115                 120                 125

GGA CAA AAA TAT GTA TAT TCA GGG CTT TAT TAT ATT CAA TCG TGG AGT      432
Gly Gln Lys Tyr Val Tyr Ser Gly Leu Tyr Tyr Ile Gln Ser Trp Ser
                130                 135                 140

CTA AGA GAT TTA CCA AAT AAA AAG TTT TAT TCA GGT TAC TAT GGA TAT      480
Leu Arg Asp Leu Pro Asn Lys Lys Phe Tyr Ser Gly Tyr Tyr Gly Tyr
            145                 150                 155
```

```
GCG TAT TAC TTT GGC AAT ACA ACT GCC TCT GCA TTA CCT GTA GGT GGC    528
Ala Tyr Tyr Phe Gly Asn Thr Thr Ala Ser Ala Leu Pro Val Gly Gly
        160                 165                 170

GTA GCA ACG TAT AAA GGA ACT TGG AGC TTC ATC ACC GCA GCT GAA AAT    576
Val Ala Thr Tyr Lys Gly Thr Trp Ser Phe Ile Thr Ala Ala Glu Asn
175                 180                 185

GGC AAG AAT TAT GAA TTG TTA AGA AAT TCT GGT GGC GGT CAA GCT TAT    624
Gly Lys Asn Tyr Glu Leu Leu Arg Asn Ser Gly Gly Gly Gln Ala Tyr
190                 195                 200                 205

TCT CGA CGT AGT GCT ACT CCA GAA GAT ATT GAT TTA GAT CGT AAG ACG    672
Ser Arg Arg Ser Ala Thr Pro Glu Asp Ile Asp Leu Asp Arg Lys Thr
                210                 215                 220

GGC TTA ACA AGT GAA TTT ACT GTC AAT TTT GGT ACA AAA AAG CTC ACT    720
Gly Leu Thr Ser Glu Phe Thr Val Asn Phe Gly Thr Lys Lys Leu Thr
                225                 230                 235

GGA GGA CTT TAT TAT AAT TTA CGT GAA ACA GAT GCT AAT AAA TCA CAA    768
Gly Gly Leu Tyr Tyr Asn Leu Arg Glu Thr Asp Ala Asn Lys Ser Gln
                240                 245                 250

AAT AGA ACA CAT AAA CTC TAC GAT CTA GAA GCT GAT GTT CAT AGC AAC    816
Asn Arg Thr His Lys Leu Tyr Asp Leu Glu Ala Asp Val His Ser Asn
        255                 260                 265

CGA TTC AGG GGT AAA GTA AAG CCA ACC AAA AAA GAG TCT TCT GAA GAA    864
Arg Phe Arg Gly Lys Val Lys Pro Thr Lys Lys Glu Ser Ser Glu Glu
270                 275                 280                 285

CAT CCC TTT ACC AGC GAG GGA ACA TTA GAA GGT GGT TTT TAC GGG CCT    912
His Pro Phe Thr Ser Glu Gly Thr Leu Glu Gly Gly Phe Tyr Gly Pro
                290                 295                 300

GAG GGT CAA GAA TTA GGA GGA AAG TTT TTA GCT CAC GAC AAA AAA GTT    960
Glu Gly Gln Glu Leu Gly Gly Lys Phe Leu Ala His Asp Lys Lys Val
                305                 310                 315

TTG GGG GTA TTT AGT GCC AAA GAA CAG CAA GAA ACG TCA GAA AAC AAA   1008
Leu Gly Val Phe Ser Ala Lys Glu Gln Gln Glu Thr Ser Glu Asn Lys
                320                 325                 330

AAA TTA CCC AAA GAA ACC TTA ATT GAT GGC AAG CTA ACT ACT TTT AAA   1056
Lys Leu Pro Lys Glu Thr Leu Ile Asp Gly Lys Leu Thr Thr Phe Lys
        335                 340                 345

ACA ACC AAT GCA ACA GCC AAT GCA ACA ACC GAT GCA ACA ACC AGT ACA   1104
Thr Thr Asn Ala Thr Ala Asn Ala Thr Thr Asp Ala Thr Thr Ser Thr
350                 355                 360                 365

ACA GCC AGT ACA AAA ACC GAT ACA ACA ACC AAT GCA ACA GCC AAT ACA   1152
Thr Ala Ser Thr Lys Thr Asp Thr Thr Thr Asn Ala Thr Ala Asn Thr
                370                 375                 380

GAA AAC TTT ACG ACA AAA GAT ATA CCA AGT TTG GGT GAA GCT GAT TAT   1200
Glu Asn Phe Thr Thr Lys Asp Ile Pro Ser Leu Gly Glu Ala Asp Tyr
                385                 390                 395

CTT TTA ATT GAT AAT TAC CCT GTT CCT CTT TTC CCT GAG AGT GGT GAT   1248
Leu Leu Ile Asp Asn Tyr Pro Val Pro Leu Phe Pro Glu Ser Gly Asp
                400                 405                 410

TTC ATA AGT AGT AAG CAC CAT ACT GTA GGA AAG AAA ACC TAT CAA GTA   1296
Phe Ile Ser Ser Lys His His Thr Val Gly Lys Lys Thr Tyr Gln Val
        415                 420                 425

GAA GCA TGT TGC AGT AAT CTA AGC TAT GTA AAA TTT GGT ATG TAT TAT   1344
Glu Ala Cys Cys Ser Asn Leu Ser Tyr Val Lys Phe Gly Met Tyr Tyr
430                 435                 440                 445

GAA GCC CCA CCT AAA GAA GAA GAA AAA GAA AAA GAA AAA GAC AAA GAC   1392
Glu Ala Pro Pro Lys Glu Glu Glu Lys Glu Lys Glu Lys Asp Lys Asp
                450                 455                 460

AAA GAA AAA GAA AAA CAA GCG ACA ACA TCT ATC AAG ACT TAT TAT CAA   1440
Lys Glu Lys Glu Lys Gln Ala Thr Thr Ser Ile Lys Thr Tyr Tyr Gln
        465                 470                 475
```

| | |
|---|---|
| TTC TTA TTA GGT CTC CGT ACT CCC AGT TCT GAA ATA CCT AAA GAA GGA<br>Phe Leu Leu Gly Leu Arg Thr Pro Ser Ser Glu Ile Pro Lys Glu Gly<br>480 485 490 | 1488 |
| AGT GCA AAA TAT CAT GGT AAT TGG TTT GGT TAT ATT AGT GAT GGC GAG<br>Ser Ala Lys Tyr His Gly Asn Trp Phe Gly Tyr Ile Ser Asp Gly Glu<br>495 500 505 | 1536 |
| ACA TCT TAC TCC GCC AGT GGT GAT AAG GAA CGC AGT AAA AAT GCT GTC<br>Thr Ser Tyr Ser Ala Ser Gly Asp Lys Glu Arg Ser Lys Asn Ala Val<br>510 515 520 525 | 1584 |
| GCC GAG TTT AAT GTA AAT TTT GCC GAG AAA ACA TTA ACA GGC GAA TTA<br>Ala Glu Phe Asn Val Asn Phe Ala Glu Lys Thr Leu Thr Gly Glu Leu<br>530 535 540 | 1632 |
| AAA CGA CAC GAT ACT CAA AAT CCC GTA TTT AAA ATT AAT GCA ACC TTT<br>Lys Arg His Asp Thr Gln Asn Pro Val Phe Lys Ile Asn Ala Thr Phe<br>545 550 555 | 1680 |
| CAA AGT GGT AAG AAT GAC TTC ACT GGT ACA GCA ACC GCA AAA GAT TTA<br>Gln Ser Gly Lys Asn Asp Phe Thr Gly Thr Ala Thr Ala Lys Asp Leu<br>560 565 570 | 1728 |
| GCA ATA GAT GGT AAA AAT ACA CAA GGC ACA TCT AAA GTC AAT TTC ACG<br>Ala Ile Asp Gly Lys Asn Thr Gln Gly Thr Ser Lys Val Asn Phe Thr<br>575 580 585 | 1776 |
| GCA ACA GTA AAC GGG GCA TTT TAT GGT CCG CAC GCT ACA GAA TTA GGC<br>Ala Thr Val Asn Gly Ala Phe Tyr Gly Pro His Ala Thr Glu Leu Gly<br>590 595 600 605 | 1824 |
| GGT TAT TTC ACC TAT AAC GGA AAC AAT CCT ACA GAT AAA AAT TCA TCA<br>Gly Tyr Phe Thr Tyr Asn Gly Asn Asn Pro Thr Asp Lys Asn Ser Ser<br>610 615 620 | 1872 |
| TCC AAT TCA GAA AAG GCA AGA GCT GCC GTT GTG TTT GGA GCT AAA AAA<br>Ser Asn Ser Glu Lys Ala Arg Ala Ala Val Val Phe Gly Ala Lys Lys<br>625 630 635 | 1920 |
| CAA CAA GTA GAA ACA ACC   AA GTAATGGAAT ACTAAA A ATG ACT AAA AAA<br>Gln Gln Val Glu Thr Thr Lys                                   Met Thr Lys Lys<br>640                                                             645 | 1969 |
| CCC TAT TTT CGC CTA AGT ATT ATT TCT TGT CTT TTA ATT TCA TGC TAT<br>Pro Tyr Phe Arg Leu Ser Ile Ile Ser Cys Leu Leu Ile Ser Cys Tyr<br>650 655 660 | 2017 |
| GTA AAA GCA GAA ACT CAA AGT ATA AAA GAT ACA AAA GAA GCT ATA TCA<br>Val Lys Ala Glu Thr Gln Ser Ile Lys Asp Thr Lys Glu Ala Ile Ser<br>665 670 675 680 | 2065 |
| TCT GAA GTG GAC ACT CAA AGT ACA GAA GAT TCA GAA TTA GAA ACT ATC<br>Ser Glu Val Asp Thr Gln Ser Thr Glu Asp Ser Glu Leu Glu Thr Ile<br>685 690 695 | 2113 |
| TCA GTC ACT GCA GAA AAA GTT AGA GAT CGT AAA GAT AAT GAA GTA ACT<br>Ser Val Thr Ala Glu Lys Val Arg Asp Arg Lys Asp Asn Glu Val Thr<br>700 705 710 | 2161 |
| GGA CTT GGC AAA ATT ATA AAA ACT AGT GAA AGT ATC AGC CGA GAA CAA<br>Gly Leu Gly Lys Ile Ile Lys Thr Ser Glu Ser Ile Ser Arg Glu Gln<br>715 720 725 | 2209 |
| GTA TTA AAT ATT CGT GAT CTA ACA CGC TAT GAT CCA GGG ATT TCA GTT<br>Val Leu Asn Ile Arg Asp Leu Thr Arg Tyr Asp Pro Gly Ile Ser Val<br>730 735 740 | 2257 |
| GTA GAA CAA GGT CGC GGT GCA AGT TCT GGA TAT TCT ATT CGT GGT ATG<br>Val Glu Gln Gly Arg Gly Ala Ser Ser Gly Tyr Ser Ile Arg Gly Met<br>745 750 755 760 | 2305 |
| GAC AGA AAT AGA GTT GCT TTA TTA GTA GAT GGT TTA CCT CAA ACG CAA<br>Asp Arg Asn Arg Val Ala Leu Leu Val Asp Gly Leu Pro Gln Thr Gln<br>765 770 775 | 2353 |
| TCT TAT GTA GTG CAA AGC CCT TTA GTT GCT CGT TCA GGA TAT TCT GGC<br>Ser Tyr Val Val Gln Ser Pro Leu Val Ala Arg Ser Gly Tyr Ser Gly<br>780 785 790 | 2401 |

-continued

| | |
|---|---|
| ACT GGT GCA ATT AAT GAA ATT GAA TAT GAA AAT GTA AAG GCC GTC GAA<br>Thr Gly Ala Ile Asn Glu Ile Glu Tyr Glu Asn Val Lys Ala Val Glu<br>　　　795　　　　　　　800　　　　　　　805 | 2449 |
| ATA AGC AAG GGG GGG AGT TCT TCT GAG TAT GGT AAT GGA GCA CTA GCT<br>Ile Ser Lys Gly Gly Ser Ser Ser Glu Tyr Gly Asn Gly Ala Leu Ala<br>810　　　　　　　815　　　　　　　820 | 2497 |
| GGT TCT GTA ACA TTT CAA AGC AAA TCA GCA GCC GAT ATC TTA GAA GGA<br>Gly Ser Val Thr Phe Gln Ser Lys Ser Ala Ala Asp Ile Leu Glu Gly<br>825　　　　　　　830　　　　　　　835　　　　　　　840 | 2545 |
| GAC AAA TCA TGG GGA ATT CAA ACT AAA AAT GCT TAT TCA AGC AAA AAT<br>Asp Lys Ser Trp Gly Ile Gln Thr Lys Asn Ala Tyr Ser Ser Lys Asn<br>　　　845　　　　　　　850　　　　　　　855 | 2593 |
| AAA GGC TTT ACC CAT TCT TTA GCT GTA GCA GGA AAA CAA GGT GGA TTT<br>Lys Gly Phe Thr His Ser Leu Ala Val Ala Gly Lys Gln Gly Gly Phe<br>860　　　　　　　865　　　　　　　870 | 2641 |
| GAA GGG GTC GCC ATT TAC ACT CAC CGA AAT TCA ATT GAA ACC CAA GTC<br>Glu Gly Val Ala Ile Tyr Thr His Arg Asn Ser Ile Glu Thr Gln Val<br>875　　　　　　　880　　　　　　　885 | 2689 |
| CAT AAA GAT GCA TTA AAA GGC GTG CAA AGT TAT GAT CGA TTC ATC GCC<br>His Lys Asp Ala Leu Lys Gly Val Gln Ser Tyr Asp Arg Phe Ile Ala<br>　　　890　　　　　　　895　　　　　　　900 | 2737 |
| ACA ACA GAG GAT CAA TCT GCA TAC TTT GTG ATG CAA GAT GAG TGT CTA<br>Thr Thr Glu Asp Gln Ser Ala Tyr Phe Val Met Gln Asp Glu Cys Leu<br>905　　　　　　　910　　　　　　　915　　　　　　　920 | 2785 |
| GAT GGT TAT GAC AAG TGT AAA ACT TCA CCC AAA CGA CCT GCG ACT TTA<br>Asp Gly Tyr Asp Lys Cys Lys Thr Ser Pro Lys Arg Pro Ala Thr Leu<br>　　　925　　　　　　　930　　　　　　　935 | 2833 |
| TCC ACC CAA AGA GAA ACC GTA AGC GTT TCA GAT TAT ACG GGG GCT AAC<br>Ser Thr Gln Arg Glu Thr Val Ser Val Ser Asp Tyr Thr Gly Ala Asn<br>　　　940　　　　　　　945　　　　　　　950 | 2881 |
| CGT ATC AAA CCT AAT CCA ATG AAA TAT GAA AGC CAG TCT TGG TTT TTA<br>Arg Ile Lys Pro Asn Pro Met Lys Tyr Glu Ser Gln Ser Trp Phe Leu<br>955　　　　　　　960　　　　　　　965 | 2929 |
| AGA GGA GGT TAT CAT TTT TCT GAA CAA CAC TAT ATT GGT GGT ATT TTT<br>Arg Gly Gly Tyr His Phe Ser Glu Gln His Tyr Ile Gly Gly Ile Phe<br>970　　　　　　　975　　　　　　　980 | 2977 |
| GAA TTC ACA CAA CAA AAA TTT GAT ATC CGT GAT ATG ACA TTT CCC GCT<br>Glu Phe Thr Gln Gln Lys Phe Asp Ile Arg Asp Met Thr Phe Pro Ala<br>985　　　　　　　990　　　　　　　995　　　　　　　1000 | 3025 |
| TAT TTA AGG CCA ACA GAA GAC AAG GAT TTA CAA AGT CGC CCT TTT TAT<br>Tyr Leu Arg Pro Thr Glu Asp Lys Asp Leu Gln Ser Arg Pro Phe Tyr<br>　　　1005　　　　　　　1010　　　　　　　1015 | 3073 |
| CCA AAG CAA GAT TAT GGT GCA TAT CAA CAT ATT GGT GAT GGC AGA GGC<br>Pro Lys Gln Asp Tyr Gly Ala Tyr Gln His Ile Gly Asp Gly Arg Gly<br>　　　1020　　　　　　　1025　　　　　　　1030 | 3121 |
| GTT AAA TAT GCA AGT GGG CTT TAT TTC GAT GAA CAC CAT AGA AAA CAG<br>Val Lys Tyr Ala Ser Gly Leu Tyr Phe Asp Glu His His Arg Lys Gln<br>　　　1035　　　　　　　1040　　　　　　　1045 | 3169 |
| CGT GTA GGT ATT GAA TAT ATT TAC GAA AAT AAG AAC AAA GCG GGC ATC<br>Arg Val Gly Ile Glu Tyr Ile Tyr Glu Asn Lys Asn Lys Ala Gly Ile<br>　　　1050　　　　　　　1055　　　　　　　1060 | 3217 |
| ATT GAC AAA GCG GTG TTA AGT GCT AAT CAA CAA ACA TCA TAC TTG ACA<br>Ile Asp Lys Ala Val Leu Ser Ala Asn Gln Gln Thr Ser Tyr Leu Thr<br>1065　　　　　　　1070　　　　　　　1075　　　　　　　1080 | 3265 |
| GTT ATA TGC GAC ATA CGC ATT GCA GTC TTT ATC CAT AAT CCA AGT AAG<br>Val Ile Cys Asp Ile Arg Ile Ala Val Phe Ile His Asn Pro Ser Lys<br>　　　1085　　　　　　　1090　　　　　　　1095 | 3313 |
| AAT TGC CGC CCA ACA CTT GAT AAA CCT TAT TCA TAC TAT CAT TCT GAT<br>Asn Cys Arg Pro Thr Leu Asp Lys Pro Tyr Ser Tyr Tyr His Ser Asp<br>　　　1100　　　　　　　1105　　　　　　　1110 | 3361 |

```
AGA AAT GTT TAT AAA GAA AAA CAT AAC ATG TTG CAA TTG AAT TTA GAG       3409
Arg Asn Val Tyr Lys Glu Lys His Asn Met Leu Gln Leu Asn Leu Glu
    1115                1120                1125

AAA AAA ATT CAA CAA AAT TGG CTT ACT CAT CAA ATT GCC TTC AAT CTT       3457
Lys Lys Ile Gln Gln Asn Trp Leu Thr His Gln Ile Ala Phe Asn Leu
1130                1135                1140

GGT TTT GAT GAC TTT ACT TCC GCA CTT CAG CAT AAA GAT TAT TTA ACT       3505
Gly Phe Asp Asp Phe Thr Ser Ala Leu Gln His Lys Asp Tyr Leu Thr
1145                1150                1155                1160

CGA CGT GTT ATC GCT ACG GCA AGT AGT ATT TCA GAG AAA CGT GGT GAA       3553
Arg Arg Val Ile Ala Thr Ala Ser Ser Ile Ser Glu Lys Arg Gly Glu
                1165                1170                1175

GCA AGA AGA AAT GGT TTA CAA TCA AGT CCT TAC TTA TAC CCA ACA CCA       3601
Ala Arg Arg Asn Gly Leu Gln Ser Ser Pro Tyr Leu Tyr Pro Thr Pro
            1180                1185                1190

AAA GCA GAG TTG GTA GGA GGA GAT CTT TGT AAT TAT CAA GGT AAG TCC       3649
Lys Ala Glu Leu Val Gly Gly Asp Leu Cys Asn Tyr Gln Gly Lys Ser
        1195                1200                1205

TCT AAT TAC AGT GAC TGT AAA GTG CGG TTA ATT AAA GGG AAA AAT TAT       3697
Ser Asn Tyr Ser Asp Cys Lys Val Arg Leu Ile Lys Gly Lys Asn Tyr
    1210                1215                1220

TAT TTC GCA GCA CGC AAT AAT ATG GCA TTA GGG AAA TAC GTT GAT TTA       3745
Tyr Phe Ala Ala Arg Asn Asn Met Ala Leu Gly Lys Tyr Val Asp Leu
1225                1230                1235                1240

GGT TTA GGT ATG AGG TAT GAC GTA TCT CGT ACA AAA GCT AAT GAA TCA       3793
Gly Leu Gly Met Arg Tyr Asp Val Ser Arg Thr Lys Ala Asn Glu Ser
                1245                1250                1255

ACT ATT AGT GTT GGT AAA TTT AAA AAT TTC TCT TGG AAT ACT GGT ATT       3841
Thr Ile Ser Val Gly Lys Phe Lys Asn Phe Ser Trp Asn Thr Gly Ile
            1260                1265                1270

GTC ATA AAA CCA ACG GAA TGG CTT GAT CTT TCT TAT CGC CTT TCT ACT       3889
Val Ile Lys Pro Thr Glu Trp Leu Asp Leu Ser Tyr Arg Leu Ser Thr
        1275                1280                1285

GGA TTT AGA AAT CCT AGT TTT GCT GAA ATG TAT GGT TGG CGG TAT GGT       3937
Gly Phe Arg Asn Pro Ser Phe Ala Glu Met Tyr Gly Trp Arg Tyr Gly
    1290                1295                1300

GGC AAG GAT ACC GAT GTT TAT ATA GGT AAA TTT AAG CCT GAA ACA TCT       3985
Gly Lys Asp Thr Asp Val Tyr Ile Gly Lys Phe Lys Pro Glu Thr Ser
1305                1310                1315                1320

CGT AAC CAA GAG TTT GGT CTC GCT CTA AAA GGG GAT TTT GGT AAT ATT       4033
Arg Asn Gln Glu Phe Gly Leu Ala Leu Lys Gly Asp Phe Gly Asn Ile
                1325                1330                1335

GAG ATC AGT CAT TTT AGT AAT GCT TAT CGA AAT CTT ATC GCC TTT GCT       4081
Glu Ile Ser His Phe Ser Asn Ala Tyr Arg Asn Leu Ile Ala Phe Ala
            1340                1345                1350

GAA GAA CTT AGT AAA AAT GGA ACT ACT GGA AAG GGC AAT TAT GGA TAT       4129
Glu Glu Leu Ser Lys Asn Gly Thr Thr Gly Lys Gly Asn Tyr Gly Tyr
        1355                1360                1365

CAT AAT GCA CAA AAT GCA AAA TTA GTT GGC GTA AAT ATA ACT GCG CAA       4177
His Asn Ala Gln Asn Ala Lys Leu Val Gly Val Asn Ile Thr Ala Gln
    1370                1375                1380

TTA GAT TTT AAT GGT TTA TGG AAA CGT ATT CCC TAC GGT TGG TAT GCA       4225
Leu Asp Phe Asn Gly Leu Trp Lys Arg Ile Pro Tyr Gly Trp Tyr Ala
1385                1390                1395                1400

ACA TTT GCT TAT AAC CGA GTA AAA GTT AAA GAT CAA AAA ATC AAT GCT       4273
Thr Phe Ala Tyr Asn Arg Val Lys Val Lys Asp Gln Lys Ile Asn Ala
                1405                1410                1415

GGT TTA GCT TCC GTA AGC AGT TAT TTA TTT GAT GCC ATT CAG CCC AGC       4321
Gly Leu Ala Ser Val Ser Ser Tyr Leu Phe Asp Ala Ile Gln Pro Ser
            1420                1425                1430
```

```
CGT TAT ATC ATT GGT TTA GGC TAT GAT CAT CCA AGT AAT ACT TGG GGA    4369
Arg Tyr Ile Ile Gly Leu Gly Tyr Asp His Pro Ser Asn Thr Trp Gly
        1435                1440                1445

ATT AAG ACA ATG TTT ACT CAA TCA AAA GCA AAA TCT CAA AAT GAA TTG    4417
Ile Lys Thr Met Phe Thr Gln Ser Lys Ala Lys Ser Gln Asn Glu Leu
    1450                1455                1460

CTA GGA AAA CGT GCA TTG GGT AAC AAT TCA AGG AAT GTA AAA TCA ACA    4465
Leu Gly Lys Arg Ala Leu Gly Asn Asn Ser Arg Asn Val Lys Ser Thr
1465                1470                1475                1480

AGA AAA CTT ACT CGG GCA TGG CAT ATC TTA GAT GTA TCG GGT TAT TAC    4513
Arg Lys Leu Thr Arg Ala Trp His Ile Leu Asp Val Ser Gly Tyr Tyr
            1485                1490                1495

ATG GTG AAT AGA AGT ATT TTG TTC CGA TTA GGA GTA TAT AAT TTA TTA    4561
Met Val Asn Arg Ser Ile Leu Phe Arg Leu Gly Val Tyr Asn Leu Leu
        1500                1505                1510

AAC TAT CGC TAT GTC ACT TGG GAA GCG GTG CGT CAA ACA GCA CAA GGT    4609
Asn Tyr Arg Tyr Val Thr Trp Glu Ala Val Arg Gln Thr Ala Gln Gly
    1515                1520                1525

GCG GTC AAT CAA CAT CAA AAT GTT GGT AAC TAT ACT CGC TAC GCA GCA    4657
Ala Val Asn Gln His Gln Asn Val Gly Asn Tyr Thr Arg Tyr Ala Ala
1530                1535                1540

TCA GGA CGA AAC TAT ACC TTA ACA TTA GAA ATG AAA TTC TAA            4699
Ser Gly Arg Asn Tyr Thr Leu Thr Leu Glu Met Lys Phe
1545                1550                1555

(2) INFORMATION FOR SEQ ID NO:2:

(i) SEQUENCE CHARACTERISTICS:
        (A) LENGTH: 5033 base pairs
        (B) TYPE: nucleic acid
        (C) STRANDEDNESS: double
        (D) TOPOLOGY: linear (ix) FEATURE:
        (A) NAME/KEY: CDS
        (B) LOCATION: join(169..2148, 2165..4900)

(xi) SEQUENCE DESCRIPTION: SEQ ID NO:2:

GCCCAAGCTA CATTGGTTAA TGATAAGCCT ATAAATGATA AGAAAGAAAT TTGTTTTACG     60

CCATTTTTCA TATTTTATCC ATGAACTTAA AAAACTCTAA CTTGACATTA TTACAAAAAA    120

AGATCAATAA TGCGAATTAT TATCAATTTT GTATGAGTAT ATAATTCT ATG AAA TCT    177
                                                    Met Lys Ser
                                                      1

GTA CCT CTT ATC TCT GGT GGA CTT TCC TTT TTA CTA AGT GCT TGT AGC      225
Val Pro Leu Ile Ser Gly Gly Leu Ser Phe Leu Leu Ser Ala Cys Ser
      5                  10                  15

GGA GGG GGG TCT TTT GAT GTA GAT AAC GTC TCT AAT ACC CCC TCT TCT      273
Gly Gly Gly Ser Phe Asp Val Asp Asn Val Ser Asn Thr Pro Ser Ser
 20                  25                  30                  35

AAA CCA CGT TAT CAA GAC GAT ACC TCG AAT CAA AGA AAA AAA TCT AAT      321
Lys Pro Arg Tyr Gln Asp Asp Thr Ser Asn Gln Arg Lys Lys Ser Asn
                 40                  45                  50

TTG AAA AAG TTG TTC ATT CCT TCT TTA GGA GGA GGG ATG AAA TTG GTG      369
Leu Lys Lys Leu Phe Ile Pro Ser Leu Gly Gly Gly Met Lys Leu Val
             55                  60                  65

GCT CAG AAT CTT CGT GGT AAT AAA GAA CCT AGT TTC TTA AAT GAA GAT      417
Ala Gln Asn Leu Arg Gly Asn Lys Glu Pro Ser Phe Leu Asn Glu Asp
         70                  75                  80

GAC TAT ATA TCA TAT TTT TCC TCA CTT TCT ACG ATT GAA AAG GAT GTT      465
Asp Tyr Ile Ser Tyr Phe Ser Ser Leu Ser Thr Ile Glu Lys Asp Val
     85                  90                  95

AAA GAT AAC AAT AAA AAC GGG GCG GAC CTT ATT GGC TCA ATA GAC GAG      513
```

-continued

| | | | | | | | | | | | | | | |
|---|---|---|---|---|---|---|---|---|---|---|---|---|---|---|
| Lys | Asp | Asn | Asn | Lys | Asn | Gly | Ala | Asp | Leu | Ile | Gly | Ser | Ile | Asp | Glu |
| 100 | | | | | 105 | | | | 110 | | | | | 115 | |

```
CCT AGT ACA ACA AAT CCA CCC GAA AAG CAT CAT GGA CAA AAA TAT GTA        561
Pro Ser Thr Thr Asn Pro Pro Glu Lys His His Gly Gln Lys Tyr Val
            120                 125                 130

TAT TCA GGG CTT TAT TAT ACT CCA TCG TGG AGT TTA AAC GAT TCT AAA        609
Tyr Ser Gly Leu Tyr Tyr Thr Pro Ser Trp Ser Leu Asn Asp Ser Lys
            135                 140                 145

AAC AAG TTT TAT TTA GGT TAC TAT GGA TAT GCG TTT TAT TAT GGT AAT        657
Asn Lys Phe Tyr Leu Gly Tyr Tyr Gly Tyr Ala Phe Tyr Tyr Gly Asn
            150                 155                 160

AAA ACT GCA ACA AAC TTG CCA GTA AAC GGT GTA GCT AAA TAC AAA GGA        705
Lys Thr Ala Thr Asn Leu Pro Val Asn Gly Val Ala Lys Tyr Lys Gly
            165                 170                 175

ACT TGG GAT TTC ATC ACT GCA ACT AAA AAT GGC AAA CGT TAT CCT TTG        753
Thr Trp Asp Phe Ile Thr Ala Thr Lys Asn Gly Lys Arg Tyr Pro Leu
180                 185                 190                 195

TTA AGT AAT GGC AGT CAC GCT TAT TAT CGA CGT AGT GCA ATT CCA GAA        801
Leu Ser Asn Gly Ser His Ala Tyr Tyr Arg Arg Ser Ala Ile Pro Glu
                200                 205                 210

GAT ATT GAT TTA GAA AAT GAT TCA AAG AAT GGT GAT ATA GGC TTA ATA        849
Asp Ile Asp Leu Glu Asn Asp Ser Lys Asn Gly Asp Ile Gly Leu Ile
            215                 220                 225

AGT GAA TTT AGT GCA GAT TTT GGG ACT AAA AAA CTG ACA GGA CAA CTG        897
Ser Glu Phe Ser Ala Asp Phe Gly Thr Lys Lys Leu Thr Gly Gln Leu
            230                 235                 240

TCT TAC ACC AAA AGA AAA ACT AAT AAT CAA CCA TAT GAA AAG AAA AAA        945
Ser Tyr Thr Lys Arg Lys Thr Asn Asn Gln Pro Tyr Glu Lys Lys Lys
            245                 250                 255

CTC TAT GAT ATA GAT GCC GAT ATT TAT AGT AAT AGA TTC AGG GGT ACA        993
Leu Tyr Asp Ile Asp Ala Asp Ile Tyr Ser Asn Arg Phe Arg Gly Thr
260                 265                 270                 275

GTA AAG CCA ACC GAA AAA GAT TCT GAA GAA CAT CCC TTT ACC AGC GAG       1041
Val Lys Pro Thr Glu Lys Asp Ser Glu Glu His Pro Phe Thr Ser Glu
            280                 285                 290

GGA ACA TTA GAA GGT GGT TTT TAT GGG CCT AAT GCT GAA GAA CTA GGG       1089
Gly Thr Leu Glu Gly Gly Phe Tyr Gly Pro Asn Ala Glu Glu Leu Gly
            295                 300                 305

GGG AAA TTT TTA GCT ACG GAT AAC CGA GTT TTT GGG GTA TTT AGT GCC       1137
Gly Lys Phe Leu Ala Thr Asp Asn Arg Val Phe Gly Val Phe Ser Ala
            310                 315                 320

AAA GAA ACG GAA GAA ACA AAA AAG GAA GCG TTA TCC AAG GAA ACC TTA       1185
Lys Glu Thr Glu Glu Thr Lys Lys Glu Ala Leu Ser Lys Glu Thr Leu
            325                 330                 335

ATT GAT GGC AAG CTA ATT ACT TTC TCT ACT AAA AAA ACC GAT GCA AAA       1233
Ile Asp Gly Lys Leu Ile Thr Phe Ser Thr Lys Lys Thr Asp Ala Lys
340                 345                 350                 355

ACC AAT GCA ACA ACC AGT ACC GCA GCT AAT ACA ACA ACC GAT ACA ACC       1281
Thr Asn Ala Thr Thr Ser Thr Ala Ala Asn Thr Thr Thr Asp Thr Thr
            360                 365                 370

GCC AAT ACA ATA ACC GAT GAA AAA AAC TTT AAG ACG GAA GAT ATA TCA       1329
Ala Asn Thr Ile Thr Asp Glu Lys Asn Phe Lys Thr Glu Asp Ile Ser
            375                 380                 385

AGT TTT GGT GAA GCT GAT TAT CTG TTA ATT GAC AAA TAT CCT ATT CCA       1377
Ser Phe Gly Glu Ala Asp Tyr Leu Leu Ile Asp Lys Tyr Pro Ile Pro
            390                 395                 400

CTT TTA CCT GAT AAA AAT ACT AAT GAT TTC ATA AGT AGT AAG CAT CAT       1425
Leu Leu Pro Asp Lys Asn Thr Asn Asp Phe Ile Ser Ser Lys His His
405                 410                 415

ACT GTA GGA AAT AAA CGC TAT AAA GTG GAA GCA TGT TGC AGT AAT CTA       1473
```

```
            Thr Val Gly Asn Lys Arg Tyr Lys Val Glu Ala Cys Cys Ser Asn Leu
            420                 425                 430                 435

AGC TAT GTG AAA TTT GGT ATG TAT TAT GAA GAC CCA CTT AAA GAA AAA            1521
Ser Tyr Val Lys Phe Gly Met Tyr Tyr Glu Asp Pro Leu Lys Glu Lys
            440                 445                 450

GAA ACA GAA ACA GAA ACA GAA ACA GAA AAA GAC AAA GAA AAA GAA AAA            1569
Glu Thr Glu Thr Glu Thr Glu Thr Glu Lys Asp Lys Glu Lys Glu Lys
            455                 460                 465

GAA AAA GAC AAA GAC AAA GAA AAA CAA ACG GCG GCA ACG ACC AAC ACT            1617
Glu Lys Asp Lys Asp Lys Glu Lys Gln Thr Ala Ala Thr Thr Asn Thr
            470                 475                 480

TAT TAT CAA TTC TTA TTA GGT CAC CGT ACT CCC AAG GAC GAC ATA CCT            1665
Tyr Tyr Gln Phe Leu Leu Gly His Arg Thr Pro Lys Asp Asp Ile Pro
            485                 490                 495

AAA ACA GGA AGT GCA AAA TAT CAT GGT AGT TGG TTT GGT TAT ATT ACT            1713
Lys Thr Gly Ser Ala Lys Tyr His Gly Ser Trp Phe Gly Tyr Ile Thr
500                 505                 510                 515

GAC GGT AAG ACA TCT TAC TCC CCC AGT GGT GAT AAG AAA CGC GAT AAA            1761
Asp Gly Lys Thr Ser Tyr Ser Pro Ser Gly Asp Lys Lys Arg Asp Lys
                    520                 525                 530

AAT GCT GTC GCC GAG TTT AAT GTT GAT TTT GCC GAG AAA AAG CTA ACA            1809
Asn Ala Val Ala Glu Phe Asn Val Asp Phe Ala Glu Lys Lys Leu Thr
                535                 540                 545

GGC GAA TTA AAA CGA CAC GAT ACT GGA AAT CCC GTA TTT AGT ATT GAG            1857
Gly Glu Leu Lys Arg His Asp Thr Gly Asn Pro Val Phe Ser Ile Glu
            550                 555                 560

GCA AAC TTT AAT AAT AGT AGT AAT GCC TTC ACT GGT ACA GCA ACC GCA            1905
Ala Asn Phe Asn Asn Ser Ser Asn Ala Phe Thr Gly Thr Ala Thr Ala
            565                 570                 575

ACA AAT TTT GTA ATA GAT GGT AAA AAT AGT CAA AAT AAA AAT ACC CCA            1953
Thr Asn Phe Val Ile Asp Gly Lys Asn Ser Gln Asn Lys Asn Thr Pro
580                 585                 590                 595

ATT AAT ATT ACA ACT AAA GTA AAC GGG GCA TTT TAT GGA CCT AAG GCT            2001
Ile Asn Ile Thr Thr Lys Val Asn Gly Ala Phe Tyr Gly Pro Lys Ala
                    600                 605                 610

TCT GAA TTA GGC GGT TAT TTC ACT TAT AAC GGA AAT TCT ACA GCT ACA            2049
Ser Glu Leu Gly Gly Tyr Phe Thr Tyr Asn Gly Asn Ser Thr Ala Thr
                615                 620                 625

AAT TCT GAA AGT TCC TCA ACC GTA TCT TCA TCA TCC AAT TCA AAA AAT            2097
Asn Ser Glu Ser Ser Ser Thr Val Ser Ser Ser Ser Asn Ser Lys Asn
            630                 635                 640

GCA AGA GCT GCA GTT GTC TTT GGT GCG AGA CAA CAA GTA GAA ACA ACC            2145
Ala Arg Ala Ala Val Val Phe Gly Ala Arg Gln Gln Val Glu Thr Thr
            645                 650                 655

AAA TAATGGAATA CTAAAA ATG ACT AAA AAA CCC TAT TTT CGC CTA AGT            2194
Lys                     Met Thr Lys Lys Pro Tyr Phe Arg Leu Ser
660                             665                 670

ATT ATT TCT TGT CTT TTA ATT TCA TGC TAT GTA AAA GCA GAA ACT CAA            2242
Ile Ile Ser Cys Leu Leu Ile Ser Cys Tyr Val Lys Ala Glu Thr Gln
                675                 680                 685

AGT ATA AAA GAT ACA AAA GAA GCT ATA TCA TCT GAA GTG GAC ACT CAA            2290
Ser Ile Lys Asp Thr Lys Glu Ala Ile Ser Ser Glu Val Asp Thr Gln
            690                 695                 700

AGT ACA GAA GAT TCA GAA TTA GAA ACT ATC TCA GTC ACT GCA GAA AAA            2338
Ser Thr Glu Asp Ser Glu Leu Glu Thr Ile Ser Val Thr Ala Glu Lys
            705                 710                 715

ATA AGA GAT CGT AAA GAT AAT GAA GTA ACT GGA CTT GGC AAA ATT ATC            2386
Ile Arg Asp Arg Lys Asp Asn Glu Val Thr Gly Leu Gly Lys Ile Ile
            720                 725                 730

AAA ACT AGT GAA AGT ATC AGC CGA GAA CAA GTA TTA AAT ATT CGT GAT            2434
```

```
                Lys Thr Ser Glu Ser Ile Ser Arg Glu Gln Val Leu Asn Ile Arg Asp
                735                 740                 745                 750

CTA ACA CGC TAT GAT CCA GGG ATT TCA GTT GTA GAA CAA GGT CGC GGT              2482
Leu Thr Arg Tyr Asp Pro Gly Ile Ser Val Val Glu Gln Gly Arg Gly
                    755                 760                 765

GCA AGT TCT GGA TAT TCT ATT CGT GGT ATG GAC AGA AAT AGA GTT GCT              2530
Ala Ser Ser Gly Tyr Ser Ile Arg Gly Met Asp Arg Asn Arg Val Ala
            770                 775                 780

TTA TTA GTA GAT GGT TTA CCT CAA ACG CAA TCT TAT GTA GTG CAA AGC              2578
Leu Leu Val Asp Gly Leu Pro Gln Thr Gln Ser Tyr Val Val Gln Ser
        785                 790                 795

CCT TTA GTT GCT CGT TCA GGA TAT TCT GGC ACT GGT GCA ATT AAT GAA              2626
Pro Leu Val Ala Arg Ser Gly Tyr Ser Gly Thr Gly Ala Ile Asn Glu
    800                 805                 810

ATT GAA TAT GAA AAT GTA AAG GCC GTC GAA ATA AGC AAG GGG GGG AGT              2674
Ile Glu Tyr Glu Asn Val Lys Ala Val Glu Ile Ser Lys Gly Gly Ser
815                 820                 825                 830

TCT TCT GAG TAT GGT AAT GGA GCA CTA GCT GGT TCT GTA ACA TTT CAA              2722
Ser Ser Glu Tyr Gly Asn Gly Ala Leu Ala Gly Ser Val Thr Phe Gln
                835                 840                 845

AGC AAA TCA GCA GCC GAT ATC TTA GAA GGA GAC AAA TCA TGG GGA ATT              2770
Ser Lys Ser Ala Ala Asp Ile Leu Glu Gly Asp Lys Ser Trp Gly Ile
            850                 855                 860

CAA ACT AAA AAT GCT TAT TCA AGC AAA AAT AAA GGC TTT ACC CAT TCT              2818
Gln Thr Lys Asn Ala Tyr Ser Ser Lys Asn Lys Gly Phe Thr His Ser
        865                 870                 875

TTA GCT GTA GCA GGA AAA CAA GGT GGA TTT GAA GGG CTA GCC ATT TAC              2866
Leu Ala Val Ala Gly Lys Gln Gly Gly Phe Glu Gly Leu Ala Ile Tyr
    880                 885                 890

ACT CAA CGA AAT TCA ATT GAA ACC CAA GTC CAT AAA GAT GCA TTA AAA              2914
Thr Gln Arg Asn Ser Ile Glu Thr Gln Val His Lys Asp Ala Leu Lys
895                 900                 905                 910

GGC GTA CAA AGT TAT GAT CGA TTA ATC GCC ACA ACA GAT AAA TCT TCA              2962
Gly Val Gln Ser Tyr Asp Arg Leu Ile Ala Thr Thr Asp Lys Ser Ser
                915                 920                 925

GGA TAC TTT GTG ATA CAA GGT GAG TGT CCA AAT GGT GAT GAC AAG TGT              3010
Gly Tyr Phe Val Ile Gln Gly Glu Cys Pro Asn Gly Asp Asp Lys Cys
            930                 935                 940

GCA GCC AAG CCA CCT GCG ACT TTA TCC ACC CAA AGC GAA ACC GTA AGC              3058
Ala Ala Lys Pro Pro Ala Thr Leu Ser Thr Gln Ser Glu Thr Val Ser
        945                 950                 955

GTT TCA GAT TAT ACG GGG GCT AAC CGT ATC AAA CCT AAT CCA ATG AAA              3106
Val Ser Asp Tyr Thr Gly Ala Asn Arg Ile Lys Pro Asn Pro Met Lys
    960                 965                 970

TAT GAA AGC CAG TCT TGG TTT TTA AGA GGA GGG TAT CAT TTT TCT GAA              3154
Tyr Glu Ser Gln Ser Trp Phe Leu Arg Gly Gly Tyr His Phe Ser Glu
975                 980                 985                 990

CAA CAT TAT ATT GGT GGT ATT TTT GAA TTC ACA CAA CAA AAA TTT GAT              3202
Gln His Tyr Ile Gly Gly Ile Phe Glu Phe Thr Gln Gln Lys Phe Asp
                995                 1000                1005

ATC CGT GAT ATG ACA TTT CCC GCT TAT TTA AGC CCA ACA GAA AGA CGG              3250
Ile Arg Asp Met Thr Phe Pro Ala Tyr Leu Ser Pro Thr Glu Arg Arg
            1010                1015                1020

GAT GAT AGT AGT CGT TCT TTT TAT CCA ATG CAA GAT CAT GGT GCA TAT              3298
Asp Asp Ser Ser Arg Ser Phe Tyr Pro Met Gln Asp His Gly Ala Tyr
        1025                1030                1035

CAA CAT ATT GAG GAT GGC AGA GGC GTT AAA TAT GCA AGT GGG CTT TAT              3346
Gln His Ile Glu Asp Gly Arg Gly Val Lys Tyr Ala Ser Gly Leu Tyr
    1040                1045                1050

TTC GAT GAA CAC CAT AGA AAA CAG CGT GTA GGT ATT GAA TAT ATT TAC              3394
```

```
Phe Asp Glu His His Arg Lys Gln Arg Val Gly Ile Glu Tyr Ile Tyr
1055                1060                1065                1070

GAA AAT AAG AAC AAA GCG GGC ATC ATT GAC AAA GCA GTG TTA AGT GCT    3442
Glu Asn Lys Asn Lys Ala Gly Ile Ile Asp Lys Ala Val Leu Ser Ala
            1075                1080                1085

AAT CAA CAA AAC ATC ATA CTT GAC AGT TAT ATG CGA CAT ACG CAT TGC    3490
Asn Gln Gln Asn Ile Ile Leu Asp Ser Tyr Met Arg His Thr His Cys
            1090                1095                1100

AGT CTT TAT CCT AAT CCA AGT AAG AAT TGC CGC CCA ACA CTT GAT AAA    3538
Ser Leu Tyr Pro Asn Pro Ser Lys Asn Cys Arg Pro Thr Leu Asp Lys
            1105                1110                1115

CCT TAT TCA TAC TAT CGT TCT GAT AGA AAT GTT TAT AAA GAA AAA CAT    3586
Pro Tyr Ser Tyr Tyr Arg Ser Asp Arg Asn Val Tyr Lys Glu Lys His
            1120                1125                1130

AAT ATG TTG CAA TTG AAT TTA GAG AAA AAA ATT CAA CAA AAT TGG CTT    3634
Asn Met Leu Gln Leu Asn Leu Glu Lys Lys Ile Gln Gln Asn Trp Leu
1135                1140                1145                1150

ACT CAT CAA ATT GTC TTC AAT CTT GGT TTT GAT GAC TTT ACT TCA GCG    3682
Thr His Gln Ile Val Phe Asn Leu Gly Phe Asp Asp Phe Thr Ser Ala
            1155                1160                1165

CTT CAG CAT AAA GAT TAT TTA ACT CGA CGT GTT ATC GCT ACG GCA GAT    3730
Leu Gln His Lys Asp Tyr Leu Thr Arg Arg Val Ile Ala Thr Ala Asp
            1170                1175                1180

AGT ATT CCA AGG AAA CCT GGT GAA ACT GGT AAA CCA AGA AAT GGT TTG    3778
Ser Ile Pro Arg Lys Pro Gly Glu Thr Gly Lys Pro Arg Asn Gly Leu
            1185                1190                1195

CAA TCA CAA CCT TAC TTA TAC CCA AAA CCA GAG CCA TAT TTT GCA GGA    3826
Gln Ser Gln Pro Tyr Leu Tyr Pro Lys Pro Glu Pro Tyr Phe Ala Gly
            1200                1205                1210

CAA GAT CAT TGT AAT TAT CAA GGT AGC TCC TCT AAT TAC AGA GAC TGT    3874
Gln Asp His Cys Asn Tyr Gln Gly Ser Ser Ser Asn Tyr Arg Asp Cys
1215                1220                1225                1230

AAA GTG CGG TTA ATT AAA GGG AAA AAT TAT TAT TTC GCA GCA CGC AAT    3922
Lys Val Arg Leu Ile Lys Gly Lys Asn Tyr Tyr Phe Ala Ala Arg Asn
            1235                1240                1245

AAT ATG GCA TTA GGG AAA TAC GTT GAT TTA GGT TTA GGT ATT CGG TAT    3970
Asn Met Ala Leu Gly Lys Tyr Val Asp Leu Gly Leu Gly Ile Arg Tyr
            1250                1255                1260

GAC GTA TCT CGT ACA AAA GCT AAT GAA TCA ACT ATT AGT GTT GGT AAA    4018
Asp Val Ser Arg Thr Lys Ala Asn Glu Ser Thr Ile Ser Val Gly Lys
            1265                1270                1275

TTT AAA AAT TTC TCT TGG AAT ACT GGT ATT GTC ATA AAA CCA ACG GAA    4066
Phe Lys Asn Phe Ser Trp Asn Thr Gly Ile Val Ile Lys Pro Thr Glu
            1280                1285                1290

TGG CTT GAT CTT TCT TAT CGC CTT TCT ACT GGA TTT AGA AAT CCT AGT    4114
Trp Leu Asp Leu Ser Tyr Arg Leu Ser Thr Gly Phe Arg Asn Pro Ser
1295                1300                1305                1310

TTT TCT GAA ATG TAT GGT TGG CGG TAT GGT GGC AAG AAT GAC GAG GTT    4162
Phe Ser Glu Met Tyr Gly Trp Arg Tyr Gly Gly Lys Asn Asp Glu Val
            1315                1320                1325

TAT GTA GGT AAA TTT AAG CCT GAA ACA TCT CGT AAC CAA GAG TTT GGT    4210
Tyr Val Gly Lys Phe Lys Pro Glu Thr Ser Arg Asn Gln Glu Phe Gly
            1330                1335                1340

CTC GCT CTA AAA GGG GAT TTT GGT AAT ATT GAG ATC AGT CAT TTT AGT    4258
Leu Ala Leu Lys Gly Asp Phe Gly Asn Ile Glu Ile Ser His Phe Ser
            1345                1350                1355

AAT GCT TAT CGA AAT CTT ATC GCC TTT GCT GAA GAA CTT AGT AAA AAT    4306
Asn Ala Tyr Arg Asn Leu Ile Ala Phe Ala Glu Glu Leu Ser Lys Asn
            1360                1365                1370

GGA ACT GGA AAG GGC AAT TAT GGA TAT CAT AAT GCA CAA AAT GCA AAA    4354
```

| | | |
|---|---|---|
| Gly Thr Gly Lys Gly Asn Tyr Gly Tyr His Asn Ala Gln Asn Ala Lys<br>1375                  1380                  1385                  1390 | |

```
TTA GTT GGC GTA AAT ATA ACT GCA CAA TTA GAT TTT AAT GGT TTA TGG        4402
Leu Val Gly Val Asn Ile Thr Ala Gln Leu Asp Phe Asn Gly Leu Trp
                1395                1400                1405

AAA CGT ATT CCC TAC GGT TGG TAT GCA ACA TTT GCT TAT AAC CAA GTA        4450
Lys Arg Ile Pro Tyr Gly Trp Tyr Ala Thr Phe Ala Tyr Asn Gln Val
            1410                1415                1420

AAA GTT AAA GAT CAA AAA ATC AAT GCT GGT TTA GCC TCC GTA AGC AGT        4498
Lys Val Lys Asp Gln Lys Ile Asn Ala Gly Leu Ala Ser Val Ser Ser
        1425                1430                1435

TAT TTA TTT GAT GCC ATT CAG CCC AGC CGT TAT ATC ATT GGT TTA GGC        4546
Tyr Leu Phe Asp Ala Ile Gln Pro Ser Arg Tyr Ile Ile Gly Leu Gly
    1440                1445                1450

TAT GAT CAT CCA AGT AAT ACT TGG GGA ATT AAT ACA ATG TTT ACT CAA        4594
Tyr Asp His Pro Ser Asn Thr Trp Gly Ile Asn Thr Met Phe Thr Gln
1455                1460                1465                1470

TCA AAA GCA AAA TCT CAA AAT GAA TTG CTA GGA AAA CGT GCA TTA GGT        4642
Ser Lys Ala Lys Ser Gln Asn Glu Leu Leu Gly Lys Arg Ala Leu Gly
                1475                1480                1485

AAC AAT TCA AGG GAT GTA AAA TCA ACA AGA AAA CTT ACT CGG GCA TGG        4690
Asn Asn Ser Arg Asp Val Lys Ser Thr Arg Lys Leu Thr Arg Ala Trp
            1490                1495                1500

CAT ATC TTA GAT GTA TCG GGT TAT TAC ATG GCG AAT AAA AAT ATT ATG        4738
His Ile Leu Asp Val Ser Gly Tyr Tyr Met Ala Asn Lys Asn Ile Met
        1505                1510                1515

CTT CGA TTA GGG ATA TAT AAT TTA TTC AAC TAT CGC TAT GTT ACT TGG        4786
Leu Arg Leu Gly Ile Tyr Asn Leu Phe Asn Tyr Arg Tyr Val Thr Trp
    1520                1525                1530

GAA GCG GTG CGT CAA ACA GCA CAA GGT GCG GTC AAT CAA CAT CAA AAT        4834
Glu Ala Val Arg Gln Thr Ala Gln Gly Ala Val Asn Gln His Gln Asn
1535                1540                1545                1550

GTT GGT AGC TAT ACT CGC TAC GCA GCA TCA GGA CGA AAC TAT ACC TTA        4882
Val Gly Ser Tyr Thr Arg Tyr Ala Ala Ser Gly Arg Asn Tyr Thr Leu
                1555                1560                1565

ACA TTA GAA ATG AAA TTC TAAATTAAAA TGCGCCAGAT GGACTAGATA               4930
Thr Leu Glu Met Lys Phe
            1570

TGCTATATCT ATACCTTACT GGCGCATCTT TTTCTGTTCT ATAATCTGCT TAAGTGAAAA     4990

ACCAAACTTG GATTTTTTAC AAGATCTTTT CACACATTTA TTG                        5033

(2) INFORMATION FOR SEQ ID NO:3:

(i) SEQUENCE CHARACTERISTICS:
        (A) LENGTH: 5009 base pairs
        (B) TYPE: nucleic acid
        (C) STRANDEDNESS: double
        (D) TOPOLOGY: linear (ix) FEATURE:
        (A) NAME/KEY: CDS
        (B) LOCATION: join(121..2100, 2117..4852)

(xi) SEQUENCE DESCRIPTION: SEQ ID NO:3:

ATTTGTTTTA CGCCATTTTT CATATTTTAT CCATGAACTT AAAAAACTCT AACTTGACAT       60

TATTACAAAA AAAGATCAAT AATGCGAATT ATTATCAATT TTGTATGAGT ATATAATTCT      120

ATG AAA TCT GTA CCT CTT ATC TCT GGT GGA CTT TCC TTT TTA CTA AGT        168
Met Lys Ser Val Pro Leu Ile Ser Gly Gly Leu Ser Phe Leu Leu Ser
  1               5                  10                  15

GCT TGT AGC GGA GGG GGG TCT TTT GAT GTA GAT AAC GTC TCT AAT ACC        216
Ala Cys Ser Gly Gly Gly Ser Phe Asp Val Asp Asn Val Ser Asn Thr
```

```
                        20                      25                      30
CCC TCT TCT AAA CCA CGT TAT CAA GAC GAT ACC TCG AAT CAA AGA AAA            264
Pro Ser Ser Lys Pro Arg Tyr Gln Asp Asp Thr Ser Asn Gln Arg Lys
            35                      40                      45

AAA TCT AAT TTG AAA AAG TTG TTC ATT CCT TCT TTA GGA GGA GGG ATG            312
Lys Ser Asn Leu Lys Lys Leu Phe Ile Pro Ser Leu Gly Gly Gly Met
        50                      55                      60

AAA TTG GTG GCT CAG AAT CTT CGT GGT AAT AAA GAA CCT AGT TTC TTA            360
Lys Leu Val Ala Gln Asn Leu Arg Gly Asn Lys Glu Pro Ser Phe Leu
65                      70                      75                      80

AAT GAA GAT GAC TAT ATA TCA TAT TTT TCC TCA CTT TCT ACG ATT GAA            408
Asn Glu Asp Asp Tyr Ile Ser Tyr Phe Ser Ser Leu Ser Thr Ile Glu
                    85                      90                      95

AAG GAT GTT AAA GAT AAC AAT AAA AAC GGG GCG GAC CTT ATT GGC TCA            456
Lys Asp Val Lys Asp Asn Asn Lys Asn Gly Ala Asp Leu Ile Gly Ser
                100                     105                     110

ATA GAC GAG CCT AGT ACA ACA AAT CCA CCC GAA AAG CAT CAT GGA CAA            504
Ile Asp Glu Pro Ser Thr Thr Asn Pro Pro Glu Lys His His Gly Gln
            115                     120                     125

AAA TAT GTA TAT TCA GGG CTT TAT TAT ACT CCA TCG TGG AGT TTA AAC            552
Lys Tyr Val Tyr Ser Gly Leu Tyr Tyr Thr Pro Ser Trp Ser Leu Asn
130                     135                     140

GAT TCT AAA AAC AAG TTT TAT TTA GGT TAC TAT GGA TAT GCG TTT TAT            600
Asp Ser Lys Asn Lys Phe Tyr Leu Gly Tyr Tyr Gly Tyr Ala Phe Tyr
145                     150                     155                     160

TAT GGT AAT AAA ACT GCA ACA AAC TTG CCA GTA AAC GGT GTA GCT AAA            648
Tyr Gly Asn Lys Thr Ala Thr Asn Leu Pro Val Asn Gly Val Ala Lys
                165                     170                     175

TAC AAA GGA ACT TGG GAT TTC ATC ACT GCA ACT AAA AAT GGC AAA CGT            696
Tyr Lys Gly Thr Trp Asp Phe Ile Thr Ala Thr Lys Asn Gly Lys Arg
            180                     185                     190

TAT CCT TTG TTA AGT AAT GGC AGT CAC GCT TAT TAT CGA CGT AGT GCA            744
Tyr Pro Leu Leu Ser Asn Gly Ser His Ala Tyr Tyr Arg Arg Ser Ala
        195                     200                     205

ATT CCA GAA GAT ATT GAT TTA GAA AAT GAT TCA AAG AAT GGT GAT ATA            792
Ile Pro Glu Asp Ile Asp Leu Glu Asn Asp Ser Lys Asn Gly Asp Ile
    210                     215                     220

GGC TTA ATA AGT GAA TTT AGT GCA GAT TTT GGG ACT AAA AAA CTG ACA            840
Gly Leu Ile Ser Glu Phe Ser Ala Asp Phe Gly Thr Lys Lys Leu Thr
225                     230                     235                     240

GGA CAA CTG TCT TAC ACC AAA AGA AAA ACT AAT AAT CAA CCA TAT GAA            888
Gly Gln Leu Ser Tyr Thr Lys Arg Lys Thr Asn Asn Gln Pro Tyr Glu
                245                     250                     255

AAG AAA AAA CTC TAT GAT ATA GAT GCC GAT ATT TAT AGT AAT AGA TTC            936
Lys Lys Lys Leu Tyr Asp Ile Asp Ala Asp Ile Tyr Ser Asn Arg Phe
            260                     265                     270

AGG GGT ACA GTA AAG CCA ACC GAA AAA GAT TCT GAA GAA CAT CCC TTT            984
Arg Gly Thr Val Lys Pro Thr Glu Lys Asp Ser Glu Glu His Pro Phe
        275                     280                     285

ACC AGC GAG GGA ACA TTA GAA GGT GGT TTT TAT GGG CCT AAT GCT GAA           1032
Thr Ser Glu Gly Thr Leu Glu Gly Gly Phe Tyr Gly Pro Asn Ala Glu
    290                     295                     300

GAA CTA GGG GGG AAA TTT TTA GCT ACG GAT AAC CGA GTT TTT GGG GTA           1080
Glu Leu Gly Gly Lys Phe Leu Ala Thr Asp Asn Arg Val Phe Gly Val
305                     310                     315                     320

TTT AGT GCC AAA GAA ACG GAA GAA ACA AAA AAG GAA GCG TTA TCC AAG           1128
Phe Ser Ala Lys Glu Thr Glu Glu Thr Lys Lys Glu Ala Leu Ser Lys
                325                     330                     335

GAA ACC TTA ATT GAT GGC AAG CTA ATT ACT TTC TCT ACT AAA AAA ACC           1176
Glu Thr Leu Ile Asp Gly Lys Leu Ile Thr Phe Ser Thr Lys Lys Thr
```

-continued

|  |  |  |  |  |  |  |  |  |  |  |  |  |  |  |  |
|---|---|---|---|---|---|---|---|---|---|---|---|---|---|---|---|

```
                  340                      345                      350
GAT GCA AAA ACC AAT GCA ACA ACC AGT ACC GCA GCT AAT ACA ACA ACC      1224
Asp Ala Lys Thr Asn Ala Thr Thr Ser Thr Ala Ala Asn Thr Thr Thr
        355                      360                      365

GAT ACA ACC GCC AAT ACA ATA ACC GAT GAA AAA AAC TTT AAG ACG GAA      1272
Asp Thr Thr Ala Asn Thr Ile Thr Asp Glu Lys Asn Phe Lys Thr Glu
    370                      375                      380

GAT ATA TCA AGT TTT GGT GAA GCT GAT TAT CTG TTA ATT GAC AAA TAT      1320
Asp Ile Ser Ser Phe Gly Glu Ala Asp Tyr Leu Leu Ile Asp Lys Tyr
385                      390                      395                 400

CCT ATT CCA CTT TTA CCT GAT AAA AAT ACT AAT GAT TTC ATA AGT AGT      1368
Pro Ile Pro Leu Leu Pro Asp Lys Asn Thr Asn Asp Phe Ile Ser Ser
                405                      410                      415

AAG CAT CAT ACT GTA GGA AAT AAA CGC TAT AAA GTG GAA GCA TGT TGC      1416
Lys His His Thr Val Gly Asn Lys Arg Tyr Lys Val Glu Ala Cys Cys
            420                      425                      430

AGT AAT CTA AGC TAT GTG AAA TTT GGT ATG TAT TAT GAA GAC CCA CTT      1464
Ser Asn Leu Ser Tyr Val Lys Phe Gly Met Tyr Tyr Glu Asp Pro Leu
        435                      440                      445

AAA GAA AAA GAA ACA GAA ACA GAA ACA GAA ACA GAA AAA GAC AAA GAA      1512
Lys Glu Lys Glu Thr Glu Thr Glu Thr Glu Thr Glu Lys Asp Lys Glu
    450                      455                      460

AAA GAA AAA GAA AAA GAC AAA GAC AAA GAA AAA CAA ACG GCG GCA ACG      1560
Lys Glu Lys Glu Lys Asp Lys Asp Lys Glu Lys Gln Thr Ala Ala Thr
465                      470                      475                 480

ACC AAC ACT TAT TAT CAA TTC TTA TTA GGT CAC CGT ACT CCC AAG GAC      1608
Thr Asn Thr Tyr Tyr Gln Phe Leu Leu Gly His Arg Thr Pro Lys Asp
                485                      490                      495

GAC ATA CCT AAA ACA GGA AGT GCA AAA TAT CAT GGT AGT TGG TTT GGT      1656
Asp Ile Pro Lys Thr Gly Ser Ala Lys Tyr His Gly Ser Trp Phe Gly
            500                      505                      510

TAT ATT ACT GAC GGT AAG ACA TCT TAC TCC CCC AGT GGT GAT AAG AAA      1704
Tyr Ile Thr Asp Gly Lys Thr Ser Tyr Ser Pro Ser Gly Asp Lys Lys
        515                      520                      525

CGC GAT AAA AAT GCT GTC GCC GAG TTT AAT GTT GAT TTT GCC GAG AAA      1752
Arg Asp Lys Asn Ala Val Ala Glu Phe Asn Val Asp Phe Ala Glu Lys
    530                      535                      540

AAG CTA ACA GGC GAA TTA AAA CGA CAC GAT ACT GGA AAT CCC GTA TTT      1800
Lys Leu Thr Gly Glu Leu Lys Arg His Asp Thr Gly Asn Pro Val Phe
545                      550                      555                 560

AGT ATT GAG GCA AAC TTT AAT AAT AGT AGT AAT GCC TTC ACT GGT ACA      1848
Ser Ile Glu Ala Asn Phe Asn Asn Ser Ser Asn Ala Phe Thr Gly Thr
                565                      570                      575

GCA ACC GCA ACA AAT TTT GTA ATA GAT GGT AAA AAT AGT CAA AAT AAA      1896
Ala Thr Ala Thr Asn Phe Val Ile Asp Gly Lys Asn Ser Gln Asn Lys
            580                      585                      590

AAT ACC CCA ATT AAT ATT ACA ACT AAA GTA AAC GGG GCA TTT TAT GGA      1944
Asn Thr Pro Ile Asn Ile Thr Thr Lys Val Asn Gly Ala Phe Tyr Gly
        595                      600                      605

CCT AAG GCT TCT GAA TTA GGC GGT TAT TTC ACT TAT AAC GGA AAT TCT      1992
Pro Lys Ala Ser Glu Leu Gly Gly Tyr Phe Thr Tyr Asn Gly Asn Ser
    610                      615                      620

ACA GCT ACA AAT TCT GAA AGT TCC TCA ACC GTA TCT TCA TCA TCC AAT      2040
Thr Ala Thr Asn Ser Glu Ser Ser Ser Thr Val Ser Ser Ser Ser Asn
625                      630                      635                 640

TCA AAA AAT GCA AGA GCT GCA GTT GTC TTT GGT GCG AGA CAA CAA GTA      2088
Ser Lys Asn Ala Arg Ala Ala Val Val Phe Gly Ala Arg Gln Gln Val
                645                      650                      655

GAA ACA ACC AAA TAATGGAATA CTAAAA ATG ACT AAA AAA CCC TAT TTT        2137
Glu Thr Thr Lys                        Met Thr Lys Lys Pro Tyr Phe
```

-continued

```
                 660                               665
CGC CTA AGT ATT ATT TCT TGT CTT TTA ATT TCA TGC TAT GTA AAA GCA    2185
Arg Leu Ser Ile Ile Ser Cys Leu Leu Ile Ser Cys Tyr Val Lys Ala
            670             675             680

GAA ACT CAA AGT ATA AAA GAT ACA AAA GAA GCT ATA TCA TCT GAA GTG    2233
Glu Thr Gln Ser Ile Lys Asp Thr Lys Glu Ala Ile Ser Ser Glu Val
        685             690             695

GAC ACT CAA AGT ACA GAA GAT TCA GAA TTA GAA ACT ATC TCA GTC ACT    2281
Asp Thr Gln Ser Thr Glu Asp Ser Glu Leu Glu Thr Ile Ser Val Thr
700             705             710             715

GCA GAA AAA ATA AGA GAT CGT AAA GAT AAT GAA GTA ACT GGA CTT GGC    2329
Ala Glu Lys Ile Arg Asp Arg Lys Asp Asn Glu Val Thr Gly Leu Gly
            720             725             730

AAA ATT ATC AAA ACT AGT GAA AGT ATC AGC CGA GAA CAA GTA TTA AAT    2377
Lys Ile Ile Lys Thr Ser Glu Ser Ile Ser Arg Glu Gln Val Leu Asn
        735             740             745

ATT CGT GAT CTA ACA CGC TAT GAT CCA GGG ATT TCA GTT GTA GAA CAA    2425
Ile Arg Asp Leu Thr Arg Tyr Asp Pro Gly Ile Ser Val Val Glu Gln
            750             755             760

GGT CGC GGT GCA AGT TCT GGA TAT TCT ATT CGT GGT ATG GAC AGA AAT    2473
Gly Arg Gly Ala Ser Ser Gly Tyr Ser Ile Arg Gly Met Asp Arg Asn
765             770             775

AGA GTT GCT TTA TTA GTA GAT GGT TTA CCT CAA ACG CAA TCT TAT GTA    2521
Arg Val Ala Leu Leu Val Asp Gly Leu Pro Gln Thr Gln Ser Tyr Val
780             785             790             795

GTG CAA AGC CCT TTA GTT GCT CGT TCA GGA TAT TCT GGC ACT GGT GCA    2569
Val Gln Ser Pro Leu Val Ala Arg Ser Gly Tyr Ser Gly Thr Gly Ala
            800             805             810

ATT AAT GAA ATT GAA TAT GAA AAT GTA AAG GCC GTC GAA ATA AGC AAG    2617
Ile Asn Glu Ile Glu Tyr Glu Asn Val Lys Ala Val Glu Ile Ser Lys
        815             820             825

GGG GGG AGT TCT TCT GAG TAT GGT AAT GGA GCA CTA GCT GGT TCT GTA    2665
Gly Gly Ser Ser Ser Glu Tyr Gly Asn Gly Ala Leu Ala Gly Ser Val
            830             835             840

ACA TTT CAA AGC AAA TCA GCA GCC GAT ATC TTA GAA GGA GAC AAA TCA    2713
Thr Phe Gln Ser Lys Ser Ala Ala Asp Ile Leu Glu Gly Asp Lys Ser
845             850             855

TGG GGA ATT CAA ACT AAA AAT GCT TAT TCA AGC AAA AAT AAA GGC TTT    2761
Trp Gly Ile Gln Thr Lys Asn Ala Tyr Ser Ser Lys Asn Lys Gly Phe
860             865             870             875

ACC CAT TCT TTA GCT GTA GCA GGA AAA CAA GGT GGA TTT GAA GGG CTA    2809
Thr His Ser Leu Ala Val Ala Gly Lys Gln Gly Gly Phe Glu Gly Leu
            880             885             890

GCC ATT TAC ACT CAA CGA AAT TCA ATT GAA ACC CAA GTC CAT AAA GAT    2857
Ala Ile Tyr Thr Gln Arg Asn Ser Ile Glu Thr Gln Val His Lys Asp
        895             900             905

GCA TTA AAA GGC GTA CAA AGT TAT GAT CGA TTA ATC GCC ACA ACA GAT    2905
Ala Leu Lys Gly Val Gln Ser Tyr Asp Arg Leu Ile Ala Thr Thr Asp
            910             915             920

AAA TCT TCA GGA TAC TTT GTG ATA CAA GGT GAG TGT CCA AAT GGT GAT    2953
Lys Ser Ser Gly Tyr Phe Val Ile Gln Gly Glu Cys Pro Asn Gly Asp
        925             930             935

GAC AAG TGT GCA GCC AAG CCA CCT GCG ACT TTA TCC ACC CAA AGC GAA    3001
Asp Lys Cys Ala Ala Lys Pro Pro Ala Thr Leu Ser Thr Gln Ser Glu
940             945             950             955

ACC GTA AGC GTT TCA GAT TAT ACG GGG GCT AAC CGT ATC AAA CCT AAT    3049
Thr Val Ser Val Ser Asp Tyr Thr Gly Ala Asn Arg Ile Lys Pro Asn
            960             965             970

CCA ATG AAA TAT GAA AGC CAG TCT TGG TTT TTA AGA GGA GGG TAT CAT    3097
Pro Met Lys Tyr Glu Ser Gln Ser Trp Phe Leu Arg Gly Gly Tyr His
```

```
                   975                 980                 985
TTT TCT GAA CAA CAT TAT ATT GGT GGT ATT TTT GAA TTC ACA CAA CAA       3145
Phe Ser Glu Gln His Tyr Ile Gly Gly Ile Phe Glu Phe Thr Gln Gln
        990                 995                 1000

AAA TTT GAT ATC CGT GAT ATG ACA TTT CCC GCT TAT TTA AGC CCA ACA       3193
Lys Phe Asp Ile Arg Asp Met Thr Phe Pro Ala Tyr Leu Ser Pro Thr
        1005                1010                1015

GAA AGA CGG GAT GAT AGT AGT CGT TCT TTT TAT CCA ATG CAA GAT CAT       3241
Glu Arg Arg Asp Asp Ser Ser Arg Ser Phe Tyr Pro Met Gln Asp His
1020                1025                1030                1035

GGT GCA TAT CAA CAT ATT GAG GAT GGC AGA GGC GTT AAA TAT GCA AGT       3289
Gly Ala Tyr Gln His Ile Glu Asp Gly Arg Gly Val Lys Tyr Ala Ser
            1040                1045                1050

GGG CTT TAT TTC GAT GAA CAC CAT AGA AAA CAG CGT GTA GGT ATT GAA       3337
Gly Leu Tyr Phe Asp Glu His His Arg Lys Gln Arg Val Gly Ile Glu
                1055                1060                1065

TAT ATT TAC GAA AAT AAG AAC AAA GCG GGC ATC ATT GAC AAA GCA GTG       3385
Tyr Ile Tyr Glu Asn Lys Asn Lys Ala Gly Ile Ile Asp Lys Ala Val
                    1070                1075                1080

TTA AGT GCT AAT CAA CAA AAC ATC ATA CTT GAC AGT TAT ATG CGA CAT       3433
Leu Ser Ala Asn Gln Gln Asn Ile Ile Leu Asp Ser Tyr Met Arg His
                        1085                1090                1095

ACG CAT TGC AGT CTT TAT CCT AAT CCA AGT AAG AAT TGC CGC CCA ACA       3481
Thr His Cys Ser Leu Tyr Pro Asn Pro Ser Lys Asn Cys Arg Pro Thr
1100                1105                1110                1115

CTT GAT AAA CCT TAT TCA TAC TAT CGT TCT GAT AGA AAT GTT TAT AAA       3529
Leu Asp Lys Pro Tyr Ser Tyr Tyr Arg Ser Asp Arg Asn Val Tyr Lys
            1120                1125                1130

GAA AAA CAT AAT ATG TTG CAA TTG AAT TTA GAG AAA AAA ATT CAA CAA       3577
Glu Lys His Asn Met Leu Gln Leu Asn Leu Glu Lys Lys Ile Gln Gln
                1135                1140                1145

AAT TGG CTT ACT CAT CAA ATT GTC TTC AAT CTT GGT TTT GAT GAC TTT       3625
Asn Trp Leu Thr His Gln Ile Val Phe Asn Leu Gly Phe Asp Asp Phe
                    1150                1155                1160

ACT TCA GCG CTT CAG CAT AAA GAT TAT TTA ACT CGA CGT GTT ATC GCT       3673
Thr Ser Ala Leu Gln His Lys Asp Tyr Leu Thr Arg Arg Val Ile Ala
                        1165                1170                1175

ACG GCA GAT AGT ATT CCA AGG AAA CCT GGT GAA ACT GGT AAA CCA AGA       3721
Thr Ala Asp Ser Ile Pro Arg Lys Pro Gly Glu Thr Gly Lys Pro Arg
1180                1185                1190                1195

AAT GGT TTG CAA TCA CAA CCT TAC TTA TAC CCA AAA CCA GAG CCA TAT       3769
Asn Gly Leu Gln Ser Gln Pro Tyr Leu Tyr Pro Lys Pro Glu Pro Tyr
            1200                1205                1210

TTT GCA GGA CAA GAT CAT TGT AAT TAT CAA GGT AGC TCC TCT AAT TAC       3817
Phe Ala Gly Gln Asp His Cys Asn Tyr Gln Gly Ser Ser Ser Asn Tyr
                1215                1220                1225

AGA GAC TGT AAA GTG CGG TTA ATT AAA GGG AAA AAT TAT TAT TTC GCA       3865
Arg Asp Cys Lys Val Arg Leu Ile Lys Gly Lys Asn Tyr Tyr Phe Ala
                    1230                1235                1240

GCA CGC AAT AAT ATG GCA TTA GGG AAA TAC GTT GAT TTA GGT TTA GGT       3913
Ala Arg Asn Asn Met Ala Leu Gly Lys Tyr Val Asp Leu Gly Leu Gly
                        1245                1250                1255

ATT CGG TAT GAC GTA TCT CGT ACA AAA GCT AAT GAA TCA ACT ATT AGT       3961
Ile Arg Tyr Asp Val Ser Arg Thr Lys Ala Asn Glu Ser Thr Ile Ser
1260                1265                1270                1275

GTT GGT AAA TTT AAA AAT TTC TCT TGG AAT ACT GGT ATT GTC ATA AAA       4009
Val Gly Lys Phe Lys Asn Phe Ser Trp Asn Thr Gly Ile Val Ile Lys
            1280                1285                1290

CCA ACG GAA TGG CTT GAT CTT TCT TAT CGC CTT TCT ACT GGA TTT AGA       4057
Pro Thr Glu Trp Leu Asp Leu Ser Tyr Arg Leu Ser Thr Gly Phe Arg
```

```
                  1295                1300                1305
AAT CCT AGT TTT TCT GAA ATG TAT GGT TGG CGG TAT GGT GGC AAG AAT       4105
Asn Pro Ser Phe Ser Glu Met Tyr Gly Trp Arg Tyr Gly Gly Lys Asn
        1310                1315                1320

GAC GAG GTT TAT GTA GGT AAA TTT AAG CCT GAA ACA TCT CGT AAC CAA       4153
Asp Glu Val Tyr Val Gly Lys Phe Lys Pro Glu Thr Ser Arg Asn Gln
    1325                1330                1335

GAG TTT GGT CTC GCT CTA AAA GGG GAT TTT GGT AAT ATT GAG ATC AGT       4201
Glu Phe Gly Leu Ala Leu Lys Gly Asp Phe Gly Asn Ile Glu Ile Ser
1340                1345                1350                1355

CAT TTT AGT AAT GCT TAT CGA AAT CTT ATC GCC TTT GCT GAA GAA CTT       4249
His Phe Ser Asn Ala Tyr Arg Asn Leu Ile Ala Phe Ala Glu Glu Leu
            1360                1365                1370

AGT AAA AAT GGA ACT GGA AAG GGC AAT TAT GGA TAT CAT AAT GCA CAA       4297
Ser Lys Asn Gly Thr Gly Lys Gly Asn Tyr Gly Tyr His Asn Ala Gln
        1375                1380                1385

AAT GCA AAA TTA GTT GGC GTA AAT ATA ACT GCA CAA TTA GAT TTT AAT       4345
Asn Ala Lys Leu Val Gly Val Asn Ile Thr Ala Gln Leu Asp Phe Asn
    1390                1395                1400

GGT TTA TGG AAA CGT ATT CCC TAC GGT TGG TAT GCA ACA TTT GCT TAT       4393
Gly Leu Trp Lys Arg Ile Pro Tyr Gly Trp Tyr Ala Thr Phe Ala Tyr
1405                1410                1415

AAC CAA GTA AAA GTT AAA GAT CAA AAA ATC AAT GCT GGT TTA GCC TCC       4441
Asn Gln Val Lys Val Lys Asp Gln Lys Ile Asn Ala Gly Leu Ala Ser
1420                1425                1430                1435

GTA AGC AGT TAT TTA TTT GAT GCC ATT CAG CCC AGC CGT TAT ATC ATT       4489
Val Ser Ser Tyr Leu Phe Asp Ala Ile Gln Pro Ser Arg Tyr Ile Ile
            1440                1445                1450

GGT TTA GGC TAT GAT CAT CCA AGT AAT ACT TGG GGA ATT AAT ACA ATG       4537
Gly Leu Gly Tyr Asp His Pro Ser Asn Thr Trp Gly Ile Asn Thr Met
        1455                1460                1465

TTT ACT CAA TCA AAA GCA AAA TCT CAA AAT GAA TTG CTA GGA AAA CGT       4585
Phe Thr Gln Ser Lys Ala Lys Ser Gln Asn Glu Leu Leu Gly Lys Arg
    1470                1475                1480

GCA TTA GGT AAC AAT TCA AGG GAT GTA AAA TCA ACA AGA AAA CTT ACT       4633
Ala Leu Gly Asn Asn Ser Arg Asp Val Lys Ser Thr Arg Lys Leu Thr
1485                1490                1495

CGG GCA TGG CAT ATC TTA GAT GTA TCG GGT TAT TAC ATG GCG AAT AAA       4681
Arg Ala Trp His Ile Leu Asp Val Ser Gly Tyr Tyr Met Ala Asn Lys
1500                1505                1510                1515

AAT ATT ATG CTT CGA TTA GGG ATA TAT AAT TTA TTC AAC TAT CGC TAT       4729
Asn Ile Met Leu Arg Leu Gly Ile Tyr Asn Leu Phe Asn Tyr Arg Tyr
            1520                1525                1530

GTT ACT TGG GAA GCG GTG CGT CAA ACA GCA CAA GGT GCG GTC AAT CAA       4777
Val Thr Trp Glu Ala Val Arg Gln Thr Ala Gln Gly Ala Val Asn Gln
        1535                1540                1545

CAT CAA AAT GTT GGT AGC TAT ACT CGC TAC GCA GCA TCA GGA CGA AAC       4825
His Gln Asn Val Gly Ser Tyr Thr Arg Tyr Ala Ala Ser Gly Arg Asn
    1550                1555                1560

TAT ACC TTA ACA TTA GAA ATG AAA TTC TAAATTAAAA TGCGCCAGAT            4872
Tyr Thr Leu Thr Leu Glu Met Lys Phe
    1565                1570

GGACTAGATA TGCTATATCT ATACCTTACT GGCGCATCTT TTTCTGTTCT ATAATCTGCT    4932

TAAGTGAAAA ACCAAACTTG GATTTTTTAC AAGATCTTTT CACACATTTA TTGTAAAATC    4992

TCCGACAATT TTGACCG                                                   5009

(2) INFORMATION FOR SEQ ID NO:4:

(i) SEQUENCE CHARACTERISTICS:
```

(A) LENGTH: 5099 base pairs
(B) TYPE: nucleic acid
(C) STRANDEDNESS: double
(D) TOPOLOGY: linear (ix) FEATURE:
(A) NAME/KEY: CDS
(B) LOCATION: join(160..2121, 2152..4890)

(xi) SEQUENCE DESCRIPTION: SEQ ID NO:4:

```
AAAATTCGGT AATGATAACC CTATAAATGA TAAGAGAGAA AGTTGTTTTA CGCCATTTTT         60

CATATTTTAT CCATGAACTT AAAAAATTCT AAGTTGACAT TATTACAAAA AAAGAACAAT        120

AATGCGAATT ATTATCAATT TTGTATAAGT ATTAATTCT ATG AAA TCT GTA CCT          174
                                            Met Lys Ser Val Pro
                                             1               5

CTT ATC ACT GGT GGA CTT TCC TTT TTA CTA AGC GCT TGT AGC GGG GGA          222
Leu Ile Thr Gly Gly Leu Ser Phe Leu Leu Ser Ala Cys Ser Gly Gly
                 10                  15                  20

GGT GGT TCT TTT GAT GTA GAT GAC GTC TCT AAT CCC TCC TCT TCT AAA          270
Gly Gly Ser Phe Asp Val Asp Asp Val Ser Asn Pro Ser Ser Ser Lys
         25                  30                  35

CCA CGT TAT CAA GAC GAT ACC TCG AAT CAA AGA ACA AAA TCT GAT TTG          318
Pro Arg Tyr Gln Asp Asp Thr Ser Asn Gln Arg Thr Lys Ser Asp Leu
     40                  45                  50

GAA AAG TTG TTC ATT CCT TCT TTA GGG GGA GGG ATG AAG TTA GTG GCT          366
Glu Lys Leu Phe Ile Pro Ser Leu Gly Gly Gly Met Lys Leu Val Ala
 55                  60                  65

CAA AAT TTT ATT GGT GCT AGA GAA CCT AGT TTC TTA AAT GAA GAT GGC          414
Gln Asn Phe Ile Gly Ala Arg Glu Pro Ser Phe Leu Asn Glu Asp Gly
 70                  75                  80                  85

TAT ATG ATA TTT TCC TCA CTT TCT ACG ATT GAA GAG GAT GTT GAA AAA          462
Tyr Met Ile Phe Ser Ser Leu Ser Thr Ile Glu Glu Asp Val Glu Lys
                 90                  95                 100

GTT AAA AAT AAC AAT AAA AAC GGG GGG AGG CTT ATT GGC TCA ATT GAG          510
Val Lys Asn Asn Asn Lys Asn Gly Gly Arg Leu Ile Gly Ser Ile Glu
                105                 110                 115

GAA CCT AAT GGA ACA TCA CAA AAT TCT AAT TCA CAA GAA TAC GTT TAT          558
Glu Pro Asn Gly Thr Ser Gln Asn Ser Asn Ser Gln Glu Tyr Val Tyr
        120                 125                 130

TCT GGT TTG TAT TAT ATC GAT AGT TGG CGT GAT TAT AAG AAG GAA GAG          606
Ser Gly Leu Tyr Tyr Ile Asp Ser Trp Arg Asp Tyr Lys Lys Glu Glu
135                 140                 145

CAA AAA GCT TAT ACT GGC TAT TAT GGT TAT GCA TTT TAT TAT GGT AAT          654
Gln Lys Ala Tyr Thr Gly Tyr Tyr Gly Tyr Ala Phe Tyr Tyr Gly Asn
150                 155                 160                 165

GAA ACT GCA AAA AAC TTG CCA GTA AAA GGT GTA GCT AAA TAC AAA GGA          702
Glu Thr Ala Lys Asn Leu Pro Val Lys Gly Val Ala Lys Tyr Lys Gly
                170                 175                 180

ACG TGG AAC TTC ATC ACT GCA ACT GAA AAT GGC AAA CGT TAT TCT TTG          750
Thr Trp Asn Phe Ile Thr Ala Thr Glu Asn Gly Lys Arg Tyr Ser Leu
                185                 190                 195

TTC AGT AAT TCT ATC GGT CAA GCT TAT TCC AGA CGC AGC GCT ATT TCA          798
Phe Ser Asn Ser Ile Gly Gln Ala Tyr Ser Arg Arg Ser Ala Ile Ser
            200                 205                 210

GAA GAT ATC TAT AAT TTA GAA AAC GGT GAC GCG GGC TTA ATA AGT GAA          846
Glu Asp Ile Tyr Asn Leu Glu Asn Gly Asp Ala Gly Leu Ile Ser Glu
    215                 220                 225

TTT AGT GTA GAT TTT GGT AAG AAA GAG CTC ACT GGA GAA CTT TAT TAT          894
Phe Ser Val Asp Phe Gly Lys Lys Glu Leu Thr Gly Glu Leu Tyr Tyr
230                 235                 240                 245

AAT GAA AGG AAA ACA AGT GTT AAT GAA TCA CAA AAT ACA ACA CAT AAA          942
```

```
Asn Glu Arg Lys Thr Ser Val Asn Glu Ser Gln Asn Thr Thr His Lys
            250                 255                 260

CTC TAC ACT CTA GAA GCT AAA GTG TAT AGC AAC CGA TTC AGA GGT AAA    990
Leu Tyr Thr Leu Glu Ala Lys Val Tyr Ser Asn Arg Phe Arg Gly Lys
            265                 270                 275

GTA AAG CCA ACC AAA ACA AAG TCT GAA GAT CAT CCC TTT ACC AGC GAG   1038
Val Lys Pro Thr Lys Thr Lys Ser Glu Asp His Pro Phe Thr Ser Glu
            280                 285                 290

GGA ACA TTA GAA GGT GGT TTT TAT GGG CCT AAT GCT GAA GAA CTA GGG   1086
Gly Thr Leu Glu Gly Gly Phe Tyr Gly Pro Asn Ala Glu Glu Leu Gly
            295                 300                 305

GGA AAG TTT TTA GCT AAC GAC GAA AAA GTT TTT GGG GTA TTT AGT GCC   1134
Gly Lys Phe Leu Ala Asn Asp Glu Lys Val Phe Gly Val Phe Ser Ala
310             315                 320                 325

AAA GAA GAC CCA CAA AAC CCA GAA AAC CAA AAA TTA TCC ACA GAA ACC   1182
Lys Glu Asp Pro Gln Asn Pro Glu Asn Gln Lys Leu Ser Thr Glu Thr
                330                 335                 340

TTA ATT GAT GGC AAG CTA ATT ACT TTT AAA AGA ACT GAT GCA ACA ACC   1230
Leu Ile Asp Gly Lys Leu Ile Thr Phe Lys Arg Thr Asp Ala Thr Thr
                345                 350                 355

AAT GCA ACA ACC GAT GCA AAA ACC AGT GCA ACA ACC GAT GCA ACC AGT   1278
Asn Ala Thr Thr Asp Ala Lys Thr Ser Ala Thr Thr Asp Ala Thr Ser
            360                 365                 370

ACA ACA GCC AAT AAA AAA ACC GAT GCA GAA AAC TTT AAG ACG GAA GAT   1326
Thr Thr Ala Asn Lys Lys Thr Asp Ala Glu Asn Phe Lys Thr Glu Asp
375             380                 385

ATA CCA AGT TTT GGT GAA GCT GAT TAC CTT TTA ATT GGC AAT CAG CCT   1374
Ile Pro Ser Phe Gly Glu Ala Asp Tyr Leu Leu Ile Gly Asn Gln Pro
390             395                 400                 405

ATT CCT CTT TTA CCT GAA AAA AAT ACT GAT GAT TTC ATA AGT AGT AAG   1422
Ile Pro Leu Leu Pro Glu Lys Asn Thr Asp Asp Phe Ile Ser Ser Lys
                410                 415                 420

CAC CAT ACG GTA GGA GGT AAA ACC TAT AAA GTA GAA GCA TGT TGC AAG   1470
His His Thr Val Gly Gly Lys Thr Tyr Lys Val Glu Ala Cys Cys Lys
                425                 430                 435

AAT CTA AGC TAT GTG AAA TTT GGT ATG TAT TAT GAG GAT AAA GAT AAG   1518
Asn Leu Ser Tyr Val Lys Phe Gly Met Tyr Tyr Glu Asp Lys Asp Lys
            440                 445                 450

GAC AAC AAA AAT GAA ACA GAC AAA GAA AAA GGC AAA GAA AAA CCA ACG   1566
Asp Asn Lys Asn Glu Thr Asp Lys Glu Lys Gly Lys Glu Lys Pro Thr
455             460                 465

ACG ACA ACA TCT ATC AAC ACT TAT TAT CAA TTC TTA TTA GGT CTC CGT   1614
Thr Thr Thr Ser Ile Asn Thr Tyr Tyr Gln Phe Leu Leu Gly Leu Arg
470             475                 480                 485

ACT CCC AAG GAC GAA ATA CCT AAA GAA GGA AGT GCA AAA TAT CAT GGT   1662
Thr Pro Lys Asp Glu Ile Pro Lys Glu Gly Ser Ala Lys Tyr His Gly
                490                 495                 500

AAT TGG TTT GGT TAT ATT AGT GAT GGC GAG ACA TCT TAC TCC GCC AGT   1710
Asn Trp Phe Gly Tyr Ile Ser Asp Gly Glu Thr Ser Tyr Ser Ala Ser
            505                 510                 515

GGT GAT AAG GAA CGC AGT AAA AAT GCT GTC GCC GAG TTT GAT GTA AGT   1758
Gly Asp Lys Glu Arg Ser Lys Asn Ala Val Ala Glu Phe Asp Val Ser
            520                 525                 530

TTT GCC AAT AAA ACA TTA ACA GGC GAA TTA AAA CGA CAC GAT AAT GGA   1806
Phe Ala Asn Lys Thr Leu Thr Gly Glu Leu Lys Arg His Asp Asn Gly
535             540                 545

AAT ACC GTA TTT AAA ATT AAT GCA GAA TTA AAT GGT AGT AAT GAC TTC   1854
Asn Thr Val Phe Lys Ile Asn Ala Glu Leu Asn Gly Ser Asn Asp Phe
550             555                 560                 565

ACT GGT ACA GCA ACC GCA ACA AAT TTT GTA ATA GAT GGT AAC AAT AGT   1902
```

-continued

```
Thr Gly Thr Ala Thr Ala Thr Asn Phe Val Ile Asp Gly Asn Asn Ser
        570                 575                 580

CAA ACT TCA AAT GCC AAA ATT AAT ATT ACA ACT AAA GTA AAT GGG GCA    1950
Gln Thr Ser Asn Ala Lys Ile Asn Ile Thr Thr Lys Val Asn Gly Ala
            585                 590                 595

TTT TAT GGA CCT AAG GCT TCT GAA TTA GGA GGG TAT TTC ACC TAT AAC    1998
Phe Tyr Gly Pro Lys Ala Ser Glu Leu Gly Gly Tyr Phe Thr Tyr Asn
            600                 605                 610

GGA AAA AAT CCT ACA GCT ACA AAT TCT GAA AGT TCC TCA ACC GTA CCT    2046
Gly Lys Asn Pro Thr Ala Thr Asn Ser Glu Ser Ser Ser Thr Val Pro
            615                 620                 625

TCA CCA CCC AAT TCA CCA AAT GCA AGC GCT GCA GTT GTC TTT GGT GCT    2094
Ser Pro Pro Asn Ser Pro Asn Ala Ser Ala Ala Val Val Phe Gly Ala
630                 635                 640                 645

AAA AAA CAA GTA GAA ACA ACC AAC AAG TAAAAACAAC CAAGTAATGG          2141
Lys Lys Gln Val Glu Thr Thr Asn Lys
                650

AATACTAAAA ATG ACT AAA AAA CCC TAT TTT CGC CTA AGT ATT ATT TCT     2190
           Met Thr Lys Lys Pro Tyr Phe Arg Leu Ser Ile Ile Ser
               655                 660                 665

TGT CTT TTA ATT TCA TGC TAT GTA AAA GCA GAA ACT CAA AGT ATA AAA    2238
Cys Leu Leu Ile Ser Cys Tyr Val Lys Ala Glu Thr Gln Ser Ile Lys
            670                 675                 680

GAT ACA AAA GAA GCT ATA TCA TCT GAA GTG GAC ACT CAA AGT ACA GAA    2286
Asp Thr Lys Glu Ala Ile Ser Ser Glu Val Asp Thr Gln Ser Thr Glu
            685                 690                 695

GAT TCA GAA TTA GAA ACT ATC TCA GTC ACT GCA GAA AAA ATA AGA GAT    2334
Asp Ser Glu Leu Glu Thr Ile Ser Val Thr Ala Glu Lys Ile Arg Asp
700                 705                 710                 715

CGT AAA GAT AAT GAA GTA ACT GGA CTT GGC AAA ATT ATC AAA ACT AGT    2382
Arg Lys Asp Asn Glu Val Thr Gly Leu Gly Lys Ile Ile Lys Thr Ser
            720                 725                 730

GAA AGT ATC AGC CGA GAA CAA GTA TTA AAT ATT CGT GAT CTA ACA CGC    2430
Glu Ser Ile Ser Arg Glu Gln Val Leu Asn Ile Arg Asp Leu Thr Arg
            735                 740                 745

TAT GAT CCA GGC ATT TCA GTT GTA GAA CAA GGC CGT GGT GCA AGT TCT    2478
Tyr Asp Pro Gly Ile Ser Val Val Glu Gln Gly Arg Gly Ala Ser Ser
            750                 755                 760

GGA TAT TCT ATT CGT GGT ATG GAC AGA AAT AGA GTT GCT TTA TTA GTA    2526
Gly Tyr Ser Ile Arg Gly Met Asp Arg Asn Arg Val Ala Leu Leu Val
765                 770                 775

GAT GGT TTA CCT CAA ACG CAA TCT TAT GTA GTG CAA AGC CCT TTA GTT    2574
Asp Gly Leu Pro Gln Thr Gln Ser Tyr Val Val Gln Ser Pro Leu Val
780                 785                 790                 795

GCT CGT TCA GGA TAT TCT GGC ACT GGT GCA ATT AAT GAA ATT GAA TAT    2622
Ala Arg Ser Gly Tyr Ser Gly Thr Gly Ala Ile Asn Glu Ile Glu Tyr
            800                 805                 810

GAA AAT GTA AAG GCC GTC GAA ATA AGC AAG GGG GGG AGT TCT TCT GAG    2670
Glu Asn Val Lys Ala Val Glu Ile Ser Lys Gly Gly Ser Ser Ser Glu
            815                 820                 825

TAT GGT AAT GGA GCA CTA GCT GGT TCT GTA ACA TTT CAA AGC AAA TCA    2718
Tyr Gly Asn Gly Ala Leu Ala Gly Ser Val Thr Phe Gln Ser Lys Ser
            830                 835                 840

GCA GCC GAT ATC TTA GAA GGA GAC AAA TCA TGG GGA ATT CAA ACT AAA    2766
Ala Ala Asp Ile Leu Glu Gly Asp Lys Ser Trp Gly Ile Gln Thr Lys
            845                 850                 855

AAT GCT TAT TCA AGC AAA AAT AAA GGC TTT ACC CAT TCT TTA GCT GTA    2814
Asn Ala Tyr Ser Ser Lys Asn Lys Gly Phe Thr His Ser Leu Ala Val
860                 865                 870                 875

GCT GGA AAA CAA GGG GGA TTT GAC GGG GTC GCC ATT TAT ACT CAA CGA    2862
```

```
                Ala Gly Lys Gln Gly Gly Phe Asp Gly Val Ala Ile Tyr Thr Gln Arg
                            880                 885                 890

AAT TCA ATT GAA ACC CAA GTC CAT AAA GAT GCA TTA AAA GGC GTA CAA              2910
Asn Ser Ile Glu Thr Gln Val His Lys Asp Ala Leu Lys Gly Val Gln
            895                 900                 905

AGT TAT CAT CGA TTA ATC GCC AAA CCA GAG GAT CAA TCT GCA TAC TTT              2958
Ser Tyr His Arg Leu Ile Ala Lys Pro Glu Asp Gln Ser Ala Tyr Phe
            910                 915                 920

GTG ATG CAA GAT GAG TGT CCA AAG CCA GAT GAT TAT AAC AGT TGT TTA              3006
Val Met Gln Asp Glu Cys Pro Lys Pro Asp Asp Tyr Asn Ser Cys Leu
925                 930                 935

CCT TTC GCC AAA CGA CCT GCG ATT TTA TCC TCC CAA AGA GAA ACC GTA              3054
Pro Phe Ala Lys Arg Pro Ala Ile Leu Ser Ser Gln Arg Glu Thr Val
940                 945                 950                 955

AGC GTT TCA GAT TAT ACG GGG GCT AAC CGT ATC AAA CCT AAT CCA ATG              3102
Ser Val Ser Asp Tyr Thr Gly Ala Asn Arg Ile Lys Pro Asn Pro Met
            960                 965                 970

AAA TAT GAA AGC CAG TCT TGG TTT TTA AGA GGA GGG TAT CAT TTT TCT              3150
Lys Tyr Glu Ser Gln Ser Trp Phe Leu Arg Gly Gly Tyr His Phe Ser
            975                 980                 985

GAA CAA CAT TAT ATT GGT GGT ATT TTT GAA TTC ACA CAA CAA AAA TTT              3198
Glu Gln His Tyr Ile Gly Gly Ile Phe Glu Phe Thr Gln Gln Lys Phe
            990                 995                 1000

GAT ATC CGT GAT ATG ACA TTT CCC GCT TAT TTA AGA TCA ACA GAA AAA              3246
Asp Ile Arg Asp Met Thr Phe Pro Ala Tyr Leu Arg Ser Thr Glu Lys
            1005                1010                1015

CGG GAT GAT AGC AGT GGC TCT TTT TAT CCA AAG CAA GAT TAT GGT GCA              3294
Arg Asp Asp Ser Ser Gly Ser Phe Tyr Pro Lys Gln Asp Tyr Gly Ala
1020                1025                1030                1035

TAT CAA CGT ATT GAG GAT GGC CGA GGC GTT AAC TAT GCA AGT GGG CTT              3342
Tyr Gln Arg Ile Glu Asp Gly Arg Gly Val Asn Tyr Ala Ser Gly Leu
            1040                1045                1050

TAT TTC GAT GAA CAC CAT AGA AAA CAG CGT GTA GGT ATT GAA TAT ATT              3390
Tyr Phe Asp Glu His His Arg Lys Gln Arg Val Gly Ile Glu Tyr Ile
            1055                1060                1065

TAC GAA AAT AAG AAC AAA GCG GGC ATC ATT GAC AAA GCA GTG TTA AGT              3438
Tyr Glu Asn Lys Asn Lys Ala Gly Ile Ile Asp Lys Ala Val Leu Ser
            1070                1075                1080

GCT AAT CAA CAA AAC ATC ATA CTT GAC AGT TAT ATG CAA CAT ACG CAT              3486
Ala Asn Gln Gln Asn Ile Ile Leu Asp Ser Tyr Met Gln His Thr His
            1085                1090                1095

TGC AGT CTT TAT CCT AAT CCA AGT AAG AAT TGC CGC CCA ACA CGT GAT              3534
Cys Ser Leu Tyr Pro Asn Pro Ser Lys Asn Cys Arg Pro Thr Arg Asp
1100                1105                1110                1115

AAA CCT TAT TCA TAC TAT CAT TCT GAT AGA AAT GTT TAT AAA GAA AAA              3582
Lys Pro Tyr Ser Tyr Tyr His Ser Asp Arg Asn Val Tyr Lys Glu Lys
            1120                1125                1130

CAT AAT ATG TTG CAA TTG AAT TTA GAG AAA AAA ATT CAA CAA AAT TGG              3630
His Asn Met Leu Gln Leu Asn Leu Glu Lys Lys Ile Gln Gln Asn Trp
            1135                1140                1145

CTT ACT CAT CAA ATT GTC TTC AAT CTT GGT TTT GAT GAC TTT ACT TCA              3678
Leu Thr His Gln Ile Val Phe Asn Leu Gly Phe Asp Asp Phe Thr Ser
            1150                1155                1160

GCG CTT CAG CAT AAA GAT TAT TTA ACT CGA CGT GTT ACC GCT ACG GCA              3726
Ala Leu Gln His Lys Asp Tyr Leu Thr Arg Arg Val Thr Ala Thr Ala
            1165                1170                1175

AAG AGT ATT TCA GAG AAA GCT AAT GAA ACA AGA AGA AAT GGT TAC AAA              3774
Lys Ser Ile Ser Glu Lys Ala Asn Glu Thr Arg Arg Asn Gly Tyr Lys
1180                1185                1190                1195

AAA CAA CCT TAC TTA TAC CCA AAA CCA ACA GTA GGT TTT GTA GTA CAA              3822
```

```
                Lys Gln Pro Tyr Leu Tyr Pro Lys Pro Thr Val Gly Phe Val Val Gln
                            1200                1205                    1210

GAT CAT TGT GAT TAT AAA GGT AAC TCC TCT AAT TAC AGA GAC TGT AAA             3870
Asp His Cys Asp Tyr Lys Gly Asn Ser Ser Asn Tyr Arg Asp Cys Lys
                1215                1220                1225

GTG CGG TTA ATT AAA GGG AAA AAT TAT TAT TTC GCA GCA CGC AAT AAT             3918
Val Arg Leu Ile Lys Gly Lys Asn Tyr Tyr Phe Ala Ala Arg Asn Asn
                1230                1235                1240

ATG GCA TTA GGG AAA TAC GTT GAT TTA GGT TTA GGT ATT CGG TAT GAC             3966
Met Ala Leu Gly Lys Tyr Val Asp Leu Gly Leu Gly Ile Arg Tyr Asp
                1245                1250                1255

GTA TCT CGC ACA AAA GCT AAT GAA TCA ACT ATT AGT GTT GGT AAA TTT             4014
Val Ser Arg Thr Lys Ala Asn Glu Ser Thr Ile Ser Val Gly Lys Phe
1260                1265                1270                1275

AAA AAT TTC TCT TGG AAT ACT GGT ATT GTC ATA AAA CCA ACG GAA TGG             4062
Lys Asn Phe Ser Trp Asn Thr Gly Ile Val Ile Lys Pro Thr Glu Trp
                1280                1285                1290

CTT GAT CTT TCT TAT CGC CTT TCT ACT GGA TTT AGA AAT CCT AGT TTT             4110
Leu Asp Leu Ser Tyr Arg Leu Ser Thr Gly Phe Arg Asn Pro Ser Phe
                1295                1300                1305

GCT GAA ATG TAT GGT TGG CGG TAT GGT GGC AAT AAT AGC GAG GTT TAT             4158
Ala Glu Met Tyr Gly Trp Arg Tyr Gly Gly Asn Asn Ser Glu Val Tyr
                1310                1315                1320

GTA GGT AAA TTT AAG CCT GAA ACA TCT CGT AAC CAA GAG TTT GGT CTC             4206
Val Gly Lys Phe Lys Pro Glu Thr Ser Arg Asn Gln Glu Phe Gly Leu
        1325                1330                1335

GCT CTA AAA GGG GAT TTT GGT AAT ATT GAG ATC AGT CAT TTT AGT AAT             4254
Ala Leu Lys Gly Asp Phe Gly Asn Ile Glu Ile Ser His Phe Ser Asn
1340                1345                1350                1355

GCT TAT CGA AAT CTT ATC GCC TTT GCT GAA GAA CTT AAT AAA AAT GGA             4302
Ala Tyr Arg Asn Leu Ile Ala Phe Ala Glu Glu Leu Asn Lys Asn Gly
                1360                1365                1370

ACT GGA AAG GCC AAT TAT GGA TAT CAT AAT GCA CAA AAT GCA AAA TTA             4350
Thr Gly Lys Ala Asn Tyr Gly Tyr His Asn Ala Gln Asn Ala Lys Leu
                1375                1380                1385

GTT GGC GTA AAT ATA ACT GCG CAA TTA GAT TTT AAT GGT TTA TGG AAA             4398
Val Gly Val Asn Ile Thr Ala Gln Leu Asp Phe Asn Gly Leu Trp Lys
                1390                1395                1400

CGT ATT CCC TAC GGT TGG TAT GCA ACA TTT GCT TAT AAC CGA GTA AAA             4446
Arg Ile Pro Tyr Gly Trp Tyr Ala Thr Phe Ala Tyr Asn Arg Val Lys
        1405                1410                1415

GTT AAA GAT CAA AAA ATC AAT GCT GGT TTG GCC TCC GTA AGC AGT TAT             4494
Val Lys Asp Gln Lys Ile Asn Ala Gly Leu Ala Ser Val Ser Ser Tyr
1420                1425                1430                1435

TTA TTT GAT GCC ATT CAG CCC AGC CGT TAT ATC ATT GGT TTA GGC TAT             4542
Leu Phe Asp Ala Ile Gln Pro Ser Arg Tyr Ile Ile Gly Leu Gly Tyr
                1440                1445                1450

GAT CAT CCA AGT AAT ACT TGG GGA ATT AAT ACA ATG TTT ACT CAA TCA             4590
Asp His Pro Ser Asn Thr Trp Gly Ile Asn Thr Met Phe Thr Gln Ser
                1455                1460                1465

AAA GCA AAA TCT CAA AAT GAA TTG CTA GGA AAA CGT GCA TTG GGT AAC             4638
Lys Ala Lys Ser Gln Asn Glu Leu Leu Gly Lys Arg Ala Leu Gly Asn
                1470                1475                1480

AAT TCA AGG GAT GTA AAA TCA ACA AGA AAA CTT ACT CGG GCA TGG CAT             4686
Asn Ser Arg Asp Val Lys Ser Thr Arg Lys Leu Thr Arg Ala Trp His
        1485                1490                1495

ATC TTA GAT GTA TCG GGT TAT TAC ATG GCG AAT AAA AAT ATT ATG CTT             4734
Ile Leu Asp Val Ser Gly Tyr Tyr Met Ala Asn Lys Asn Ile Met Leu
1500                1505                1510                1515

CGA TTA GGG ATA TAT AAT TTA TTC AAC TAT CGC TAT GTT ACT TGG GAA             4782
```

```
Arg Leu Gly Ile Tyr Asn Leu Phe Asn Tyr Arg Tyr Val Thr Trp Glu
            1520                1525                1530

GCG GTG CGT CAA ACA GCA CAA GGT GCG GTC AAT CAA CAT CAA AAT GTT         4830
Ala Val Arg Gln Thr Ala Gln Gly Ala Val Asn Gln His Gln Asn Val
        1535                1540                1545

GGT AGC TAT ACT CGC TAC GCA GCA TCA GGA CGA AAC TAT ACC TTA ACA         4878
Gly Ser Tyr Thr Arg Tyr Ala Ala Ser Gly Arg Asn Tyr Thr Leu Thr
        1550                1555                1560

TTA GAA ATG AAA TTCTAAATTA AAATGCGCCA GATGGACTAG ACATGCTATA              4930
Leu Glu Met Lys
    1565

TCTATACCTT ACTGGCGCAT CTTTTTCTGT TCTATAATCT GGTTAAGTGA AAAACCAAAC        4990

TTGGATTTTT TAGAAGATCT TTCCACGCAT TTATTGTAAA ATCTCCGACA ATTTTTACCG        5050

CACTTTTCTC TATTACAAAA ACAATAAGGA TCCTTTTGTG AATCTCTCA                    5099

(2) INFORMATION FOR SEQ ID NO:5:

(i) SEQUENCE CHARACTERISTICS:
        (A) LENGTH: 913 amino acids
        (B) TYPE: amino acid
        (C) STRANDEDNESS: single
        (D) TOPOLOGY: linear (xi) SEQUENCE DESCRIPTION: SEQ ID NO:5:

Met Thr Lys Lys Pro Tyr Phe Arg Leu Ser Ile Ile Ser Cys Leu Leu
1               5                   10                  15

Ile Ser Cys Tyr Val Lys Ala Glu Thr Gln Ser Ile Lys Asp Thr Lys
            20                  25                  30

Glu Ala Ile Ser Ser Glu Val Asp Thr Gln Ser Thr Glu Asp Ser Glu
        35                  40                  45

Leu Glu Thr Ile Ser Val Thr Ala Glu Lys Val Arg Asp Arg Lys Asp
    50                  55                  60

Asn Glu Val Thr Gly Leu Gly Lys Ile Ile Lys Thr Ser Glu Ser Ile
65                  70                  75                  80

Ser Arg Glu Gln Val Leu Asn Ile Arg Asp Leu Thr Arg Tyr Asp Pro
                85                  90                  95

Gly Ile Ser Val Val Glu Gln Gly Arg Gly Ala Ser Ser Gly Tyr Ser
            100                 105                 110

Ile Arg Gly Met Asp Arg Asn Arg Val Ala Leu Leu Val Asp Gly Leu
        115                 120                 125

Pro Gln Thr Gln Ser Tyr Val Gln Ser Pro Leu Val Ala Arg Ser
    130                 135                 140

Gly Tyr Ser Gly Thr Gly Ala Ile Asn Glu Ile Glu Tyr Glu Asn Val
145                 150                 155                 160

Lys Ala Val Glu Ile Ser Lys Gly Gly Ser Ser Glu Tyr Gly Asn
                165                 170                 175

Gly Ala Leu Ala Gly Ser Val Thr Phe Gln Ser Lys Ser Ala Ala Asp
            180                 185                 190

Ile Leu Glu Gly Asp Lys Ser Trp Gly Ile Gln Thr Lys Asn Ala Tyr
        195                 200                 205

Ser Ser Lys Asn Lys Gly Phe Thr His Ser Leu Ala Val Ala Gly Lys
    210                 215                 220

Gln Gly Gly Phe Glu Gly Val Ala Ile Tyr Thr His Arg Asn Ser Ile
225                 230                 235                 240

Glu Thr Gln Val His Lys Asp Ala Leu Lys Gly Val Gln Ser Tyr Asp
                245                 250                 255
```

-continued

```
Arg Phe Ile Ala Thr Thr Glu Asp Gln Ser Ala Tyr Phe Val Met Gln
            260                 265                 270

Asp Glu Cys Leu Asp Gly Tyr Asp Lys Cys Lys Thr Ser Pro Lys Arg
            275                 280                 285

Pro Ala Thr Leu Ser Thr Gln Arg Glu Thr Val Ser Val Ser Asp Tyr
            290                 295                 300

Thr Gly Ala Asn Arg Ile Lys Pro Asn Pro Met Lys Tyr Glu Ser Gln
305                 310                 315                 320

Ser Trp Phe Leu Arg Gly Gly Tyr His Phe Ser Glu Gln His Tyr Ile
                    325                 330                 335

Gly Gly Ile Phe Glu Phe Thr Gln Gln Lys Phe Asp Ile Arg Asp Met
                340                 345                 350

Thr Phe Pro Ala Tyr Leu Arg Pro Thr Glu Asp Lys Asp Leu Gln Ser
            355                 360                 365

Arg Pro Phe Tyr Pro Lys Gln Asp Tyr Gly Ala Tyr Gln His Ile Gly
            370                 375                 380

Asp Gly Arg Gly Val Lys Tyr Ala Ser Gly Leu Tyr Phe Asp Glu His
385                 390                 395                 400

His Arg Lys Gln Arg Val Gly Ile Glu Tyr Ile Tyr Glu Asn Lys Asn
                    405                 410                 415

Lys Ala Gly Ile Ile Asp Lys Ala Val Leu Ser Ala Asn Gln Gln Asn
                420                 425                 430

Ile Ile Leu Asp Ser Tyr Met Arg His Thr His Cys Ser Leu Tyr Pro
            435                 440                 445

Asn Pro Ser Lys Asn Cys Arg Pro Thr Leu Asp Lys Pro Tyr Ser Tyr
            450                 455                 460

Tyr His Ser Asp Arg Asn Val Tyr Lys Glu Lys His Asn Met Leu Gln
465                 470                 475                 480

Leu Asn Leu Glu Lys Lys Ile Gln Gln Asn Trp Leu Thr His Gln Ile
                    485                 490                 495

Ala Phe Asn Leu Gly Phe Asp Asp Phe Thr Ser Ala Leu Gln His Lys
                500                 505                 510

Asp Tyr Leu Thr Arg Arg Val Ile Ala Thr Ala Ser Ser Ile Ser Glu
            515                 520                 525

Lys Arg Gly Glu Ala Arg Arg Asn Gly Leu Gln Ser Ser Pro Tyr Leu
530                 535                 540

Tyr Pro Thr Pro Lys Ala Glu Leu Val Gly Gly Asp Leu Cys Asn Tyr
545                 550                 555                 560

Gln Gly Lys Ser Ser Asn Tyr Ser Asp Cys Lys Val Arg Leu Ile Lys
                    565                 570                 575

Gly Lys Asn Tyr Tyr Phe Ala Ala Arg Asn Asn Met Ala Leu Gly Lys
                580                 585                 590

Tyr Val Asp Leu Gly Leu Gly Met Arg Tyr Asp Val Ser Arg Thr Lys
            595                 600                 605

Ala Asn Glu Ser Thr Ile Ser Val Gly Lys Phe Lys Asn Phe Ser Trp
610                 615                 620

Asn Thr Gly Ile Val Ile Lys Pro Thr Glu Trp Leu Asp Leu Ser Tyr
625                 630                 635                 640

Arg Leu Ser Thr Gly Phe Arg Asn Pro Ser Phe Ala Glu Met Tyr Gly
                    645                 650                 655

Trp Arg Tyr Gly Gly Lys Asp Thr Asp Val Tyr Ile Gly Lys Phe Lys
                660                 665                 670

Pro Glu Thr Ser Arg Asn Gln Glu Phe Gly Leu Ala Leu Lys Gly Asp
            675                 680                 685
```

```
Phe Gly Asn Ile Glu Ile Ser His Phe Ser Asn Ala Tyr Arg Asn Leu
        690                 695                 700

Ile Ala Phe Ala Glu Glu Leu Ser Lys Asn Gly Thr Thr Gly Lys Gly
705                 710                 715                 720

Asn Tyr Gly Tyr His Asn Ala Gln Asn Ala Lys Leu Val Gly Val Asn
                725                 730                 735

Ile Thr Ala Gln Leu Asp Phe Asn Gly Leu Trp Lys Arg Ile Pro Tyr
            740                 745                 750

Gly Trp Tyr Ala Thr Phe Ala Tyr Asn Arg Val Lys Val Lys Asp Gln
        755                 760                 765

Lys Ile Asn Ala Gly Leu Ala Ser Val Ser Ser Tyr Leu Phe Asp Ala
        770                 775                 780

Ile Gln Pro Ser Arg Tyr Ile Ile Gly Leu Gly Tyr Asp His Pro Ser
785                 790                 795                 800

Asn Thr Trp Gly Ile Lys Thr Met Phe Thr Gln Ser Lys Ala Lys Ser
                805                 810                 815

Gln Asn Glu Leu Leu Gly Lys Arg Ala Leu Gly Asn Asn Ser Arg Asn
            820                 825                 830

Val Lys Ser Thr Arg Lys Leu Thr Arg Ala Trp His Ile Leu Asp Val
        835                 840                 845

Ser Gly Tyr Tyr Met Val Asn Arg Ser Ile Leu Phe Arg Leu Gly Val
        850                 855                 860

Tyr Asn Leu Leu Asn Tyr Arg Tyr Val Thr Trp Glu Ala Val Arg Gln
865                 870                 875                 880

Thr Ala Gln Gly Ala Val Asn Gln His Gln Asn Val Gly Asn Tyr Thr
                885                 890                 895

Arg Tyr Ala Ala Ser Gly Arg Asn Tyr Thr Leu Thr Leu Glu Met Lys
            900                 905                 910

Phe (2) INFORMATION FOR SEQ ID NO:6:

(i) SEQUENCE CHARACTERISTICS:
        (A) LENGTH: 644 amino acids
        (B) TYPE: amino acid
        (C) STRANDEDNESS: single
        (D) TOPOLOGY: linear (xi) SEQUENCE DESCRIPTION: SEQ ID NO:6:

Met Lys Ser Val Pro Leu Ile Ser Gly Gly Leu Ser Phe Leu Leu Ser
1               5                   10                  15

Ala Cys Ser Gly Gly Gly Ser Phe Asp Val Asp Asn Val Ser Asn Thr
            20                  25                  30

Pro Ser Ser Lys Pro Arg Tyr Gln Asp Asp Thr Ser Ser Ser Arg Thr
        35                  40                  45

Lys Ser Lys Leu Glu Lys Leu Ser Ile Pro Ser Leu Gly Gly Gly Met
    50                  55                  60

Lys Leu Ala Ala Leu Asn Leu Phe Asp Arg Asn Lys Pro Ser Leu Leu
65                  70                  75                  80

Asn Glu Asp Ser Tyr Met Ile Phe Ser Ser Arg Ser Thr Ile Glu Glu
                85                  90                  95

Asp Val Lys Asn Asp Asn Gln Asn Gly Glu His Pro Ile Asp Ser Ile
            100                 105                 110

Val Asp Pro Arg Ala Pro Asn Ser Asn Glu Asn Arg His Gly Gln Lys
        115                 120                 125
```

-continued

```
Tyr Val Tyr Ser Gly Leu Tyr Tyr Ile Gln Ser Trp Ser Leu Arg Asp
    130                 135                 140

Leu Pro Asn Lys Lys Phe Tyr Ser Gly Tyr Tyr Gly Tyr Ala Tyr Tyr
145                 150                 155                 160

Phe Gly Asn Thr Thr Ala Ser Ala Leu Pro Val Gly Val Ala Thr
                165                 170                 175

Tyr Lys Gly Thr Trp Ser Phe Ile Thr Ala Ala Glu Asn Gly Lys Asn
            180                 185                 190

Tyr Glu Leu Leu Arg Asn Ser Gly Gly Gln Ala Tyr Ser Arg Arg
            195                 200                 205

Ser Ala Thr Pro Glu Asp Ile Asp Leu Asp Arg Lys Thr Gly Leu Thr
    210                 215                 220

Ser Glu Phe Thr Val Asn Phe Gly Thr Lys Lys Leu Thr Gly Gly Leu
225                 230                 235                 240

Tyr Tyr Asn Leu Arg Glu Thr Asp Ala Asn Lys Ser Gln Asn Arg Thr
                245                 250                 255

His Lys Leu Tyr Asp Leu Glu Ala Asp Val His Ser Asn Arg Phe Arg
            260                 265                 270

Gly Lys Val Lys Pro Thr Lys Lys Glu Ser Ser Glu His Pro Phe
            275                 280                 285

Thr Ser Glu Gly Thr Leu Glu Gly Gly Phe Tyr Gly Pro Glu Gly Gln
    290                 295                 300

Glu Leu Gly Gly Lys Phe Leu Ala His Asp Lys Lys Val Leu Gly Val
305                 310                 315                 320

Phe Ser Ala Lys Glu Gln Gln Glu Thr Ser Glu Asn Lys Lys Leu Pro
                325                 330                 335

Lys Glu Thr Leu Ile Asp Gly Lys Leu Thr Thr Phe Lys Thr Thr Asn
            340                 345                 350

Ala Thr Ala Asn Ala Thr Thr Asp Ala Thr Ser Thr Thr Ala Ser
    355                 360                 365

Thr Lys Thr Asp Thr Thr Thr Asn Ala Thr Ala Asn Thr Glu Asn Phe
    370                 375                 380

Thr Thr Lys Asp Ile Pro Ser Leu Gly Glu Ala Asp Tyr Leu Leu Ile
385                 390                 395                 400

Asp Asn Tyr Pro Val Pro Leu Phe Pro Glu Ser Gly Asp Phe Ile Ser
                405                 410                 415

Ser Lys His His Thr Val Gly Lys Lys Thr Tyr Gln Val Glu Ala Cys
            420                 425                 430

Cys Ser Asn Leu Ser Tyr Val Lys Phe Gly Met Tyr Tyr Glu Ala Pro
            435                 440                 445

Pro Lys Glu Glu Glu Lys Glu Lys Glu Lys Asp Lys Asp Lys Glu Lys
    450                 455                 460

Glu Lys Gln Ala Thr Thr Ser Ile Lys Thr Tyr Tyr Gln Phe Leu Leu
465                 470                 475                 480

Gly Leu Arg Thr Pro Ser Ser Glu Ile Pro Lys Glu Gly Ser Ala Lys
                485                 490                 495

Tyr His Gly Asn Trp Phe Gly Tyr Ile Ser Asp Gly Glu Thr Ser Tyr
            500                 505                 510

Ser Ala Ser Gly Asp Lys Glu Arg Ser Lys Asn Ala Val Ala Glu Phe
            515                 520                 525

Asn Val Asn Phe Ala Glu Lys Thr Leu Thr Gly Glu Leu Lys Arg His
    530                 535                 540

Asp Thr Gln Asn Pro Val Phe Lys Ile Asn Ala Thr Phe Gln Ser Gly
545                 550                 555                 560
```

```
Lys Asn Asp Phe Thr Gly Thr Ala Thr Ala Lys Asp Leu Ala Ile Asp
            565                 570                 575

Gly Lys Asn Thr Gln Gly Thr Ser Lys Val Asn Phe Thr Ala Thr Val
            580                 585                 590

Asn Gly Ala Phe Tyr Gly Pro His Ala Thr Glu Leu Gly Gly Tyr Phe
            595                 600                 605

Thr Tyr Asn Gly Asn Asn Pro Thr Asp Lys Asn Ser Ser Ser Asn Ser
            610                 615                 620

Glu Lys Ala Arg Ala Ala Val Val Phe Gly Ala Lys Lys Gln Gln Val
625                 630                 635                 640

Glu Thr Thr Lys (2) INFORMATION FOR SEQ ID NO:7:

(i) SEQUENCE CHARACTERISTICS:
        (A) LENGTH: 912 amino acids
        (B) TYPE: amino acid
        (C) STRANDEDNESS: single
        (D) TOPOLOGY: linear (xi) SEQUENCE DESCRIPTION: SEQ ID NO:7:

Met Thr Lys Lys Pro Tyr Phe Arg Leu Ser Ile Ile Ser Cys Leu Leu
1               5                   10                  15

Ile Ser Cys Tyr Val Lys Ala Glu Thr Gln Ser Ile Lys Asp Thr Lys
                20                  25                  30

Glu Ala Ile Ser Ser Glu Val Asp Thr Gln Ser Thr Glu Asp Ser Glu
            35                  40                  45

Leu Glu Thr Ile Ser Val Thr Ala Glu Lys Ile Arg Asp Arg Lys Asp
50                  55                  60

Asn Glu Val Thr Gly Leu Gly Lys Ile Ile Lys Thr Ser Glu Ser Ile
65                  70                  75                  80

Ser Arg Glu Gln Val Leu Asn Ile Arg Asp Leu Thr Arg Tyr Asp Pro
                85                  90                  95

Gly Ile Ser Val Val Glu Gln Gly Arg Gly Ala Ser Ser Gly Tyr Ser
                100                 105                 110

Ile Arg Gly Met Asp Arg Asn Arg Val Ala Leu Leu Val Asp Gly Leu
            115                 120                 125

Pro Gln Thr Gln Ser Tyr Val Val Gln Ser Pro Leu Val Ala Arg Ser
130                 135                 140

Gly Tyr Ser Gly Thr Gly Ala Ile Asn Glu Ile Glu Tyr Glu Asn Val
145                 150                 155                 160

Lys Ala Val Glu Ile Ser Lys Gly Gly Ser Ser Glu Tyr Gly Asn
                165                 170                 175

Gly Ala Leu Ala Gly Ser Val Thr Phe Gln Ser Lys Ser Ala Ala Asp
            180                 185                 190

Ile Leu Glu Gly Asp Lys Ser Trp Gly Ile Gln Thr Lys Asn Ala Tyr
            195                 200                 205

Ser Ser Lys Asn Lys Gly Phe Thr His Ser Leu Ala Val Ala Gly Lys
            210                 215                 220

Gln Gly Gly Phe Glu Gly Leu Ala Ile Tyr Thr Gln Arg Asn Ser Ile
225                 230                 235                 240

Glu Thr Gln Val His Lys Asp Ala Leu Lys Gly Val Gln Ser Tyr Asp
                245                 250                 255

Arg Leu Ile Ala Thr Thr Asp Lys Ser Ser Gly Tyr Phe Val Ile Gln
            260                 265                 270
```

```
Gly Glu Cys Pro Asn Gly Asp Asp Lys Cys Ala Ala Lys Pro Pro Ala
            275                 280                 285

Thr Leu Ser Thr Gln Ser Glu Thr Val Ser Val Ser Asp Tyr Thr Gly
        290                 295                 300

Ala Asn Arg Ile Lys Pro Asn Pro Met Lys Tyr Glu Ser Gln Ser Trp
305                 310                 315                 320

Phe Leu Arg Gly Gly Tyr His Phe Ser Glu Gln His Tyr Ile Gly Gly
                325                 330                 335

Ile Phe Glu Phe Thr Gln Gln Lys Phe Asp Ile Arg Asp Met Thr Phe
                340                 345                 350

Pro Ala Tyr Leu Ser Pro Thr Glu Arg Arg Asp Asp Ser Ser Arg Ser
            355                 360                 365

Phe Tyr Pro Met Gln Asp His Gly Ala Tyr Gln His Ile Glu Asp Gly
370                 375                 380

Arg Gly Val Lys Tyr Ala Ser Gly Leu Tyr Phe Asp Glu His His Arg
385                 390                 395                 400

Lys Gln Arg Val Gly Ile Glu Tyr Ile Tyr Glu Asn Lys Asn Lys Ala
                405                 410                 415

Gly Ile Ile Asp Lys Ala Val Leu Ser Ala Asn Gln Gln Asn Ile Ile
                420                 425                 430

Leu Asp Ser Tyr Met Arg His Thr His Cys Ser Leu Tyr Pro Asn Pro
            435                 440                 445

Ser Lys Asn Cys Arg Pro Thr Leu Asp Lys Pro Tyr Ser Tyr Tyr Arg
450                 455                 460

Ser Asp Arg Asn Val Tyr Lys Glu Lys His Asn Met Leu Gln Leu Asn
465                 470                 475                 480

Leu Glu Lys Lys Ile Gln Gln Asn Trp Leu Thr His Gln Ile Val Phe
                485                 490                 495

Asn Leu Gly Phe Asp Asp Phe Thr Ser Ala Leu Gln His Lys Asp Tyr
                500                 505                 510

Leu Thr Arg Arg Val Ile Ala Thr Ala Asp Ser Ile Pro Arg Lys Pro
            515                 520                 525

Gly Glu Thr Gly Lys Pro Arg Asn Gly Leu Gln Ser Gln Pro Tyr Leu
            530                 535                 540

Tyr Pro Lys Pro Glu Pro Tyr Phe Ala Gly Gln Asp His Cys Asn Tyr
545                 550                 555                 560

Gln Gly Ser Ser Asn Tyr Arg Asp Cys Lys Val Arg Leu Ile Lys
                565                 570                 575

Gly Lys Asn Tyr Tyr Phe Ala Ala Arg Asn Asn Met Ala Leu Gly Lys
                580                 585                 590

Tyr Val Asp Leu Gly Leu Gly Ile Arg Tyr Asp Val Ser Arg Thr Lys
            595                 600                 605

Ala Asn Glu Ser Thr Ile Ser Val Gly Lys Phe Lys Asn Phe Ser Trp
610                 615                 620

Asn Thr Gly Ile Val Ile Lys Pro Thr Glu Trp Leu Asp Leu Ser Tyr
625                 630                 635                 640

Arg Leu Ser Thr Gly Phe Arg Asn Pro Ser Phe Ser Glu Met Tyr Gly
                645                 650                 655

Trp Arg Tyr Gly Gly Lys Asn Asp Glu Val Tyr Val Gly Lys Phe Lys
                660                 665                 670

Pro Glu Thr Ser Arg Asn Gln Glu Phe Gly Leu Ala Leu Lys Gly Asp
            675                 680                 685

Phe Gly Asn Ile Glu Ile Ser His Phe Ser Asn Ala Tyr Arg Asn Leu
690                 695                 700
```

Ile Ala Phe Ala Glu Glu Leu Ser Lys Asn Gly Thr Gly Lys Gly Asn
705                 710                 715                 720

Tyr Gly Tyr His Asn Ala Gln Asn Ala Lys Leu Val Gly Val Asn Ile
            725                 730                 735

Thr Ala Gln Leu Asp Phe Asn Gly Leu Trp Lys Arg Ile Pro Tyr Gly
            740                 745                 750

Trp Tyr Ala Thr Phe Ala Tyr Asn Gln Val Lys Val Lys Asp Gln Lys
            755                 760                 765

Ile Asn Ala Gly Leu Ala Ser Val Ser Ser Tyr Leu Phe Asp Ala Ile
770                 775                 780

Gln Pro Ser Arg Tyr Ile Ile Gly Leu Gly Tyr Asp His Pro Ser Asn
785                 790                 795                 800

Thr Trp Gly Ile Asn Thr Met Phe Thr Gln Ser Lys Ala Lys Ser Gln
                805                 810                 815

Asn Glu Leu Leu Gly Lys Arg Ala Leu Gly Asn Asn Ser Arg Asp Val
            820                 825                 830

Lys Ser Thr Arg Lys Leu Thr Arg Ala Trp His Ile Leu Asp Val Ser
            835                 840                 845

Gly Tyr Tyr Met Ala Asn Lys Asn Ile Met Leu Arg Leu Gly Ile Tyr
850                 855                 860

Asn Leu Phe Asn Tyr Arg Tyr Val Thr Trp Glu Ala Val Arg Gln Thr
865                 870                 875                 880

Ala Gln Gly Ala Val Asn Gln His Gln Asn Val Gly Ser Tyr Thr Arg
            885                 890                 895

Tyr Ala Ala Ser Gly Arg Asn Tyr Thr Leu Thr Leu Glu Met Lys Phe
            900                 905                 910

(2) INFORMATION FOR SEQ ID NO:8:

(i) SEQUENCE CHARACTERISTICS:
        (A) LENGTH: 660 amino acids
        (B) TYPE: amino acid
        (C) STRANDEDNESS: single
        (D) TOPOLOGY: linear (xi) SEQUENCE DESCRIPTION: SEQ ID NO:8:

Met Lys Ser Val Pro Leu Ile Ser Gly Gly Leu Ser Phe Leu Leu Ser
1               5                   10                  15

Ala Cys Ser Gly Gly Gly Ser Phe Asp Val Asp Asn Val Ser Asn Thr
            20                  25                  30

Pro Ser Ser Lys Pro Arg Tyr Gln Asp Asp Thr Ser Asn Gln Arg Lys
            35                  40                  45

Lys Ser Asn Leu Lys Lys Leu Phe Ile Pro Ser Leu Gly Gly Gly Met
50                  55                  60

Lys Leu Val Ala Gln Asn Leu Arg Gly Asn Lys Glu Pro Ser Phe Leu
65                  70                  75                  80

Asn Glu Asp Asp Tyr Ile Ser Tyr Phe Ser Ser Leu Ser Thr Ile Glu
                85                  90                  95

Lys Asp Val Lys Asp Asn Asn Lys Asn Gly Ala Asp Leu Ile Gly Ser
            100                 105                 110

Ile Asp Glu Pro Ser Thr Thr Asn Pro Pro Glu Lys His His Gly Gln
            115                 120                 125

Lys Tyr Val Tyr Ser Gly Leu Tyr Tyr Thr Pro Ser Trp Ser Leu Asn
            130                 135                 140

Asp Ser Lys Asn Lys Phe Tyr Leu Gly Tyr Tyr Gly Tyr Ala Phe Tyr
145                 150                 155                 160

```
Tyr Gly Asn Lys Thr Ala Thr Asn Leu Pro Val Asn Gly Val Ala Lys
                165                 170                 175
Tyr Lys Gly Thr Trp Asp Phe Ile Thr Ala Thr Lys Asn Gly Lys Arg
            180                 185                 190
Tyr Pro Leu Leu Ser Asn Gly Ser His Ala Tyr Tyr Arg Arg Ser Ala
        195                 200                 205
Ile Pro Glu Asp Ile Asp Leu Glu Asn Asp Ser Lys Asn Gly Asp Ile
    210                 215                 220
Gly Leu Ile Ser Glu Phe Ser Ala Asp Phe Gly Thr Lys Lys Leu Thr
225                 230                 235                 240
Gly Gln Leu Ser Tyr Thr Lys Arg Lys Thr Asn Asn Gln Pro Tyr Glu
                245                 250                 255
Lys Lys Lys Leu Tyr Asp Ile Asp Ala Asp Ile Tyr Ser Asn Arg Phe
            260                 265                 270
Arg Gly Thr Val Lys Pro Thr Glu Lys Asp Ser Glu Glu His Pro Phe
        275                 280                 285
Thr Ser Glu Gly Thr Leu Glu Gly Gly Phe Tyr Gly Pro Asn Ala Glu
    290                 295                 300
Glu Leu Gly Gly Lys Phe Leu Ala Thr Asp Asn Arg Val Phe Gly Val
305                 310                 315                 320
Phe Ser Ala Lys Glu Thr Glu Thr Lys Lys Glu Ala Leu Ser Lys
                325                 330                 335
Glu Thr Leu Ile Asp Gly Lys Leu Ile Thr Phe Ser Thr Lys Lys Thr
            340                 345                 350
Asp Ala Lys Thr Asn Ala Thr Thr Ser Thr Ala Ala Asn Thr Thr Thr
        355                 360                 365
Asp Thr Thr Ala Asn Thr Ile Thr Asp Glu Lys Asn Phe Lys Thr Glu
    370                 375                 380
Asp Ile Ser Ser Phe Gly Glu Ala Asp Tyr Leu Leu Ile Asp Lys Tyr
385                 390                 395                 400
Pro Ile Pro Leu Leu Pro Asp Lys Asn Thr Asn Asp Phe Ile Ser Ser
                405                 410                 415
Lys His His Thr Val Gly Asn Lys Arg Tyr Lys Val Glu Ala Cys Cys
            420                 425                 430
Ser Asn Leu Ser Tyr Val Lys Phe Gly Met Tyr Tyr Glu Asp Pro Leu
        435                 440                 445
Lys Glu Lys Glu Thr Glu Thr Glu Thr Glu Thr Glu Lys Asp Lys Glu
    450                 455                 460
Lys Glu Lys Glu Lys Asp Lys Asp Lys Glu Lys Gln Thr Ala Ala Thr
465                 470                 475                 480
Thr Asn Thr Tyr Tyr Gln Phe Leu Leu Gly His Arg Thr Pro Lys Asp
                485                 490                 495
Asp Ile Pro Lys Thr Gly Ser Ala Lys Tyr His Gly Ser Trp Phe Gly
            500                 505                 510
Tyr Ile Thr Asp Gly Lys Thr Ser Tyr Ser Pro Ser Gly Asp Lys Lys
        515                 520                 525
Arg Asp Lys Asn Ala Val Ala Glu Phe Asn Val Asp Phe Ala Glu Lys
    530                 535                 540
Lys Leu Thr Gly Glu Leu Lys Arg His Asp Thr Gly Asn Pro Val Phe
545                 550                 555                 560
Ser Ile Glu Ala Asn Phe Asn Asn Ser Ser Asn Ala Phe Thr Gly Thr
                565                 570                 575
Ala Thr Ala Thr Asn Phe Val Ile Asp Gly Lys Asn Ser Gln Asn Lys
```

```
                580                 585                 590
Asn Thr Pro Ile Asn Ile Thr Thr Lys Val Asn Gly Ala Phe Tyr Gly
            595                 600                 605

Pro Lys Ala Ser Glu Leu Gly Gly Tyr Phe Thr Tyr Asn Gly Asn Ser
610                 615                 620

Thr Ala Thr Asn Ser Glu Ser Ser Ser Thr Val Ser Ser Ser Ser Asn
625                 630                 635                 640

Ser Lys Asn Ala Arg Ala Ala Val Val Phe Gly Ala Arg Gln Gln Val
                645                 650                 655

Glu Thr Thr Lys
            660

(2) INFORMATION FOR SEQ ID NO:9:

(i) SEQUENCE CHARACTERISTICS:
        (A) LENGTH: 912 amino acids
        (B) TYPE: amino acid
        (C) STRANDEDNESS: single
        (D) TOPOLOGY: linear (xi) SEQUENCE DESCRIPTION: SEQ ID NO:9:

Met Thr Lys Lys Pro Tyr Phe Arg Leu Ser Ile Ile Ser Cys Leu Leu
1               5                   10                  15

Ile Ser Cys Tyr Val Lys Ala Glu Thr Gln Ser Ile Lys Asp Thr Lys
                20                  25                  30

Glu Ala Ile Ser Ser Glu Val Asp Thr Gln Ser Thr Glu Asp Ser Glu
            35                  40                  45

Leu Glu Thr Ile Ser Val Thr Ala Glu Lys Ile Arg Asp Arg Lys Asp
    50                  55                  60

Asn Glu Val Thr Gly Leu Gly Lys Ile Ile Lys Thr Ser Glu Ser Ile
65                  70                  75                  80

Ser Arg Glu Gln Val Leu Asn Ile Arg Asp Leu Thr Arg Tyr Asp Pro
                85                  90                  95

Gly Ile Ser Val Val Glu Gln Gly Arg Gly Ala Ser Ser Gly Tyr Ser
                100                 105                 110

Ile Arg Gly Met Asp Arg Asn Arg Val Ala Leu Leu Val Asp Gly Leu
            115                 120                 125

Pro Gln Thr Gln Ser Tyr Val Val Gln Ser Pro Leu Val Ala Arg Ser
    130                 135                 140

Gly Tyr Ser Gly Thr Gly Ala Ile Asn Glu Ile Glu Tyr Glu Asn Val
145                 150                 155                 160

Lys Ala Val Glu Ile Ser Lys Gly Gly Ser Ser Glu Tyr Gly Asn
                165                 170                 175

Gly Ala Leu Ala Gly Ser Val Thr Phe Gln Ser Lys Ser Ala Ala Asp
                180                 185                 190

Ile Leu Glu Gly Asp Lys Ser Trp Gly Ile Gln Thr Lys Asn Ala Tyr
            195                 200                 205

Ser Ser Lys Asn Lys Gly Phe Thr His Ser Leu Ala Val Ala Gly Lys
    210                 215                 220

Gln Gly Gly Phe Glu Gly Leu Ala Ile Tyr Thr Gln Arg Asn Ser Ile
225                 230                 235                 240

Glu Thr Gln Val His Lys Asp Ala Leu Lys Gly Val Gln Ser Tyr Asp
                245                 250                 255

Arg Leu Ile Ala Thr Thr Asp Lys Ser Ser Gly Tyr Phe Val Ile Gln
            260                 265                 270

Gly Glu Cys Pro Asn Gly Asp Asp Lys Cys Ala Ala Lys Pro Pro Ala
```

-continued

```
                275                 280                 285
Thr Leu Ser Thr Gln Ser Glu Thr Val Ser Val Ser Asp Tyr Thr Gly
    290                 295                 300
Ala Asn Arg Ile Lys Pro Asn Pro Met Lys Tyr Glu Ser Gln Ser Trp
305                 310                 315                 320
Phe Leu Arg Gly Tyr His Phe Ser Glu Gln His Tyr Ile Gly Gly
                325                 330                 335
Ile Phe Glu Phe Thr Gln Gln Lys Phe Asp Ile Arg Asp Met Thr Phe
            340                 345                 350
Pro Ala Tyr Leu Ser Pro Thr Glu Arg Asp Asp Ser Ser Arg Ser
            355                 360                 365
Phe Tyr Pro Met Gln Asp His Gly Ala Tyr Gln His Ile Glu Asp Gly
370                 375                 380
Arg Gly Val Lys Tyr Ala Ser Gly Leu Tyr Phe Asp Glu His His Arg
385                 390                 395                 400
Lys Gln Arg Val Gly Ile Glu Tyr Ile Tyr Glu Asn Lys Asn Lys Ala
                405                 410                 415
Gly Ile Ile Asp Lys Ala Val Leu Ser Ala Asn Gln Gln Asn Ile Ile
                420                 425                 430
Leu Asp Ser Tyr Met Arg His Thr His Cys Ser Leu Tyr Pro Asn Pro
            435                 440                 445
Ser Lys Asn Cys Arg Pro Thr Leu Asp Lys Pro Tyr Ser Tyr Tyr Arg
450                 455                 460
Ser Asp Arg Asn Val Tyr Lys Glu Lys His Asn Met Leu Gln Leu Asn
465                 470                 475                 480
Leu Glu Lys Lys Ile Gln Gln Asn Trp Leu Thr His Gln Ile Val Phe
                485                 490                 495
Asn Leu Gly Phe Asp Asp Phe Thr Ser Ala Leu Gln His Lys Asp Tyr
            500                 505                 510
Leu Thr Arg Arg Val Ile Ala Thr Asp Ser Ile Pro Arg Lys Pro
            515                 520                 525
Gly Glu Thr Gly Lys Pro Arg Asn Gly Leu Gln Ser Gln Pro Tyr Leu
    530                 535                 540
Tyr Pro Lys Pro Glu Pro Tyr Phe Ala Gly Gln Asp His Cys Asn Tyr
545                 550                 555                 560
Gln Gly Ser Ser Asn Tyr Arg Asp Cys Lys Val Arg Leu Ile Lys
                565                 570                 575
Gly Lys Asn Tyr Tyr Phe Ala Ala Arg Asn Asn Met Ala Leu Gly Lys
            580                 585                 590
Tyr Val Asp Leu Gly Leu Gly Ile Arg Tyr Asp Val Ser Arg Thr Lys
            595                 600                 605
Ala Asn Glu Ser Thr Ile Ser Val Gly Lys Phe Lys Asn Phe Ser Trp
610                 615                 620
Asn Thr Gly Ile Val Ile Lys Pro Thr Glu Trp Leu Asp Leu Ser Tyr
625                 630                 635                 640
Arg Leu Ser Thr Gly Phe Arg Asn Pro Ser Phe Ser Glu Met Tyr Gly
                645                 650                 655
Trp Arg Tyr Gly Gly Lys Asn Asp Glu Val Tyr Val Gly Lys Phe Lys
            660                 665                 670
Pro Glu Thr Ser Arg Asn Gln Glu Phe Gly Leu Ala Leu Lys Gly Asp
            675                 680                 685
Phe Gly Asn Ile Glu Ile Ser His Phe Ser Asn Ala Tyr Arg Asn Leu
    690                 695                 700
```

```
Ile Ala Phe Ala Glu Glu Leu Ser Lys Asn Gly Thr Gly Lys Gly Asn
705                 710                 715                 720

Tyr Gly Tyr His Asn Ala Gln Asn Ala Lys Leu Val Gly Val Asn Ile
            725                 730                 735

Thr Ala Gln Leu Asp Phe Asn Gly Leu Trp Lys Arg Ile Pro Tyr Gly
        740                 745                 750

Trp Tyr Ala Thr Phe Ala Tyr Asn Gln Val Lys Val Lys Asp Gln Lys
    755                 760                 765

Ile Asn Ala Gly Leu Ala Ser Val Ser Tyr Leu Phe Asp Ala Ile
770                 775                 780

Gln Pro Ser Arg Tyr Ile Ile Gly Leu Gly Tyr Asp His Pro Ser Asn
785                 790                 795                 800

Thr Trp Gly Ile Asn Thr Met Phe Thr Gln Ser Lys Ala Lys Ser Gln
            805                 810                 815

Asn Glu Leu Leu Gly Lys Arg Ala Leu Gly Asn Asn Ser Arg Asp Val
        820                 825                 830

Lys Ser Thr Arg Lys Leu Thr Arg Ala Trp His Ile Leu Asp Val Ser
    835                 840                 845

Gly Tyr Tyr Met Ala Asn Lys Asn Ile Met Leu Arg Leu Gly Ile Tyr
    850                 855                 860

Asn Leu Phe Asn Tyr Arg Tyr Val Thr Trp Glu Ala Val Arg Gln Thr
865                 870                 875                 880

Ala Gln Gly Ala Val Asn Gln His Gln Asn Val Gly Ser Tyr Thr Arg
            885                 890                 895

Tyr Ala Ala Ser Gly Arg Asn Tyr Thr Leu Thr Leu Glu Met Lys Phe
        900                 905                 910

(2) INFORMATION FOR SEQ ID NO:10:

(i) SEQUENCE CHARACTERISTICS:
        (A) LENGTH: 660 amino acids
        (B) TYPE: amino acid
        (C) STRANDEDNESS: single
        (D) TOPOLOGY: linear (xi) SEQUENCE DESCRIPTION: SEQ ID NO:10:

Met Lys Ser Val Pro Leu Ile Ser Gly Gly Leu Ser Phe Leu Leu Ser
1                   5                   10                  15

Ala Cys Ser Gly Gly Ser Phe Asp Val Asp Asn Val Ser Asn Thr
            20                  25                  30

Pro Ser Ser Lys Pro Arg Tyr Gln Asp Asp Thr Ser Asn Gln Arg Lys
        35                  40                  45

Lys Ser Asn Leu Lys Lys Leu Phe Ile Pro Ser Leu Gly Gly Gly Met
50                  55                  60

Lys Leu Val Ala Gln Asn Leu Arg Gly Asn Lys Glu Pro Ser Phe Leu
65                  70                  75                  80

Asn Glu Asp Asp Tyr Ile Ser Tyr Phe Ser Ser Leu Ser Thr Ile Glu
            85                  90                  95

Lys Asp Val Lys Asp Asn Asn Lys Asn Gly Ala Asp Leu Ile Gly Ser
        100                 105                 110

Ile Asp Glu Pro Ser Thr Thr Asn Pro Pro Glu Lys His His Gly Gln
    115                 120                 125

Lys Tyr Val Tyr Ser Gly Leu Tyr Tyr Thr Pro Ser Trp Ser Leu Asn
    130                 135                 140

Asp Ser Lys Asn Lys Phe Tyr Leu Gly Tyr Gly Tyr Ala Phe Tyr
145                 150                 155                 160
```

-continued

```
Tyr Gly Asn Lys Thr Ala Thr Asn Leu Pro Val Asn Gly Val Ala Lys
            165                 170                 175

Tyr Lys Gly Thr Trp Asp Phe Ile Thr Ala Thr Lys Asn Gly Lys Arg
            180                 185                 190

Tyr Pro Leu Leu Ser Asn Gly Ser His Ala Tyr Tyr Arg Arg Ser Ala
            195                 200                 205

Ile Pro Glu Asp Ile Asp Leu Glu Asn Asp Ser Lys Asn Gly Asp Ile
210                 215                 220

Gly Leu Ile Ser Glu Phe Ser Ala Asp Phe Gly Thr Lys Lys Leu Thr
225                 230                 235                 240

Gly Gln Leu Ser Tyr Thr Lys Arg Lys Thr Asn Asn Gln Pro Tyr Glu
            245                 250                 255

Lys Lys Lys Leu Tyr Asp Ile Asp Ala Asp Ile Tyr Ser Asn Arg Phe
            260                 265                 270

Arg Gly Thr Val Lys Pro Thr Glu Lys Asp Ser Glu Glu His Pro Phe
            275                 280                 285

Thr Ser Glu Gly Thr Leu Glu Gly Gly Phe Tyr Gly Pro Asn Ala Glu
290                 295                 300

Glu Leu Gly Gly Lys Phe Leu Ala Thr Asp Asn Arg Val Phe Gly Val
305                 310                 315                 320

Phe Ser Ala Lys Glu Thr Glu Thr Lys Lys Glu Ala Leu Ser Lys
            325                 330                 335

Glu Thr Leu Ile Asp Gly Lys Leu Ile Thr Phe Ser Thr Lys Lys Thr
            340                 345                 350

Asp Ala Lys Thr Asn Ala Thr Thr Ser Thr Ala Ala Asn Thr Thr Thr
            355                 360                 365

Asp Thr Thr Ala Asn Thr Ile Thr Asp Glu Lys Asn Phe Lys Thr Glu
            370                 375                 380

Asp Ile Ser Ser Phe Gly Glu Ala Asp Tyr Leu Leu Ile Asp Lys Tyr
385                 390                 395                 400

Pro Ile Pro Leu Leu Pro Asp Lys Asn Thr Asn Asp Phe Ile Ser Ser
            405                 410                 415

Lys His His Thr Val Gly Asn Lys Arg Tyr Lys Val Glu Ala Cys Cys
            420                 425                 430

Ser Asn Leu Ser Tyr Val Lys Phe Gly Met Tyr Tyr Glu Asp Pro Leu
            435                 440                 445

Lys Glu Lys Glu Thr Glu Thr Glu Thr Glu Thr Glu Lys Asp Lys Glu
            450                 455                 460

Lys Glu Lys Glu Lys Asp Lys Asp Lys Glu Lys Gln Thr Ala Ala Thr
465                 470                 475                 480

Thr Asn Thr Tyr Tyr Gln Phe Leu Leu Gly His Arg Thr Pro Lys Asp
            485                 490                 495

Asp Ile Pro Lys Thr Gly Ser Ala Lys Tyr His Gly Ser Trp Phe Gly
            500                 505                 510

Tyr Ile Thr Asp Gly Lys Thr Ser Tyr Ser Pro Ser Gly Asp Lys Lys
            515                 520                 525

Arg Asp Lys Asn Ala Val Ala Glu Phe Asn Val Asp Phe Ala Glu Lys
            530                 535                 540

Lys Leu Thr Gly Glu Leu Lys Arg His Asp Thr Gly Asn Pro Val Phe
545                 550                 555                 560

Ser Ile Glu Ala Asn Phe Asn Asn Ser Ser Asn Ala Phe Thr Gly Thr
            565                 570                 575

Ala Thr Ala Thr Asn Phe Val Ile Asp Gly Lys Asn Ser Gln Asn Lys
            580                 585                 590
```

Asn Thr Pro Ile Asn Ile Thr Thr Lys Val Asn Gly Ala Phe Tyr Gly
            595                 600                 605

Pro Lys Ala Ser Glu Leu Gly Gly Tyr Phe Thr Tyr Asn Gly Asn Ser
            610                 615                 620

Thr Ala Thr Asn Ser Glu Ser Ser Ser Thr Val Ser Ser Ser Ser Asn
625                 630                 635                 640

Ser Lys Asn Ala Arg Ala Ala Val Val Phe Gly Ala Arg Gln Gln Val
            645                 650                 655

Glu Thr Thr Lys
            660

(2) INFORMATION FOR SEQ ID NO:11:

(i) SEQUENCE CHARACTERISTICS:
        (A) LENGTH: 914 amino acids
        (B) TYPE: amino acid
        (C) STRANDEDNESS: single
        (D) TOPOLOGY: linear (xi) SEQUENCE DESCRIPTION: SEQ ID NO:11:

Met Thr Lys Lys Pro Tyr Phe Arg Leu Ser Ile Ile Ser Cys Leu Leu
1               5                   10                  15

Ile Ser Cys Tyr Val Lys Ala Glu Thr Gln Ser Ile Lys Asp Thr Lys
            20                  25                  30

Glu Ala Ile Ser Ser Glu Val Asp Thr Gln Ser Thr Glu Asp Ser Glu
            35                  40                  45

Leu Glu Thr Ile Ser Val Thr Ala Glu Lys Ile Arg Asp Arg Lys Asp
        50                  55                  60

Asn Glu Val Thr Gly Leu Gly Lys Ile Lys Thr Ser Glu Ser Ile
65                  70                  75                  80

Ser Arg Glu Gln Val Leu Asn Ile Arg Asp Leu Thr Arg Tyr Asp Pro
            85                  90                  95

Gly Ile Ser Val Val Glu Gln Gly Arg Gly Ala Ser Ser Gly Tyr Ser
            100                 105                 110

Ile Arg Gly Met Asp Arg Asn Arg Val Ala Leu Leu Val Asp Gly Leu
            115                 120                 125

Pro Gln Thr Gln Ser Tyr Val Val Gln Ser Pro Leu Val Ala Arg Ser
        130                 135                 140

Gly Tyr Ser Gly Thr Gly Ala Ile Asn Glu Ile Glu Tyr Glu Asn Val
145                 150                 155                 160

Lys Ala Val Glu Ile Ser Lys Gly Gly Ser Ser Glu Tyr Gly Asn
            165                 170                 175

Gly Ala Leu Ala Gly Ser Val Thr Phe Gln Ser Lys Ser Ala Ala Asp
            180                 185                 190

Ile Leu Glu Gly Asp Lys Ser Trp Gly Ile Gln Thr Lys Asn Ala Tyr
        195                 200                 205

Ser Ser Lys Asn Lys Gly Phe Thr His Ser Leu Ala Val Ala Gly Lys
        210                 215                 220

Gln Gly Gly Phe Asp Gly Val Ala Ile Tyr Thr Gln Arg Asn Ser Ile
225                 230                 235                 240

Glu Thr Gln Val His Lys Asp Ala Leu Lys Gly Val Gln Ser Tyr His
            245                 250                 255

Arg Leu Ile Ala Lys Pro Glu Asp Gln Ser Ala Tyr Phe Val Met Gln
            260                 265                 270

Asp Glu Cys Pro Lys Pro Asp Asp Tyr Asn Ser Cys Leu Pro Phe Ala
            275                 280                 285

```
Lys Arg Pro Ala Ile Leu Ser Ser Gln Arg Glu Thr Val Ser Val Ser
    290                 295                 300

Asp Tyr Thr Gly Ala Asn Arg Ile Lys Pro Asn Pro Met Lys Tyr Glu
305             310                 315                 320

Ser Gln Ser Trp Phe Leu Arg Gly Tyr His Phe Ser Glu Gln His
            325                 330                 335

Tyr Ile Gly Gly Ile Phe Glu Phe Thr Gln Gln Lys Phe Asp Ile Arg
            340                 345                 350

Asp Met Thr Phe Pro Ala Tyr Leu Arg Ser Thr Glu Lys Arg Asp Asp
        355                 360                 365

Ser Ser Gly Ser Phe Tyr Pro Lys Gln Asp Tyr Gly Ala Tyr Gln Arg
    370                 375                 380

Ile Glu Asp Gly Arg Gly Val Asn Tyr Ala Ser Gly Leu Tyr Phe Asp
385                 390                 395                 400

Glu His His Arg Lys Gln Arg Val Gly Ile Glu Tyr Ile Tyr Glu Asn
                405                 410                 415

Lys Asn Lys Ala Gly Ile Ile Asp Lys Ala Val Leu Ser Ala Asn Gln
            420                 425                 430

Gln Asn Ile Ile Leu Asp Ser Tyr Met Gln His Thr His Cys Ser Leu
        435                 440                 445

Tyr Pro Asn Pro Ser Lys Asn Cys Arg Pro Thr Arg Asp Lys Pro Tyr
450                 455                 460

Ser Tyr Tyr His Ser Asp Arg Asn Val Tyr Lys Glu Lys His Asn Met
465                 470                 475                 480

Leu Gln Leu Asn Leu Glu Lys Lys Ile Gln Gln Asn Trp Leu Thr His
                485                 490                 495

Gln Ile Val Phe Asn Leu Gly Phe Asp Asp Phe Thr Ser Ala Leu Gln
                500                 505                 510

His Lys Asp Tyr Leu Thr Arg Arg Val Thr Ala Thr Lys Ser Ile
            515                 520                 525

Ser Glu Lys Ala Asn Glu Thr Arg Arg Asn Gly Tyr Lys Lys Gln Pro
    530                 535                 540

Tyr Leu Tyr Pro Lys Pro Thr Val Gly Phe Val Val Gln Asp His Cys
545                 550                 555                 560

Asp Tyr Lys Gly Asn Ser Ser Asn Tyr Arg Asp Cys Lys Val Arg Leu
                565                 570                 575

Ile Lys Gly Lys Asn Tyr Tyr Phe Ala Ala Arg Asn Asn Met Ala Leu
            580                 585                 590

Gly Lys Tyr Val Asp Leu Gly Leu Gly Ile Arg Tyr Asp Val Ser Arg
        595                 600                 605

Thr Lys Ala Asn Glu Ser Thr Ile Ser Val Gly Lys Phe Lys Asn Phe
610                 615                 620

Ser Trp Asn Thr Gly Ile Val Ile Lys Pro Thr Glu Trp Leu Asp Leu
625                 630                 635                 640

Ser Tyr Arg Leu Ser Thr Gly Phe Arg Asn Pro Ser Phe Ala Glu Met
            645                 650                 655

Tyr Gly Trp Arg Tyr Gly Gly Asn Asn Ser Glu Val Tyr Val Gly Lys
                660                 665                 670

Phe Lys Pro Glu Thr Ser Arg Asn Gln Glu Phe Gly Leu Ala Leu Lys
            675                 680                 685

Gly Asp Phe Gly Asn Ile Glu Ile Ser His Phe Ser Asn Ala Tyr Arg
        690                 695                 700

Asn Leu Ile Ala Phe Ala Glu Glu Leu Asn Lys Asn Gly Thr Gly Lys
```

```
                    705                 710                 715                 720
Ala Asn Tyr Gly Tyr His Asn Ala Gln Asn Ala Lys Leu Val Gly Val
                725                 730                 735

Asn Ile Thr Ala Gln Leu Asp Phe Asn Gly Leu Trp Lys Arg Ile Pro
            740                 745                 750

Tyr Gly Trp Tyr Ala Thr Phe Ala Tyr Asn Arg Val Lys Val Lys Asp
        755                 760                 765

Gln Lys Ile Asn Ala Gly Leu Ala Ser Val Ser Ser Tyr Leu Phe Asp
    770                 775                 780

Ala Ile Gln Pro Ser Arg Tyr Ile Ile Gly Leu Gly Tyr Asp His Pro
785                 790                 795                 800

Ser Asn Thr Trp Gly Ile Asn Thr Met Phe Thr Gln Ser Lys Ala Lys
                805                 810                 815

Ser Gln Asn Glu Leu Leu Gly Lys Arg Ala Leu Gly Asn Asn Ser Arg
            820                 825                 830

Asp Val Lys Ser Thr Arg Lys Leu Thr Arg Ala Trp His Ile Leu Asp
        835                 840                 845

Val Ser Gly Tyr Tyr Met Ala Asn Lys Asn Ile Met Leu Arg Leu Gly
    850                 855                 860

Ile Tyr Asn Leu Phe Asn Tyr Arg Tyr Val Thr Trp Glu Ala Val Arg
865                 870                 875                 880

Gln Thr Ala Gln Gly Ala Val Asn Gln His Gln Asn Val Gly Ser Tyr
                885                 890                 895

Thr Arg Tyr Ala Ala Ser Gly Arg Asn Tyr Thr Leu Thr Leu Glu Met
            900                 905                 910

Lys Phe (2) INFORMATION FOR SEQ ID NO:12:

(i) SEQUENCE CHARACTERISTICS:
        (A) LENGTH: 654 amino acids
        (B) TYPE: amino acid
        (C) STRANDEDNESS: single
        (D) TOPOLOGY: linear (xi) SEQUENCE DESCRIPTION: SEQ ID NO:12:

Met Lys Ser Val Pro Leu Ile Thr Gly Gly Leu Ser Phe Leu Leu Ser
1               5                   10                  15

Ala Cys Ser Gly Gly Gly Gly Ser Phe Asp Val Asp Asp Val Ser Asn
            20                  25                  30

Pro Ser Ser Ser Lys Pro Arg Tyr Gln Asp Asp Thr Ser Asn Gln Arg
        35                  40                  45

Thr Lys Ser Asp Leu Glu Lys Leu Phe Ile Pro Ser Leu Gly Gly Gly
    50                  55                  60

Met Lys Leu Val Ala Gln Asn Phe Ile Gly Ala Arg Glu Pro Ser Phe
65                  70                  75                  80

Leu Asn Glu Asp Gly Tyr Met Ile Phe Ser Ser Leu Ser Thr Ile Glu
                85                  90                  95

Glu Asp Val Glu Lys Val Lys Asn Asn Asn Lys Asn Gly Gly Arg Leu
            100                 105                 110

Ile Gly Ser Ile Glu Glu Pro Asn Gly Thr Ser Gln Asn Ser Asn Ser
        115                 120                 125

Gln Glu Tyr Val Tyr Ser Gly Leu Tyr Tyr Ile Asp Ser Trp Arg Asp
    130                 135                 140

Tyr Lys Lys Glu Glu Gln Lys Ala Tyr Thr Gly Tyr Tyr Gly Tyr Ala
145                 150                 155                 160
```

```
Phe Tyr Tyr Gly Asn Glu Thr Ala Lys Asn Leu Pro Val Lys Gly Val
                165                 170                 175
Ala Lys Tyr Lys Gly Thr Trp Asn Phe Ile Thr Ala Thr Glu Asn Gly
            180                 185                 190
Lys Arg Tyr Ser Leu Phe Ser Asn Ser Ile Gly Gln Ala Tyr Ser Arg
        195                 200                 205
Arg Ser Ala Ile Ser Glu Asp Ile Tyr Asn Leu Glu Asn Gly Asp Ala
210                 215                 220
Gly Leu Ile Ser Glu Phe Ser Val Asp Phe Gly Lys Lys Glu Leu Thr
225                 230                 235                 240
Gly Glu Leu Tyr Tyr Asn Glu Arg Lys Thr Ser Val Asn Glu Ser Gln
            245                 250                 255
Asn Thr Thr His Lys Leu Tyr Thr Leu Glu Ala Lys Val Tyr Ser Asn
        260                 265                 270
Arg Phe Arg Gly Lys Val Lys Pro Thr Lys Thr Lys Ser Glu Asp His
    275                 280                 285
Pro Phe Thr Ser Glu Gly Thr Leu Glu Gly Phe Tyr Gly Pro Asn
290                 295                 300
Ala Glu Glu Leu Gly Gly Lys Phe Leu Ala Asn Asp Glu Lys Val Phe
305                 310                 315                 320
Gly Val Phe Ser Ala Lys Glu Asp Pro Gln Asn Pro Glu Asn Gln Lys
                325                 330                 335
Leu Ser Thr Glu Thr Leu Ile Asp Gly Lys Leu Ile Thr Phe Lys Arg
            340                 345                 350
Thr Asp Ala Thr Thr Asn Ala Thr Thr Asp Ala Lys Thr Ser Ala Thr
        355                 360                 365
Thr Asp Ala Thr Ser Thr Thr Ala Asn Lys Lys Thr Asp Ala Glu Asn
370                 375                 380
Phe Lys Thr Glu Asp Ile Pro Ser Phe Gly Glu Ala Asp Tyr Leu Leu
385                 390                 395                 400
Ile Gly Asn Gln Pro Ile Pro Leu Leu Pro Glu Lys Asn Thr Asp Asp
            405                 410                 415
Phe Ile Ser Ser Lys His His Thr Val Gly Gly Lys Thr Tyr Lys Val
        420                 425                 430
Glu Ala Cys Cys Lys Asn Leu Ser Tyr Val Lys Phe Gly Met Tyr Tyr
    435                 440                 445
Glu Asp Lys Asp Lys Asp Asn Lys Asn Glu Thr Asp Lys Glu Lys Gly
450                 455                 460
Lys Glu Lys Pro Thr Thr Thr Ser Ile Asn Thr Tyr Tyr Gln Phe
465                 470                 475                 480
Leu Leu Gly Leu Arg Thr Pro Lys Asp Glu Ile Pro Lys Glu Gly Ser
            485                 490                 495
Ala Lys Tyr His Gly Asn Trp Phe Gly Tyr Ile Ser Asp Gly Glu Thr
        500                 505                 510
Ser Tyr Ser Ala Ser Gly Asp Lys Glu Arg Ser Lys Asn Ala Val Ala
    515                 520                 525
Glu Phe Asp Val Ser Phe Ala Asn Lys Thr Leu Thr Gly Glu Leu Lys
530                 535                 540
Arg His Asp Asn Gly Asn Thr Val Phe Lys Ile Asn Ala Glu Leu Asn
545                 550                 555                 560
Gly Ser Asn Asp Phe Thr Gly Thr Ala Thr Ala Thr Asn Phe Val Ile
            565                 570                 575
Asp Gly Asn Asn Ser Gln Thr Ser Asn Ala Lys Ile Asn Ile Thr Thr
```

```
                      580              585               590
Lys Val Asn Gly Ala Phe Tyr Gly Pro Lys Ala Ser Glu Leu Gly Gly
                595              600              605

Tyr Phe Thr Tyr Asn Gly Lys Asn Pro Thr Ala Thr Asn Ser Glu Ser
            610              615              620

Ser Ser Thr Val Pro Ser Pro Pro Asn Ser Pro Asn Ala Ser Ala Ala
625              630              635              640

Val Val Phe Gly Ala Lys Lys Gln Val Glu Thr Thr Asn Lys
                645              650
```

(2) INFORMATION FOR SEQ ID NO:13:

(i) SEQUENCE CHARACTERISTICS:
        (A) LENGTH: 36 amino acids
        (B) TYPE: amino acid
        (C) STRANDEDNESS: single
        (D) TOPOLOGY: linear (xi) SEQUENCE DESCRIPTION: SEQ ID NO:13:

```
Ala Glu Thr Gln Ser Ile Lys Asp Thr Lys Glu Ala Ile Ser Ser Glu
1               5                  10                  15

Val Asp Thr Gln Ser Thr Glu Asp Ser Glu Leu Glu Thr Ile Ser Val
                20                  25                  30

Thr Ala Glu Lys
            35
```

(2) INFORMATION FOR SEQ ID NO:14:

(i) SEQUENCE CHARACTERISTICS:
        (A) LENGTH: 36 amino acids
        (B) TYPE: amino acid
        (C) STRANDEDNESS: single
        (D) TOPOLOGY: linear (xi) SEQUENCE DESCRIPTION: SEQ ID NO:14:

```
Ser Val Thr Ala Glu Lys Val Arg Asp Arg Lys Asp Asn Glu Val Thr
1               5                  10                  15

Gly Leu Gly Lys Ile Ile Lys Thr Ser Glu Ser Ile Ser Arg Glu Gln
                20                  25                  30

Val Leu Asn Ile
            35
```

(2) INFORMATION FOR SEQ ID NO:15:

(i) SEQUENCE CHARACTERISTICS:
        (A) LENGTH: 36 amino acids
        (B) TYPE: amino acid
        (C) STRANDEDNESS: single
        (D) TOPOLOGY: linear (xi) SEQUENCE DESCRIPTION: SEQ ID NO:15:

```
Ser Arg Glu Gln Val Leu Asn Ile Arg Asp Leu Thr Arg Tyr Asp Pro
1               5                  10                  15

Gly Ile Ser Val Val Glu Gln Gly Arg Gly Ala Ser Ser Gly Tyr Ser
                20                  25                  30

Ile Arg Gly Met
            35
```

(2) INFORMATION FOR SEQ ID NO:16:

(i) SEQUENCE CHARACTERISTICS:
        (A) LENGTH: 36 amino acids
        (B) TYPE: amino acid (C) STRANDEDNESS: single
            (D) TOPOLOGY: linear (xi) SEQUENCE DESCRIPTION: SEQ ID NO:16:

Gly Tyr Ser Ile Arg Gly Met Asp Arg Asn Arg Val Ala Leu Val
1               5                   10                  15

Asp Gly Leu Pro Gln Thr Gln Ser Tyr Val Val Gln Ser Pro Leu Val
            20                  25                  30

Ala Arg Ser Gly
        35

(2) INFORMATION FOR SEQ ID NO:17:

(i) SEQUENCE CHARACTERISTICS:
        (A) LENGTH: 36 amino acids
        (B) TYPE: amino acid
        (C) STRANDEDNESS: single
        (D) TOPOLOGY: linear (xi) SEQUENCE DESCRIPTION: SEQ ID NO:17:

Pro Leu Val Ala Arg Ser Gly Tyr Gly Thr Gly Ala Ile Asn Glu Ile
1               5                   10                  15

Glu Tyr Glu Asn Val Lys Ala Val Glu Ile Ser Lys Gly Gly Ser Ser
            20                  25                  30

Ser Glu Tyr Gly
        35

(2) INFORMATION FOR SEQ ID NO:18:

(i) SEQUENCE CHARACTERISTICS:
        (A) LENGTH: 36 amino acids
        (B) TYPE: amino acid
        (C) STRANDEDNESS: single
        (D) TOPOLOGY: linear (xi) SEQUENCE DESCRIPTION: SEQ ID NO:18:

Ser Ser Ser Glu Tyr Gly Asn Gly Ala Leu Ala Gly Ser Val Thr Phe
1               5                   10                  15

Gln Ser Lys Ser Ala Ala Asp Ile Leu Glu Gly Asp Lys Ser Trp Gly
            20                  25                  30

Ile Gln Thr Lys
        35

(2) INFORMATION FOR SEQ ID NO:19:

(i) SEQUENCE CHARACTERISTICS:
        (A) LENGTH: 36 amino acids
        (B) TYPE: amino acid
        (C) STRANDEDNESS: single
        (D) TOPOLOGY: linear (xi) SEQUENCE DESCRIPTION: SEQ ID NO:19:

Gly Ile Gln Thr Lys Asn Ala Tyr Ser Ser Lys Asn Lys Gly Phe Thr
1               5                   10                  15

His Ser Leu Ala Val Ala Gly Lys Gln Gly Gly Phe Glu Gly Val Ala
            20                  25                  30

Ile Tyr Thr His
        35

(2) INFORMATION FOR SEQ ID NO:20:

(i) SEQUENCE CHARACTERISTICS:
        (A) LENGTH: 36 amino acids
        (B) TYPE: amino acid (C) STRANDEDNESS: single
(D) TOPOLOGY: linear (xi) SEQUENCE DESCRIPTION: SEQ ID NO:20:

Gly Val Ala Ile Tyr Thr His Arg Asn Ser Ile Glu Thr Gln Val His
1               5                   10                  15

Lys Asp Ala Leu Lys Gly Val Gln Ser Tyr Asp Arg Phe Ile Ala Thr
                20                  25                  30

Thr Glu Asp Gln
        35

(2) INFORMATION FOR SEQ ID NO:21:

(i) SEQUENCE CHARACTERISTICS:
        (A) LENGTH: 36 amino acids
        (B) TYPE: amino acid
        (C) STRANDEDNESS: single
        (D) TOPOLOGY: linear (xi) SEQUENCE DESCRIPTION: SEQ ID NO:21:

Ile Ala Thr Thr Glu Asp Gln Ser Ala Tyr Phe Val Met Gln Asp Glu
1               5                   10                  15

Cys Leu Asp Gly Tyr Asp Lys Cys Lys Thr Ser Pro Lys Arg Pro Ala
                20                  25                  30

Thr Leu Ser Thr
        35

(2) INFORMATION FOR SEQ ID NO:22:

(i) SEQUENCE CHARACTERISTICS:
        (A) LENGTH: 36 amino acids
        (B) TYPE: amino acid
        (C) STRANDEDNESS: single
        (D) TOPOLOGY: linear (xi) SEQUENCE DESCRIPTION: SEQ ID NO:22:

Pro Ala Thr Leu Ser Thr Gln Arg Glu Thr Val Ser Val Ser Asp Tyr
1               5                   10                  15

Thr Gly Ala Asn Arg Ile Lys Pro Asn Pro Met Lys Tyr Glu Ser Gln
                20                  25                  30

Ser Trp Phe Leu
        35

(2) INFORMATION FOR SEQ ID NO:23:

(i) SEQUENCE CHARACTERISTICS:
        (A) LENGTH: 36 amino acids
        (B) TYPE: amino acid
        (C) STRANDEDNESS: single
        (D) TOPOLOGY: linear (xi) SEQUENCE DESCRIPTION: SEQ ID NO:23:

Tyr Glu Ser Gln Ser Trp Phe Leu Arg Gly Tyr His Phe Ser Glu
1               5                   10                  15

Gln His Tyr Ile Gly Gly Ile Phe Glu Phe Thr Gln Gln Lys Phe Asp
                20                  25                  30

Ile Arg Asp Met
        35

(2) INFORMATION FOR SEQ ID NO:24:

(i) SEQUENCE CHARACTERISTICS:
        (A) LENGTH: 36 amino acids
        (B) TYPE: amino acid (C) STRANDEDNESS: single
            (D) TOPOLOGY: linear (xi) SEQUENCE DESCRIPTION: SEQ ID NO:24:

Lys Phe Asp Ile Arg Asp Met Thr Phe Pro Ala Tyr Leu Arg Pro Thr
1               5                   10                  15

Glu Asp Lys Asp Leu Gln Ser Arg Pro Phe Tyr Pro Lys Gln Asp Tyr
            20                  25                  30

Gly Ala Tyr Gln
        35

(2) INFORMATION FOR SEQ ID NO:25:

(i) SEQUENCE CHARACTERISTICS:
        (A) LENGTH: 36 amino acids
        (B) TYPE: amino acid
        (C) STRANDEDNESS: single
        (D) TOPOLOGY: linear (xi) SEQUENCE DESCRIPTION: SEQ ID NO:25:

Asp Tyr Gly Ala Tyr Gln His Ile Gly Asp Gly Arg Gly Val Lys Tyr
1               5                   10                  15

Ala Ser Gly Leu Tyr Phe Asp Glu His His Arg Lys Gln Arg Val Gly
            20                  25                  30

Ile Glu Tyr Ile
        35

(2) INFORMATION FOR SEQ ID NO:26:

(i) SEQUENCE CHARACTERISTICS:
        (A) LENGTH: 36 amino acids
        (B) TYPE: amino acid
        (C) STRANDEDNESS: single
        (D) TOPOLOGY: linear (xi) SEQUENCE DESCRIPTION: SEQ ID NO:26:

Gly Ile Glu Tyr Ile Tyr Glu Asn Lys Asn Lys Ala Gly Ile Ile Asp
1               5                   10                  15

Lys Ala Val Leu Ser Ala Asn Gln Gln Asn Ile Ile Leu Asp Ser Tyr
            20                  25                  30

Met Arg His Thr
        35

(2) INFORMATION FOR SEQ ID NO:27:

(i) SEQUENCE CHARACTERISTICS:
        (A) LENGTH: 36 amino acids
        (B) TYPE: amino acid
        (C) STRANDEDNESS: single
        (D) TOPOLOGY: linear (xi) SEQUENCE DESCRIPTION: SEQ ID NO:27:

Asp Ser Tyr Met Arg His Thr His Cys Ser Leu Tyr Pro Asn Pro Ser
1               5                   10                  15

Lys Asn Cys Arg Pro Thr Leu Asp Lys Pro Tyr Ser Tyr Tyr His Ser
            20                  25                  30

Asp Arg Asn Val
        35

(2) INFORMATION FOR SEQ ID NO:28:

(i) SEQUENCE CHARACTERISTICS:
        (A) LENGTH: 36 amino acids
        (B) TYPE: amino acid (C) STRANDEDNESS: single
            (D) TOPOLOGY: linear (xi) SEQUENCE DESCRIPTION: SEQ ID NO:28:

Ser Asp Arg Asn Val Tyr Lys Glu Lys His Asn Met Leu Gln Leu Asn
1               5                   10                  15

Leu Glu Lys Lys Ile Gln Gln Asn Trp Leu Thr His Gln Ile Ala Phe
            20                  25                  30

Asn Leu Gly Phe
        35

(2) INFORMATION FOR SEQ ID NO:29:

(i) SEQUENCE CHARACTERISTICS:
        (A) LENGTH: 36 amino acids
        (B) TYPE: amino acid
        (C) STRANDEDNESS: single
        (D) TOPOLOGY: linear (xi) SEQUENCE DESCRIPTION: SEQ ID NO:29:

Thr His Gln Ile Ala Phe Asn Leu Gly Phe Asp Asp Phe Thr Ser Ala
1               5                   10                  15

Leu Gln His Lys Asp Tyr Leu Thr Arg Arg Val Ile Ala Thr Ala Ser
            20                  25                  30

Ser Ile Ser Glu
        35

(2) INFORMATION FOR SEQ ID NO:30:

(i) SEQUENCE CHARACTERISTICS:
        (A) LENGTH: 37 amino acids
        (B) TYPE: amino acid
        (C) STRANDEDNESS: single
        (D) TOPOLOGY: linear (xi) SEQUENCE DESCRIPTION: SEQ ID NO:30:

Thr Ala Ser Ser Ile Ser Glu Lys Arg Gly Glu Ala Arg Arg Asn Gly
1               5                   10                  15

Leu Gln Ser Ser Pro Tyr Leu Tyr Pro Thr Pro Lys Ala Glu Leu Val
            20                  25                  30

Gly Gly Asp Leu Cys
        35

(2) INFORMATION FOR SEQ ID NO:31:

(i) SEQUENCE CHARACTERISTICS:
        (A) LENGTH: 36 amino acids
        (B) TYPE: amino acid
        (C) STRANDEDNESS: single
        (D) TOPOLOGY: linear (xi) SEQUENCE DESCRIPTION: SEQ ID NO:31:

Leu Val Gly Gly Asp Leu Cys Asn Tyr Gln Gly Lys Ser Ser Asn Tyr
1               5                   10                  15

Ser Asp Cys Lys Val Arg Leu Ile Lys Gly Lys Asn Tyr Tyr Phe Ala
            20                  25                  30

Ala Arg Asn Asn
        35

(2) INFORMATION FOR SEQ ID NO:32:

(i) SEQUENCE CHARACTERISTICS:
        (A) LENGTH: 36 amino acids
        (B) TYPE: amino acid (C) STRANDEDNESS: single
            (D) TOPOLOGY: linear (xi) SEQUENCE DESCRIPTION: SEQ ID NO:32:

Phe Ala Ala Arg Asn Asn Met Ala Leu Gly Lys Tyr Val Asp Leu Gly
1               5                   10                  15

Leu Gly Met Arg Tyr Asp Val Ser Arg Thr Lys Ala Asn Glu Ser Thr
            20                  25                  30

Ile Ser Val Gly
        35

(2) INFORMATION FOR SEQ ID NO:33:

(i) SEQUENCE CHARACTERISTICS:
        (A) LENGTH: 36 amino acids
        (B) TYPE: amino acid
        (C) STRANDEDNESS: single
        (D) TOPOLOGY: linear (xi) SEQUENCE DESCRIPTION: SEQ ID NO:33:

Ser Thr Ile Ser Val Gly Lys Phe Lys Asn Phe Ser Trp Asn Thr Gly
1               5                   10                  15

Ile Val Ile Lys Pro Thr Glu Trp Leu Asp Leu Ser Tyr Arg Leu Ser
            20                  25                  30

Thr Gly Phe Arg
        35

(2) INFORMATION FOR SEQ ID NO:34:

(i) SEQUENCE CHARACTERISTICS:
        (A) LENGTH: 36 amino acids
        (B) TYPE: amino acid
        (C) STRANDEDNESS: single
        (D) TOPOLOGY: linear (xi) SEQUENCE DESCRIPTION: SEQ ID NO:34:

Leu Ser Thr Gly Phe Arg Asn Pro Ser Phe Ala Glu Met Tyr Gly Trp
1               5                   10                  15

Arg Tyr Gly Gly Lys Asp Thr Asp Val Tyr Ile Gly Lys Phe Lys Pro
            20                  25                  30

Glu Thr Ser Arg
        35

(2) INFORMATION FOR SEQ ID NO:35:

(i) SEQUENCE CHARACTERISTICS:
        (A) LENGTH: 36 amino acids
        (B) TYPE: amino acid
        (C) STRANDEDNESS: single
        (D) TOPOLOGY: linear (xi) SEQUENCE DESCRIPTION: SEQ ID NO:35:

Lys Pro Glu Thr Ser Arg Asn Gln Glu Phe Gly Leu Ala Leu Lys Gly
1               5                   10                  15

Asp Phe Gly Asn Ile Glu Ile Ser His Phe Ser Asn Ala Tyr Arg Asn
            20                  25                  30

Leu Ile Ala Phe
        35

(2) INFORMATION FOR SEQ ID NO:36:

(i) SEQUENCE CHARACTERISTICS:
        (A) LENGTH: 36 amino acids
        (B) TYPE: amino acid (C) STRANDEDNESS: single
        (D) TOPOLOGY: linear (xi) SEQUENCE DESCRIPTION: SEQ ID NO:36:

Tyr Arg Asn Leu Ile Ala Phe Ala Glu Glu Leu Ser Lys Asn Gly Thr
1               5                   10                  15

Thr Gly Lys Gly Asn Tyr Gly Tyr His Asn Ala Gln Asn Ala Lys Leu
            20                  25                  30

Val Gly Val Asn
            35

(2) INFORMATION FOR SEQ ID NO:37:

(i) SEQUENCE CHARACTERISTICS:
        (A) LENGTH: 36 amino acids
        (B) TYPE: amino acid
        (C) STRANDEDNESS: single
        (D) TOPOLOGY: linear (xi) SEQUENCE DESCRIPTION: SEQ ID NO:37:

Ala Lys Leu Val Gly Val Asn Ile Thr Ala Gln Leu Asp Phe Asn Gly
1               5                   10                  15

Leu Trp Lys Arg Ile Pro Tyr Gly Trp Tyr Ala Thr Phe Ala Tyr Asn
            20                  25                  30

Arg Val Lys Val
            35

(2) INFORMATION FOR SEQ ID NO:38:

(i) SEQUENCE CHARACTERISTICS:
        (A) LENGTH: 36 amino acids
        (B) TYPE: amino acid
        (C) STRANDEDNESS: single
        (D) TOPOLOGY: linear (xi) SEQUENCE DESCRIPTION: SEQ ID NO:38:

Ala Tyr Asn Arg Val Lys Val Lys Asp Gln Lys Ile Asn Ala Gly Leu
1               5                   10                  15

Ala Ser Val Ser Ser Tyr Leu Phe Asp Ala Ile Gln Pro Ser Arg Tyr
            20                  25                  30

Ile Ile Gly Leu
            35

(2) INFORMATION FOR SEQ ID NO:39:

(i) SEQUENCE CHARACTERISTICS:
        (A) LENGTH: 36 amino acids
        (B) TYPE: amino acid
        (C) STRANDEDNESS: single
        (D) TOPOLOGY: linear (xi) SEQUENCE DESCRIPTION: SEQ ID NO:39:

Ser Arg Tyr Ile Ile Gly Leu Asp Tyr Asp His Pro Ser Asn Thr Trp
1               5                   10                  15

Gly Ile Lys Thr Met Phe Thr Gln Ser Lys Ala Lys Ser Gln Asn Glu
            20                  25                  30

Leu Leu Gly Lys
            35

(2) INFORMATION FOR SEQ ID NO:40:

(i) SEQUENCE CHARACTERISTICS:
        (A) LENGTH: 36 amino acids
        (B) TYPE: amino acid

```
            (C) STRANDEDNESS: single
            (D) TOPOLOGY: linear (xi) SEQUENCE DESCRIPTION: SEQ ID NO:40:

Asn Glu Leu Leu Gly Lys Arg Ala Leu Gly Asn Asn Ser Arg Asn Val
1               5                   10                  15

Lys Ser Thr Arg Lys Leu Thr Arg Ala Trp His Ile Leu Asp Val Ser
                20                  25                  30

Gly Tyr Tyr Met
            35

(2) INFORMATION FOR SEQ ID NO:41:

(i) SEQUENCE CHARACTERISTICS:
        (A) LENGTH: 30 amino acids
        (B) TYPE: amino acid
        (C) STRANDEDNESS: single
        (D) TOPOLOGY: linear (xi) SEQUENCE DESCRIPTION: SEQ ID NO:41:

Ser Gly Tyr Tyr Met Val Asn Arg Ser Ile Leu Phe Arg Leu Gly Val
1               5                   10                  15

Tyr Asn Leu Leu Asn Tyr Arg Tyr Val Thr Trp Glu Ala Val
                20                  25                  30

(2) INFORMATION FOR SEQ ID NO:42:

(i) SEQUENCE CHARACTERISTICS:
        (A) LENGTH: 23 amino acids
        (B) TYPE: amino acid
        (C) STRANDEDNESS: single
        (D) TOPOLOGY: linear (xi) SEQUENCE DESCRIPTION: SEQ ID NO:42:

Leu Leu Asn Tyr Arg Tyr Val Thr Trp Glu Ala Val Arg Gln Thr Ala
1               5                   10                  15

Gln Gly Ala Glu Phe Asp Ile
                20

(2) INFORMATION FOR SEQ ID NO:43:

(i) SEQUENCE CHARACTERISTICS:
        (A) LENGTH: 9 amino acids
        (B) TYPE: amino acid
        (C) STRANDEDNESS: single
        (D) TOPOLOGY: linear (xi) SEQUENCE DESCRIPTION: SEQ ID NO:43:

Asp Asn Glu Val Thr Gly Leu Gly Lys
1               5

(2) INFORMATION FOR SEQ ID NO:44:

(i) SEQUENCE CHARACTERISTICS:
        (A) LENGTH: 16 amino acids
        (B) TYPE: amino acid
        (C) STRANDEDNESS: single
        (D) TOPOLOGY: linear (xi) SEQUENCE DESCRIPTION: SEQ ID NO:44:

Glu Gln Val Leu Asn Ile Arg Asp Leu Thr Arg Tyr Asp Pro Gly Ile
1               5                   10                  15

(2) INFORMATION FOR SEQ ID NO:45:

(i) SEQUENCE CHARACTERISTICS:
```

(A) LENGTH: 35 amino acids
        (B) TYPE: amino acid
        (C) STRANDEDNESS: single
        (D) TOPOLOGY: linear (xi) SEQUENCE DESCRIPTION: SEQ ID NO:45:

Glu Gln Val Leu Asn Ile Arg Asp Leu Thr Arg Tyr Asp Pro Gly Ile
1               5                   10                  15

Ser Val Val Glu Gln Gly Arg Gly Ala Ser Ser Gly Tyr Ser Ile Arg
            20                  25                  30

Gly Met Asp
        35

(2) INFORMATION FOR SEQ ID NO:46:

(i) SEQUENCE CHARACTERISTICS:
        (A) LENGTH: 19 amino acids
        (B) TYPE: amino acid
        (C) STRANDEDNESS: single
        (D) TOPOLOGY: linear (xi) SEQUENCE DESCRIPTION: SEQ ID NO:46:

Gly Ala Ile Asn Glu Ile Glu Tyr Glu Asn Val Lys Ala Val Glu Ile
1               5                   10                  15

Ser Lys Gly (2) INFORMATION FOR SEQ ID NO:47:

(i) SEQUENCE CHARACTERISTICS:
        (A) LENGTH: 7 amino acids
        (B) TYPE: amino acid
        (C) STRANDEDNESS: single
        (D) TOPOLOGY: linear (xi) SEQUENCE DESCRIPTION: SEQ ID NO:47:

Gly Ala Leu Ala Gly Ser Val
1               5

(2) INFORMATION FOR SEQ ID NO:48:

(i) SEQUENCE CHARACTERISTICS:
        (A) LENGTH: 15 amino acids
        (B) TYPE: amino acid
        (C) STRANDEDNESS: single
        (D) TOPOLOGY: linear (xi) SEQUENCE DESCRIPTION: SEQ ID NO:48:

Ala Glu Thr Gln Ser Ile Lys Asp Thr Lys Glu Ala Ile Ser Cys
1               5                   10                  15

(2) INFORMATION FOR SEQ ID NO:49:

(i) SEQUENCE CHARACTERISTICS:
        (A) LENGTH: 14 amino acids
        (B) TYPE: amino acid
        (C) STRANDEDNESS: single
        (D) TOPOLOGY: linear (xi) SEQUENCE DESCRIPTION: SEQ ID NO:49:

Cys Ser Gly Gly Gly Ser Phe Asp Val Asp Asn Val Ser Asn
1               5                   10

(2) INFORMATION FOR SEQ ID NO:50:

(i) SEQUENCE CHARACTERISTICS:
        (A) LENGTH: 31 amino acids
        (B) TYPE: amino acid (C) STRANDEDNESS: single
        (D) TOPOLOGY: linear (xi) SEQUENCE DESCRIPTION: SEQ ID NO:50:

Leu Glu Gly Gly Phe Tyr Gly Pro Lys Gly Glu Leu Gly Phe Arg
1               5                   10                  15

Phe Leu Ala Gly Asp Lys Lys Val Phe Gly Val Phe Ser Ala Lys
            20                  25                  30

(2) INFORMATION FOR SEQ ID NO:51:

(i) SEQUENCE CHARACTERISTICS:
        (A) LENGTH: 23 amino acids
        (B) TYPE: amino acid
        (C) STRANDEDNESS: single
        (D) TOPOLOGY: linear (xi) SEQUENCE DESCRIPTION: SEQ ID NO:51:

Thr Val Gly Lys Lys Thr Tyr Gln Val Glu Ala Cys Cys Ser Asn Leu
1               5                   10                  15

Ser Tyr Val Lys Phe Gly Met
            20

(2) INFORMATION FOR SEQ ID NO:52:

(i) SEQUENCE CHARACTERISTICS:
        (A) LENGTH: 23 amino acids
        (B) TYPE: amino acid
        (C) STRANDEDNESS: single
        (D) TOPOLOGY: linear (xi) SEQUENCE DESCRIPTION: SEQ ID NO:52:

Ala Thr Val Lys Gly Ala Phe Tyr Gly Pro Lys Ala Ser Glu Leu Gly
1               5                   10                  15

Gly Tyr Phe Thr Tyr Asn Gly
            20

(2) INFORMATION FOR SEQ ID NO:53:

(i) SEQUENCE CHARACTERISTICS:
        (A) LENGTH: 35 amino acids
        (B) TYPE: amino acid
        (C) STRANDEDNESS: single
        (D) TOPOLOGY: linear (xi) SEQUENCE DESCRIPTION: SEQ ID NO:53:

Met Lys Leu Ala Ala Leu Asn Leu Phe Asp Arg Asn Lys Pro Ser Leu
1               5                   10                  15

Leu Asn Glu Asp Ser Tyr Met Ile Phe Ser Ser Arg Ser Thr Ile Glu
            20                  25                  30

Glu Asp Val
        35

(2) INFORMATION FOR SEQ ID NO:54:

(i) SEQUENCE CHARACTERISTICS:
        (A) LENGTH: 35 amino acids
        (B) TYPE: amino acid
        (C) STRANDEDNESS: single
        (D) TOPOLOGY: linear (xi) SEQUENCE DESCRIPTION: SEQ ID NO:54:

Ser Thr Ile Glu Glu Asp Val Lys Asn Asp Asn Gln Asn Gly Glu His
1               5                   10                  15

Pro Ile Asp Ser Ile Val Asp Pro Arg Ala Pro Asn Ser Asn Glu Asn

```
                    20                  25                  30
Arg His Gly
        35

(2) INFORMATION FOR SEQ ID NO:55:

(i) SEQUENCE CHARACTERISTICS:
        (A) LENGTH: 35 amino acids
        (B) TYPE: amino acid
        (C) STRANDEDNESS: single
        (D) TOPOLOGY: linear (xi) SEQUENCE DESCRIPTION: SEQ ID NO:55:

Ser Asn Glu Asn Arg His Gly Gln Lys Tyr Val Tyr Ser Gly Leu Tyr
1               5                   10                  15

Tyr Ile Gln Ser Trp Ser Leu Arg Asp Leu Pro Asn Lys Lys Phe Tyr
                20                  25                  30

Ser Gly Tyr
        35

(2) INFORMATION FOR SEQ ID NO:56:

(i) SEQUENCE CHARACTERISTICS:
        (A) LENGTH: 35 amino acids
        (B) TYPE: amino acid
        (C) STRANDEDNESS: single
        (D) TOPOLOGY: linear (xi) SEQUENCE DESCRIPTION: SEQ ID NO:56:

Lys Lys Phe Tyr Ser Gly Tyr Tyr Gly Tyr Ala Tyr Tyr Phe Gly Asn
1               5                   10                  15

Thr Thr Ala Ser Ala Leu Pro Val Gly Gly Val Ala Thr Tyr Lys Gly
                20                  25                  30

Thr Trp Ser
        35

(2) INFORMATION FOR SEQ ID NO:57:

(i) SEQUENCE CHARACTERISTICS:
        (A) LENGTH: 35 amino acids
        (B) TYPE: amino acid
        (C) STRANDEDNESS: single
        (D) TOPOLOGY: linear (xi) SEQUENCE DESCRIPTION: SEQ ID NO:57:

Thr Tyr Lys Gly Thr Trp Ser Phe Ile Thr Ala Ala Glu Asn Gly Lys
1               5                   10                  15

Asn Tyr Glu Leu Leu Arg Asn Ser Gly Gly Gln Ala Tyr Ser Arg
                20                  25                  30

Arg Ser Ala
        35

(2) INFORMATION FOR SEQ ID NO:58:

(i) SEQUENCE CHARACTERISTICS:
        (A) LENGTH: 35 amino acids
        (B) TYPE: amino acid
        (C) STRANDEDNESS: single
        (D) TOPOLOGY: linear (xi) SEQUENCE DESCRIPTION: SEQ ID NO:58:

Ala Tyr Ser Arg Arg Ser Ala Thr Pro Glu Asp Ile Asp Leu Asp Arg
1               5                   10                  15

Lys Thr Gly Leu Thr Ser Glu Phe Thr Val Asn Phe Gly Thr Lys Lys
```

```
                        20                  25                  30
Leu Thr Gly
        35

(2) INFORMATION FOR SEQ ID NO:59:

(i) SEQUENCE CHARACTERISTICS:
        (A) LENGTH: 35 amino acids
        (B) TYPE: amino acid
        (C) STRANDEDNESS: single
        (D) TOPOLOGY: linear (xi) SEQUENCE DESCRIPTION: SEQ ID NO:59:

Gly Thr Lys Lys Leu Thr Gly Gly Leu Tyr Tyr Asn Leu Arg Glu Thr
1               5                   10                  15

Asp Ala Asn Lys Ser Gln Asn Arg Thr His Lys Leu Tyr Asp Leu Glu
                20                  25                  30

Ala Asp Val
        35

(2) INFORMATION FOR SEQ ID NO:60:

(i) SEQUENCE CHARACTERISTICS:
        (A) LENGTH: 35 amino acids
        (B) TYPE: amino acid
        (C) STRANDEDNESS: single
        (D) TOPOLOGY: linear (xi) SEQUENCE DESCRIPTION: SEQ ID NO:60:

Tyr Asp Leu Glu Ala Asp Val His Ser Asn Arg Phe Arg Gly Lys Val
1               5                   10                  15

Lys Pro Thr Lys Lys Glu Ser Ser Glu Glu His Pro Phe Thr Ser Glu
                20                  25                  30

Gly Thr Leu
        35

(2) INFORMATION FOR SEQ ID NO:61:

(i) SEQUENCE CHARACTERISTICS:
        (A) LENGTH: 35 amino acids
        (B) TYPE: amino acid
        (C) STRANDEDNESS: single
        (D) TOPOLOGY: linear (xi) SEQUENCE DESCRIPTION: SEQ ID NO:61:

Phe Thr Ser Glu Gly Thr Leu Glu Gly Gly Phe Tyr Gly Pro Glu Gly
1               5                   10                  15

Gln Glu Leu Gly Gly Lys Phe Leu Ala His Asp Lys Lys Val Leu Gly
                20                  25                  30

Val Phe Ser
        35

(2) INFORMATION FOR SEQ ID NO:62:

(i) SEQUENCE CHARACTERISTICS:
        (A) LENGTH: 35 amino acids
        (B) TYPE: amino acid
        (C) STRANDEDNESS: single
        (D) TOPOLOGY: linear (xi) SEQUENCE DESCRIPTION: SEQ ID NO:62:

Lys Val Leu Gly Val Phe Ser Ala Lys Glu Gln Gln Glu Thr Ser Glu
1               5                   10                  15

Asn Lys Lys Leu Pro Lys Glu Thr Leu Ile Asp Gly Lys Leu Thr Thr
```

```
                    20                  25                  30
Phe Lys Thr
        35

(2) INFORMATION FOR SEQ ID NO:63:

(i) SEQUENCE CHARACTERISTICS:
        (A) LENGTH: 35 amino acids
        (B) TYPE: amino acid
        (C) STRANDEDNESS: single
        (D) TOPOLOGY: linear (xi) SEQUENCE DESCRIPTION: SEQ ID NO:63:

Lys Leu Thr Thr Phe Lys Thr Thr Asn Ala Thr Ala Asn Ala Thr Thr
1               5                   10                  15

Asp Ala Thr Thr Ser Thr Thr Ala Ser Thr Lys Thr Asp Thr Thr Thr
                20                  25                  30

Asn Ala Thr
        35

(2) INFORMATION FOR SEQ ID NO:64:

(i) SEQUENCE CHARACTERISTICS:
        (A) LENGTH: 35 amino acids
        (B) TYPE: amino acid
        (C) STRANDEDNESS: single
        (D) TOPOLOGY: linear (xi) SEQUENCE DESCRIPTION: SEQ ID NO:64:

Asp Thr Thr Thr Asn Ala Thr Ala Asn Thr Glu Asn Phe Thr Thr Lys
1               5                   10                  15

Asp Ile Pro Ser Leu Gly Glu Ala Asp Tyr Leu Leu Ile Asp Asn Tyr
                20                  25                  30

Pro Val Pro
        35

(2) INFORMATION FOR SEQ ID NO:65:

(i) SEQUENCE CHARACTERISTICS:
        (A) LENGTH: 35 amino acids
        (B) TYPE: amino acid
        (C) STRANDEDNESS: single
        (D) TOPOLOGY: linear (xi) SEQUENCE DESCRIPTION: SEQ ID NO:65:

Ile Asp Asn Tyr Pro Val Pro Leu Phe Pro Glu Ser Gly Asp Phe Ile
1               5                   10                  15

Ser Ser Lys His His Thr Val Gly Lys Lys Thr Tyr Gln Val Glu Ala
                20                  25                  30

Cys Cys Ser
        35

(2) INFORMATION FOR SEQ ID NO:66:

(i) SEQUENCE CHARACTERISTICS:
        (A) LENGTH: 36 amino acids
        (B) TYPE: amino acid
        (C) STRANDEDNESS: single
        (D) TOPOLOGY: linear (xi) SEQUENCE DESCRIPTION: SEQ ID NO:66:

Cys Ser Asn Leu Ser Tyr Val Lys Phe Gly Met Tyr Tyr Glu Ala Pro
1               5                   10                  15

Pro Lys Glu Glu Glu Lys Glu Lys Glu Lys Asp Lys Asp Lys Glu Lys
```

```
                    20                  25                  30

Glu Lys Gln Ala
             35

(2) INFORMATION FOR SEQ ID NO:67:

(i) SEQUENCE CHARACTERISTICS:
        (A) LENGTH: 35 amino acids
        (B) TYPE: amino acid
        (C) STRANDEDNESS: single
        (D) TOPOLOGY: linear (xi) SEQUENCE DESCRIPTION: SEQ ID NO:67:

Lys Glu Lys Asp Lys Asp Lys Glu Lys Glu Lys Gln Ala Thr Thr Ser
1               5                  10                  15

Ile Lys Thr Tyr Tyr Gln Phe Leu Leu Gly Leu Arg Thr Pro Ser Ser
                20                  25                  30

Glu Ile Pro
         35

(2) INFORMATION FOR SEQ ID NO:68:

(i) SEQUENCE CHARACTERISTICS:
        (A) LENGTH: 35 amino acids
        (B) TYPE: amino acid
        (C) STRANDEDNESS: single
        (D) TOPOLOGY: linear (xi) SEQUENCE DESCRIPTION: SEQ ID NO:68:

Thr Pro Ser Ser Glu Ile Pro Lys Glu Gly Ser Ala Lys Tyr His Gly
1               5                  10                  15

Asn Trp Phe Gly Tyr Ile Ser Asp Gly Glu Thr Ser Tyr Ser Ala Ser
                20                  25                  30

Gly Asp Lys
         35

(2) INFORMATION FOR SEQ ID NO:69:

(i) SEQUENCE CHARACTERISTICS:
        (A) LENGTH: 35 amino acids
        (B) TYPE: amino acid
        (C) STRANDEDNESS: single
        (D) TOPOLOGY: linear (xi) SEQUENCE DESCRIPTION: SEQ ID NO:69:

Tyr Ser Ala Ser Gly Asp Lys Glu Arg Ser Lys Asn Ala Val Ala Glu
1               5                  10                  15

Phe Asn Val Asn Phe Ala Glu Lys Thr Leu Thr Gly Glu Leu Lys Arg
                20                  25                  30

His Asp Thr
         35

(2) INFORMATION FOR SEQ ID NO:70:

(i) SEQUENCE CHARACTERISTICS:
        (A) LENGTH: 35 amino acids
        (B) TYPE: amino acid
        (C) STRANDEDNESS: single
        (D) TOPOLOGY: linear (xi) SEQUENCE DESCRIPTION: SEQ ID NO:70:

Glu Leu Lys Arg His Asp Thr Gln Asn Pro Val Phe Lys Ile Asn Ala
1               5                  10                  15

Thr Phe Gln Ser Gly Lys Asn Asp Phe Thr Gly Thr Ala Thr Ala Lys
```

```
                        20                  25                  30
Asp Leu Ala
        35
```

(2) INFORMATION FOR SEQ ID NO:71:

(i) SEQUENCE CHARACTERISTICS:
        (A) LENGTH: 35 amino acids
        (B) TYPE: amino acid
        (C) STRANDEDNESS: single
        (D) TOPOLOGY: linear (xi) SEQUENCE DESCRIPTION: SEQ ID NO:71:

```
Ala Thr Ala Lys Asp Leu Ala Ile Asp Gly Lys Asn Thr Gln Gly Thr
1               5                  10                  15
Ser Lys Val Asn Phe Thr Ala Thr Val Asn Gly Ala Phe Tyr Gly Pro
                20                  25                  30
His Ala Thr
        35
```

(2) INFORMATION FOR SEQ ID NO:72:

(i) SEQUENCE CHARACTERISTICS:
        (A) LENGTH: 26 amino acids
        (B) TYPE: amino acid
        (C) STRANDEDNESS: single
        (D) TOPOLOGY: linear (xi) SEQUENCE DESCRIPTION: SEQ ID NO:72:

```
Phe Tyr Gly Pro His Ala Thr Glu Leu Gly Gly Tyr Phe Thr Tyr Asn
1               5                  10                  15
Gly Asn Asn Pro Thr Asp Lys Asn Ser Ser
                20                  25
```

(2) INFORMATION FOR SEQ ID NO:73:

(i) SEQUENCE CHARACTERISTICS:
        (A) LENGTH: 31 amino acids
        (B) TYPE: amino acid
        (C) STRANDEDNESS: single
        (D) TOPOLOGY: linear (xi) SEQUENCE DESCRIPTION: SEQ ID NO:73:

```
Cys Pro Thr Asp Lys Asn Ser Ser Asn Ser Glu Lys Ala Arg Ala
1               5                  10                  15
Ala Val Val Phe Gly Ala Lys Lys Gln Gln Val Glu Thr Thr Lys
                20                  25                  30
```

(2) INFORMATION FOR SEQ ID NO:74:

(i) SEQUENCE CHARACTERISTICS:
        (A) LENGTH: 8 amino acids
        (B) TYPE: amino acid
        (C) STRANDEDNESS: single
        (D) TOPOLOGY: linear (xi) SEQUENCE DESCRIPTION: SEQ ID NO:74:

```
Leu Glu Gly Gly Phe Tyr Gly Pro
1               5
```

(2) INFORMATION FOR SEQ ID NO:75:

(i) SEQUENCE CHARACTERISTICS:
        (A) LENGTH: 8 amino acids
        (B) TYPE: amino acid
        (C) STRANDEDNESS: single (D) TOPOLOGY: linear (xi) SEQUENCE DESCRIPTION: SEQ ID NO:75:

Cys Ser Gly Gly Gly Ser Phe Asp
1               5

(2) INFORMATION FOR SEQ ID NO:76:

(i) SEQUENCE CHARACTERISTICS:
        (A) LENGTH: 6 amino acid
        (B) TYPE: amino acid
        (C) STRANDEDNESS: single
        (D) TOPOLOGY: linear (xi) SEQUENCE DESCRIPTION: SEQ ID NO:76:

Tyr Val Tyr Ser Gly Leu
1               5

(2) INFORMATION FOR SEQ ID NO:77:

(i) SEQUENCE CHARACTERISTICS:
        (A) LENGTH: 11 amino acids
        (B) TYPE: amino acid
        (C) STRANDEDNESS: single
        (D) TOPOLOGY: linear (xi) SEQUENCE DESCRIPTION: SEQ ID NO:77:

Cys Cys Ser Asn Leu Ser Tyr Val Lys Phe Gly
1               5                   10

(2) INFORMATION FOR SEQ ID NO:78:

(i) SEQUENCE CHARACTERISTICS:
        (A) LENGTH: 7 amino acids
        (B) TYPE: amino acid
        (C) STRANDEDNESS: single
        (D) TOPOLOGY: linear (xi) SEQUENCE DESCRIPTION: SEQ ID NO:78:

Phe Leu Leu Gly His Arg Thr
1               5

(2) INFORMATION FOR SEQ ID NO:79:

(i) SEQUENCE CHARACTERISTICS:
        (A) LENGTH: 6 amino acids
        (B) TYPE: amino acid
        (C) STRANDEDNESS: single
        (D) TOPOLOGY: linear (xi) SEQUENCE DESCRIPTION: SEQ ID NO:79:

Glu Phe Asn Val Asp Phe
1               5

(2) INFORMATION FOR SEQ ID NO:80:

(i) SEQUENCE CHARACTERISTICS:
        (A) LENGTH: 7 amino acids
        (B) TYPE: amino acid
        (C) STRANDEDNESS: single
        (D) TOPOLOGY: linear (xi) SEQUENCE DESCRIPTION: SEQ ID NO:80:

Asn Ala Phe Thr Gly Thr Ala
1               5

(2) INFORMATION FOR SEQ ID NO:81:

(i) SEQUENCE CHARACTERISTICS:
    (A) LENGTH: 7 amino acids
    (B) TYPE: amino acid
    (C) STRANDEDNESS: single
    (D) TOPOLOGY: linear (xi) SEQUENCE DESCRIPTION: SEQ ID NO:81:

Val Asn Gly Ala Phe Tyr Gly
1               5

(2) INFORMATION FOR SEQ ID NO:82:

(i) SEQUENCE CHARACTERISTICS:
        (A) LENGTH: 6 amino acids
        (B) TYPE: amino acid
        (C) STRANDEDNESS: single
        (D) TOPOLOGY: linear (xi) SEQUENCE DESCRIPTION: SEQ ID NO:82:

Glu Leu Gly Gly Tyr Phe
1               5

(2) INFORMATION FOR SEQ ID NO:83:

(i) SEQUENCE CHARACTERISTICS:
        (A) LENGTH: 6 amino acids
        (B) TYPE: amino acid
        (C) STRANDEDNESS: single
        (D) TOPOLOGY: linear (xi) SEQUENCE DESCRIPTION: SEQ ID NO:83:

Val Val Phe Gly Ala Arg
1               5

(2) INFORMATION FOR SEQ ID NO:84:

(i) SEQUENCE CHARACTERISTICS:
        (A) LENGTH: 6 amino acids
        (B) TYPE: amino acid
        (C) STRANDEDNESS: single
        (D) TOPOLOGY: linear (xi) SEQUENCE DESCRIPTION: SEQ ID NO:84:

Val Val Phe Gly Ala Lys
1               5

(2) INFORMATION FOR SEQ ID NO:85:

(i) SEQUENCE CHARACTERISTICS:
        (A) LENGTH: 7 amino acids
        (B) TYPE: amino acid
        (C) STRANDEDNESS: single
        (D) TOPOLOGY: linear (xi) SEQUENCE DESCRIPTION: SEQ ID NO:85:

Leu Glu Gly Gly Phe Tyr Gly
1               5

(2) INFORMATION FOR SEQ ID NO:86:

(i) SEQUENCE CHARACTERISTICS:
        (A) LENGTH: 103 base pairs
        (B) TYPE: nucleic acid
        (C) STRANDEDNESS: single
        (D) TOPOLOGY: linear (xi) SEQUENCE DESCRIPTION: SEQ ID NO:86:

TATGGAAACT CAAAGTATAA AAGATACAAA AGAAGCTATA TCATCTGAAG TGGACACTCA        60

AAGTACAGAA GATTCAGAAT TAGAAACTAT CTCAGTCACT GCA                103

(2) INFORMATION FOR SEQ ID NO:87:

(i) SEQUENCE CHARACTERISTICS:
        (A) LENGTH: 97 base pairs
        (B) TYPE: nucleic acid
        (C) STRANDEDNESS: single
        (D) TOPOLOGY: linear (xi) SEQUENCE DESCRIPTION: SEQ ID NO:87:

ACCTTTGAGT TTCATATTTT CTATGTTTTC TTCGATATAG TAGACTTCAC CTGTGAGTTT    60

CATGTCTTCT AAGTCTTAAT CTTTGATAGA GTCAGTG                             97

(2) INFORMATION FOR SEQ ID NO:88:

(i) SEQUENCE CHARACTERISTICS:
        (A) LENGTH: 115 base pairs
        (B) TYPE: nucleic acid
        (C) STRANDEDNESS: single
        (D) TOPOLOGY: linear (xi) SEQUENCE DESCRIPTION: SEQ ID NO:88:

TATGAAAGCT ACTAAACTGG TTCTGGGTGC TGTTATCCTG GGTTCCACTC TGCTGGCTGG    60

TTGTAGCGGA GGTGGTTGTT TTGATGTAGA TAACGTCTCT AATACCCCCT CTTCT        115

(2) INFORMATION FOR SEQ ID NO:89:

(i) SEQUENCE CHARACTERISTICS:
        (A) LENGTH: 116 base pairs
        (B) TYPE: nucleic acid
        (C) STRANDEDNESS: single
        (D) TOPOLOGY: linear (xi) SEQUENCE DESCRIPTION: SEQ ID NO:89:

ACTTTCGATG ATTTGACCAA GACCCACGAC AATAGGACCC AAGGTGAGAC GACCGACCAA    60

CATCGCCTCC ACCAACAAAA CTACATCTAT TGCAGAGATT ATGGGGAGA AGATTT        116

(2) INFORMATION FOR SEQ ID NO:90:

(i) SEQUENCE CHARACTERISTICS:
        (A) LENGTH: 109 base pairs
        (B) TYPE: nucleic acid
        (C) STRANDEDNESS: single
        (D) TOPOLOGY: linear (xi) SEQUENCE DESCRIPTION: SEQ ID NO:90:

TATGCGATAT CTGGCAACAT TGTTGTTATC TCTGGCGGTG TTAATCACCG CTGGTTGTAG    60

CGGAGGTGGT TCTTTTGATG TAGATAACGT CTCTAATACC CCCTCTTCT              109

(2) INFORMATION FOR SEQ ID NO:91:

(i) SEQUENCE CHARACTERISTICS:
        (A) LENGTH: 110 base pairs
        (B) TYPE: nucleic acid
        (C) STRANDEDNESS: single
        (D) TOPOLOGY: linear (xi) SEQUENCE DESCRIPTION: SEQ ID NO:91:

ACGCTATAGA CCGTTGTAAC AACAATAGAG ACCGCCACAA TTAGTGGCGA CCAACATCGC    60

CTCCACCAAG AAAACTACAT CTATTGCAGA GATTATGGGG GAGAAGATTT              110

(2) INFORMATION FOR SEQ ID NO:92:

(i) SEQUENCE CHARACTERISTICS:
    (A) LENGTH: 117 base pairs
    (B) TYPE: nucleic acid
    (C) STRANDEDNESS: single
    (D) TOPOLOGY: linear (xi) SEQUENCE DESCRIPTION: SEQ ID NO:92:

```
TATGCAACTG AACAAAGTGC TGAAAGGGCT GATGATTGCT CTGCCTGTTA TGGCAATGCT      60

GGTTGTAGCG GAGGTGGTTC TTTTGATGTA GATAACGTCT CTAATACCCC CTCTTCT       117
```

(2) INFORMATION FOR SEQ ID NO:93:

(i) SEQUENCE CHARACTERISTICS:
        (A) LENGTH: 119 base pairs
        (B) TYPE: nucleic acid
        (C) STRANDEDNESS: single
        (D) TOPOLOGY: linear (xi) SEQUENCE DESCRIPTION: SEQ ID NO:93:

```
ACGTTGACTT GTTTCACGAC TTTCCCGACT ACTAACGAGA CGGACAATAC CGTTAACGAC      60

CAACATCGCC TCCACCAAGA AAACTACATC TATTGCAGAG ATTATGGGGG AGAAGATTT     119
```

(2) INFORMATION FOR SEQ ID NO:94:

(i) SEQUENCE CHARACTERISTICS:
        (A) LENGTH: 908 amino acids
        (B) TYPE: amino acid
        (C) STRANDEDNESS: single
        (D) TOPOLOGY: linear (xi) SEQUENCE DESCRIPTION: SEQ ID NO:94:

```
Met Gln Gln Gln His Leu Phe Arg Leu Asn Ile Leu Cys Leu Ser Leu
1               5                   10                  15

Met Thr Ala Leu Pro Val Tyr Ala Glu Asn Val Gln Ala Glu Gln Ala
            20                  25                  30

Gln Glu Lys Gln Leu Asp Thr Ile Gln Val Lys Ala Lys Lys Gln Lys
        35                  40                  45

Thr Arg Arg Asp Asn Glu Val Thr Gly Leu Gly Lys Leu Val Lys Ser
50                  55                  60

Ser Asp Thr Leu Ser Lys Glu Gln Val Leu Asn Ile Arg Asp Leu Thr
65                  70                  75                  80

Arg Tyr Asp Pro Gly Ile Ala Val Val Glu Gln Gly Arg Gly Ala Ser
                85                  90                  95

Ser Gly Tyr Ser Ile Arg Gly Met Asp Lys Asn Arg Val Ser Leu Thr
            100                 105                 110

Val Asp Gly Val Ser Gln Ile Gln Ser Tyr Thr Ala Gln Ala Ala Leu
        115                 120                 125

Gly Gly Thr Arg Thr Ala Gly Ser Ser Gly Ala Ile Asn Glu Ile Glu
    130                 135                 140

Tyr Glu Asn Val Lys Ala Val Glu Ile Ser Lys Gly Ser Asn Ser Ser
145                 150                 155                 160

Glu Tyr Gly Asn Gly Ala Leu Ala Gly Ser Val Ala Phe Gln Thr Lys
                165                 170                 175

Thr Ala Ala Asp Ile Ile Gly Glu Gly Lys Gln Trp Gly Ile Gln Ser
            180                 185                 190

Lys Thr Ala Tyr Ser Gly Lys Asp His Ala Leu Thr Gln Ser Leu Ala
        195                 200                 205

Leu Ala Gly Arg Ser Gly Gly Ala Glu Ala Leu Leu Ile Tyr Thr Lys
    210                 215                 220
```

```
Arg Arg Gly Arg Glu Ile His Ala His Lys Asp Ala Gly Lys Gly Val
225                 230                 235                 240

Gln Ser Phe Asn Arg Leu Val Leu Asp Glu Asp Lys Lys Glu Gly Gly
                245                 250                 255

Ser Gln Tyr Arg Tyr Phe Ile Val Glu Glu Cys His Asn Gly Tyr
                260                 265                 270

Ala Ala Cys Lys Asn Lys Leu Lys Glu Asp Ala Ser Val Lys Asp Glu
            275                 280                 285

Arg Lys Thr Val Ser Thr Gln Asp Tyr Thr Gly Ser Asn Arg Leu Leu
        290                 295                 300

Ala Asn Pro Leu Glu Tyr Gly Ser Gln Ser Trp Leu Phe Arg Pro Gly
305                 310                 315                 320

Trp His Leu Asp Asn Arg His Tyr Val Gly Ala Val Leu Glu Arg Thr
                325                 330                 335

Gln Gln Thr Phe Asp Thr Arg Asp Met Thr Val Pro Ala Tyr Phe Thr
                340                 345                 350

Ser Glu Asp Tyr Val Pro Gly Ser Leu Lys Gly Leu Gly Lys Tyr Ser
            355                 360                 365

Gly Asp Asn Lys Ala Glu Arg Leu Phe Val Gln Glu Gly Ser Thr
        370                 375                 380

Leu Gln Gly Ile Gly Tyr Gly Thr Gly Val Phe Tyr Asp Glu Arg His
385                 390                 395                 400

Thr Lys Asn Arg Tyr Gly Val Glu Tyr Val Tyr His Asn Ala Asp Lys
                405                 410                 415

Asp Thr Trp Ala Asp Tyr Ala Arg Leu Ser Tyr Asp Arg Gln Gly Ile
                420                 425                 430

Asp Leu Asp Asn Arg Leu Gln Gln Thr His Cys Ser His Asp Gly Ser
            435                 440                 445

Asp Lys Asn Cys Arg Pro Asp Gly Asn Lys Pro Tyr Ser Phe Tyr Lys
        450                 455                 460

Ser Asp Arg Met Ile Tyr Glu Glu Ser Arg Asn Leu Phe Gln Ala Val
465                 470                 475                 480

Phe Lys Lys Ala Phe Asp Thr Ala Lys Ile Arg His Asn Leu Ser Ile
                485                 490                 495

Asn Leu Gly Tyr Asp Arg Phe Lys Ser Gln Leu Ser His Ser Asp Tyr
                500                 505                 510

Tyr Leu Gln Asn Ala Val Gln Ala Tyr Asp Leu Ile Thr Pro Lys Lys
            515                 520                 525

Pro Pro Phe Pro Asn Gly Ser Lys Asp Asn Pro Tyr Arg Val Ser Ile
        530                 535                 540

Gly Lys Thr Thr Val Asn Thr Ser Pro Ile Cys Arg Phe Gly Asn Asn
545                 550                 555                 560

Thr Tyr Thr Asp Cys Thr Pro Arg Asn Ile Gly Gly Asn Gly Tyr Tyr
                565                 570                 575

Ala Ala Val Gln Asp Asn Val Arg Leu Gly Arg Trp Ala Asp Val Gly
            580                 585                 590

Ala Gly Ile Arg Tyr Asp Tyr Arg Ser Thr His Ser Glu Asp Lys Ser
        595                 600                 605

Val Ser Thr Gly Thr His Arg Asn Leu Ser Trp Asn Ala Gly Val Val
    610                 615                 620

Leu Lys Pro Phe Thr Trp Met Asp Leu Thr Tyr Arg Ala Ser Thr Gly
625                 630                 635                 640

Phe Arg Leu Pro Ser Phe Ala Glu Met Tyr Gly Trp Arg Ala Gly Glu
                645                 650                 655
```

```
Ser Leu Lys Thr Leu Asp Leu Lys Pro Glu Lys Ser Phe Asn Arg Glu
            660                 665                 670

Ala Gly Ile Val Phe Lys Gly Asp Phe Gly Asn Leu Glu Ala Ser Tyr
            675                 680                 685

Phe Asn Asn Ala Tyr Arg Asp Leu Ile Ala Phe Gly Tyr Glu Thr Arg
            690                 695                 700

Thr Gln Asn Gly Gln Thr Ser Ala Ser Gly Asp Pro Gly Tyr Arg Asn
705                 710                 715                 720

Ala Gln Asn Ala Arg Ile Ala Gly Ile Asn Ile Leu Gly Lys Ile Asp
                725                 730                 735

Trp His Gly Val Trp Gly Leu Pro Asp Gly Leu Tyr Ser Thr Leu
            740                 745                 750

Ala Tyr Asn Arg Ile Lys Val Lys Asp Ala Asp Ile Arg Ala Asp Arg
            755                 760                 765

Thr Phe Val Thr Ser Tyr Leu Phe Asp Ala Val Gln Pro Ser Arg Tyr
            770                 775                 780

Val Leu Gly Leu Gly Tyr Asp His Pro Asp Gly Ile Trp Gly Ile Asn
785                 790                 795                 800

Thr Met Phe Thr Tyr Ser Lys Ala Lys Ser Val Asp Glu Leu Leu Gly
                805                 810                 815

Ser Gln Ala Leu Leu Asn Gly Asn Ala Asn Ala Lys Lys Ala Ala Ser
            820                 825                 830

Arg Arg Thr Arg Pro Trp Tyr Val Thr Asp Val Ser Gly Tyr Tyr Asn
            835                 840                 845

Ile Lys Lys His Leu Thr Leu Arg Ala Gly Val Tyr Asn Leu Leu Asn
850                 855                 860

Tyr Arg Tyr Val Thr Trp Glu Asn Val Arg Gln Thr Ala Gly Gly Ala
865                 870                 875                 880

Val Asn Gln His Lys Asn Val Gly Val Tyr Asn Arg Tyr Ala Ala Pro
                885                 890                 895

Gly Arg Asn Tyr Thr Phe Ser Leu Glu Met Lys Phe
            900                 905

(2) INFORMATION FOR SEQ ID NO:95:

(i) SEQUENCE CHARACTERISTICS:
        (A) LENGTH: 911 amino acids
        (B) TYPE: amino acid
        (C) STRANDEDNESS: single
        (D) TOPOLOGY: linear (xi) SEQUENCE DESCRIPTION: SEQ ID NO:95:

Met Gln Gln Gln His Leu Phe Arg Leu Asn Ile Leu Cys Leu Ser Leu
1               5                   10                  15

Met Thr Ala Leu Pro Ala Tyr Ala Glu Asn Val Gln Ala Gly Gln Ala
            20                  25                  30

Gln Glu Lys Gln Leu Asp Thr Ile Gln Val Lys Ala Lys Lys Gln Lys
            35                  40                  45

Thr Arg Arg Asp Asn Glu Val Thr Gly Leu Gly Lys Leu Val Lys Thr
50                  55                  60

Ala Asp Thr Leu Ser Lys Glu Gln Val Leu Asp Ile Arg Asp Leu Thr
65                  70                  75                  80

Arg Tyr Asp Pro Gly Ile Ala Val Val Glu Gln Gly Arg Gly Ala Ser
                85                  90                  95

Ser Gly Tyr Ser Ile Arg Gly Met Asp Lys Asn Arg Val Ser Leu Thr
            100                 105                 110
```

```
Val Asp Gly Leu Ala Gln Ile Gln Ser Tyr Thr Ala Gln Ala Ala Leu
        115                 120                 125

Gly Gly Thr Arg Thr Ala Gly Ser Ser Gly Ala Ile Asn Glu Ile Glu
130                 135                 140

Tyr Glu Asn Val Lys Ala Val Glu Ile Ser Lys Gly Ser Asn Ser Val
145                 150                 155                 160

Glu Gln Gly Ser Gly Ala Leu Ala Gly Ser Val Ala Phe Gln Thr Lys
                165                 170                 175

Thr Ala Asp Asp Val Ile Gly Glu Gly Arg Gln Trp Gly Ile Gln Ser
                180                 185                 190

Lys Thr Ala Tyr Ser Gly Lys Asn Arg Gly Leu Thr Gln Ser Ile Ala
        195                 200                 205

Leu Ala Gly Arg Ile Gly Gly Ala Glu Ala Leu Leu Ile His Thr Gly
        210                 215                 220

Arg Arg Ala Gly Glu Ile Arg Ala His Glu Asp Ala Gly Arg Gly Val
225                 230                 235                 240

Gln Ser Phe Asn Arg Leu Val Pro Val Glu Asp Ser Ser Glu Tyr Ala
                245                 250                 255

Tyr Phe Ile Val Glu Asp Glu Cys Glu Gly Lys Asn Tyr Glu Thr Cys
                260                 265                 270

Lys Ser Lys Pro Lys Lys Asp Val Gly Lys Asp Glu Arg Gln Thr
                275                 280                 285

Val Ser Thr Arg Asp Tyr Thr Gly Pro Asn Arg Phe Leu Ala Asp Pro
290                 295                 300

Leu Ser Tyr Glu Ser Arg Ser Trp Leu Phe Arg Pro Gly Phe Arg Phe
305                 310                 315                 320

Glu Asn Lys Arg His Tyr Ile Gly Gly Ile Leu Glu His Thr Gln Gln
                325                 330                 335

Thr Phe Asp Thr Arg Asp Met Thr Val Pro Ala Phe Leu Thr Lys Ala
                340                 345                 350

Val Phe Asp Ala Asn Ser Lys Gln Ala Gly Ser Leu Pro Gly Asn Gly
                355                 360                 365

Lys Tyr Ala Gly Asn His Lys Tyr Gly Gly Leu Phe Thr Asn Gly Glu
370                 375                 380

Asn Gly Ala Leu Val Gly Ala Glu Tyr Gly Thr Gly Val Phe Tyr Asp
385                 390                 395                 400

Glu Thr His Thr Lys Ser Arg Tyr Gly Leu Glu Tyr Val Tyr Thr Asn
                405                 410                 415

Ala Asp Lys Asp Thr Trp Ala Asp Tyr Ala Arg Leu Ser Tyr Asp Arg
                420                 425                 430

Gln Gly Ile Gly Leu Asp Asn His Phe Gln Gln Thr His Cys Ser Ala
        435                 440                 445

Asp Gly Ser Asp Lys Tyr Cys Arg Pro Ser Ala Asp Lys Pro Phe Ser
        450                 455                 460

Tyr Tyr Lys Ser Asp Arg Val Ile Tyr Gly Glu Ser His Arg Leu Leu
465                 470                 475                 480

Gln Ala Ala Phe Lys Lys Ser Phe Asp Thr Ala Lys Ile Arg His Asn
                485                 490                 495

Leu Ser Val Asn Leu Gly Phe Asp Arg Phe Asp Ser Asn Leu Arg His
                500                 505                 510

Gln Asp Tyr Tyr Gln His Ala Asn Arg Ala Tyr Ser Ser Lys Thr
                515                 520                 525

Pro Pro Lys Thr Ala Asn Pro Asn Gly Asp Lys Ser Lys Pro Tyr Trp
```

530                 535                 540
Val Ser Ile Gly Gly Gly Asn Val Val Thr Gly Gln Ile Cys Leu Phe
545                 550                 555                 560

Gly Asn Asn Thr Tyr Thr Asp Cys Thr Pro Arg Ser Ile Asn Gly Lys
                565                 570                 575

Ser Tyr Tyr Ala Ala Val Arg Asp Asn Val Arg Leu Gly Arg Trp Ala
                580                 585                 590

Asp Val Gly Ala Gly Leu Arg Tyr Asp Tyr Arg Ser Thr His Ser Asp
                595                 600                 605

Asp Gly Ser Val Ser Thr Gly Thr His Arg Thr Leu Ser Trp Asn Ala
610                 615                 620

Gly Ile Val Leu Lys Pro Ala Asp Trp Leu Asp Leu Thr Tyr Arg Thr
625                 630                 635                 640

Ser Thr Gly Phe Arg Leu Pro Ser Phe Ala Glu Met Tyr Gly Trp Arg
                645                 650                 655

Ser Gly Val Gln Ser Lys Ala Val Lys Ile Asp Pro Glu Lys Ser Phe
                660                 665                 670

Asn Lys Glu Ala Gly Ile Val Phe Lys Gly Asp Phe Gly Asn Leu Glu
                675                 680                 685

Ala Ser Trp Phe Asn Asn Ala Tyr Arg Asp Leu Ile Val Arg Gly Tyr
690                 695                 700

Glu Ala Gln Ile Lys Asn Gly Lys Glu Ala Lys Gly Asp Pro Ala
705                 710                 715                 720

Tyr Leu Asn Ala Gln Ser Ala Arg Ile Thr Gly Ile Asn Ile Leu Gly
                725                 730                 735

Lys Ile Asp Trp Asn Gly Val Trp Asp Lys Leu Pro Glu Gly Trp Tyr
                740                 745                 750

Ser Thr Phe Ala Tyr Asn Arg Val His Val Arg Asp Ile Lys Lys Arg
                755                 760                 765

Ala Asp Arg Thr Asp Ile Gln Ser His Leu Phe Asp Ala Ile Gln Pro
770                 775                 780

Ser Arg Tyr Val Val Gly Leu Gly Tyr Asp Gln Pro Glu Gly Lys Trp
785                 790                 795                 800

Gly Val Asn Gly Met Leu Thr Tyr Ser Lys Ala Lys Glu Ile Thr Glu
                805                 810                 815

Leu Leu Gly Ser Arg Ala Leu Leu Asn Gly Asn Ser Arg Asn Thr Lys
                820                 825                 830

Ala Thr Ala Arg Arg Thr Arg Pro Trp Tyr Ile Val Asp Val Ser Gly
                835                 840                 845

Tyr Tyr Thr Ile Lys Lys His Phe Thr Leu Arg Ala Gly Val Tyr Asn
850                 855                 860

Leu Leu Asn Tyr Arg Tyr Val Thr Trp Glu Asn Val Arg Gln Thr Ala
865                 870                 875                 880

Gly Gly Ala Val Asn Gln His Lys Asn Val Gly Val Tyr Asn Arg Tyr
                885                 890                 895

Ala Ala Pro Gly Arg Asn Tyr Thr Phe Ser Leu Glu Met Lys Phe
                900                 905                 910

(2) INFORMATION FOR SEQ ID NO:96:

(i) SEQUENCE CHARACTERISTICS:
        (A) LENGTH: 915 amino acids
        (B) TYPE: amino acid
        (C) STRANDEDNESS: single
        (D) TOPOLOGY: linear (xi) SEQUENCE DESCRIPTION: SEQ ID NO:96:

```
Met Gln Gln Gln His Leu Phe Arg Leu Asn Ile Leu Cys Leu Ser Leu
 1               5                  10                  15

Met Thr Ala Leu Pro Ala Tyr Ala Glu Asn Val Gln Ala Gly Gln Ala
                20                  25                  30

Gln Glu Lys Gln Leu Asp Thr Ile Gln Val Lys Ala Lys Lys Gln Lys
            35                  40                  45

Thr Arg Arg Asp Asn Glu Val Thr Gly Leu Gly Lys Leu Val Lys Thr
        50                  55                  60

Ala Asp Thr Leu Ser Lys Glu Gln Val Leu Asp Ile Arg Asp Leu Thr
 65                  70                  75                  80

Arg Tyr Asp Pro Gly Ile Ala Val Val Glu Gln Gly Arg Gly Ala Ser
                85                  90                  95

Ser Gly Tyr Ser Ile Arg Gly Met Asp Lys Asn Arg Val Ser Leu Thr
            100                 105                 110

Val Asp Gly Leu Ala Gln Ile Gln Ser Tyr Thr Ala Gln Ala Ala Leu
        115                 120                 125

Gly Gly Thr Arg Thr Ala Gly Ser Ser Gly Ala Ile Asn Glu Ile Glu
    130                 135                 140

Tyr Glu Asn Val Lys Ala Val Glu Ile Ser Lys Gly Ser Asn Ser Val
145                 150                 155                 160

Glu Gln Gly Ser Gly Ala Leu Ala Gly Ser Val Ala Phe Gln Thr Lys
                165                 170                 175

Thr Ala Asp Asp Val Ile Gly Glu Gly Arg Gln Trp Gly Ile Gln Ser
            180                 185                 190

Lys Thr Ala Tyr Ser Gly Lys Asn Arg Gly Leu Thr Gln Ser Ile Ala
        195                 200                 205

Leu Ala Gly Arg Ile Gly Gly Ala Glu Ala Leu Leu Ile Arg Thr Gly
    210                 215                 220

Arg His Ala Gly Glu Ile Arg Ala His Glu Ala Gly Arg Gly Val
225                 230                 235                 240

Gln Ser Phe Asn Arg Leu Ala Pro Val Asp Asp Gly Ser Lys Tyr Ala
                245                 250                 255

Tyr Phe Ile Val Glu Glu Glu Cys Lys Asn Gly Gly His Glu Lys Cys
            260                 265                 270

Lys Ala Asn Pro Lys Lys Asp Val Val Gly Glu Asp Lys Arg Gln Thr
        275                 280                 285

Val Ser Thr Arg Asp Tyr Thr Gly Pro Asn Arg Phe Leu Ala Asp Pro
    290                 295                 300

Leu Ser Tyr Glu Ser Arg Ser Trp Leu Phe Arg Pro Gly Phe Arg Phe
305                 310                 315                 320

Glu Asn Lys Arg His Tyr Ile Gly Gly Ile Leu Glu Arg Thr Gln Gln
                325                 330                 335

Thr Phe Asp Thr Arg Asp Met Thr Val Pro Ala Phe Leu Thr Lys Ala
            340                 345                 350

Val Phe Asp Ala Asn Gln Lys Gln Ala Gly Ser Leu Arg Gly Asn Gly
        355                 360                 365

Lys Tyr Ala Gly Asn His Lys Tyr Gly Gly Leu Phe Thr Ser Gly Glu
    370                 375                 380

Asn Asn Ala Pro Val Gly Ala Glu Tyr Gly Thr Gly Val Phe Tyr Asp
385                 390                 395                 400

Glu Thr His Thr Lys Ser Arg Tyr Gly Leu Glu Tyr Val Tyr Thr Asn
                405                 410                 415
```

-continued

```
Ala Asp Lys Asp Thr Trp Ala Asp Tyr Ala Arg Leu Ser Tyr Asp Arg
        420                 425                 430

Gln Gly Ile Gly Leu Asp Asn His Phe Gln Gln Thr His Cys Ser Ala
            435                 440                 445

Asp Gly Ser Asp Lys Tyr Cys Arg Pro Ser Ala Asp Lys Pro Phe Ser
    450                 455                 460

Tyr Tyr Lys Ser Asp Arg Val Ile Tyr Gly Glu Ser His Lys Leu Leu
465                 470                 475                 480

Gln Ala Ala Phe Lys Lys Ser Phe Asp Thr Ala Lys Ile Arg His Asn
                485                 490                 495

Leu Ser Val Asn Leu Gly Tyr Asp Arg Phe Gly Ser Asn Leu Arg His
            500                 505                 510

Gln Asp Tyr Tyr Tyr Gln Ser Ala Asn Arg Ala Tyr Ser Leu Lys Thr
        515                 520                 525

Pro Pro Gln Asn Asn Gly Lys Lys Thr Ser Pro Asn Gly Arg Glu Lys
    530                 535                 540

Asn Pro Tyr Trp Val Ser Ile Gly Arg Gly Asn Val Val Thr Arg Gln
545                 550                 555                 560

Ile Cys Leu Phe Gly Asn Asn Thr Tyr Thr Asp Cys Thr Pro Arg Ser
                565                 570                 575

Ile Asn Gly Lys Ser Tyr Tyr Ala Ala Val Arg Asp Asn Val Arg Leu
            580                 585                 590

Gly Arg Trp Ala Asp Val Gly Ala Gly Leu Arg Tyr Asp Tyr Arg Ser
        595                 600                 605

Thr His Ser Asp Asp Gly Ser Val Ser Thr Gly Thr His Arg Thr Leu
    610                 615                 620

Ser Trp Asn Ala Gly Ile Val Leu Lys Pro Ala Asp Trp Leu Asp Leu
625                 630                 635                 640

Thr Tyr Arg Thr Ser Thr Gly Phe Arg Leu Pro Ser Phe Ala Glu Met
                645                 650                 655

Tyr Gly Trp Arg Ser Gly Asp Lys Ile Lys Ala Val Lys Ile Asp Pro
            660                 665                 670

Glu Lys Ser Phe Asn Lys Glu Ala Gly Ile Val Phe Lys Gly Asp Phe
        675                 680                 685

Gly Asn Leu Glu Ala Ser Trp Phe Asn Asn Ala Tyr Arg Asp Leu Ile
    690                 695                 700

Val Arg Gly Tyr Glu Ala Gln Ile Lys Asp Gly Lys Glu Gln Val Lys
705                 710                 715                 720

Gly Asn Pro Ala Tyr Leu Asn Ala Gln Ser Ala Arg Ile Thr Gly Ile
                725                 730                 735

Asn Ile Leu Gly Lys Ile Asp Trp Asn Gly Val Trp Asp Lys Leu Pro
            740                 745                 750

Glu Gly Trp Tyr Ser Thr Phe Ala Tyr Asn Arg Val Arg Val Arg Asp
        755                 760                 765

Ile Lys Lys Arg Ala Asp Arg Thr Asp Ile Gln Ser His Leu Phe Asp
    770                 775                 780

Ala Ile Gln Pro Ser Arg Tyr Val Val Gly Ser Gly Tyr Asp Gln Pro
785                 790                 795                 800

Glu Gly Lys Trp Gly Val Asn Gly Met Leu Thr Tyr Ser Lys Ala Lys
                805                 810                 815

Glu Ile Thr Glu Leu Leu Gly Ser Arg Ala Leu Leu Asn Gly Asn Ser
            820                 825                 830

Arg Asn Thr Lys Ala Thr Ala Arg Arg Thr Arg Pro Trp Tyr Ile Val
        835                 840                 845
```

Asp Val Ser Gly Tyr Tyr Thr Val Lys Lys His Phe Thr Leu Arg Ala
    850                 855                 860

Gly Val Tyr Asn Leu Leu Asn His Arg Tyr Val Thr Trp Glu Asn Val
865                 870                 875                 880

Arg Gln Thr Ala Ala Gly Ala Val Asn Gln His Lys Asn Val Gly Val
                885                 890                 895

Tyr Asn Arg Tyr Ala Ala Pro Gly Arg Asn Tyr Thr Phe Ser Leu Glu
            900                 905                 910

Met Lys Phe
        915

(2) INFORMATION FOR SEQ ID NO:97:

(i) SEQUENCE CHARACTERISTICS:
        (A) LENGTH: 598 amino acids
        (B) TYPE: amino acid
        (C) STRANDEDNESS: single
        (D) TOPOLOGY: linear (xi) SEQUENCE DESCRIPTION: SEQ ID NO:97:

Met Asn Asn Pro Leu Val Asn Gln Ala Ala Met Val Leu Pro Val Phe
1               5                   10                  15

Leu Leu Ser Ala Cys Leu Gly Gly Gly Ser Phe Asp Leu Asp Ser
            20                  25                  30

Val Glu Thr Val Gln Asp Met His Ser Lys Pro Lys Tyr Glu Asp Glu
            35                  40                  45

Lys Ser Gln Pro Glu Ser Gln Gln Asp Val Ser Glu Asn Ser Gly Ala
        50                  55                  60

Ala Tyr Gly Phe Ala Val Lys Leu Pro Arg Arg Asn Ala His Phe Asn
65                  70                  75                  80

Pro Lys Tyr Lys Glu Lys His Lys Pro Leu Gly Ser Met Asp Trp Lys
                85                  90                  95

Lys Leu Gln Arg Gly Glu Pro Asn Ser Phe Ser Glu Arg Asp Glu Leu
                100                 105                 110

Glu Lys Lys Arg Gly Ser Ser Glu Leu Ile Glu Ser Lys Trp Glu Asp
            115                 120                 125

Gly Gln Ser Arg Val Val Gly Tyr Thr Asn Phe Thr Tyr Val Arg Ser
130                 135                 140

Gly Tyr Val Tyr Leu Asn Lys Asn Asn Ile Asp Ile Lys Asn Asn Ile
145                 150                 155                 160

Val Leu Phe Gly Pro Asp Gly Tyr Leu Tyr Tyr Lys Gly Lys Glu Pro
                165                 170                 175

Ser Lys Glu Leu Pro Ser Glu Lys Ile Thr Tyr Lys Gly Thr Trp Asp
            180                 185                 190

Tyr Val Thr Asp Ala Met Glu Lys Gln Arg Phe Glu Gly Leu Gly Ser
            195                 200                 205

Ala Ala Gly Gly Asp Lys Ser Gly Ala Leu Ser Ala Leu Glu Glu Gly
        210                 215                 220

Val Leu Arg Asn Gln Ala Glu Ala Ser Ser Gly His Thr Asp Phe Gly
225                 230                 235                 240

Met Thr Ser Glu Phe Glu Val Asp Phe Ser Asp Lys Thr Ile Lys Gly
                245                 250                 255

Thr Leu Tyr Arg Asn Asn Arg Ile Thr Gln Asn Asn Ser Glu Asn Lys
            260                 265                 270

Gln Ile Lys Thr Thr Arg Tyr Thr Ile Gln Ala Thr Leu His Gly Asn
        275                 280                 285

```
Arg Phe Lys Gly Lys Ala Leu Ala Ala Asp Lys Gly Ala Thr Asn Gly
    290                 295                 300

Ser His Pro Phe Ile Ser Asp Ser Asp Ser Leu Glu Gly Gly Phe Tyr
305                 310                 315                 320

Gly Pro Lys Gly Glu Glu Leu Ala Gly Lys Phe Leu Ser Asn Asp Asn
                325                 330                 335

Lys Val Ala Ala Val Phe Gly Ala Lys Gln Lys Asp Lys Lys Asp Gly
            340                 345                 350

Glu Asn Ala Ala Gly Pro Ala Thr Glu Val Ile Asp Ala Tyr Arg Ile
        355                 360                 365

Thr Gly Glu Glu Phe Lys Lys Glu Gln Ile Asp Ser Phe Gly Asp Val
    370                 375                 380

Lys Lys Leu Leu Val Asp Gly Val Glu Leu Ser Leu Leu Pro Ser Glu
385                 390                 395                 400

Gly Asn Lys Ala Ala Phe Gln His Glu Ile Glu Gln Asn Gly Val Lys
                405                 410                 415

Ala Thr Val Cys Cys Ser Asn Leu Asp Tyr Met Ser Phe Gly Lys Leu
            420                 425                 430

Ser Lys Glu Asn Lys Asp Asp Met Phe Leu Gln Gly Val Arg Thr Pro
        435                 440                 445

Val Ser Asp Val Ala Ala Arg Thr Glu Ala Asn Ala Lys Tyr Arg Gly
    450                 455                 460

Thr Trp Tyr Gly Tyr Ile Ala Asn Gly Thr Ser Trp Ser Gly Glu Ala
465                 470                 475                 480

Ser Asn Gln Glu Gly Gly Asn Arg Ala Glu Phe Asp Val Asp Phe Ser
                485                 490                 495

Thr Lys Lys Ile Ser Gly Thr Leu Thr Ala Lys Asp Arg Thr Ser Pro
            500                 505                 510

Ala Phe Thr Ile Thr Ala Met Ile Lys Asp Asn Gly Phe Ser Gly Val
        515                 520                 525

Ala Lys Thr Gly Glu Asn Gly Phe Ala Leu Asp Pro Gln Asn Thr Gly
    530                 535                 540

Asn Ser His Tyr Thr His Ile Glu Ala Thr Val Ser Gly Gly Phe Tyr
545                 550                 555                 560

Gly Lys Asn Ala Ile Glu Met Gly Gly Ser Phe Ser Phe Pro Gly Asn
                565                 570                 575

Ala Pro Glu Gly Lys Gln Glu Lys Ala Ser Val Val Phe Gly Ala Lys
            580                 585                 590

Arg Gln Gln Leu Val Gln
        595
```

(2) INFORMATION FOR SEQ ID NO:98:

(i) SEQUENCE CHARACTERISTICS:
        (A) LENGTH: 711 amino acids
        (B) TYPE: amino acid
        (C) STRANDEDNESS: single
        (D) TOPOLOGY: linear (xi) SEQUENCE DESCRIPTION: SEQ ID NO:98:

```
Met Asn Asn Pro Leu Val Asn Gln Ala Ala Met Val Leu Pro Val Phe
1                   5                   10                  15

Leu Leu Ser Ala Cys Leu Gly Gly Gly Ser Phe Asp Leu Asp Ser
                20                  25                  30

Val Asp Thr Glu Ala Pro Arg Pro Ala Pro Lys Tyr Gln Asp Val Ser
            35                  40                  45
```

Ser Glu Lys Pro Gln Ala Gln Lys Asp Gln Gly Tyr Gly Phe Ala
    50                  55                  60

Met Arg Leu Lys Arg Arg Asn Trp Tyr Pro Gly Ala Glu Ser Glu
65                  70                  75                  80

Val Lys Leu Asn Glu Ser Asp Trp Glu Ala Thr Gly Leu Pro Thr Lys
                85                  90                  95

Pro Lys Glu Leu Pro Lys Arg Gln Lys Ser Val Ile Glu Lys Val Glu
            100                 105                 110

Thr Asp Gly Asp Ser Asp Ile Tyr Ser Ser Pro Tyr Leu Thr Pro Ser
            115                 120                 125

Asn His Gln Asn Gly Ser Ala Gly Asn Gly Val Asn Gln Pro Lys Asn
            130                 135                 140

Gln Ala Thr Gly His Glu Asn Phe Gln Tyr Val Tyr Ser Gly Trp Phe
145                 150                 155                 160

Tyr Lys His Ala Ala Ser Glu Lys Asp Phe Ser Asn Lys Lys Ile Lys
                165                 170                 175

Ser Gly Asp Asp Gly Tyr Ile Phe Tyr His Gly Glu Lys Pro Ser Arg
            180                 185                 190

Gln Leu Pro Ala Ser Gly Lys Val Ile Tyr Lys Gly Val Trp His Phe
            195                 200                 205

Val Thr Asp Thr Lys Lys Gly Gln Asp Phe Arg Glu Ile Ile Gln Pro
            210                 215                 220

Ser Lys Lys Gln Gly Asp Arg Tyr Ser Gly Phe Ser Gly Asp Gly Ser
225                 230                 235                 240

Glu Glu Tyr Ser Asn Lys Asn Glu Ser Thr Leu Lys Asp Asp His Glu
                245                 250                 255

Gly Tyr Gly Phe Thr Ser Asn Leu Glu Val Asp Phe Gly Asn Lys Lys
            260                 265                 270

Leu Thr Gly Lys Leu Ile Arg Asn Asn Ala Ser Leu Asn Asn Asn Thr
            275                 280                 285

Asn Asn Asp Lys His Thr Thr Gln Tyr Tyr Ser Leu Asp Ala Gln Ile
            290                 295                 300

Thr Gly Asn Arg Phe Asn Gly Thr Ala Thr Asp Lys Lys Glu
305                 310                 315                 320

Asn Glu Thr Lys Leu His Pro Phe Val Ser Asp Ser Ser Leu Ser
                325                 330                 335

Gly Gly Phe Phe Gly Pro Gln Gly Glu Glu Leu Gly Phe Arg Phe Leu
            340                 345                 350

Ser Asp Asp Gln Lys Val Ala Val Gly Ser Ala Lys Thr Lys Asp
            355                 360                 365

Lys Leu Glu Asn Gly Ala Ala Ala Ser Gly Ser Thr Gly Ala Ala Ala
            370                 375                 380

Ser Gly Gly Ala Ala Gly Thr Ser Ser Glu Asn Ser Lys Leu Thr Thr
385                 390                 395                 400

Val Leu Asp Ala Val Glu Leu Thr Leu Asn Asp Lys Lys Ile Lys Asn
                405                 410                 415

Leu Asp Asn Phe Ser Asn Ala Ala Gln Leu Val Val Asp Gly Ile Met
            420                 425                 430

Ile Pro Leu Leu Pro Lys Asp Ser Glu Ser Gly Asn Thr Gln Ala Asp
            435                 440                 445

Lys Gly Lys Asn Gly Gly Thr Glu Phe Thr Arg Lys Phe Glu His Thr
            450                 455                 460

Pro Glu Ser Asp Lys Lys Asp Ala Gln Ala Gly Thr Gln Thr Asn Gly

```
                465                 470                 475                 480
Ala Gln Thr Ala Ser Asn Thr Ala Gly Asp Thr Asn Gly Lys Thr Lys
                    485                 490                 495

Thr Tyr Glu Val Glu Val Cys Cys Ser Asn Leu Asn Tyr Leu Lys Tyr
        500                 505                 510

Gly Met Leu Thr Arg Lys Asn Ser Lys Ser Ala Met Gln Ala Gly Gly
            515                 520                 525

Asn Ser Ser Gln Ala Asp Ala Lys Thr Glu Gln Val Glu Gln Ser Met
        530                 535                 540

Phe Leu Gln Gly Glu Arg Thr Asp Glu Lys Glu Ile Pro Thr Asp Gln
545                 550                 555                 560

Asn Val Val Tyr Arg Gly Ser Trp Tyr Gly His Ile Ala Asn Gly Thr
                565                 570                 575

Ser Trp Ser Gly Asn Ala Ser Asp Lys Glu Gly Gly Asn Arg Ala Glu
            580                 585                 590

Phe Thr Val Asn Phe Ala Asp Lys Lys Ile Thr Gly Lys Leu Thr Ala
                595                 600                 605

Glu Asn Arg Gln Ala Gln Thr Phe Thr Ile Glu Gly Met Ile Gln Gly
            610                 615                 620

Asn Gly Phe Glu Gly Thr Ala Lys Thr Ala Glu Ser Gly Phe Asp Leu
625                 630                 635                 640

Asp Gln Lys Asn Thr Thr Arg Thr Pro Lys Ala Tyr Ile Thr Asp Ala
                645                 650                 655

Lys Val Lys Gly Gly Phe Tyr Gly Pro Lys Ala Glu Glu Leu Gly Gly
                660                 665                 670

Trp Phe Ala Tyr Pro Gly Asp Lys Gln Thr Glu Lys Ala Thr Ala Thr
            675                 680                 685

Ser Ser Asp Gly Asn Ser Ala Ser Ser Ala Thr Val Val Phe Gly Ala
        690                 695                 700

Lys Arg Gln Gln Pro Val Gln
705                 710

(2) INFORMATION FOR SEQ ID NO:99:

(i) SEQUENCE CHARACTERISTICS:
        (A) LENGTH: 546 amino acids
        (B) TYPE: amino acid
        (C) STRANDEDNESS: single
        (D) TOPOLOGY: linear (xi) SEQUENCE DESCRIPTION: SEQ ID NO:99:

Met His Phe Lys Leu Asn Pro Tyr Ala Leu Ala Phe Thr Ser Leu Phe
1               5                   10                  15

Leu Val Ala Cys Ser Gly Gly Lys Gly Ser Phe Asp Leu Glu Asp Val
            20                  25                  30

Arg Pro Asn Lys Thr Thr Gly Val Ser Lys Glu Glu Tyr Lys Asp Val
        35                  40                  45

Glu Thr Ala Lys Lys Glu Lys Glu Gln Leu Gly Glu Leu Met Glu Pro
    50                  55                  60

Ala Leu Gly Tyr Val Val Lys Val Pro Val Ser Ser Phe Glu Asn Lys
65                  70                  75                  80

Lys Val Asp Ile Ser Asp Ile Glu Val Ile Thr Asn Gly Asn Leu Asp
                85                  90                  95

Asp Val Pro Tyr Lys Ala Asn Ser Ser Lys Tyr Asn Tyr Pro Asp Ile
            100                 105                 110

Lys Thr Lys Asp Ser Ser Leu Gln Tyr Val Arg Ser Gly Tyr Val Ile
```

-continued

```
                115                 120                 125
Asp Gly Glu His Ser Gly Ser Asn Glu Lys Gly Tyr Val Tyr Tyr Lys
    130                 135                 140
Gly Asn Ser Pro Ala Lys Glu Leu Pro Val Asn Gln Leu Leu Thr Tyr
145                 150                 155                 160
Thr Gly Ser Trp Asp Phe Thr Ser Asn Ala Asn Leu Asn Asn Glu Glu
                165                 170                 175
Gly Arg Pro Asn Tyr Leu Asn Asp Asp Tyr Tyr Thr Lys Phe Ile Gly
            180                 185                 190
Lys Arg Val Gly Leu Val Ser Gly Asp Ala Lys Pro Ala Lys His Lys
        195                 200                 205
Tyr Thr Ser Gln Phe Glu Val Asp Phe Ala Thr Lys Lys Met Thr Gly
    210                 215                 220
Lys Ser Asp Lys Glu Lys Thr Ile Tyr Thr Val Asn Ala Asp Ile Arg
225                 230                 235                 240
Gly Asn Arg Phe Thr Gly Ala Ala Thr Ala Ser Asp Lys Asn Lys Gly
                245                 250                 255
Lys Gly Glu Ser Tyr Asn Phe Phe Ser Ala Asp Ser Gln Ser Leu Glu
            260                 265                 270
Gly Gly Phe Tyr Gly Pro Lys Ala Glu Glu Met Ala Gly Lys Phe Val
        275                 280                 285
Ala Asn Asp Lys Ser Leu Phe Ala Val Phe Ser Ala Lys His Asn Gly
    290                 295                 300
Ser Asn Val Asn Thr Val Arg Ile Ile Asp Ala Ser Lys Ile Asp Leu
305                 310                 315                 320
Thr Asn Phe Ser Ile Ser Glu Leu Asn Asn Phe Gly Asp Ala Ser Val
                325                 330                 335
Leu Ile Ile Asp Gly Lys Lys Ile Lys Leu Ala Gly Ser Gly Phe Thr
            340                 345                 350
Asn Lys His Thr Ile Glu Ile Asn Gly Lys Thr Met Val Ala Val Ala
        355                 360                 365
Cys Cys Ser Asn Leu Glu Tyr Met Lys Phe Gly Gln Leu Trp Gln Gln
    370                 375                 380
Ala Glu Gly Gly Lys Pro Glu Asn Asn Ser Leu Phe Leu Gln Gly Glu
385                 390                 395                 400
Arg Thr Ala Thr Asp Lys Met Pro Lys Gly Gly Asn Tyr Lys Tyr Ile
                405                 410                 415
Gly Thr Trp Asp Ala Gln Val Ser Lys Glu Asn Asn Trp Val Ala Thr
            420                 425                 430
Ala Asp Asp Asp Arg Lys Ala Gly Tyr Arg Thr Glu Phe Asp Val Asp
        435                 440                 445
Phe Gly Asn Lys Asn Leu Ser Gly Lys Leu Phe Asp Lys Asn Gly Val
    450                 455                 460
Asn Pro Val Phe Thr Val Asp Ala Lys Ile Asp Gly Asn Gly Phe Thr
465                 470                 475                 480
Gly Lys Ala Lys Thr Ser Asp Glu Gly Phe Ala Leu Asp Ser Gly Ser
                485                 490                 495
Ser Arg Tyr Glu Asn Val Lys Phe Asn Asp Val Ala Val Ser Gly Gly
            500                 505                 510
Phe Tyr Gly Pro Thr Ala Ala Glu Leu Gly Gly Gln Phe His His Lys
        515                 520                 525
Ser Glu Asn Gly Ser Val Gly Ala Val Phe Gly Ala Lys Gln Gln Val
    530                 535                 540
```

Lys Lys
545

(2) INFORMATION FOR SEQ ID NO:100:

(i) SEQUENCE CHARACTERISTICS:
        (A) LENGTH: 593 amino acids
        (B) TYPE: amino acid
        (C) STRANDEDNESS: single
        (D) TOPOLOGY: linear (xi) SEQUENCE DESCRIPTION: SEQ ID NO:100:

```
Met His Phe Lys Leu Asn Pro Tyr Ala Leu Ala Phe Thr Ser Leu Phe
 1               5                  10                  15

Leu Val Ala Cys Ser Gly Gly Lys Gly Ser Phe Asp Leu Glu Asp Val
            20                  25                  30

Arg Pro Asn Gln Thr Ala Lys Ala Glu Lys Ala Thr Thr Ser Tyr Gln
            35                  40                  45

Asp Glu Glu Thr Lys Lys Thr Lys Glu Glu Leu Asp Lys Leu Met
        50                  55                  60

Glu Pro Ala Leu Gly Tyr Glu Thr Gln Ile Leu Arg Arg Asn Lys Ala
65                  70                  75                  80

Pro Lys Thr Glu Thr Gly Glu Lys Arg Asn Glu Arg Val Val Glu Leu
                85                  90                  95

Ser Glu Asp Lys Ile Thr Lys Leu Tyr Gln Glu Ser Val Glu Ile Ile
                100                 105                 110

Pro His Leu Asp Glu Leu Asn Gly Lys Thr Thr Ser Asn Asp Val Tyr
            115                 120                 125

His Ser His Asp Ser Lys Arg Leu Asp Lys Asn Arg Asp Leu Lys Tyr
        130                 135                 140

Val Arg Ser Gly Tyr Val Tyr Asp Gly Ser Phe Asn Glu Ile Arg Arg
145                 150                 155                 160

Asn Asp Ser Gly Phe His Val Phe Lys Gln Gly Ile Asp Gly Tyr Val
                165                 170                 175

Tyr Tyr Leu Gly Val Thr Pro Ser Lys Glu Leu Pro Lys Gly Lys Val
                180                 185                 190

Ile Ser Tyr Lys Gly Thr Trp Asp Phe Val Ser Asn Ile Asn Leu Glu
                195                 200                 205

Arg Glu Ile Asp Gly Phe Asp Thr Ser Gly Asp Gly Lys Asn Val Ser
210                 215                 220

Ala Thr Ser Ile Thr Glu Thr Val Asn Arg Asp His Lys Val Gly Glu
225                 230                 235                 240

Lys Leu Gly Asp Asn Glu Val Lys Gly Val Ala His Ser Ser Glu Phe
                245                 250                 255

Ala Val Asp Phe Asp Asn Lys Lys Leu Thr Gly Ser Leu Tyr Arg Asn
                260                 265                 270

Gly Tyr Ile Asn Arg Asn Lys Ala Gln Glu Val Thr Lys Arg Tyr Ser
            275                 280                 285

Ile Glu Ala Asp Ile Ala Gly Asn Arg Phe Arg Gly Lys Ala Lys Ala
            290                 295                 300

Glu Lys Ala Gly Asp Pro Ile Phe Thr Asp Ser Asn Tyr Leu Glu Gly
305                 310                 315                 320

Gly Phe Tyr Gly Pro Lys Ala Glu Glu Met Ala Gly Lys Phe Phe Thr
                325                 330                 335

Asn Asn Lys Ser Leu Phe Ala Val Phe Ala Ala Lys Ser Glu Asn Gly
            340                 345                 350
```

-continued

```
Glu Thr Thr Thr Glu Arg Ile Ile Asp Ala Thr Lys Ile Asp Leu Thr
         355                 360                 365

Gln Phe Asn Ala Lys Glu Leu Asn Asn Phe Gly Asp Ala Ser Val Leu
         370                 375                 380

Ile Ile Asp Gly Gln Lys Ile Asp Leu Ala Gly Val Asn Phe Lys Asn
385                 390                 395                 400

Ser Lys Thr Val Glu Ile Asn Gly Lys Thr Met Val Ala Val Ala Cys
                 405                 410                 415

Cys Ser Asn Leu Glu Tyr Met Lys Phe Gly Gln Leu Trp Gln Lys Glu
         420                 425                 430

Gly Lys Gln Gln Val Lys Asp Asn Ser Leu Phe Leu Gln Gly Glu Arg
         435                 440                 445

Thr Ala Thr Asp Lys Met Pro Ala Gly Gly Asn Tyr Lys Tyr Val Gly
         450                 455                 460

Thr Trp Asp Ala Leu Val Ser Lys Gly Thr Asn Trp Ile Ala Glu Ala
465                 470                 475                 480

Asp Asn Asn Arg Glu Ser Gly Tyr Arg Thr Glu Phe Asp Val Asn Phe
                 485                 490                 495

Ser Asp Lys Lys Val Asn Gly Lys Leu Phe Asp Lys Gly Gly Val Asn
                 500                 505                 510

Pro Val Phe Thr Val Asp Ala Thr Ile Asn Gly Asn Gly Phe Ile Gly
         515                 520                 525

Ser Ala Lys Thr Ser Asp Ser Gly Phe Ala Leu Asp Ala Gly Ser Ser
530                 535                 540

Gln His Gly Asn Ala Val Phe Ser Asp Ile Lys Val Asn Gly Gly Phe
545                 550                 555                 560

Tyr Gly Pro Thr Ala Gly Glu Leu Gly Gly Gln Phe His His Lys Ser
                 565                 570                 575

Asp Asn Gly Ser Val Gly Ala Val Phe Gly Ala Lys Arg Gln Ile Glu
                 580                 585                 590

Lys
```

(2) INFORMATION FOR SEQ ID NO:101:

(i) SEQUENCE CHARACTERISTICS:
        (A) LENGTH: 18 amino acids
        (B) TYPE: amino acid
        (C) STRANDEDNESS: single
        (D) TOPOLOGY: linear (xi) SEQUENCE DESCRIPTION: SEQ ID NO:101:

```
Glu Thr Gln Ser Ile Lys Asp Thr Lys Glu Ala Ile Ser Ser Glu Val
1                 5                  10                 15

Asp Thr
```

(2) INFORMATION FOR SEQ ID NO:102:

(i) SEQUENCE CHARACTERISTICS:
        (A) LENGTH: 20 amino acids
        (B) TYPE: amino acid
        (C) STRANDEDNESS: single
        (D) TOPOLOGY: linear (xi) SEQUENCE DESCRIPTION: SEQ ID NO:102:

```
Leu Gln Leu Asn Leu Glu Lys Lys Ile Gln Gln Asn Trp Leu Thr His
1                 5                  10                 15

Gln Ile Ala Phe
                 20
```

(2) INFORMATION FOR SEQ ID NO:103:

(i) SEQUENCE CHARACTERISTICS:
        (A) LENGTH: 23 amino acids
        (B) TYPE: amino acid
        (C) STRANDEDNESS: single
        (D) TOPOLOGY: linear (xi) SEQUENCE DESCRIPTION: SEQ ID NO:103:

```
Met Thr Lys Lys Pro Tyr Phe Arg Leu Ser Ile Ile Ser Cys Leu Leu
 1               5                  10                  15

Ile Ser Cys Tyr Val Lys Ala
            20
```

(2) INFORMATION FOR SEQ ID NO:104:

(i) SEQUENCE CHARACTERISTICS:
        (A) LENGTH: 17 amino acids
        (B) TYPE: amino acid
        (C) STRANDEDNESS: single
        (D) TOPOLOGY: linear (xi) SEQUENCE DESCRIPTION: SEQ ID NO:104:

```
Met Lys Ser Val Pro Leu Ile Ser Gly Gly Leu Ser Phe Leu Leu Ser
 1               5                  10                  15

Ala
```

(2) INFORMATION FOR SEQ ID NO: 105:

(i) SEQUENCE CHARACTERISTICS:
        (A) LENGTH: 5144 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: join(192..695, 2135..4867)

(xi) SEQUENCE DESCRIPTION: SEQ ID NO: 105:

```
CAACATCTGC CCAAGCTATA TTCGTTAATG ATAAGCCTAT TAATGATAAG CCTATTAATG      60

ATAAGAAAGA AATTTGTTTT ACGCCATTTT TCATATTTTA TCCATGAACT TAAAAAATTC     120

TAAGTTGACA TTATTACAAA AAAAGAACAA TAATGCGAAT TATTATCAAT TTTGTATAAG     180

AATATAATTC T ATG AAA TCT GTA CCT CTT ATC TCT GGT GGA CTT TCC TTT     230
            Met Lys Ser Val Pro Leu Ile Ser Gly Gly Leu Ser Phe
             1               5                  10

TTA TTA AGT GCT TGT AGC GGA GGA GGG TCT TTT GAT GTA GAT AAC GTC     278
Leu Leu Ser Ala Cys Ser Gly Gly Gly Ser Phe Asp Val Asp Asn Val
         15                  20                  25

TCT AAT CCC TCC TCT TCT AAA CCA CGT TAT CAA GAC GAT ACC TCG AAT     326
Ser Asn Pro Ser Ser Ser Lys Pro Arg Tyr Gln Asp Asp Thr Ser Asn
 30                  35                  40                  45

CAA AGA ACA AAA TCT GAT TTG CAA AAG TTG TCC ATT CCT TCT TTA GGG     374
Gln Arg Thr Lys Ser Asp Leu Gln Lys Leu Ser Ile Pro Ser Leu Gly
                 50                  55                  60

GGA GGG ATG AAG TTA GTG GCT CAG AAT CTT CTT GGT AAG AAA GAA CCT     422
Gly Gly Met Lys Leu Val Ala Gln Asn Leu Leu Gly Lys Lys Glu Pro
         65                  70                  75

AGT CTC TTA AAT AAT GAA GAT GGC TAT ATG ATA TTT TCC TCA CTT TCT     470
Ser Leu Leu Asn Asn Glu Asp Gly Tyr Met Ile Phe Ser Ser Leu Ser
     80                  85                  90

ACG ATT GAA GAG GAT GTT ACA AAA GAA AAT AAA TCT CAG GAA CCC ACT     518
Thr Ile Glu Glu Asp Val Thr Lys Glu Asn Lys Ser Gln Glu Pro Thr
```

```
              95                  100                 105
ATT GGC TCA ATA GAC GAG CCT AGC AAA ACA AAT TCA CCC CAA AAT CAT      566
Ile Gly Ser Ile Asp Glu Pro Ser Lys Thr Asn Ser Pro Gln Asn His
110             115                 120                 125

CAT GGC AAT ATG TAT ATT CGG GTC TTT ATT ATA TTC AAT CGT GGC GTA      614
His Gly Asn Met Tyr Ile Arg Val Phe Ile Ile Phe Asn Arg Gly Val
            130                 135                 140

ATT CCT CAA ATG GCA AGT TTT ATT CAG GTT ACT ATG GAT ATG CGT ATT      662
Ile Pro Gln Met Ala Ser Phe Ile Gln Val Thr Met Asp Met Arg Ile
                145                 150                 155

ACT TTG GCA AGC AAA CAG CCA CTA CAT TAC CTG TAGATGGCGA AGCAACGTAT    715
Thr Leu Ala Ser Lys Gln Pro Leu His Tyr Leu
                160                 165

AAAGGAACTT GGCACTTCAT CACCGCAACT GAAAATGGCA AAAAGTATTC TTTGTTCAGT    775

AATGATAGCG GTCAAGCTTA TCGCAGACGT AGTGCAATTC CAGAAGATAT TGATTTAGAA    835

AAAAATGATT CAACTAATGG TGACAAGGGC TTAATAAGTG AATTTAGTGT CAATTTTGGT    895

ACAAAAAAGC TCACTGGAAA ACTTTATTAT AATGAAAGAG AAACAGAACT TAATAAATCA    955

AAAGATAGAA AACATACACT CTACAATCTA GAAGCTGAAG TGTATAGTAA CCGATTCAGG   1015

GGTACAGTAA AGCCAACCGA AAAAGATTCT ACAGATCATC CCTTTACCAG CGAGGGAACA   1075

TTAGAAGGTG GTTTTTATGG GCCTAAAGGT GAAGAACTAG GAGGAAAGTT TTTAGCTGGC   1135

GATAAAAAAG TTTTTGGGGT ATTTAGTGCC AAAGAAACGG AAGAAACAAA AAAGAAAGCG   1195

TTATCCAAGG AAACCTTAAT TGATGGCAAG CTAACTACTT TTAAAACAAC CAATGCAACA   1255

ACCAATGCAA CAGCCAATGC AACAACCAGT ACAACAGCCA GTACAACAAC CGATGCAGAA   1315

AACTTTACGA CGAAAGATAT ACCAAGTTTT GGTGAAGCTG ATTACCTTTT AATTGATAAT   1375

TACCCTGTTC CTCTTTTACC TGAGAGTGGT GATTTCATAA GTAGTAAGCA CCATACTGTA   1435

GGAAAGAAAA CCTATCAAGT AGAAGCATGT TGCAGTAATC TAAGCTATGT GAAATTTGGT   1495

ATGTTTTATG AAGACCCACT TAAAGAAGAA AAAGACAAAG AAAAAGAAGA AGACAAAGAA   1555

AAACAAACGG CGGCAACGAC CAACACTTAT TATCAATTCT TATTAGGTCT CCGTACTGCC   1615

AGTTCTGAAA TTCCTAAAAT GGGAAACGTG GAATATCGCG GTAATTGGTT TGGTTATATT   1675

AGTGATGGCA CGACATCTTA CTCCCCCAGT GGTGATAAGG AACGCAATAA AAATGCTCCC   1735

GCCGATTTTA ATGTTGATTT TGTCAATAAA AAGCTAACAG GCACATTAAA ACGACACGAT   1795

AATGGAAATA CCGTATTTAG TATTGAGGCA ACTTTAACA GTGGGAATGA CTTCACTGGT   1855

AAAGCAACCG CAAAAGATTT AGTAATAGAT GGTAAAAGTA CACAAGCCAC ATCTAAAGTC   1915

AATTTCACGG CAACAGTAAA AGGGGCATTT TATGGACCTG ATGCTTCTGA ATTAGGCGGT   1975

TATTTCACCT ATAACGGAAA AAATCCTACA GCTACAAATT CCCCAACCGT ATCTTCACCA   2035

TCCAATTCAG CAAATGCTCG TGCTGCCGTT GTGTTTGGAG CTAAAAAACA AGTAGACACA   2095

ACCAACAAGT AGAAAAAACC AAATAATGGA ATACTAAAA ATG ACT AAA AAA CCC     2149
                                            Met Thr Lys Lys Pro
                                                170

TAT TTT CGC CTA AGT ATT ATT TCT TGT CTT TTA ATT TCA TGC TAT GTA    2197
Tyr Phe Arg Leu Ser Ile Ile Ser Cys Leu Leu Ile Ser Cys Tyr Val
175                 180                 185

AAA GCA GAA ACT CAA AGT ATA AAA GAT ACA AAA GAA GCT ATA TCA TCT    2245
Lys Ala Glu Thr Gln Ser Ile Lys Asp Thr Lys Glu Ala Ile Ser Ser
190                 195                 200                 205

GAA GTG GAC ACT CAA AGT ACA GAA GAT TCA GAA TTA GAA ACT ATC TCA    2293
Glu Val Asp Thr Gln Ser Thr Glu Asp Ser Glu Leu Glu Thr Ile Ser
                210                 215                 220
```

```
GTC ACT GCA GAA AAA ATA AGA GAT CGT AAA GAT AAT GAA GTA ACT GGA        2341
Val Thr Ala Glu Lys Ile Arg Asp Arg Lys Asp Asn Glu Val Thr Gly
            225                 230                 235

CTT GGC AAA ATT ATA AAA ACG AGT GAA AGT ATC AGC CGA GAA CAA GTA        2389
Leu Gly Lys Ile Ile Lys Thr Ser Glu Ser Ile Ser Arg Glu Gln Val
        240                 245                 250

TTA AAT ATT CGT GAT CTA ACA CGC TAT GAT CCA GGC ATT TCA GTT GTA        2437
Leu Asn Ile Arg Asp Leu Thr Arg Tyr Asp Pro Gly Ile Ser Val Val
255                 260                 265

GAA CAA GGT CGC GGT GCA AGT TCT GGA TAT TCT ATT CGT GGT ATG GAC        2485
Glu Gln Gly Arg Gly Ala Ser Ser Gly Tyr Ser Ile Arg Gly Met Asp
270                 275                 280                 285

AGA AAT AGA GTT GCT TTA TTA GTA GAT GGT TTA CCT CAA ACG CAA TCT        2533
Arg Asn Arg Val Ala Leu Leu Val Asp Gly Leu Pro Gln Thr Gln Ser
                290                 295                 300

TAT GTA GTG CAA AGC CCT TTA GTT GCT CGT TCA GGA TAT TCT GGC ACT        2581
Tyr Val Val Gln Ser Pro Leu Val Ala Arg Ser Gly Tyr Ser Gly Thr
            305                 310                 315

GGT GCA ATT AAT GAA ATT GAA TAT GAA AAT GTA AAG GCC GTC GAA ATA        2629
Gly Ala Ile Asn Glu Ile Glu Tyr Glu Asn Val Lys Ala Val Glu Ile
        320                 325                 330

AGC AAG GGG GGG AGT TCT TCT GAG TAT GGT AAT GGA GCA CTA GCT GGT        2677
Ser Lys Gly Gly Ser Ser Ser Glu Tyr Gly Asn Gly Ala Leu Ala Gly
    335                 340                 345

TCT GTA ACA TTT CAA AGC AAA TCC GCA GCC GAT ATC TTA GAA GGA GAC        2725
Ser Val Thr Phe Gln Ser Lys Ser Ala Ala Asp Ile Leu Glu Gly Asp
350                 355                 360                 365

AAA TCA TGG GGA ATT CAA ACT AAA AAT GCT TAT TCA AGC AAA AAT AAA        2773
Lys Ser Trp Gly Ile Gln Thr Lys Asn Ala Tyr Ser Ser Lys Asn Lys
                370                 375                 380

GGC TTT ACC CAT TCT TTA GCT GTA GCA GGA AAA CAA GGT GGA TTT GAA        2821
Gly Phe Thr His Ser Leu Ala Val Ala Gly Lys Gln Gly Gly Phe Glu
            385                 390                 395

GGG GTC GCC ATT TAC ACT CAA CGA AAT TCG GAG GAA ACC CAA GTC CAT        2869
Gly Val Ala Ile Tyr Thr Gln Arg Asn Ser Glu Glu Thr Gln Val His
        400                 405                 410

AAA GAT GCA TTA AAA GGC GTA CAA AGT TAT GAG CGA TTC ATC GCC ACA        2917
Lys Asp Ala Leu Lys Gly Val Gln Ser Tyr Glu Arg Phe Ile Ala Thr
    415                 420                 425

ACA GAT AAA TCT TCA GGA TAC TTT GTG ATA CAA GGT GAG TGT CCA AAT        2965
Thr Asp Lys Ser Ser Gly Tyr Phe Val Ile Gln Gly Glu Cys Pro Asn
430                 435                 440                 445

GGT GAT GAC AAG TGT GCA GCC AAA CCA CCT GCA AAG TTA TCC CCC CAA        3013
Gly Asp Asp Lys Cys Ala Ala Lys Pro Pro Ala Lys Leu Ser Pro Gln
                450                 455                 460

AGC GAA ACC GTA AGC GTT TCA GAT TAT ACG GGG GCT AAC CGT ATC AAA        3061
Ser Glu Thr Val Ser Val Ser Asp Tyr Thr Gly Ala Asn Arg Ile Lys
            465                 470                 475

CCT AAT CCA ATG AAA TAT GAA AGC CAG TCT TGG TTT TTA AGA GGA GGG        3109
Pro Asn Pro Met Lys Tyr Glu Ser Gln Ser Trp Phe Leu Arg Gly Gly
        480                 485                 490

TAT CAT TTT TCT GAA CAA CAC TAT ATT GGT GGT ATT TTT GAA TTC ACA        3157
Tyr His Phe Ser Glu Gln His Tyr Ile Gly Gly Ile Phe Glu Phe Thr
    495                 500                 505

CAA CAA AAA TTT GAT ATC CGT GAT ATG ACA TTT CCC GCT TAT TTA AGA        3205
Gln Gln Lys Phe Asp Ile Arg Asp Met Thr Phe Pro Ala Tyr Leu Arg
510                 515                 520                 525

TCA ACA GAA AAA CGG GAT GAT AGA ACT GGC CCT TTT TAT CCA AAG CAA        3253
Ser Thr Glu Lys Arg Asp Asp Arg Thr Gly Pro Phe Tyr Pro Lys Gln
                530                 535                 540
```

```
GAT TAT GGT GCA TAT CAA CGT ATT GAG GAT GGC CGA GGC GTT AAC TAT      3301
Asp Tyr Gly Ala Tyr Gln Arg Ile Glu Asp Gly Arg Gly Val Asn Tyr
        545                 550                 555

GCA AGT GGG CTT TAT TTC GAT GAA CAC CAT AGA AAA CAG CGT GTA GGT      3349
Ala Ser Gly Leu Tyr Phe Asp Glu His His Arg Lys Gln Arg Val Gly
        560                 565                 570

ATT GAA TAT ATT TAC GAA AAT AAG AAC AAA GCG GGC ATC ATT GAC AAA      3397
Ile Glu Tyr Ile Tyr Glu Asn Lys Asn Lys Ala Gly Ile Ile Asp Lys
575                 580                 585

GCA GTG TTA AGT GCT AAT CAA CAA AAC ATC ATA CTT GAC AGT TAT ATG      3445
Ala Val Leu Ser Ala Asn Gln Gln Asn Ile Ile Leu Asp Ser Tyr Met
590                 595                 600                 605

CGA CAT ACG CAT TGC AGT CTT TAT CCT AAT CCA AGT AAG AAT TGC CGC      3493
Arg His Thr His Cys Ser Leu Tyr Pro Asn Pro Ser Lys Asn Cys Arg
                610                 615                 620

CCG ACA CTT GAT AAA CCT TAT TCA TAC TAT CGT TCT GAT AGA AAT GTT      3541
Pro Thr Leu Asp Lys Pro Tyr Ser Tyr Tyr Arg Ser Asp Arg Asn Val
            625                 630                 635

TAT AAA GAA AAA CAT AAT ATG TTG CAA TTG AAT TTA GAG AAA AAA ATT      3589
Tyr Lys Glu Lys His Asn Met Leu Gln Leu Asn Leu Glu Lys Lys Ile
                640                 645                 650

CAA CAA AAT TGG CTT ACT CAT CAA ATT GTC TTC AAT CTT GGT TTT GAT      3637
Gln Gln Asn Trp Leu Thr His Gln Ile Val Phe Asn Leu Gly Phe Asp
        655                 660                 665

GAC TTT ACT TCA GCG CTT CAG CAT AAA GAT TAT TTA ACT CGA CGT GTT      3685
Asp Phe Thr Ser Ala Leu Gln His Lys Asp Tyr Leu Thr Arg Arg Val
670                 675                 680                 685

ACC GCT ACG GCA AAT ATT ATT TCA GGG ACA GTT GCT GGT AAA CGA AGA      3733
Thr Ala Thr Ala Asn Ile Ile Ser Gly Thr Val Ala Gly Lys Arg Arg
                690                 695                 700

AAT GGT TAC GAA AAA CAA CCT TAC TTA TAC TCA AAA CCA AAA GTA GAT      3781
Asn Gly Tyr Glu Lys Gln Pro Tyr Leu Tyr Ser Lys Pro Lys Val Asp
            705                 710                 715

TTT GTA GGA CAA GAT CAT TGT AAT TAT AAA GGT AGC TCC TCT AAT TAC      3829
Phe Val Gly Gln Asp His Cys Asn Tyr Lys Gly Ser Ser Ser Asn Tyr
            720                 725                 730

AGC GAC TGT AAA GTG CGG TTA ATT AAA GGG AAA AAT TAT TAT TTC GCA      3877
Ser Asp Cys Lys Val Arg Leu Ile Lys Gly Lys Asn Tyr Tyr Phe Ala
        735                 740                 745

GCA CGC AAT AAT ATG GCA TTA GGG AAA TAC ATT GAT TTA GGT TTA GGT      3925
Ala Arg Asn Asn Met Ala Leu Gly Lys Tyr Ile Asp Leu Gly Leu Gly
750                 755                 760                 765

ATT CGG TAT GAC GTA TCT CGT ACA AAA GCT AAT GAA TCA ACT ATT AGT      3973
Ile Arg Tyr Asp Val Ser Arg Thr Lys Ala Asn Glu Ser Thr Ile Ser
                770                 775                 780

GTT GGT AAA TTT AAA AAT TTC TCT TGG AAT ACT GGT ATT GTC ATA AAA      4021
Val Gly Lys Phe Lys Asn Phe Ser Trp Asn Thr Gly Ile Val Ile Lys
            785                 790                 795

CCA ACG GAA TGG CTT GAT CTT TCT TAT CGC CTT TCT ACT GGA TTT AGA      4069
Pro Thr Glu Trp Leu Asp Leu Ser Tyr Arg Leu Ser Thr Gly Phe Arg
            800                 805                 810

AAT CCT AGT TTT GCT GAA ATG TAT GGT TGG CGG TAT GGT GGC AAT AAT      4117
Asn Pro Ser Phe Ala Glu Met Tyr Gly Trp Arg Tyr Gly Gly Asn Asn
815                 820                 825

AGC GAT GTT TAT GTA GGT AAA TTT AAG CCT GAA ACA TCT CGT AAC CAA      4165
Ser Asp Val Tyr Val Gly Lys Phe Lys Pro Glu Thr Ser Arg Asn Gln
830                 835                 840                 845

GAG TTT GGT CTC GCT CTA AAA GGG GAT TTT GGT AAT ATT GAG ATC AGT      4213
Glu Phe Gly Leu Ala Leu Lys Gly Asp Phe Gly Asn Ile Glu Ile Ser
                850                 855                 860
```

| | | | | | | | | | | | | | | | | |
|---|---|---|---|---|---|---|---|---|---|---|---|---|---|---|---|---|
| CAT | TTT | AGT | AAT | GCT | TAT | CGA | AAT | CTT | ATC | GCC | TTT | GCT | GAA | GAA | CTT | 4261 |
| His | Phe | Ser | Asn | Ala | Tyr | Arg | Asn | Leu | Ile | Ala | Phe | Ala | Glu | Glu | Leu | |
| | | 865 | | | | 870 | | | | 875 | | | | | | |
| AGT | AAA | AAT | GGA | ACT | ACT | GGA | AAG | GGC | AAT | TAT | GGA | TAT | CAT | AAT | GCA | 4309 |
| Ser | Lys | Asn | Gly | Thr | Thr | Gly | Lys | Gly | Asn | Tyr | Gly | Tyr | His | Asn | Ala | |
| | 880 | | | | | 885 | | | | | 890 | | | | | |
| CAA | AAT | GCA | AAA | TTA | GTT | GGC | GTA | AAT | ATA | ACT | GCG | CAA | TTA | GAT | TTT | 4357 |
| Gln | Asn | Ala | Lys | Leu | Val | Gly | Val | Asn | Ile | Thr | Ala | Gln | Leu | Asp | Phe | |
| | 895 | | | | | 900 | | | | | 905 | | | | | |
| AAT | GGT | TTA | TGG | AAA | CGT | ATT | CCC | TAC | GGT | TGG | TAT | GCA | ACA | TTT | GCT | 4405 |
| Asn | Gly | Leu | Trp | Lys | Arg | Ile | Pro | Tyr | Gly | Trp | Tyr | Ala | Thr | Phe | Ala | |
| 910 | | | | | 915 | | | | | 920 | | | | | 925 | |
| TAT | AAC | CGA | GTA | AAA | GTT | AAA | GAT | CAA | AAA | ATC | AAT | GCT | GGT | TTG | GCC | 4453 |
| Tyr | Asn | Arg | Val | Lys | Val | Lys | Asp | Gln | Lys | Ile | Asn | Ala | Gly | Leu | Ala | |
| | | | 930 | | | | | 935 | | | | | 940 | | | |
| TCC | GTA | AGC | AGT | TAT | TTA | TTT | GAT | GCC | ATT | CAG | CCC | AGC | CGT | TAT | ATC | 4501 |
| Ser | Val | Ser | Ser | Tyr | Leu | Phe | Asp | Ala | Ile | Gln | Pro | Ser | Arg | Tyr | Ile | |
| | | | 945 | | | | | 950 | | | | | 955 | | | |
| ATT | GGT | TTA | GGC | TAT | GAT | CAT | CCA | AGT | AAT | ACT | TGG | GGA | ATT | AAT | ACA | 4549 |
| Ile | Gly | Leu | Gly | Tyr | Asp | His | Pro | Ser | Asn | Thr | Trp | Gly | Ile | Asn | Thr | |
| | | 960 | | | | | 965 | | | | | 970 | | | | |
| ATG | TTT | ACT | CAA | TCA | AAA | GCA | AAA | TCT | CAA | AAT | GAA | TTG | CTA | GGA | CAA | 4597 |
| Met | Phe | Thr | Gln | Ser | Lys | Ala | Lys | Ser | Gln | Asn | Glu | Leu | Leu | Gly | Gln | |
| | 975 | | | | | 980 | | | | | 985 | | | | | |
| CGT | GCA | TTG | GGT | AAC | AAT | TCA | AGG | AAT | GTA | AAA | TCA | ACA | AGA | AAA | CTT | 4645 |
| Arg | Ala | Leu | Gly | Asn | Asn | Ser | Arg | Asn | Val | Lys | Ser | Thr | Arg | Lys | Leu | |
| 990 | | | | | 995 | | | | | 1000 | | | | | 1005 | |
| ACT | CGG | GCA | TGG | CAT | ATC | TTA | GAT | GTA | TCG | GGT | TAT | TAC | ATG | GCG | AAT | 4693 |
| Thr | Arg | Ala | Trp | His | Ile | Leu | Asp | Val | Ser | Gly | Tyr | Tyr | Met | Ala | Asn | |
| | | | 1010 | | | | | 1015 | | | | | 1020 | | | |
| AAA | AAT | ATT | ATG | CTT | CGA | TTA | GGG | ATA | TAT | AAT | TTA | TTC | AAC | TAT | CGC | 4741 |
| Lys | Asn | Ile | Met | Leu | Arg | Leu | Gly | Ile | Tyr | Asn | Leu | Phe | Asn | Tyr | Arg | |
| | | | 1025 | | | | | 1030 | | | | | 1035 | | | |
| TAT | GTT | ACT | TGG | GAA | GCG | GTG | CGT | CAA | ACA | GCA | CAA | GGT | GCG | GTC | AAT | 4789 |
| Tyr | Val | Thr | Trp | Glu | Ala | Val | Arg | Gln | Thr | Ala | Gln | Gly | Ala | Val | Asn | |
| | | | 1040 | | | | | 1045 | | | | | 1050 | | | |
| CAA | CAT | CAA | AAT | GTT | GGT | AGC | TAT | ACT | CGC | TAC | GCA | GCA | TCA | GGA | CGA | 4837 |
| Gln | His | Gln | Asn | Val | Gly | Ser | Tyr | Thr | Arg | Tyr | Ala | Ala | Ser | Gly | Arg | |
| | | | 1055 | | | | | 1060 | | | | | 1065 | | | |
| AAC | TAT | ACC | TTA | ACA | TTA | GAA | ATG | AAA | TTC | TAAATTAAAA | | | TGCGCCAGAT | | | 4887 |
| Asn | Tyr | Thr | Leu | Thr | Leu | Glu | Met | Lys | Phe | | | | | | | |
| 1070 | | | | | 1075 | | | | | | | | | | | |

| | |
|---|---|
| GGACTAGATA TGCTATATCT ATACCTTACT GGCGCATCTT TTTCTGTTCT ATAATCTGCT | 4947 |
| TAAGTGAAAA ACCAAACTTG GATTTTTTAC AAGATCTTTT CACGCATTTA TTGTAAAATC | 5007 |
| TCCGACAATT TTTACCGCAC TTTTCTCTAT TACAAAAACA ATAAGGATCC TTTTGTGACT | 5067 |
| CTCTCAATCT TTGGCAAGTT GCTGTTACAA CTTCAGATCA AGTTTCAGCC AGCGATCTTA | 5127 |
| GGCACTTGGG TTCGGCC | 5144 |

(2) INFORMATION FOR SEQ ID NO: 106:

(i) SEQUENCE CHARACTERISTICS:
        (A) LENGTH: 168 amino acids
        (B) TYPE: amino acid
        (D) TOPOLOGY: linear (xi) SEQUENCE DESCRIPTION: SEQ ID NO: 106:

Met Lys Ser Val Pro Leu Ile Ser Gly Gly Leu Ser Phe Leu Leu Ser
  1            5                10                15

Ala Cys Ser Gly Gly Gly Ser Phe Asp Val Asp Asn Val Ser Asn Pro

```
                    20                  25                  30
Ser Ser Ser Lys Pro Arg Tyr Gln Asp Asp Thr Ser Asn Gln Arg Thr
            35                  40                  45

Lys Ser Asp Leu Gln Lys Leu Ser Ile Pro Ser Leu Gly Gly Gly Met
 50                  55                  60

Lys Leu Val Ala Gln Asn Leu Leu Gly Lys Lys Glu Pro Ser Leu Leu
 65                  70                  75                  80

Asn Asn Glu Asp Gly Tyr Met Ile Phe Ser Ser Leu Ser Thr Ile Glu
                85                  90                  95

Glu Asp Val Thr Lys Glu Asn Lys Ser Gln Gly Pro Thr Ile Gly Ser
            100                 105                 110

Ile Asp Glu Pro Ser Lys Thr Asn Ser Pro Gln Asn His His Gly Asn
            115                 120                 125

Met Tyr Ile Arg Val Phe Ile Ile Phe Asn Arg Gly Val Ile Pro Gln
            130                 135                 140

Met Ala Ser Phe Ile Gln Val Thr Met Asp Met Arg Ile Thr Leu Ala
145                 150                 155                 160

Ser Lys Gln Pro Leu His Tyr Leu
                165

(2) INFORMATION FOR SEQ ID NO: 107:

(i) SEQUENCE CHARACTERISTICS:
        (A) LENGTH: 911 amino acids
        (B) TYPE: amino acid
        (C) STRANDEDNESS: single
        (D) TOPOLOGY: linear (xi) SEQUENCE DESCRIPTION: SEQ ID NO: 107:

Met Thr Lys Lys Pro Tyr Phe Arg Leu Ser Ile Ile Ser Cys Leu Leu
     1               5                  10                  15

Ile Ser Cys Tyr Val Lys Ala Glu Thr Gln Ser Ile Lys Asp Thr Lys
                    20                  25                  30

Glu Ala Ile Ser Ser Glu Val Asp Thr Gln Ser Thr Glu Asp Ser Glu
                35                  40                  45

Leu Glu Thr Ile Ser Val Thr Ala Glu Lys Ile Arg Asp Arg Lys Asp
     50                  55                  60

Asn Glu Val Thr Gly Leu Gly Lys Ile Ile Lys Thr Ser Glu Ser Ile
    65                   70                  75                  80

Ser Arg Glu Gln Val Leu Asn Ile Arg Asp Leu Thr Arg Tyr Asp Pro
                    85                  90                  95

Gly Ile Ser Val Val Glu Gln Gly Arg Gly Ala Ser Ser Gly Tyr Ser
                    100                 105                 110

Ile Arg Gly Met Asp Arg Asn Arg Val Ala Leu Leu Val Asp Gly Leu
                    115                 120                 125

Pro Gln Thr Gln Ser Tyr Val Val Gln Ser Pro Leu Val Ala Arg Ser
                    130                 135                 140

Gly Tyr Ser Gly Thr Gly Ala Ile Asn Glu Ile Glu Tyr Glu Asn Val
    145                 150                 155                 160

Lys Ala Val Glu Ile Ser Lys Gly Gly Ser Ser Ser Glu Tyr Gly Asn
                    165                 170                 175

Gly Ala Leu Ala Gly Ser Val Thr Phe Gln Ser Lys Ser Ala Ala Asp
                    180                 185                 190

Ile Leu Glu Gly Asp Lys Ser Trp Gly Ile Gln Thr Lys Asn Ala Tyr
                    195                 200                 205

Ser Ser Lys Asn Lys Gly Phe Thr His Ser Leu Ala Val Ala Gly Lys
```

```
                210                 215                 220
Gln Gly Gly Phe Glu Gly Val Ala Ile Tyr Thr Gln Arg Asn Ser Glu
225                 230                 235                 240

Glu Thr Gln Val His Lys Asp Ala Leu Lys Gly Val Gln Ser Tyr Glu
                245                 250                 255

Arg Phe Ile Ala Thr Thr Asp Lys Ser Ser Gly Tyr Phe Val Ile Gln
                260                 265                 270

Gly Glu Cys Pro Asn Gly Asp Asp Lys Cys Ala Ala Lys Pro Pro Ala
                275                 280                 285

Lys Leu Ser Pro Gln Ser Glu Thr Val Ser Val Ser Asp Tyr Thr Gly
290                 295                 300

Ala Asn Arg Ile Lys Pro Asn Pro Met Lys Tyr Glu Ser Gln Ser Trp
305                 310                 315                 320

Phe Leu Arg Gly Gly Tyr His Phe Ser Glu Gln His Tyr Ile Gly Gly
                325                 330                 335

Ile Phe Glu Phe Thr Gln Gln Lys Phe Asp Ile Arg Asp Met Thr Phe
                340                 345                 350

Pro Ala Tyr Leu Arg Ser Thr Glu Lys Arg Asp Asp Arg Thr Gly Pro
                355                 360                 365

Phe Tyr Pro Lys Gln Asp Tyr Gly Ala Tyr Gln Arg Ile Glu Asp Gly
                370                 375                 380

Arg Gly Val Asn Tyr Ala Ser Gly Leu Tyr Phe Asp Glu His His Arg
385                 390                 395                 400

Lys Gln Arg Val Gly Ile Glu Tyr Ile Tyr Glu Asn Lys Asn Lys Ala
                405                 410                 415

Gly Ile Ile Asp Lys Ala Val Leu Ser Ala Asn Gln Gln Asn Ile Ile
                420                 425                 430

Leu Asp Ser Tyr Met Arg His Thr His Cys Ser Leu Tyr Pro Asn Pro
                435                 440                 445

Ser Lys Asn Cys Arg Pro Thr Leu Asp Lys Pro Tyr Ser Tyr Tyr Arg
450                 455                 460

Ser Asp Arg Asn Val Tyr Lys Glu Lys His Asn Met Leu Gln Leu Asn
465                 470                 475                 480

Leu Glu Lys Lys Ile Gln Gln Asn Trp Leu Thr His Gln Ile Val Phe
                485                 490                 495

Asn Leu Gly Phe Asp Asp Phe Thr Ser Ala Leu Gln His Lys Asp Tyr
                500                 505                 510

Leu Thr Arg Arg Val Thr Ala Thr Ala Asn Ile Ile Ser Gly Thr Val
                515                 520                 525

Ala Gly Lys Arg Arg Asn Gly Tyr Glu Lys Gln Pro Tyr Leu Tyr Ser
530                 535                 540

Lys Pro Lys Val Asp Phe Val Gly Gln Asp His Cys Asn Tyr Lys Gly
545                 550                 555                 560

Ser Ser Ser Asn Tyr Ser Asp Cys Lys Val Arg Leu Ile Lys Gly Lys
                565                 570                 575

Asn Tyr Tyr Phe Ala Ala Arg Asn Asn Met Ala Leu Gly Lys Tyr Ile
                580                 585                 590

Asp Leu Gly Leu Gly Ile Arg Tyr Asp Val Ser Arg Thr Lys Ala Asn
                595                 600                 605

Glu Ser Thr Ile Ser Val Gly Lys Phe Lys Asn Phe Ser Trp Asn Thr
610                 615                 620

Gly Ile Val Ile Lys Pro Thr Glu Trp Leu Asp Leu Ser Tyr Arg Leu
625                 630                 635                 640
```

```
        Ser Thr Gly Phe Arg Asn Pro Ser Phe Ala Glu Met Tyr Gly Trp Arg
                        645                 650                 655

Tyr Gly Gly Asn Asn Ser Asp Val Tyr Val Gly Lys Phe Lys Pro Glu
                    660                 665                 670

Thr Ser Arg Asn Gln Glu Phe Gly Leu Ala Leu Lys Gly Asp Phe Gly
                675                 680                 685

Asn Ile Glu Ile Ser His Phe Ser Asn Ala Tyr Arg Asn Leu Ile Ala
            690                 695                 700

Phe Ala Glu Glu Leu Ser Lys Asn Gly Thr Thr Gly Lys Gly Asn Tyr
        705                 710                 715                 720

Gly Tyr His Asn Ala Gln Asn Ala Lys Leu Val Gly Val Asn Ile Thr
                        725                 730                 735

Ala Gln Leu Asp Phe Asn Gly Leu Trp Lys Arg Ile Pro Tyr Gly Trp
                    740                 745                 750

Tyr Ala Thr Phe Ala Tyr Asn Arg Val Lys Val Lys Asp Gln Lys Ile
                755                 760                 765

Asn Ala Gly Leu Ala Ser Val Ser Ser Tyr Leu Phe Asp Ala Ile Gln
            770                 775                 780

Pro Ser Arg Tyr Ile Ile Gly Leu Gly Tyr Asp His Pro Ser Asn Thr
        785                 790                 795                 800

Trp Gly Ile Asn Thr Met Phe Thr Gln Ser Lys Ala Lys Ser Gln Asn
                        805                 810                 815

Glu Leu Leu Gly Gln Arg Ala Leu Gly Asn Asn Ser Arg Asn Val Lys
                    820                 825                 830

Ser Thr Arg Lys Leu Thr Arg Ala Trp His Ile Leu Asp Val Ser Gly
                835                 840                 845

Tyr Tyr Met Ala Asn Lys Asn Ile Met Leu Arg Leu Gly Ile Tyr Asn
            850                 855                 860

Leu Phe Asn Tyr Arg Tyr Val Thr Trp Glu Ala Val Arg Gln Thr Ala
        865                 870                 875                 880

Gln Gly Ala Val Asn Gln His Gln Asn Val Gly Ser Tyr Thr Arg Tyr
                        885                 890                 895

Ala Ala Ser Gly Arg Asn Tyr Thr Leu Thr Leu Glu Met Lys Phe
                    900                 905                 910

(2) INFORMATION FOR SEQ ID NO: 108:

(i) SEQUENCE CHARACTERISTICS:
        (A) LENGTH: 1993 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 3..1946

(xi) SEQUENCE DESCRIPTION: SEQ ID NO: 108:

AT ATG AAA TCT GTA CCT CTT ATC TCT GGT GGA CTT TCC TTT TTA TTA        47
   Met Lys Ser Val Pro Leu Ile Ser Gly Gly Leu Ser Phe Leu Leu
    1               5                   10                  15

AGT GCT TGT AGC GGG GGA GGT GGT TCT TTT GAT GTA GAT GAC GTC TCT       95
Ser Ala Cys Ser Gly Gly Gly Gly Ser Phe Asp Val Asp Asp Val Ser
                20                  25                  30

AAT CCC TCC TCT TCT AAA CCA CGT TAT CAA GAC GAT ACT TCA AGT TCA      143
Asn Pro Ser Ser Ser Lys Pro Arg Tyr Gln Asp Asp Thr Ser Ser Ser
            35                  40                  45

AGA ACA AAA TCT AAA TTG GAA AAT TTG TCC ATT CCT TCT TTA GGG GGA      191
Arg Thr Lys Ser Lys Leu Glu Asn Leu Ser Ile Pro Ser Leu Gly Gly
```

|  |  |  |  |  |  |  |  |  |  |  |  |  |  |  |  |
|---|---|---|---|---|---|---|---|---|---|---|---|---|---|---|---|
| | | | 50 | | | | 55 | | | | 60 | | | | |
| GGG | ATG | AAG | TTA | GTG | GCT | CAG | AAT | CTT | CGT | GAT | AGG | ACA | AAA | CCT | AGT | 239 |
| Gly | Met | Lys | Leu | Val | Ala | Gln | Asn | Leu | Arg | Asp | Arg | Thr | Lys | Pro | Ser |
| | 65 | | | | 70 | | | | 75 | | | | | | |
| CTC | TTA | AAT | GAA | GAT | GAC | TAT | ATG | ATA | TTT | TCC | TCA | CTT | TCA | ACG | ATT | 287 |
| Leu | Leu | Asn | Glu | Asp | Asp | Tyr | Met | Ile | Phe | Ser | Ser | Leu | Ser | Thr | Ile |
| 80 | | | | | 85 | | | | | 90 | | | | | 95 |
| AAA | GCT | GAT | GTT | GAA | AAA | GAA | AAT | AAA | CAC | TAT | ACA | AGT | CCA | GTT | GGC | 335 |
| Lys | Ala | Asp | Val | Glu | Lys | Glu | Asn | Lys | His | Tyr | Thr | Ser | Pro | Val | Gly |
| | | | | 100 | | | | | 105 | | | | | 110 | |
| TCA | ATA | GAC | GAG | CCT | AGT | ACA | ACA | AAT | CCA | AAA | GAA | AAT | GAT | CAT | GGA | 383 |
| Ser | Ile | Asp | Glu | Pro | Ser | Thr | Thr | Asn | Pro | Lys | Glu | Asn | Asp | His | Gly |
| | | | 115 | | | | | 120 | | | | | 125 | | |
| CAA | AGA | TAT | GTA | TAT | TCA | GGA | CTT | TAT | TAT | ATT | CCA | TCG | TGG | AAT | TTA | 431 |
| Gln | Arg | Tyr | Val | Tyr | Ser | Gly | Leu | Tyr | Tyr | Ile | Pro | Ser | Trp | Asn | Leu |
| | | 130 | | | | | 135 | | | | | 140 | | | |
| AAC | GAT | CTT | AAA | AAT | AAC | AAG | TAT | TAT | TAT | TCT | GGT | TAC | TAT | GGA | TAT | 479 |
| Asn | Asp | Leu | Lys | Asn | Asn | Lys | Tyr | Tyr | Tyr | Ser | Gly | Tyr | Tyr | Gly | Tyr |
| | 145 | | | | | 150 | | | | | 155 | | | | |
| GCG | TAT | TAC | TTT | GGC | AAG | CAA | ACA | GCC | ACT | ACA | TTA | CCT | GTA | AAT | GGC | 527 |
| Ala | Tyr | Tyr | Phe | Gly | Lys | Gln | Thr | Ala | Thr | Thr | Leu | Pro | Val | Asn | Gly |
| 160 | | | | | 165 | | | | | 170 | | | | | 175 |
| AAA | GTA | ACG | TAT | AAA | GGA | ACT | TGG | AGC | TTC | ATC | ACC | GCA | GCT | GAA | AAT | 575 |
| Lys | Val | Thr | Tyr | Lys | Gly | Thr | Trp | Ser | Phe | Ile | Thr | Ala | Ala | Glu | Asn |
| | | | | 180 | | | | | 185 | | | | | 190 | |
| GGC | AAA | AGG | TAT | CCT | TTG | TTA | AGT | AAT | GGC | AGT | CAA | GCT | TAT | TTT | CGA | 623 |
| Gly | Lys | Arg | Tyr | Pro | Leu | Leu | Ser | Asn | Gly | Ser | Gln | Ala | Tyr | Phe | Arg |
| | | | 195 | | | | | 200 | | | | | 205 | | |
| CGT | AGT | GCA | ATT | CCA | GAA | GAT | ATT | GAT | TTA | GAA | GTT | AAA | AAT | GAT | GAG | 671 |
| Arg | Ser | Ala | Ile | Pro | Glu | Asp | Ile | Asp | Leu | Glu | Val | Lys | Asn | Asp | Glu |
| | | 210 | | | | | 215 | | | | | 220 | | | |
| AAT | AGA | GAA | AAA | GGG | CTA | GTG | AGT | GAA | TTT | AGT | GCA | GAT | TTT | GGG | ACT | 719 |
| Asn | Arg | Glu | Lys | Gly | Leu | Val | Ser | Glu | Phe | Ser | Ala | Asp | Phe | Gly | Thr |
| | 225 | | | | | 230 | | | | | 235 | | | | |
| AAA | AAA | CTG | ACA | GGA | GGA | CTG | TTT | TAC | ACC | AAA | AGA | CAA | ACT | CAT | ATT | 767 |
| Lys | Lys | Leu | Thr | Gly | Gly | Leu | Phe | Tyr | Thr | Lys | Arg | Gln | Thr | His | Ile |
| 240 | | | | | 245 | | | | | 250 | | | | | 255 |
| CAA | AAC | CAT | GAA | AAG | AAA | AAA | CTC | TAT | GAT | ATA | GAT | GCC | CAT | ATT | TAT | 815 |
| Gln | Asn | His | Glu | Lys | Lys | Lys | Leu | Tyr | Asp | Ile | Asp | Ala | His | Ile | Tyr |
| | | | | 260 | | | | | 265 | | | | | 270 | |
| AGT | AAT | AGA | TTC | AGA | GGT | AAA | GTA | AAT | CCT | ACC | CAA | AAA | GAT | TCT | AAA | 863 |
| Ser | Asn | Arg | Phe | Arg | Gly | Lys | Val | Asn | Pro | Thr | Gln | Lys | Asp | Ser | Lys |
| | | | 275 | | | | | 280 | | | | | 285 | | |
| GAA | CAT | CCC | TTT | ACC | AGC | GAG | GGA | ACA | TTA | GAA | GGT | GGT | TTT | TAC | GGG | 911 |
| Glu | His | Pro | Phe | Thr | Ser | Glu | Gly | Thr | Leu | Glu | Gly | Gly | Phe | Tyr | Gly |
| | | 290 | | | | | 295 | | | | | 300 | | | |
| CCT | GAA | GGT | CAA | GAA | TTA | GGA | GGA | AAG | TTT | TTA | GCT | GGC | GAC | AAA | AAA | 959 |
| Pro | Glu | Gly | Gln | Glu | Leu | Gly | Gly | Lys | Phe | Leu | Ala | Gly | Asp | Lys | Lys |
| | 305 | | | | | 310 | | | | | 315 | | | | |
| GTT | TTT | GGG | GTA | TTT | AGT | GCC | AAA | GGA | ACG | GAA | GAA | AAC | AAA | AAA | TTA | 1007 |
| Val | Phe | Gly | Val | Phe | Ser | Ala | Lys | Gly | Thr | Glu | Glu | Asn | Lys | Lys | Leu |
| 320 | | | | | 325 | | | | | 330 | | | | | 335 |
| CCC | AAA | GAA | ACC | TTA | ATT | GAT | GGC | AAG | CTA | ACT | ACT | TTC | TCT | ACT | AAA | 1055 |
| Pro | Lys | Glu | Thr | Leu | Ile | Asp | Gly | Lys | Leu | Thr | Thr | Phe | Ser | Thr | Lys |
| | | | | 340 | | | | | 345 | | | | | 350 | |
| ACA | ACC | GAT | GCA | AAA | ACC | AAT | GCA | ACA | GCC | AAT | GCA | ACA | ACC | AGT | ACC | 1103 |
| Thr | Thr | Asp | Ala | Lys | Thr | Asn | Ala | Thr | Ala | Asn | Ala | Thr | Thr | Ser | Thr |
| | | | 355 | | | | | 360 | | | | | 365 | | |
| GCA | GCC | AAT | ACA | ACA | ACC | GAT | ACA | ACA | GCC | AAT | ACA | ATA | ACC | GAT | GCA | 1151 |
| Ala | Ala | Asn | Thr | Thr | Thr | Asp | Thr | Thr | Ala | Asn | Thr | Ile | Thr | Asp | Ala |

|                                                                                          |      |
|------------------------------------------------------------------------------------------|------|
|            370          375          380 | |
| GAA AAC TTT AAG ACG AAA GAT ATA TCA AGT TTT GGT GAA GCT GAT TAC<br>Glu Asn Phe Lys Thr Lys Asp Ile Ser Ser Phe Gly Glu Ala Asp Tyr<br>385                    390                    395 | 1199 |
| CTT TTA ATT GAT AAT TAC CCT GTT CCT CTT TTA CCT GAG AGT GGT GAT<br>Leu Leu Ile Asp Asn Tyr Pro Val Pro Leu Leu Pro Glu Ser Gly Asp<br>400                    405                    410                    415 | 1247 |
| TTC ATA AGT AGT AAG CAC CAT ACT GTA GGA AAG AAA ACC TAT CAA GTA<br>Phe Ile Ser Ser Lys His His Thr Val Gly Lys Lys Thr Tyr Gln Val<br>                    420                    425                    430 | 1295 |
| AAA GCA TGT TGC AGT AAT CTA AGC TAT GTG AAA TTT GGT ATG TAT TAT<br>Lys Ala Cys Cys Ser Asn Leu Ser Tyr Val Lys Phe Gly Met Tyr Tyr<br>                435                    440                    445 | 1343 |
| GAA GTC CCA CCT AAA GAA GAA GAA AAA GAC AAA GAA AAA AAA GAA AAA<br>Glu Val Pro Pro Lys Glu Glu Glu Lys Asp Lys Glu Lys Lys Glu Lys<br>            450                    455                    460 | 1391 |
| GAA AAA GAA AAA CAA GCG ACA AAT CTA TCG AAC ACT TAT TAT CAA TTC<br>Glu Lys Glu Lys Gln Ala Thr Asn Leu Ser Asn Thr Tyr Tyr Gln Phe<br>465                      470                    475 | 1439 |
| TTA TTA GGT CTC CGT ACT CCC AGT TCT GAA ATT CCT AAA GGA GGA AGT<br>Leu Leu Gly Leu Arg Thr Pro Ser Ser Glu Ile Pro Lys Gly Gly Ser<br>480                    485                    490                    495 | 1487 |
| GCA AAA TAT CTC GGT AGT TGG TTT GGT TAT CTG AGC GAT GGT TCA ACA<br>Ala Lys Tyr Leu Gly Ser Trp Phe Gly Tyr Leu Ser Asp Gly Ser Thr<br>                500                    505                    510 | 1535 |
| TCT TAC TCC CCC AGT GGT GAT AAG AAA CGC GAG AAC AAT GCT CTC GCC<br>Ser Tyr Ser Pro Ser Gly Asp Lys Lys Arg Glu Asn Asn Ala Leu Ala<br>                515                    520                    525 | 1583 |
| GAG TTT AAT GTA AAT TTT GTC GAT AAA ACA TTA AAA GGC CAA TTA ATA<br>Glu Phe Asn Val Asn Phe Val Asp Lys Thr Leu Lys Gly Gln Leu Ile<br>            530                    535                    540 | 1631 |
| CGA CAC GAT AAT CAA AAT ACC GTT TTT ACA ATT GAT GCA ACC TTT AAA<br>Arg His Asp Asn Gln Asn Thr Val Phe Thr Ile Asp Ala Thr Phe Lys<br>545                      550                    555 | 1679 |
| GGT GGT AAG AAT AAC TTC ACT GGT ACA GCA ACC GCA AAC AAT GTA GCG<br>Gly Gly Lys Asn Asn Phe Thr Gly Thr Ala Thr Ala Asn Asn Val Ala<br>560                      565                    570                    575 | 1727 |
| ATT GAT CCC CAA AGT ACA CAA GGC ACA TCT AAC GTC AAT TTC ACG GCA<br>Ile Asp Pro Gln Ser Thr Gln Gly Thr Ser Asn Val Asn Phe Thr Ala<br>                580                    585                    590 | 1775 |
| ACA GTA AAT GGG GCA TTT TAT GGG CCG AAC GCT ACA GAA TTA GGC GGT<br>Thr Val Asn Gly Ala Phe Tyr Gly Pro Asn Ala Thr Glu Leu Gly Gly<br>                595                    600                    605 | 1823 |
| TAT TTC ACC TAT AAC GGA AAT CCT ACA GAT AAA AGT TCC TCA ACC GTA<br>Tyr Phe Thr Tyr Asn Gly Asn Pro Thr Asp Lys Ser Ser Ser Thr Val<br>            610                    615                    620 | 1871 |
| CCT TCA TCA TCC AAT TCA AAA AAT GCA AGA GCT GCA GTT GTC TTT GGT<br>Pro Ser Ser Ser Asn Ser Lys Asn Ala Arg Ala Ala Val Val Phe Gly<br>625                      630                    635 | 1919 |
| GCG AGA CAA CAA GTA GAA ACA ACC AAA TAATGGAATA CTAAAAATGA<br>Ala Arg Gln Gln Val Glu Thr Thr Lys<br>640                      645 | 1966 |
| CTAAAAAGC TTCTAGAAGC CGAATTC | 1993 |

(2) INFORMATION FOR SEQ ID NO: 109:

(i) SEQUENCE CHARACTERISTICS:
        (A) LENGTH: 648 amino acids
        (B) TYPE: amino acid
        (D) TOPOLOGY: linear (ii) MOLECULE TYPE: protein (xi) SEQUENCE DESCRIPTION: SEQ ID NO: 109:

```
Met Lys Ser Val Pro Leu Ile Ser Gly Gly Leu Ser Phe Leu Leu Ser
 1               5                  10                  15

Ala Cys Ser Gly Gly Gly Ser Phe Asp Val Asp Val Ser Asn
                 20                  25                  30

Pro Ser Ser Ser Lys Pro Arg Tyr Gln Asp Asp Thr Ser Ser Ser Arg
                 35                  40                  45

Thr Lys Ser Lys Leu Glu Asn Leu Ser Ile Pro Ser Leu Gly Gly Gly
     50                  55                  60

Met Lys Leu Val Ala Gln Asn Leu Arg Asp Arg Thr Lys Pro Ser Leu
 65                  70                  75                  80

Leu Asn Glu Asp Asp Tyr Met Ile Phe Ser Ser Leu Ser Thr Ile Lys
                 85                  90                  95

Ala Asp Val Glu Lys Glu Asn Lys His Tyr Thr Ser Pro Val Gly Ser
                100                 105                 110

Ile Asp Glu Pro Ser Thr Thr Asn Pro Lys Glu Asn Asp His Gly Gln
                115                 120                 125

Arg Tyr Val Tyr Ser Gly Leu Tyr Tyr Ile Pro Ser Trp Asn Leu Asn
    130                 135                 140

Asp Leu Lys Asn Asn Lys Tyr Tyr Tyr Ser Gly Tyr Tyr Gly Tyr Ala
145                 150                 155                 160

Tyr Tyr Phe Gly Lys Gln Thr Ala Thr Thr Leu Pro Val Asn Gly Lys
                165                 170                 175

Val Thr Tyr Lys Gly Thr Trp Ser Phe Ile Thr Ala Ala Glu Asn Gly
                180                 185                 190

Lys Arg Tyr Pro Leu Leu Ser Asn Gly Ser Gln Ala Tyr Phe Arg Arg
                195                 200                 205

Ser Ala Ile Pro Glu Asp Ile Asp Leu Glu Val Lys Asn Asp Glu Asn
                210                 215                 220

Arg Glu Lys Gly Leu Val Ser Glu Phe Ser Ala Asp Phe Gly Thr Lys
225                 230                 235                 240

Lys Leu Thr Gly Gly Leu Phe Tyr Thr Lys Arg Gln Thr His Ile Gln
                245                 250                 255

Asn His Glu Lys Lys Leu Tyr Asp Ile Asp Ala His Ile Tyr Ser
                260                 265                 270

Asn Arg Phe Arg Gly Lys Val Asn Pro Thr Gln Lys Asp Ser Lys Glu
                275                 280                 285

His Pro Phe Thr Ser Glu Gly Thr Leu Glu Gly Gly Phe Tyr Gly Pro
                290                 295                 300

Glu Gly Gln Glu Leu Gly Gly Lys Phe Leu Ala Gly Asp Lys Lys Val
305                 310                 315                 320

Phe Gly Val Phe Ser Ala Lys Gly Thr Glu Glu Asn Lys Lys Leu Pro
                325                 330                 335

Lys Glu Thr Leu Ile Asp Gly Lys Leu Thr Thr Phe Ser Thr Lys Thr
                340                 345                 350

Thr Asp Ala Lys Thr Asn Ala Thr Ala Asn Ala Thr Ser Thr Ala
                355                 360                 365

Ala Asn Thr Thr Thr Asp Thr Thr Ala Asn Thr Ile Thr Asp Ala Glu
    370                 375                 380

Asn Phe Lys Thr Lys Asp Ile Ser Ser Phe Gly Glu Ala Asp Tyr Leu
385                 390                 395                 400

Leu Ile Asp Asn Tyr Pro Val Pro Leu Leu Pro Glu Ser Gly Asp Phe
```

```
                            405                 410                 415
Ile Ser Ser Lys His His Thr Val Gly Lys Lys Thr Tyr Gln Val Lys
                420                 425                 430

Ala Cys Cys Ser Asn Leu Ser Tyr Val Lys Phe Gly Met Tyr Tyr Glu
        435                 440                 445

Val Pro Pro Lys Glu Glu Lys Asp Lys Glu Lys Lys Glu Lys Glu
    450                 455                 460

Lys Glu Lys Gln Ala Thr Asn Leu Ser Asn Thr Tyr Tyr Gln Phe Leu
465                 470                 475                 480

Leu Gly Leu Arg Thr Pro Ser Ser Glu Ile Pro Lys Gly Gly Ser Ala
                485                 490                 495

Lys Tyr Leu Gly Ser Trp Phe Gly Tyr Leu Ser Asp Gly Ser Thr Ser
                500                 505                 510

Tyr Ser Pro Ser Gly Asp Lys Lys Arg Glu Asn Asn Ala Leu Ala Glu
            515                 520                 525

Phe Asn Val Asn Phe Val Asp Lys Thr Leu Lys Gly Gln Leu Ile Arg
        530                 535                 540

His Asp Asn Gln Asn Thr Val Phe Thr Ile Asp Ala Thr Phe Lys Gly
545                 550                 555                 560

Gly Lys Asn Asn Phe Thr Gly Thr Ala Thr Ala Asn Val Ala Ile
                565                 570                 575

Asp Pro Gln Ser Thr Gln Gly Thr Ser Asn Val Asn Phe Thr Ala Thr
            580                 585                 590

Val Asn Gly Ala Phe Tyr Gly Pro Asn Ala Thr Glu Leu Gly Gly Tyr
                595                 600                 605

Phe Thr Tyr Asn Gly Asn Pro Thr Asp Lys Ser Ser Ser Thr Val Pro
        610                 615                 620

Ser Ser Ser Asn Ser Lys Asn Ala Arg Ala Ala Val Val Phe Gly Ala
625                 630                 635                 640

Arg Gln Gln Val Glu Thr Thr Lys
                645

(2) INFORMATION FOR SEQ ID NO: 110:

(i) SEQUENCE CHARACTERISTICS:
        (A) LENGTH: 1974 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 20..1912

(xi) SEQUENCE DESCRIPTION: SEQ ID NO: 110:

GAATTCGGCT TGGATCCAT ATG AAA TCT GTA CCT CTT ATC TCT GGT GGA CTT         52
                    Met Lys Ser Val Pro Leu Ile Ser Gly Gly Leu
                     1               5                  10

TCC TTT TTA CTA AGT GCT TGT AGC GGA GGG GGG TCT TTT GAT GTA GAT        100
Ser Phe Leu Leu Ser Ala Cys Ser Gly Gly Gly Ser Phe Asp Val Asp
            15                  20                  25

AAC GTC TCT AAT CCA TCC TCT TCT AAA CCA CGT TAT CAA GAC GAT ACT        148
Asn Val Ser Asn Pro Ser Ser Ser Lys Pro Arg Tyr Gln Asp Asp Thr
        30                  35                  40

TCA AGT TCA AGA ACA AAA TCT AAT TTG AAA AAG TTG TCC ATT CCT TCT        196
Ser Ser Ser Arg Thr Lys Ser Asn Leu Lys Lys Leu Ser Ile Pro Ser
    45                  50                  55

TTA GGG GGA GGG ATG AAG TTA GTG GCT CAG AAT CTT AGT GAT AAG AAC        244
Leu Gly Gly Gly Met Lys Leu Val Ala Gln Asn Leu Ser Asp Lys Asn
```

```
                60                   65                   70                   75
AAA CCT AGT CTC TTA AAT GAA GAT GAC TAT ATA TCA TAT TTT TCC TCA              292
Lys Pro Ser Leu Leu Asn Glu Asp Asp Tyr Ile Ser Tyr Phe Ser Ser
                        80                       85                       90

CTT TCT ACA ATT CAA GAT GAT GTT AAA AAA GAA AAT AAA CGC CAT ACA              340
Leu Ser Thr Ile Gln Asp Asp Val Lys Lys Glu Asn Lys Arg His Thr
                95                      100                      105

AAT CCA GTT GGC TCA ATA GAC GAG CCT AAC GCA ACA AAT CCA CCC GAA              388
Asn Pro Val Gly Ser Ile Asp Glu Pro Asn Ala Thr Asn Pro Pro Glu
            110                      115                      120

AAG CAT CAT GGA CAA AGA TAT GTA TAT TCA GGG CTT TAT TAT ATT CCA              436
Lys His His Gly Gln Arg Tyr Val Tyr Ser Gly Leu Tyr Tyr Ile Pro
        125                      130                      135

TCG TGG AGT CAT TCC TCA AAT GGC AAG CTT TAT TTA GGT TAC TAT GGA              484
Ser Trp Ser His Ser Ser Asn Gly Lys Leu Tyr Leu Gly Tyr Tyr Gly
140                      145                      150                      155

TAT GCG TTT TAT TAT GGT AAT AAA ACT GCA ACA AAC TTG CCA GTA AGC              532
Tyr Ala Phe Tyr Tyr Gly Asn Lys Thr Ala Thr Asn Leu Pro Val Ser
                    160                      165                      170

GGC ATA GCT AAA TAC AAA GGA ACT TGG GAT TTT ATT ACT GCA ACT AAA              580
Gly Ile Ala Lys Tyr Lys Gly Thr Trp Asp Phe Ile Thr Ala Thr Lys
                175                      180                      185

AAT GGC CAA CGT TAT TCT TTA TTT GGT AGC GCT TTT GGA GCT TAT AAT              628
Asn Gly Gln Arg Tyr Ser Leu Phe Gly Ser Ala Phe Gly Ala Tyr Asn
            190                      195                      200

AGA CGC AGT GCT ATT TCA GAA GAT ATA GAT AAT TTA GAA AAT AAT CTA              676
Arg Arg Ser Ala Ile Ser Glu Asp Ile Asp Asn Leu Glu Asn Asn Leu
        205                      210                      215

AAG AAT GGT GCG GGA TTA ACT AGT GAA TTT ACT GTC AAT TTT GGT ACG              724
Lys Asn Gly Ala Gly Leu Thr Ser Glu Phe Thr Val Asn Phe Gly Thr
220                      225                      230                      235

AAA AAG CTC ACT GGA AAA CTT TAT TAT AAT GAA AGG GAA ACA AAT CTT              772
Lys Lys Leu Thr Gly Lys Leu Tyr Tyr Asn Glu Arg Glu Thr Asn Leu
                    240                      245                      250

AAT AAA TTA CAA AAG AGA AAA CAT GAA CTC TAT GAT ATA GAT GCC GAT              820
Asn Lys Leu Gln Lys Arg Lys His Glu Leu Tyr Asp Ile Asp Ala Asp
                255                      260                      265

ATT TAT AGT AAT AGA TTC AGA GGT AAA GTA AAG CCA ACA ACC CAA AAA              868
Ile Tyr Ser Asn Arg Phe Arg Gly Lys Val Lys Pro Thr Thr Gln Lys
            270                      275                      280

GAT TCT CAA GAA CAT CCC TTT ACC AGC GAG GGA ACA TTA GAA GGT GGT              916
Asp Ser Gln Glu His Pro Phe Thr Ser Glu Gly Thr Leu Glu Gly Gly
        285                      290                      295

TTT TAT GGG CCT AAC GGT GAA GAA TTA GGA GGA AAG TTT TTA GCT GGC              964
Phe Tyr Gly Pro Asn Gly Glu Glu Leu Gly Gly Lys Phe Leu Ala Gly
300                      305                      310                      315

GAT AAC CGA GTT TTT GGG GTA TTT AGT GCC AAA GAA GAA GAA ACA AAA             1012
Asp Asn Arg Val Phe Gly Val Phe Ser Ala Lys Glu Glu Glu Thr Lys
                    320                      325                      330

GAC AAA AAA TTA TCC AGA GAA ACC TTA ATT GAT GGC AAG CTA ATT ACT             1060
Asp Lys Lys Leu Ser Arg Glu Thr Leu Ile Asp Gly Lys Leu Ile Thr
                335                      340                      345

TTT AAA AGA ACT GAT GCA ACA ACC AAT ACA GCA GCC AAT GCA AAA ACC             1108
Phe Lys Arg Thr Asp Ala Thr Thr Asn Thr Ala Ala Asn Ala Lys Thr
            350                      355                      360

GAT GAA AAA AAC TTT ACG ACG AAA GAT ATA CCA AGT TTT GGT GAA GCT             1156
Asp Glu Lys Asn Phe Thr Thr Lys Asp Ile Pro Ser Phe Gly Glu Ala
        365                      370                      375

GAT TAC CTT TTA ATT GAT AAT TAC CCT GTT CCT CTT TTC CCT GAA GAA             1204
Asp Tyr Leu Leu Ile Asp Asn Tyr Pro Val Pro Leu Phe Pro Glu Glu
```

```
                380                     385                     390                     395
AAT ACT AAT GAT TTC ATA ACT AGT AGG CAC CAT AAG GTA GGA GAT AAA      1252
Asn Thr Asn Asp Phe Ile Thr Ser Arg His His Lys Val Gly Asp Lys
                        400                     405                     410

ACC TAT AAA GTA GAA GCA TGT TGC AAG AAT CTA AGC TAT GTG AAA TTT      1300
Thr Tyr Lys Val Glu Ala Cys Cys Lys Asn Leu Ser Tyr Val Lys Phe
                415                     420                     425

GGT ATG TAT TAT GAA GAC CCA TTA AAT GGA GAA AAT GGC AAA GAA AAA      1348
Gly Met Tyr Tyr Glu Asp Pro Leu Asn Gly Glu Asn Gly Lys Glu Lys
                430                     435                     440

GAA AAA GAA AAA GAA AAA GAC AAA GAA AAA CAA GCG ACA ACA TCT ATC      1396
Glu Lys Glu Lys Glu Lys Asp Lys Glu Lys Gln Ala Thr Thr Ser Ile
            445                     450                     455

AAG ACT TAT TAT CAA TTC TTA TTA GGT CAC CGT ACT GCC AAG GCC GAC      1444
Lys Thr Tyr Tyr Gln Phe Leu Leu Gly His Arg Thr Ala Lys Ala Asp
460                     465                     470                     475

ATA CCT GCA ACG GGA AAC GTG AAA TAT CGC GGT AAT TGG TTT GGT TAT      1492
Ile Pro Ala Thr Gly Asn Val Lys Tyr Arg Gly Asn Trp Phe Gly Tyr
                    480                     485                     490

ATT GGT GAT GAC AAG ACA TCT TAC TCC ACT ACT GGA GAT AAA AAT GCT      1540
Ile Gly Asp Asp Lys Thr Ser Tyr Ser Thr Thr Gly Asp Lys Asn Ala
                495                     500                     505

GTC GCC GAG TTT GAT GTA AAT TTT GCC GAT AAA ACA TTA ACA GGC ACA      1588
Val Ala Glu Phe Asp Val Asn Phe Ala Asp Lys Thr Leu Thr Gly Thr
            510                     515                     520

TTA AAA CGA CAC GAT AAT GGA AAT CCC GTA TTT ACA ATT AAT GCA AGC      1636
Leu Lys Arg His Asp Asn Gly Asn Pro Val Phe Thr Ile Asn Ala Ser
525                     530                     535

TTT CAA AGT GGT AAG AAT GAC TTC ACT GGT ACA GCA ACC GCA AAC AAT      1684
Phe Gln Ser Gly Lys Asn Asp Phe Thr Gly Thr Ala Thr Ala Asn Asn
540                     545                     550                     555

GTA GCG ATT GAT CCC CAA AAT ACA CAA ACC ACA TCT AGA GTC AAT TTC      1732
Val Ala Ile Asp Pro Gln Asn Thr Gln Thr Thr Ser Arg Val Asn Phe
                    560                     565                     570

ACG GCA ACA GTA AAC GGG GCA TTT TAT GGA CCT AAG GCT ACA GAA TTA      1780
Thr Ala Thr Val Asn Gly Ala Phe Tyr Gly Pro Lys Ala Thr Glu Leu
                575                     580                     585

GGC GGT TAT TTC ACT TAT AAC GGA AAC AAT CCT ACA GAT AAA AAT TCC      1828
Gly Gly Tyr Phe Thr Tyr Asn Gly Asn Asn Pro Thr Asp Lys Asn Ser
            590                     595                     600

TCA ACC GTT TCA CCA TCC AAT TCA GCA AAT GCT CGT GCT GCC GTT GTG      1876
Ser Thr Val Ser Pro Ser Asn Ser Ala Asn Ala Arg Ala Ala Val Val
        605                     610                     615

TTT GGC GCT AAA AAA CAA GTA GAA ACA ACC AAC AAG TAAAAACAAC           1922
Phe Gly Ala Lys Lys Gln Val Glu Thr Thr Asn Lys
620                     625                     630

CAAGTAATGG AATACTAAAA ATGACTAAAA AAGCTTCTAG AAAGCCGAAT TC            1974

(2) INFORMATION FOR SEQ ID NO: 111:

(i) SEQUENCE CHARACTERISTICS:
        (A) LENGTH: 631 amino acids
        (B) TYPE: amino acid
        (D) TOPOLOGY: linear (ii) MOLECULE TYPE: protein (xi) SEQUENCE DESCRIPTION: SEQ ID NO: 111:

Met Lys Ser Val Pro Leu Ile Ser Gly Gly Leu Ser Phe Leu Leu Ser
  1               5                  10                  15

Ala Cys Ser Gly Gly Gly Ser Phe Asp Val Asp Asn Val Ser Asn Pro
```

-continued

```
                    20                  25                  30
Ser Ser Ser Lys Pro Arg Tyr Gln Asp Asp Thr Ser Ser Arg Thr
            35                  40                  45
Lys Ser Asn Leu Lys Lys Leu Ser Ile Pro Ser Leu Gly Gly Met
 50                  55                  60
Lys Leu Val Ala Gln Asn Leu Ser Asp Lys Asn Lys Pro Ser Leu Leu
 65                  70                  75                  80
Asn Glu Asp Asp Tyr Ile Ser Tyr Phe Ser Ser Leu Ser Thr Ile Gln
                    85                  90                  95
Asp Asp Val Lys Lys Glu Asn Lys Arg His Thr Asn Pro Val Gly Ser
                100                 105                 110
Ile Asp Glu Pro Asn Ala Thr Asn Pro Pro Glu Lys His His Gly Gln
            115                 120                 125
Arg Tyr Val Tyr Ser Gly Leu Tyr Tyr Ile Pro Ser Trp Ser His Ser
    130                 135                 140
Ser Asn Gly Lys Leu Tyr Leu Gly Tyr Tyr Gly Tyr Ala Phe Tyr Tyr
145                 150                 155                 160
Gly Asn Lys Thr Ala Thr Asn Leu Pro Val Ser Gly Ile Ala Lys Tyr
                165                 170                 175
Lys Gly Thr Trp Asp Phe Ile Thr Ala Thr Lys Asn Gly Gln Arg Tyr
            180                 185                 190
Ser Leu Phe Gly Ser Ala Phe Gly Ala Tyr Asn Arg Arg Ser Ala Ile
    195                 200                 205
Ser Glu Asp Ile Asp Asn Leu Glu Asn Asn Leu Lys Asn Gly Ala Gly
    210                 215                 220
Leu Thr Ser Glu Phe Thr Val Asn Phe Gly Thr Lys Lys Leu Thr Gly
225                 230                 235                 240
Lys Leu Tyr Tyr Asn Glu Arg Glu Thr Asn Leu Asn Lys Leu Gln Lys
                245                 250                 255
Arg Lys His Glu Leu Tyr Asp Ile Asp Ala Asp Ile Tyr Ser Asn Arg
            260                 265                 270
Phe Arg Gly Lys Val Lys Pro Thr Thr Gln Lys Asp Ser Gln Glu His
    275                 280                 285
Pro Phe Thr Ser Glu Gly Thr Leu Glu Gly Gly Phe Tyr Gly Pro Asn
    290                 295                 300
Gly Glu Glu Leu Gly Gly Lys Phe Leu Ala Gly Asp Asn Arg Val Phe
305                 310                 315                 320
Gly Val Phe Ser Ala Lys Glu Glu Thr Lys Asp Lys Lys Leu Ser
                325                 330                 335
Arg Glu Thr Leu Ile Asp Gly Lys Leu Ile Thr Phe Lys Arg Thr Asp
            340                 345                 350
Ala Thr Thr Asn Thr Ala Ala Asn Ala Lys Thr Asp Glu Lys Asn Phe
            355                 360                 365
Thr Thr Lys Asp Ile Pro Ser Phe Gly Glu Ala Asp Tyr Leu Leu Ile
    370                 375                 380
Asp Asn Tyr Pro Val Pro Leu Phe Pro Glu Glu Asn Thr Asn Asp Phe
385                 390                 395                 400
Ile Thr Ser Arg His His Lys Val Gly Asp Lys Thr Tyr Lys Val Glu
                405                 410                 415
Ala Cys Cys Lys Asn Leu Ser Tyr Val Lys Phe Gly Met Tyr Tyr Glu
            420                 425                 430
Asp Pro Leu Asn Gly Glu Asn Gly Lys Glu Lys Glu Lys Glu
            435                 440                 445
```

```
Lys Asp Lys Glu Lys Gln Ala Thr Thr Ser Ile Lys Thr Tyr Tyr Gln
    450                 455                 460

Phe Leu Leu Gly His Arg Thr Ala Lys Ala Asp Ile Pro Ala Thr Gly
465                 470                 475                 480

Asn Val Lys Tyr Arg Gly Asn Trp Phe Gly Tyr Ile Gly Asp Asp Lys
                485                 490                 495

Thr Ser Tyr Ser Thr Thr Gly Asp Lys Asn Ala Val Ala Glu Phe Asp
            500                 505                 510

Val Asn Phe Ala Asp Lys Thr Leu Thr Gly Thr Leu Lys Arg His Asp
        515                 520                 525

Asn Gly Asn Pro Val Phe Thr Ile Asn Ala Ser Phe Gln Ser Gly Lys
    530                 535                 540

Asn Asp Phe Thr Gly Thr Ala Thr Ala Asn Asn Val Ala Ile Asp Pro
545                 550                 555                 560

Gln Asn Thr Gln Thr Thr Ser Arg Val Asn Phe Thr Ala Thr Val Asn
                565                 570                 575

Gly Ala Phe Tyr Gly Pro Lys Ala Thr Glu Leu Gly Gly Tyr Phe Thr
            580                 585                 590

Tyr Asn Gly Asn Asn Pro Thr Asp Lys Asn Ser Ser Thr Val Ser Pro
        595                 600                 605

Ser Asn Ser Ala Asn Ala Arg Ala Ala Val Val Phe Gly Ala Lys Lys
    610                 615                 620

Gln Val Glu Thr Thr Asn Lys
625                 630

(2) INFORMATION FOR SEQ ID NO: 112:

(i) SEQUENCE CHARACTERISTICS:
        (A) LENGTH: 1951 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..1890

(xi) SEQUENCE DESCRIPTION: SEQ ID NO: 112:

ATG AAA TCT GTA CCT CTT ATC TCT GGT GGA CTT TCC CTT TTA TTA AGT         48
Met Lys Ser Val Pro Leu Ile Ser Gly Gly Leu Ser Leu Leu Leu Ser
 1               5                  10                  15

GCT TGT AGC GGG GGA GGT GGT TCT TTT GAT GTA GAT GAC GTC TCT AAT         96
Ala Cys Ser Gly Gly Gly Gly Ser Phe Asp Val Asp Asp Val Ser Asn
                20                  25                  30

CCC TCC TCT TCT AAA CCA CGT TAT CAA GAC GAT ACC TCG AGT CAA AGA        144
Pro Ser Ser Ser Lys Pro Arg Tyr Gln Asp Asp Thr Ser Ser Gln Arg
            35                  40                  45

ACA AAA TCT AAT TTG GAA AAG TTG TCC ATT CCT TCT TTA GGA GGA GGG        192
Thr Lys Ser Asn Leu Glu Lys Leu Ser Ile Pro Ser Leu Gly Gly Gly
        50                  55                  60

ATG AAA TTG GTG GCT CAG AAT CTG AGT GGT AAT AAA GAA CCT AGT TTC        240
Met Lys Leu Val Ala Gln Asn Leu Ser Gly Asn Lys Glu Pro Ser Phe
65                  70                  75                  80

TTA AAT GGA AAT GAC TAT ATG ATA TTT TCC TCA CGT TCT ACG ATT AAA        288
Leu Asn Gly Asn Asp Tyr Met Ile Phe Ser Ser Arg Ser Thr Ile Lys
                85                  90                  95

GAT GAT GTT GAA AAT AAC AAT ACA AAC GGG GGG GAC TAT ATT GGC TCA        336
Asp Asp Val Glu Asn Asn Asn Thr Asn Gly Gly Asp Tyr Ile Gly Ser
            100                 105                 110

ATA GAC GAG CCT AGT ACA ACA AAT CCA CTC GAA AAG CAT CAT GGA CAA        384
```

-continued

| | | | | | | | | | | | | | | |
|---|---|---|---|---|---|---|---|---|---|---|---|---|---|---|
| Ile | Asp | Glu | Pro | Ser | Thr | Thr | Asn | Pro | Leu | Glu | Lys | His | His | Gly | Gln |
| | | 115 | | | | | 120 | | | | 125 | | | | |

```
AGG TAT GTA TAT TCA GGG CTT TAT TAT ATT CAA TCG TGG AGT CTA AGA      432
Arg Tyr Val Tyr Ser Gly Leu Tyr Tyr Ile Gln Ser Trp Ser Leu Arg
    130             135             140

GAT TTA CCA AAG AAG TTT TAT TCA GGT TAC TAT GGA TAT GCG TAT TAC      480
Asp Leu Pro Lys Lys Phe Tyr Ser Gly Tyr Tyr Gly Tyr Ala Tyr Tyr
145             150             155             160

TTT GGC AAG GAA ACA GCC ACT ACA TTA CCT GTA AAT GGC GAA GCA ACG      528
Phe Gly Lys Glu Thr Ala Thr Thr Leu Pro Val Asn Gly Glu Ala Thr
                165             170             175

TAT AAA GGA ACT TGG GAT TTC ATC ACT GCA ACT AGA AAT GGC AAA AGT      576
Tyr Lys Gly Thr Trp Asp Phe Ile Thr Ala Thr Arg Asn Gly Lys Ser
            180             185             190

TAT TCT TTG TTA AGT AAT AAC CGA CAA GCT TAT TCC AAA CGT AGT GCA      624
Tyr Ser Leu Leu Ser Asn Asn Arg Gln Ala Tyr Ser Lys Arg Ser Ala
        195             200             205

ATT CCA GAA GAC ATT GAT TTA GAA AAT GAT CCA AAG AAT GGT GAG ACG      672
Ile Pro Glu Asp Ile Asp Leu Glu Asn Asp Pro Lys Asn Gly Glu Thr
    210             215             220

AGA TTA ACT AGT GAA TTT ACT GTG AAT TTT GGT ACG AAA AAG CTC ACA      720
Arg Leu Thr Ser Glu Phe Thr Val Asn Phe Gly Thr Lys Lys Leu Thr
225             230             235             240

GGT GGA CTT TAT TAC CAT TTA CGT AAA ACA AAT GCT AAT GAA AAC CAA      768
Gly Gly Leu Tyr Tyr His Leu Arg Lys Thr Asn Ala Asn Glu Asn Gln
                245             250             255

AAT AGA AAA CAT AAA CTC TAC AAT CTA GAA GCT GAT GTG TAT AGC AAC      816
Asn Arg Lys His Lys Leu Tyr Asn Leu Glu Ala Asp Val Tyr Ser Asn
            260             265             270

CGA TTC AGA GGT AAA GTA AAG CCA ACC AAA GAG TCT TCT GAA GAA CAT      864
Arg Phe Arg Gly Lys Val Lys Pro Thr Lys Glu Ser Ser Glu Glu His
        275             280             285

CCC TTT ACC AGC GAG GGA ACA TTA GAA GGT GGT TTT TAT GGG CCT AAT      912
Pro Phe Thr Ser Glu Gly Thr Leu Glu Gly Gly Phe Tyr Gly Pro Asn
    290             295             300

GCT GAA GAA CTA GGG GGA AAA TTT TTA GCT AGC GAT AAA AAA GTT TTT      960
Ala Glu Glu Leu Gly Gly Lys Phe Leu Ala Ser Asp Lys Lys Val Phe
305             310             315             320

GGG GTA TTT AGT GCC AAA GAA CAG CAA GAA ACG GAA GAA AAC AAA AAA     1008
Gly Val Phe Ser Ala Lys Glu Gln Gln Glu Thr Glu Glu Asn Lys Lys
                325             330             335

TTA CTC AAA GAA ACC TTA ATT GAT GGC AAG CTA ACT ACT TTC TCT ACT     1056
Leu Leu Lys Glu Thr Leu Ile Asp Gly Lys Leu Thr Thr Phe Ser Thr
            340             345             350

AAA AAA ACC AAT GCA ACA ACC GAT GCA ACA ACC AGT ACA ACA ACC AGT     1104
Lys Lys Thr Asn Ala Thr Thr Asp Ala Thr Thr Ser Thr Thr Thr Ser
        355             360             365

ACA GCA ACC AAT GCA ACA GCC GAT GCA GAA AAC TTT ACG ACA AAA GAT     1152
Thr Ala Thr Asn Ala Thr Ala Asp Ala Glu Asn Phe Thr Thr Lys Asp
    370             375             380

ATA TCA AGT TTT GGT GAA GCT GAT TAT CTT TTA ATT GAT AAT TAC CCT     1200
Ile Ser Ser Phe Gly Glu Ala Asp Tyr Leu Leu Ile Asp Asn Tyr Pro
385             390             395             400

GTT CCT CTT TTA CCT GAA AAT ACT AAT GAT TTC ATA AGC AGT AAG CAC     1248
Val Pro Leu Leu Pro Glu Asn Thr Asn Asp Phe Ile Ser Ser Lys His
                405             410             415

CAT GAG GTA GGA GGT AAA CAC TAT AAA GTG GAA GCA TGT TGC AAG AAT     1296
His Glu Val Gly Gly Lys His Tyr Lys Val Glu Ala Cys Cys Lys Asn
            420             425             430

CTA AGC TAT GTG AAA TTT GGT ATA TAT TAT GAG GAT AAT GAG AAG AAC     1344
```

```
Leu Ser Tyr Val Lys Phe Gly Ile Tyr Glu Asp Asn Glu Lys Asn
        435                 440                 445

ACC AAA ATT GAA ACA GAA CAA TAC CAC CAA TTT TTG TTA GGT CTC CGT        1392
Thr Lys Ile Glu Thr Glu Gln Tyr His Gln Phe Leu Leu Gly Leu Arg
        450                 455                 460

ACT CCC AGT TCT CAA ATT CCT GCA ACG GGA AAC GTG AAA TAT CGC GGT        1440
Thr Pro Ser Ser Gln Ile Pro Ala Thr Gly Asn Val Lys Tyr Arg Gly
465                 470                 475                 480

AGT TGG TTT GGT TAT ATT GGT GAT GAC AAG ACA TCT TAC TCC ACT ACT        1488
Ser Trp Phe Gly Tyr Ile Gly Asp Asp Lys Thr Ser Tyr Ser Thr Thr
                485                 490                 495

GGA GAT AAA AAT GCT CTC GCC GAG TTT GAT GTA AAT TTT ACC GAT AAA        1536
Gly Asp Lys Asn Ala Leu Ala Glu Phe Asp Val Asn Phe Thr Asp Lys
                500                 505                 510

AAG CTA ACA GGC GAA TTA AAA CGA GCC GAT AAT CAA AAT ACC GTA TTT        1584
Lys Leu Thr Gly Glu Leu Lys Arg Ala Asp Asn Gln Asn Thr Val Phe
            515                 520                 525

AGA ATT AAT GCA GAC TTT AAA AAT AAT GAT AAT GCC TTC AAA GGT ACA        1632
Arg Ile Asn Ala Asp Phe Lys Asn Asn Asp Asn Ala Phe Lys Gly Thr
        530                 535                 540

GCA ACC GCA GAA AAT TTT GTA ATA GAT GGT AAC AAT AGT CAA ACT GGA        1680
Ala Thr Ala Glu Asn Phe Val Ile Asp Gly Asn Asn Ser Gln Thr Gly
545                 550                 555                 560

AAT ACC CAA ATT AAT ATT AAA ACT GAA GTA AAT GGG GCA TTT TAT GGT        1728
Asn Thr Gln Ile Asn Ile Lys Thr Glu Val Asn Gly Ala Phe Tyr Gly
                565                 570                 575

CCG AAC GCT ACA GAA TTA GGC GGT TAT TTC ACT TAT AAC GGA AAA AAT        1776
Pro Asn Ala Thr Glu Leu Gly Gly Tyr Phe Thr Tyr Asn Gly Lys Asn
                580                 585                 590

CCT ACA GAT AAA AAT TCT GAA AGT TCC TCA ACC GTA CCT TCA CCA CCC        1824
Pro Thr Asp Lys Asn Ser Glu Ser Ser Ser Thr Val Pro Ser Pro Pro
            595                 600                 605

AAT TCA CCA AAT GCA AGA GCT GCA GTT GTC TTT GGT GCT AAA AAA CAA        1872
Asn Ser Pro Asn Ala Arg Ala Ala Val Val Phe Gly Ala Lys Lys Gln
        610                 615                 620

GTA GAA AAA AAC AAC AAG TAAAAACAAC CAAGTAATGG AATACTAAAA              1920
Val Glu Lys Asn Asn Lys
625                 630

ATGACTAAAA AAGCTTCTAG AAGCCGAATT C                                     1951

(2) INFORMATION FOR SEQ ID NO: 113:

(i) SEQUENCE CHARACTERISTICS:
        (A) LENGTH: 630 amino acids
        (B) TYPE: amino acid
        (D) TOPOLOGY: linear (ii) MOLECULE TYPE: protein (xi) SEQUENCE DESCRIPTION: SEQ ID NO: 113:

Met Lys Ser Val Pro Leu Ile Ser Gly Gly Leu Ser Leu Leu Leu Ser
1               5                   10                  15

Ala Cys Ser Gly Gly Gly Gly Ser Phe Asp Val Asp Asp Val Ser Asn
                20                  25                  30

Pro Ser Ser Ser Lys Pro Arg Tyr Gln Asp Asp Thr Ser Ser Gln Arg
            35                  40                  45

Thr Lys Ser Asn Leu Glu Lys Leu Ser Ile Pro Ser Leu Gly Gly Gly
        50                  55                  60

Met Lys Leu Val Ala Gln Asn Leu Ser Gly Asn Lys Glu Pro Ser Phe
65                  70                  75                  80
```

-continued

```
Leu Asn Gly Asn Asp Tyr Met Ile Phe Ser Ser Arg Ser Thr Ile Lys
             85                  90                  95

Asp Asp Val Glu Asn Asn Thr Asn Gly Gly Asp Tyr Ile Gly Ser
        100                 105                 110

Ile Asp Glu Pro Ser Thr Thr Asn Pro Leu Glu Lys His His Gly Gln
            115                 120                 125

Arg Tyr Val Tyr Ser Gly Leu Tyr Tyr Ile Gln Ser Trp Ser Leu Arg
        130                 135                 140

Asp Leu Pro Lys Lys Phe Tyr Ser Gly Tyr Tyr Gly Tyr Ala Tyr Tyr
145                 150                 155                 160

Phe Gly Lys Glu Thr Ala Thr Thr Leu Pro Val Asn Gly Glu Ala Thr
                165                 170                 175

Tyr Lys Gly Thr Trp Asp Phe Ile Thr Ala Thr Arg Asn Gly Lys Ser
            180                 185                 190

Tyr Ser Leu Leu Ser Asn Asn Arg Gln Ala Tyr Ser Lys Arg Ser Ala
        195                 200                 205

Ile Pro Glu Asp Ile Asp Leu Glu Asn Asp Pro Lys Asn Gly Glu Thr
    210                 215                 220

Arg Leu Thr Ser Glu Phe Thr Val Asn Phe Gly Thr Lys Lys Leu Thr
225                 230                 235                 240

Gly Gly Leu Tyr Tyr His Leu Arg Lys Thr Asn Ala Asn Glu Asn Gln
                245                 250                 255

Asn Arg Lys His Lys Leu Tyr Asn Leu Glu Ala Asp Val Tyr Ser Asn
            260                 265                 270

Arg Phe Arg Gly Lys Val Lys Pro Thr Lys Glu Ser Ser Glu Glu His
        275                 280                 285

Pro Phe Thr Ser Glu Gly Thr Leu Glu Gly Gly Phe Tyr Gly Pro Asn
    290                 295                 300

Ala Glu Glu Leu Gly Gly Lys Phe Leu Ala Ser Asp Lys Lys Val Phe
305                 310                 315                 320

Gly Val Phe Ser Ala Lys Glu Gln Gln Glu Thr Glu Glu Asn Lys Lys
                325                 330                 335

Leu Leu Lys Glu Thr Leu Ile Asp Gly Lys Leu Thr Thr Phe Ser Thr
            340                 345                 350

Lys Lys Thr Asn Ala Thr Thr Asp Ala Thr Thr Ser Thr Thr Thr Ser
        355                 360                 365

Thr Ala Thr Asn Ala Thr Ala Asp Ala Glu Asn Phe Thr Thr Lys Asp
    370                 375                 380

Ile Ser Ser Phe Gly Glu Ala Asp Tyr Leu Leu Ile Asp Asn Tyr Pro
385                 390                 395                 400

Val Pro Leu Leu Pro Glu Asn Thr Asn Asp Phe Ile Ser Ser Lys His
                405                 410                 415

His Glu Val Gly Gly Lys His Tyr Lys Val Glu Ala Cys Cys Lys Asn
            420                 425                 430

Leu Ser Tyr Val Lys Phe Gly Ile Tyr Tyr Glu Asp Asn Glu Lys Asn
        435                 440                 445

Thr Lys Ile Glu Thr Glu Gln Tyr His Gln Phe Leu Leu Gly Leu Arg
    450                 455                 460

Thr Pro Ser Ser Gln Ile Pro Ala Thr Gly Asn Val Lys Tyr Arg Gly
465                 470                 475                 480

Ser Trp Phe Gly Tyr Ile Gly Asp Lys Thr Ser Tyr Ser Thr Thr
                485                 490                 495

Gly Asp Lys Asn Ala Leu Ala Glu Phe Asp Val Asn Phe Thr Asp Lys
            500                 505                 510
```

```
Lys Leu Thr Gly Glu Leu Lys Arg Ala Asp Asn Gln Asn Thr Val Phe
            515                 520                 525

Arg Ile Asn Ala Asp Phe Lys Asn Asn Asp Asn Ala Phe Lys Gly Thr
        530                 535                 540

Ala Thr Ala Glu Asn Phe Val Ile Asp Gly Asn Asn Ser Gln Thr Gly
545                 550                 555                 560

Asn Thr Gln Ile Asn Ile Lys Thr Glu Val Asn Gly Ala Phe Tyr Gly
                565                 570                 575

Pro Asn Ala Thr Glu Leu Gly Gly Tyr Phe Thr Tyr Asn Gly Lys Asn
            580                 585                 590

Pro Thr Asp Lys Asn Ser Glu Ser Ser Ser Thr Val Pro Ser Pro Pro
            595                 600                 605

Asn Ser Pro Asn Ala Arg Ala Ala Val Val Phe Gly Ala Lys Lys Gln
        610                 615                 620

Val Glu Lys Asn Asn Lys
625                 630

(2) INFORMATION FOR SEQ ID NO: 114:

(i) SEQUENCE CHARACTERISTICS:
        (A) LENGTH: 1955 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..1893

(xi) SEQUENCE DESCRIPTION: SEQ ID NO: 114:

ATG AAA TCT GTA CCT CTT ATC TCT GGT GGA CTT TCC TTT TTA CTA AGT        48
Met Lys Ser Val Pro Leu Ile Ser Gly Gly Leu Ser Phe Leu Leu Ser
1               5                   10                  15

GCT TGT AGC GGA GGG GGG TCT TTT GAT GTA GAT AAC GTC TCT AAT ACC        96
Ala Cys Ser Gly Gly Gly Ser Phe Asp Val Asp Asn Val Ser Asn Thr
            20                  25                  30

CCC TCT TCT AAA CCA CGT TAT CAA GAC GAT ACC TCG AAT CAA AGA ACA       144
Pro Ser Ser Lys Pro Arg Tyr Gln Asp Asp Thr Ser Asn Gln Arg Thr
        35                  40                  45

AAA TCT AAA TTG GAA AAG TTG TCC ATT CCT TCT TTA GGA GGA GGG ATG       192
Lys Ser Lys Leu Glu Lys Leu Ser Ile Pro Ser Leu Gly Gly Gly Met
    50                  55                  60

AAG TTA GTT GTG CAA AAT TTT GCT GGT GCT AAA GAA CCT AGT TTC TTA       240
Lys Leu Val Val Gln Asn Phe Ala Gly Ala Lys Glu Pro Ser Phe Leu
65                  70                  75                  80

AAT GAA AAT GAC TAT ATA TCA TAT TTT TCC TCA CTT TCT ATG ATT AAA       288
Asn Glu Asn Asp Tyr Ile Ser Tyr Phe Ser Ser Leu Ser Met Ile Lys
                85                  90                  95

GAT GAT GTT GAA AAT AAC AAT AAA AAT AAG GAT ACT CCA ATT GGC TCA       336
Asp Asp Val Glu Asn Asn Asn Lys Asn Lys Asp Thr Pro Ile Gly Ser
            100                 105                 110

ATA GAC GAG CCT AGA GCA CCA AAT TCA AAC GAA AAT CAT CAA AAT CAT       384
Ile Asp Glu Pro Arg Ala Pro Asn Ser Asn Glu Asn His Gln Asn His
        115                 120                 125

CAT GGA CAG CAA TAT GTA TAT TCG GGT CTT TAT TAT ATT CCA TCG TGG       432
His Gly Gln Gln Tyr Val Tyr Ser Gly Leu Tyr Tyr Ile Pro Ser Trp
    130                 135                 140

CGT CTA ATA AAT TTA CCA AAT AAG TTT TAT TCA GGT TAC TAT GGA TAT       480
Arg Leu Ile Asn Leu Pro Asn Lys Phe Tyr Ser Gly Tyr Tyr Gly Tyr
145                 150                 155                 160
```

-continued

| | |
|---|---|
| GCG TAT TAC TTT GGC AAG CAA ACT GCC ACT ACA TTA CCT GTA AAT GGC<br>Ala Tyr Tyr Phe Gly Lys Gln Thr Ala Thr Thr Leu Pro Val Asn Gly<br>               165                     170                     175 | 528 |
| GAA GCA ACG TAT AAA GGA ACT TGG AGC TTC ATC ACC GCA ACT GAA AGA<br>Glu Ala Thr Tyr Lys Gly Thr Trp Ser Phe Ile Thr Ala Thr Glu Arg<br>               180                     185                     190 | 576 |
| GGC AAA AAT TAT TCT TTG TTC AAT AAT AGA GGT CAA GCT TAT TCT CGA<br>Gly Lys Asn Tyr Ser Leu Phe Asn Asn Arg Gly Gln Ala Tyr Ser Arg<br>               195                     200                     205 | 624 |
| CGT AGT GCT ACT CCA GGA GAT ATT GAT TTA GAA AAC GGT GAC GCA GGC<br>Arg Ser Ala Thr Pro Gly Asp Ile Asp Leu Glu Asn Gly Asp Ala Gly<br>210                     215                     220 | 672 |
| TTA ACA AGT GAA TTT ACT GTC AAT TTT GGT ACA AAA AAG CTC ACT GGA<br>Leu Thr Ser Glu Phe Thr Val Asn Phe Gly Thr Lys Lys Leu Thr Gly<br>225                     230                     235                     240 | 720 |
| GAA CCT TAT TAT AAT GAA AGG GAA ACA AAT CTT AAT CAA TCA AAA GAT<br>Glu Pro Tyr Tyr Asn Glu Arg Glu Thr Asn Leu Asn Gln Ser Lys Asp<br>                     245                     250                     255 | 768 |
| AGA AAA CAT AAA CTC TAC GAT CTA GAA GCT GAT GTG TAT AGC AAC CGA<br>Arg Lys His Lys Leu Tyr Asp Leu Glu Ala Asp Val Tyr Ser Asn Arg<br>               260                     265                     270 | 816 |
| TTC AGA GGT ACA GTA AAG CCA ACC AAA AAA GAG TCT TCT GAA GAA CAT<br>Phe Arg Gly Thr Val Lys Pro Thr Lys Lys Glu Ser Ser Glu Glu His<br>               275                     280                     285 | 864 |
| CCC TTT ACC AGC GAG GGA ACA TTA GAA GGT GGT TTT TAT GGG CCT AAT<br>Pro Phe Thr Ser Glu Gly Thr Leu Glu Gly Gly Phe Tyr Gly Pro Asn<br>               290                     295                     300 | 912 |
| GCT GAA GAA CTA GGG GGA AAA TTT TTA GCT AGC GAT AAA AAA GTT TTT<br>Ala Glu Glu Leu Gly Gly Lys Phe Leu Ala Ser Asp Lys Lys Val Phe<br>305                     310                     315                     320 | 960 |
| GGG GTA TTT AGT GCC AAA GAA ACG GAA GAA AAA CCA AAA TTA CCC AAA<br>Gly Val Phe Ser Ala Lys Glu Thr Glu Glu Lys Pro Lys Leu Pro Lys<br>                     325                     330                     335 | 1008 |
| GAA ACC TTA ATT GAT GGC AAG CTA ACT ACT TTC TCT AAA ACA ACC GAT<br>Glu Thr Leu Ile Asp Gly Lys Leu Thr Thr Phe Ser Lys Thr Thr Asp<br>                     340                     345                     350 | 1056 |
| ACA ACA ACC AAT AAA ACA ACC AGT GCA AAA ACC AAT ACA GAA AAC TTT<br>Thr Thr Thr Asn Lys Thr Thr Ser Ala Lys Thr Asn Thr Glu Asn Phe<br>               355                     360                     365 | 1104 |
| ACG ACA AAA GAT ATA CCA AGT TTT GGT GAA GCT GAT TAT CTT TTA ATT<br>Thr Thr Lys Asp Ile Pro Ser Phe Gly Glu Ala Asp Tyr Leu Leu Ile<br>370                     375                     380 | 1152 |
| GAT AAT TAC CCT ATT CCG CTT TTA CCT GAG AGT GGT GAT TTC ATA AGT<br>Asp Asn Tyr Pro Ile Pro Leu Leu Pro Glu Ser Gly Asp Phe Ile Ser<br>385                     390                     395                     400 | 1200 |
| AGT AAG CAC CAT GAG GTA GGA GGT AAA CGC TAT AAA GTG GAA GCA TGT<br>Ser Lys His His Glu Val Gly Gly Lys Arg Tyr Lys Val Glu Ala Cys<br>               405                     410                     415 | 1248 |
| TGC AAG AAT CTA TGC TAT GTG AAA TTT GGT ATG TAT TAT GAG GAT AAA<br>Cys Lys Asn Leu Cys Tyr Val Lys Phe Gly Met Tyr Tyr Glu Asp Lys<br>                     420                     425                     430 | 1296 |
| GAG AAC AAC AAA AAT GAA ACA GAC AAA GAA AAA GAA AAA CAA ACG ACA<br>Glu Asn Asn Lys Asn Glu Thr Asp Lys Glu Lys Glu Lys Gln Thr Thr<br>               435                     440                     445 | 1344 |
| ACA TCT ATC AAG ACT TAT TAT CAA TTC TTA TTA GGT CTC CGG ACT CCC<br>Thr Ser Ile Lys Thr Tyr Tyr Gln Phe Leu Leu Gly Leu Arg Thr Pro<br>450                     455                     460 | 1392 |
| AGT TCT GAA ATT CCT AAA ATG GGA AAC GTG ACA TAT CGC GGT AGT TGG<br>Ser Ser Glu Ile Pro Lys Met Gly Asn Val Thr Tyr Arg Gly Ser Trp<br>465                     470                     475                     480 | 1440 |

| | | | |
|---|---|---|---|
| TTT GGT TAT ATT GGT GAT GAC AAG ACA TCT TAC TCC GCT ACA GGA GAT | | | 1488 |
| Phe Gly Tyr Ile Gly Asp Asp Lys Thr Ser Tyr Ser Ala Thr Gly Asp | | | |
| 485 490 495 | | | |
| AAA CGA CAA GAT AAA AAT GCT CCC GCC GAG TTT AAT GCT GAT TTT AAC | | | 1536 |
| Lys Arg Gln Asp Lys Asn Ala Pro Ala Glu Phe Asn Ala Asp Phe Asn | | | |
| 500 505 510 | | | |
| AAT AAA AAG CTA ACA GGC ACA TCA AAA CGA CAC GAT AAT CAA AAT CCC | | | 1584 |
| Asn Lys Lys Leu Thr Gly Thr Ser Lys Arg His Asp Asn Gln Asn Pro | | | |
| 515 520 525 | | | |
| GTG TTT AAC ATT AAG GCA ACC TTT CAA AAT GGT CGG AAT GAC TTT GAA | | | 1632 |
| Val Phe Asn Ile Lys Ala Thr Phe Gln Asn Gly Arg Asn Asp Phe Glu | | | |
| 530 535 540 | | | |
| GGT ACA GCA ACC GCA GAA AAT TTT GTA ATA GAT GGT AAA GAT AGT CAA | | | 1680 |
| Gly Thr Ala Thr Ala Glu Asn Phe Val Ile Asp Gly Lys Asp Ser Gln | | | |
| 545 550 555 560 | | | |
| GGA AAT ACC CCA ATT AAT ATT ACA ACT AAA GTA AAC GGG GCA TTT TAT | | | 1728 |
| Gly Asn Thr Pro Ile Asn Ile Thr Thr Lys Val Asn Gly Ala Phe Tyr | | | |
| 565 570 575 | | | |
| GGA CCT GAT GCT TCT GAA TTA GGC GGT TAT TTC ACC TAT AAC GGA AAA | | | 1776 |
| Gly Pro Asp Ala Ser Glu Leu Gly Gly Tyr Phe Thr Tyr Asn Gly Lys | | | |
| 580 585 590 | | | |
| GAC ACT ATA ACT AAA AAT ACT GAA AGT TCC TCA ACC GTA CCT TCA CCA | | | 1824 |
| Asp Thr Ile Thr Lys Asn Thr Glu Ser Ser Ser Thr Val Pro Ser Pro | | | |
| 595 600 605 | | | |
| CCC AAT TCA CCA AAT GCA AGA GCT GCA GTT GTG TTT GGA GCT AAA AAA | | | 1872 |
| Pro Asn Ser Pro Asn Ala Arg Ala Ala Val Val Phe Gly Ala Lys Lys | | | |
| 610 615 620 | | | |
| CAA GTA GAA ACA ACC AAC AAG TAGAAAAAAA CAAATAATGG AATACTAAAA | | | 1923 |
| Gln Val Glu Thr Thr Asn Lys | | | |
| 625 630 | | | |
| ATGACTAAAA AAGCTTCTAG AAAGCCGAAT TC | | | 1955 |

(2) INFORMATION FOR SEQ ID NO: 115:

(i) SEQUENCE CHARACTERISTICS:
        (A) LENGTH: 631 amino acids
        (B) TYPE: amino acid
        (D) TOPOLOGY: linear (ii) MOLECULE TYPE: protein (xi) SEQUENCE DESCRIPTION: SEQ ID NO: 115:

```
Met Lys Ser Val Pro Leu Ile Ser Gly Gly Leu Ser Phe Leu Leu Ser
  1               5                  10                  15

Ala Cys Ser Gly Gly Gly Ser Phe Asp Val Asp Asn Val Ser Asn Thr
                 20                  25                  30

Pro Ser Ser Lys Pro Arg Tyr Gln Asp Thr Ser Asn Gln Arg Thr
             35                  40                  45

Lys Ser Lys Leu Glu Lys Leu Ser Ile Pro Ser Leu Gly Gly Met
         50                  55                  60

Lys Leu Val Val Gln Asn Phe Ala Gly Ala Lys Glu Pro Ser Phe Leu
 65                  70                  75                  80

Asn Glu Asn Asp Tyr Ile Ser Tyr Phe Ser Ser Leu Ser Met Ile Lys
                     85                  90                  95

Asp Asp Val Glu Asn Asn Lys Asn Lys Asp Thr Pro Ile Gly Ser
                100                 105                 110

Ile Asp Glu Pro Arg Ala Pro Asn Ser Asn Glu Asn His Gln Asn His
            115                 120                 125

His Gly Gln Gln Tyr Val Tyr Ser Gly Leu Tyr Tyr Ile Pro Ser Trp
        130                 135                 140
```

```
Arg Leu Ile Asn Leu Pro Asn Lys Phe Tyr Ser Gly Tyr Tyr Gly Tyr
145                 150                 155                 160

Ala Tyr Tyr Phe Gly Lys Gln Thr Ala Thr Thr Leu Pro Val Asn Gly
                165                 170                 175

Glu Ala Thr Tyr Lys Gly Thr Trp Ser Phe Ile Thr Ala Thr Glu Arg
                180                 185                 190

Gly Lys Asn Tyr Ser Leu Phe Asn Asn Arg Gly Gln Ala Tyr Ser Arg
                195                 200                 205

Arg Ser Ala Thr Pro Gly Asp Ile Asp Leu Glu Asn Gly Asp Ala Gly
210                 215                 220

Leu Thr Ser Glu Phe Thr Val Asn Phe Gly Thr Lys Lys Leu Thr Gly
225                 230                 235                 240

Glu Pro Tyr Tyr Asn Glu Arg Glu Thr Asn Leu Asn Gln Ser Lys Asp
                245                 250                 255

Arg Lys His Lys Leu Tyr Asp Leu Glu Ala Asp Val Tyr Ser Asn Arg
                260                 265                 270

Phe Arg Gly Thr Val Lys Pro Thr Lys Lys Glu Ser Glu Glu His
                275                 280                 285

Pro Phe Thr Ser Glu Gly Thr Leu Glu Gly Gly Phe Tyr Gly Pro Asn
290                 295                 300

Ala Glu Glu Leu Gly Gly Lys Phe Leu Ala Ser Asp Lys Lys Val Phe
305                 310                 315                 320

Gly Val Phe Ser Ala Lys Glu Thr Glu Lys Pro Lys Leu Pro Lys
                325                 330                 335

Glu Thr Leu Ile Asp Gly Lys Leu Thr Thr Phe Ser Lys Thr Thr Asp
                340                 345                 350

Thr Thr Thr Asn Lys Thr Thr Ser Ala Lys Thr Asn Thr Glu Asn Phe
                355                 360                 365

Thr Thr Lys Asp Ile Pro Ser Phe Gly Glu Ala Asp Tyr Leu Leu Ile
                370                 375                 380

Asp Asn Tyr Pro Ile Pro Leu Leu Pro Glu Ser Gly Asp Phe Ile Ser
385                 390                 395                 400

Ser Lys His His Glu Val Gly Gly Lys Arg Tyr Lys Val Glu Ala Cys
                405                 410                 415

Cys Lys Asn Leu Cys Tyr Val Lys Phe Gly Met Tyr Tyr Glu Asp Lys
                420                 425                 430

Glu Asn Asn Lys Asn Glu Thr Asp Lys Glu Lys Glu Lys Gln Thr Thr
                435                 440                 445

Thr Ser Ile Lys Thr Tyr Tyr Gln Phe Leu Leu Gly Leu Arg Thr Pro
                450                 455                 460

Ser Ser Glu Ile Pro Lys Met Gly Asn Val Thr Tyr Arg Gly Ser Trp
465                 470                 475                 480

Phe Gly Tyr Ile Gly Asp Asp Lys Thr Ser Tyr Ser Ala Thr Gly Asp
                485                 490                 495

Lys Arg Gln Asp Lys Asn Ala Pro Ala Glu Phe Asn Ala Asp Phe Asn
                500                 505                 510

Asn Lys Lys Leu Thr Gly Thr Ser Lys Arg His Asp Asn Gln Asn Pro
                515                 520                 525

Val Phe Asn Ile Lys Ala Thr Phe Gln Asn Gly Arg Asn Asp Phe Glu
                530                 535                 540

Gly Thr Ala Thr Ala Glu Asn Phe Val Ile Asp Gly Lys Asp Ser Gln
545                 550                 555                 560

Gly Asn Thr Pro Ile Asn Ile Thr Thr Lys Val Asn Gly Ala Phe Tyr
```

```
                    565                 570                 575
Gly Pro Asp Ala Ser Glu Leu Gly Gly Tyr Phe Thr Tyr Asn Gly Lys
            580                 585                 590

Asp Thr Ile Thr Lys Asn Thr Glu Ser Ser Thr Val Pro Ser Pro
        595                 600                 605

Pro Asn Ser Pro Asn Ala Arg Ala Ala Val Val Phe Gly Ala Lys Lys
    610                 615                 620

Gln Val Glu Thr Thr Asn Lys
625                 630
```

(2) INFORMATION FOR SEQ ID NO: 116:

(i) SEQUENCE CHARACTERISTICS:
        (A) LENGTH: 100 base pairs
        (B) TYPE: nucleic acid
        (C) STRANDEDNESS: single
        (D) TOPOLOGY: linear (xi) SEQUENCE DESCRIPTION: SEQ ID NO: 116:

```
TCTAACTTGA CATTATTACA AAAAAGATC AATAATGCGA ATTATTATCA ATTTTGTATG      60
AGTATATAAT TCTATGAAAT CTGTACCTCT TATCTCTGGT                          100
```

(2) INFORMATION FOR SEQ ID NO: 117:

(i) SEQUENCE CHARACTERISTICS:
        (A) LENGTH: 100 base pairs
        (B) TYPE: nucleic acid
        (C) STRANDEDNESS: single
        (D) TOPOLOGY: linear (xi) SEQUENCE DESCRIPTION: SEQ ID NO: 117:

```
TCTAACTTGA CATTATTACA AAAAAGATC AATAATGCGA ATTATTATCA ATTTTGTATG      60
AGTATATAAT TCTATGAAAT CTGTACCTCT TATCTCTGGT                          100
```

(2) INFORMATION FOR SEQ ID NO: 118:

(i) SEQUENCE CHARACTERISTICS:
        (A) LENGTH: 99 base pairs
        (B) TYPE: nucleic acid
        (C) STRANDEDNESS: single
        (D) TOPOLOGY: linear (xi) SEQUENCE DESCRIPTION: SEQ ID NO: 118:

```
TCTAAGTTGA CATTATTACA AAAAAGAAC AATAATGCGA ATTATTATCA ATTTTGTATA      60
AGTATTAATT CTATGAAATC TGTACCTCTT ATCTCTGGT                            99
```

(2) INFORMATION FOR SEQ ID NO: 119:

(i) SEQUENCE CHARACTERISTICS:
        (A) LENGTH: 100 base pairs
        (B) TYPE: nucleic acid
        (C) STRANDEDNESS: single
        (D) TOPOLOGY: linear (xi) SEQUENCE DESCRIPTION: SEQ ID NO: 119:

```
TCTAAGTTGA CATTATTACA AAAAAGAAC AATAATGCGA ATTATTATCA ATTTTGTATA      60
AGAATATAAT TCTATGAAAT CTGTACCTCT TATCTCTGGT                          100
```

(2) INFORMATION FOR SEQ ID NO: 120:

(i) SEQUENCE CHARACTERISTICS:
        (A) LENGTH: 35 base pairs
        (B) TYPE: nucleic acid (C) STRANDEDNESS: single
            (D) TOPOLOGY: linear (xi) SEQUENCE DESCRIPTION: SEQ ID NO: 120:

GGATCCATAT GAAATCTGTA CCTCTTATCT CTGGT                                    35

(2) INFORMATION FOR SEQ ID NO: 121:

(i) SEQUENCE CHARACTERISTICS:
            (A) LENGTH: 61 base pairs
            (B) TYPE: nucleic acid
            (C) STRANDEDNESS: single
            (D) TOPOLOGY: linear (xi) SEQUENCE DESCRIPTION: SEQ ID NO: 121:

GTAGAAACAA CCAAATAATG GAATACTAAA AATGACTAAA AAACCCTATT TTCGCCTAAG         60

T                                                                        61

(2) INFORMATION FOR SEQ ID NO: 122:

(i) SEQUENCE CHARACTERISTICS:
            (A) LENGTH: 61 base pairs
            (B) TYPE: nucleic acid
            (C) STRANDEDNESS: single
            (D) TOPOLOGY: linear (xi) SEQUENCE DESCRIPTION: SEQ ID NO: 122:

GTAGAAACAA CCAAATAATG GAATACTAAA AATGACTAAA AAACCCTATT TTCGCCTAAG         60

T                                                                        61

(2) INFORMATION FOR SEQ ID NO: 123:

(i) SEQUENCE CHARACTERISTICS:
            (A) LENGTH: 61 base pairs
            (B) TYPE: nucleic acid
            (C) STRANDEDNESS: single
            (D) TOPOLOGY: linear (xi) SEQUENCE DESCRIPTION: SEQ ID NO: 123:

GTAGAAACAA CCAAGTAATG GAATACTAAA AATGACTAAA AAACCCTATT TTCGCCTAAG         60

T                                                                        61

(2) INFORMATION FOR SEQ ID NO: 124:

(i) SEQUENCE CHARACTERISTICS:
            (A) LENGTH: 78 base pairs
            (B) TYPE: nucleic acid
            (C) STRANDEDNESS: single
            (D) TOPOLOGY: linear (xi) SEQUENCE DESCRIPTION: SEQ ID NO: 124:

GTAGAAACAA CCAACAAGTA AAAACAACCA AGTAATGGAA TACTAAAAAT GACTAAAAAA         60

CCCTATTTTC GCCTAAGT                                                      78

(2) INFORMATION FOR SEQ ID NO: 125:

(i) SEQUENCE CHARACTERISTICS:
            (A) LENGTH: 43 base pairs
            (B) TYPE: nucleic acid
            (C) STRANDEDNESS: single
            (D) TOPOLOGY: linear (xi) SEQUENCE DESCRIPTION: SEQ ID NO: 125:

GTAGAAACAA CCAAATAATG GAATACTAAA AATGACTAAA AAA                          43

(2) INFORMATION FOR SEQ ID NO: 126:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (xi) SEQUENCE DESCRIPTION: SEQ ID NO: 126:

```
GTAGAAACAA CCAACAAGTA AAAACAACCA AGTAATGGAA TACTAAAAAT GACTAAAAAA      60
```

(2) INFORMATION FOR SEQ ID NO: 127:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (xi) SEQUENCE DESCRIPTION: SEQ ID NO: 127:

```
GTAGAAAAAA ACAACTAGTA AAAACAACCA AGTAATGGAA TACTAAAAAT GACTAAAAAA      60
```

(2) INFORMATION FOR SEQ ID NO: 128:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (xi) SEQUENCE DESCRIPTION: SEQ ID NO: 128:

```
GTAGAAACAA CCAACAAGTA GAAAAAAACA AATAATGGAA TACTAAAAAT GACTAAAAAA      60
```

(2) INFORMATION FOR SEQ ID NO: 129:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO: 129:

```
TCTAGAAGCT TTTTTAGTCA TTTTTAGTAT TCCAT                                 35
```

(2) INFORMATION FOR SEQ ID NO: 130:

(i) SEQUENCE CHARACTERISTICS:
        (A) LENGTH: 58 base pairs
        (B) TYPE: nucleic acid
        (C) STRANDEDNESS: single
        (D) TOPOLOGY: linear (xi) SEQUENCE DESCRIPTION: SEQ ID NO: 130:

```
TATGTGTTCT GGTGGTGGTT CTTTCGACGT TGACAACGTT TCTAACACTC CCTCTTCT        58
```

(2) INFORMATION FOR SEQ ID NO: 131:

(i) SEQUENCE CHARACTERISTICS:
        (A) LENGTH: 59 base pairs
        (B) TYPE: nucleic acid
        (C) STRANDEDNESS: single
        (D) TOPOLOGY: linear (xi) SEQUENCE DESCRIPTION: SEQ ID NO: 131:

```
ACACAAGACC ACCACCAAGA AAGCTGCAAC TGTTGCAAAG ATTGTGAGGG AGAAGATTT       59
```

(2) INFORMATION FOR SEQ ID NO: 132:

(i) SEQUENCE CHARACTERISTICS:
        (A) LENGTH: 9 amino acids
        (B) TYPE: amino acid
        (C) STRANDEDNESS: single
        (D) TOPOLOGY: linear (xi) SEQUENCE DESCRIPTION: SEQ ID NO: 132:

Asn Pro Ala Ser Thr Thr Asn Lys Asp
1               5

(2) INFORMATION FOR SEQ ID NO: 133:

(i) SEQUENCE CHARACTERISTICS:
        (A) LENGTH: 17 amino acids
        (B) TYPE: amino acid
        (C) STRANDEDNESS: single
        (D) TOPOLOGY: linear (xi) SEQUENCE DESCRIPTION: SEQ ID NO: 133:

Asn Pro Ala Ser Thr Thr Ser Leu Glu Gly Gly Phe Tyr Gly Pro Lys
1               5                   10                  15
Asp (2) INFORMATION FOR SEQ ID NO: 134:

(i) SEQUENCE CHARACTERISTICS:
        (A) LENGTH: 16 amino acids
        (B) TYPE: amino acid
        (C) STRANDEDNESS: single
        (D) TOPOLOGY: linear (xi) SEQUENCE DESCRIPTION: SEQ ID NO: 134:

Asn Pro Ala Ser Thr Thr Ser Leu Glu Gly Gly Phe Tyr Gly Lys Asp
1               5                   10                  15

(2) INFORMATION FOR SEQ ID NO: 135:

(i) SEQUENCE CHARACTERISTICS:
        (A) LENGTH: 16 amino acids
        (B) TYPE: amino acid
        (C) STRANDEDNESS: single
        (D) TOPOLOGY: linear (xi) SEQUENCE DESCRIPTION: SEQ ID NO: 135:

Asn Pro Ala Ser Thr Thr Leu Glu Gly Gly Phe Tyr Gly Pro Lys Asp
1               5                   10                  15

(2) INFORMATION FOR SEQ ID NO: 136:

(i) SEQUENCE CHARACTERISTICS:
        (A) LENGTH: 15 amino acids
        (B) TYPE: amino acid
        (C) STRANDEDNESS: single
        (D) TOPOLOGY: linear (xi) SEQUENCE DESCRIPTION: SEQ ID NO: 136:

Asn Pro Ala Ser Thr Thr Leu Glu Gly Gly Phe Tyr Gly Lys Asp
1               5                   10                  15

(2) INFORMATION FOR SEQ ID NO: 137:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO: 137:

```
TCTAGAAGCT TTTTTAGTCA TTTTTAGTAT TCCAT                                35
```

(2) INFORMATION FOR SEQ ID NO: 138:

(i) SEQUENCE CHARACTERISTICS:
        (A) LENGTH: 4 amino acids
        (B) TYPE: amino acid
        (C) STRANDEDNESS: single
        (D) TOPOLOGY: linear (xi) SEQUENCE DESCRIPTION: SEQ ID NO: 138:

```
Met Thr Lys Lys
1
```

(2) INFORMATION FOR SEQ ID NO: 139:

(i) SEQUENCE CHARACTERISTICS:
        (A) LENGTH: 5 amino acids
        (B) TYPE: amino acid
        (C) STRANDEDNESS: single
        (D) TOPOLOGY: linear (xi) SEQUENCE DESCRIPTION: SEQ ID NO: 139:

```
Glu Gln Val Leu Asn
1               5
```

(2) INFORMATION FOR SEQ ID NO: 140:

(i) SEQUENCE CHARACTERISTICS:
        (A) LENGTH: 9 amino acids
        (B) TYPE: amino acid
        (C) STRANDEDNESS: single
        (D) TOPOLOGY: linear (xi) SEQUENCE DESCRIPTION: SEQ ID NO: 140:

```
Asp Ile Arg Asp Leu Thr Arg Tyr Asp
1               5
```

(2) INFORMATION FOR SEQ ID NO: 141:

(i) SEQUENCE CHARACTERISTICS:
        (A) LENGTH: 18 amino acids
        (B) TYPE: amino acid
        (C) STRANDEDNESS: single
        (D) TOPOLOGY: linear (xi) SEQUENCE DESCRIPTION: SEQ ID NO: 141:

```
Gly Ala Ile Asn Glu Ile Glu Tyr Glu Asn Val Lys Ala Val Glu Ile
1               5                   10                  15

Ser Lys
```

(2) INFORMATION FOR SEQ ID NO: 142:

(i) SEQUENCE CHARACTERISTICS:
        (A) LENGTH: 5 amino acids
        (B) TYPE: amino acid
        (C) STRANDEDNESS: single
        (D) TOPOLOGY: linear (xi) SEQUENCE DESCRIPTION: SEQ ID NO: 142:

```
Val Tyr Asn Leu Phe
1               5
```

(2) INFORMATION FOR SEQ ID NO: 143:

(i) SEQUENCE CHARACTERISTICS:
        (A) LENGTH: 9 amino acids

```
        (B) TYPE: amino acid
        (C) STRANDEDNESS: single
        (D) TOPOLOGY: linear (xi) SEQUENCE DESCRIPTION: SEQ ID NO: 143:

Leu Asn Tyr Arg Tyr Val Thr Trp Glu
1               5

(2) INFORMATION FOR SEQ ID NO: 144:

(i) SEQUENCE CHARACTERISTICS:
        (A) LENGTH: 9 amino acids
        (B) TYPE: amino acid
        (C) STRANDEDNESS: single
        (D) TOPOLOGY: linear (xi) SEQUENCE DESCRIPTION: SEQ ID NO: 144:

Cys Ser Gly Gly Gly Gly Ser Phe Asp
1               5

(2) INFORMATION FOR SEQ ID NO: 145:

(i) SEQUENCE CHARACTERISTICS:
        (A) LENGTH: 9 amino acids
        (B) TYPE: amino acid
        (C) STRANDEDNESS: single
        (D) TOPOLOGY: linear (xi) SEQUENCE DESCRIPTION: SEQ ID NO: 145:

Cys Leu Gly Gly Gly Gly Ser Phe Asp
1               5

(2) INFORMATION FOR SEQ ID NO: 146:

(i) SEQUENCE CHARACTERISTICS:
        (A) LENGTH: 8 amino acids
        (B) TYPE: amino acid
        (C) STRANDEDNESS: single
        (D) TOPOLOGY: linear (xi) SEQUENCE DESCRIPTION: SEQ ID NO: 146:

Leu Ser Gly Gly Phe Phe Gly Pro
1               5

(2) INFORMATION FOR SEQ ID NO: 147:

(i) SEQUENCE CHARACTERISTICS:
        (A) LENGTH: 10 amino acids
        (B) TYPE: amino acid
        (C) STRANDEDNESS: single
        (D) TOPOLOGY: linear (xi) SEQUENCE DESCRIPTION: SEQ ID NO: 147:

Met Lys Ser Val Pro Leu Ile Ser Gly Ser
1               5                   10
```

What we claim is:

1. A purified and isolated nucleic acid molecule encoding a fragment of a transferrin receptor protein of a strain of Haemophilus having only an amino acid sequence selected from the group consisting of SEQ ID NOS: 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84 and 85.

2. The nucleic acid molecule of claim 1, wherein the amino acid sequence is selected from the group consisting of SEQ ID NOS: 50, 61, 74 and 85.

3. A purified and isolated nucleic acid molecule having a DNA sequence selected from the group consisting of:
   (a) any one of the DNA sequences set out in FIGS. 3A to 3Q, 4A to 4Q, 5A to 5Q, 6A to 6Q, 7A to 7N, 8A to 8G, 9A to 9G, 10A to 10G or 11A to 11G (SEQ ID NOS: 1, 2, 3, 4, 105, 108, 110, 112, 114) or the complementary DNA sequence of any one of said sequences;
   (b) any one of the DNA sequences encoding one of the amino acid sequences set out in FIGS. 3A to 3Q, 4A to 4Q, 5A to 5Q, 6A to 6Q, 7A to 7N, 8A to 8G, 9A to 9G, 10A to 10G, or 11A to 11G (SEQ ID NOS: 5, 6, 7, 8, 9, 10, 11, 12, 106, 107, 109, 111, 113, 115) or the complementary DNA sequence thereto;

(c) a DNA sequence of a transferrin receptor gene from a strain of Haemophilus which has at least about 90% sequence identity with any of the DNA sequences defined in (a); and (d) a DNA sequence encoding a transferrin receptor protein from a strain of Haemophilus which has at least about 90% sequence identity with any one of the DNA sequences defined in (b).

4. A vector, comprising the nucleic acid molecule of claim 3.

5. The vector of claim 4 which is plasmid DS-712-1-3 having ATCC accession number 75603 or plasmid JB-1042-7-6 having ATCC accession number 75607.

6. An expression vector, comprising the nucleic acid molecule of claim 3 and a promoter operatively coupled to the nucleic acid molecule for expression by a host cell of a transferrin receptor protein of a strain of Haemophilus.

7. The expression vector of claim 6, wherein the nucleic acid molecule encodes an entire transferring receptor protein of the Haemophilus strain.

8. The expression vector of claim 6, wherein the nucleic acid molecule encodes only the Tbp1 protein or only the Tbp2 protein of the Haemophilus strain.

9. The expression vector of claim 6, wherein the promoter include a nucleic acid encoding a lipidation signal for expression of a lipidated form of the transferrin receptor portion from a host cell.

10. The expression vector of claim 6, wherein the promoter includes a nucleic acid encoding a lipidation signal for expression of a lipidated form of the transferrin receptor protein from a host cell.

11. The expression vector of claim 6, which is plasmid JB-1424-2-8 having ATCC Accession No. 75937, JB-1600-1 having ATCC Accession No. 75935 or JB-1468-29 having ATCC Accession No. 75936.

12. A transformed host cell containing an expression vector as claimed in claim 6.

13. The host of claim 12 which is selected from the group consisting of JB-1476-2-1, JB-1437-4-1 and JB-1607-1-1.

14. The host cell of claim 12 wherein said host cell is a Haemophilus bacteria.

15. A plasmid vector which is pT7TBP2A having ATCC Accession No. 75931, pT7TBP:2B having ATCC Accession No. 75932, pT7TBP2C having ATCC Accession No. 75933 or pT7TBP2D having ATCC Accession No. 75934.

16. A method of producing an isolated and purified Tbp1 or Tbp2 protein of a strain of Haemophilus, comprising the steps of:

(a) providing a recombinant host expressing, in inclusion bodies, Tbp1 or Tbp2 protein, but not both, wherein said Tbp1 protein has the amino acid sequence of FIGS. 3, 4, 5, 6 or 7 (SEQ ID NOS: 5, 7, 9, 11, 106) and said Tbp2 protein has the amino acid sequence of FIGS. 3, 4, 5, 6, 7, 8, 9, 10 or 11 (SEQ ID NOS: 6, 8, 10, 12, 107, 109, 111, 113, 115);

(b) growing said host to provide a cell mass;

(c) disrupting the cell mass to provide a cell lysate;

(d) fractionating the cell lysate to provide a first supernatant and a first pellet, the first supernatant comprising substantially a large proportion of soluble host proteins;

(e) separating said first supernatant from said first pellet;

(f) selectively extracting the first pellet to remove substantially all soluble host proteins and host membrane proteins therefrom to provide a second supernatant and an extracted pellet containing the inclusion bodies;

(g) separating said second supernatant from said extracted pellet;

(h) solubilizing the extracted pellet to provide a solubilized extract; and (i) fractionating the solubilized extract to provide a Tbp1 or Tbp2 protein containing fraction.

17. The method of claim 16 wherein the cell lysate is fractionated by centrifugation thereof.

18. The method of claim 17 wherein the step of selectively extracting the first pellet comprises at least one detergent extraction.

19. The method of claim 18 wherein the solubilized extract is fractionated by gel filtration to provide said Tbp1 or Tbp2 protein containing fraction.

20. The method of claim 19 including subsequently dialyzing the Tbp1 or Tbp2 protein containing fraction to remove at least said detergent to provide a further purified solution of Tbp1 or Tbp2 protein.

21. The method of claim 16 wherein said strain of Haemophilus is a strain of Haemophilus influenzae.

* * * * *